United States Patent
Itoi et al.

(10) Patent No.: US 12,284,916 B2
(45) Date of Patent: Apr. 22, 2025

(54) ORGANIC ELECTROLUMINESCENCE DEVICE AND ELECTRONIC APPARATUS PROVIDED WITH THE SAME

(71) Applicant: IDEMITSU KOSAN CO., LTD., Tokyo (JP)

(72) Inventors: Hiroaki Itoi, Sodegaura (JP); Yuki Nakano, Sodegaura (JP); Satomi Tasaki, Sodegaura (JP); Taro Yamaki, Sodegaura (JP); Tetsuya Masuda, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 844 days.

(21) Appl. No.: 17/602,273

(22) PCT Filed: Apr. 8, 2020

(86) PCT No.: PCT/JP2020/015850
§ 371 (c)(1),
(2) Date: Oct. 7, 2021

(87) PCT Pub. No.: WO2020/209299
PCT Pub. Date: Oct. 15, 2020

(65) Prior Publication Data
US 2022/0165964 A1 May 26, 2022

(30) Foreign Application Priority Data
Apr. 8, 2019 (JP) .................... 2019-073768

(51) Int. Cl.
*H01L 51/00* (2006.01)
*C07D 307/77* (2006.01)
(Continued)

(52) U.S. Cl.
CPC ....... *H10K 85/6574* (2023.02); *C07D 307/77* (2013.01); *C09K 11/06* (2013.01);
(Continued)

(58) Field of Classification Search
CPC .......... H10K 85/6574; H10K 85/6576; H10K 85/615; H10K 50/16
See application file for complete search history.

(56) References Cited

U.S. PATENT DOCUMENTS 10,763,441 B2 * 9/2020 Nakano ............... H10K 85/657
2007/0247063 A1 * 10/2007 Murase ............... C07D 209/86
548/440

(Continued)

FOREIGN PATENT DOCUMENTS

CN 106206964 A 12/2016
CN 106810457 A 6/2017
(Continued)

OTHER PUBLICATIONS

Office Action issued in corresponding Chinese Patent Application No. 202080027133.1 dated Dec. 1, 2023 (10 pages).
(Continued)

*Primary Examiner* — Michael M Dollinger
(74) *Attorney, Agent, or Firm* — Foley & Lardner LLP

(57) ABSTRACT

An organic electroluminescence device comprising: a cathode, an anode, and an organic layer disposed between the cathode and the anode, wherein the organic layer comprises an emitting layer and a first layer, the first layer is disposed between the cathode and the emitting layer, the emitting layer comprises a compound represented by the following formula (1), and the first layer comprises a compound represented by the following formula (BE1):

(Continued)

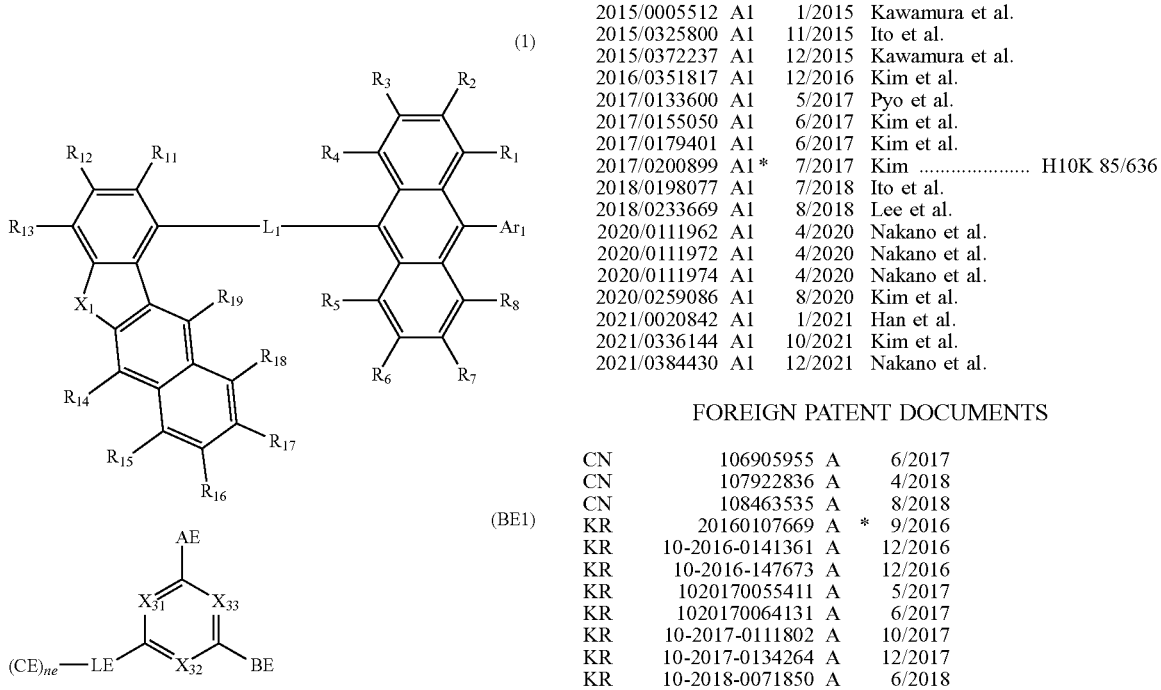

18 Claims, 1 Drawing Sheet

(51) Int. Cl.
 *C09K 11/06* (2006.01)
 *H10K 85/60* (2023.01)
 *H10K 50/11* (2023.01)
 *H10K 101/10* (2023.01)
(52) U.S. Cl.
 CPC .... *H10K 85/615* (2023.02); *C09K 2211/1018* (2013.01); *H10K 50/11* (2023.02); *H10K 2101/10* (2023.02)

(56) References Cited

U.S. PATENT DOCUMENTS

| | | | |
|---|---|---|---|
| 2012/0138907 A1* | 6/2012 | Murase | C09K 11/06 257/E51.026 |
| 2012/0138914 A1 | 6/2012 | Kawamura et al. | |
| 2014/0159005 A1 | 6/2014 | Kawamura et al. | |
| 2015/0005512 A1 | 1/2015 | Kawamura et al. | |
| 2015/0325800 A1 | 11/2015 | Ito et al. | |
| 2015/0372237 A1 | 12/2015 | Kawamura et al. | |
| 2016/0351817 A1 | 12/2016 | Kim et al. | |
| 2017/0133600 A1 | 5/2017 | Pyo et al. | |
| 2017/0155050 A1 | 6/2017 | Kim et al. | |
| 2017/0179401 A1 | 6/2017 | Kim et al. | |
| 2017/0200899 A1* | 7/2017 | Kim | H10K 85/636 |
| 2018/0198077 A1 | 7/2018 | Ito et al. | |
| 2018/0233669 A1 | 8/2018 | Lee et al. | |
| 2020/0111962 A1 | 4/2020 | Nakano et al. | |
| 2020/0111972 A1 | 4/2020 | Nakano et al. | |
| 2020/0111974 A1 | 4/2020 | Nakano et al. | |
| 2020/0259086 A1 | 8/2020 | Kim et al. | |
| 2021/0020842 A1 | 1/2021 | Han et al. | |
| 2021/0336144 A1 | 10/2021 | Kim et al. | |
| 2021/0384430 A1 | 12/2021 | Nakano et al. | |

FOREIGN PATENT DOCUMENTS

| | | | |
|---|---|---|---|
| CN | 106905955 A | | 6/2017 |
| CN | 107922836 A | | 4/2018 |
| CN | 108463535 A | | 8/2018 |
| KR | 20160107669 A | * | 9/2016 |
| KR | 10-2016-0141361 A | | 12/2016 |
| KR | 10-2016-147673 A | | 12/2016 |
| KR | 1020170055411 A | | 5/2017 |
| KR | 1020170064131 A | | 6/2017 |
| KR | 10-2017-0111802 A | | 10/2017 |
| KR | 10-2017-0134264 A | | 12/2017 |
| KR | 10-2018-0071850 A | | 6/2018 |
| KR | 1020190139783 A | | 12/2019 |
| WO | WO-2010/137285 A1 | | 12/2010 |
| WO | WO-2014/141725 A1 | | 9/2014 |
| WO | WO-2019/160335 A1 | | 8/2019 |
| WO | WO-2020/032428 A1 | | 2/2020 |
| WO | WO-2020/075769 A1 | | 4/2020 |
| WO | WO-2020/096012 A1 | | 5/2020 |
| WO | WO-2020/096021 A1 | | 5/2020 |
| WO | WO-2020/159279 A1 | | 8/2020 |

OTHER PUBLICATIONS

International Preliminary Report on Patentability (including WO-ISA) from PCT/JP2020/015850 dated Oct. 21, 2021 (6 pages).
International Search Report and Written Opinion from PCT/JP2020/015850 dated Jul. 28, 2020 (15 pages).
Notice of Submission of 3rd Party Observation issued in corresponding Korean Patent Application No. 10-2021-7032615, dated May 2, 2023.
Notice of Submission of 3rd Party Observation issued in corresponding Korean Patent Application No. 10-2021-7032634, dated Apr. 6, 2023.
Office Action issued in corresponding Korean Patent Application No. 10-2021-7032615 dated Nov. 12, 2024.

* cited by examiner

ORGANIC ELECTROLUMINESCENCE DEVICE AND ELECTRONIC APPARATUS PROVIDED WITH THE SAME

CROSS-REFERENCE TO RELATED APPLICATIONS

The present application claims priority under 37 U.S.C. § 371 to International Patent Application No PCT/JP2020/015850, filed Apr. 8, 2020, which claims priority to and the benefit of Japanese Patent Application No. 2019-073768, filed on Apr. 8, 2019. The contents of these applications are hereby incorporated by reference in their entireties.

TECHNICAL FIELD

The invention relates to an organic electroluminescence device and an electronic apparatus provided with the same.

BACKGROUND ART

When voltage is applied to an organic electroluminescence device, holes and electrons are injected into an emitting layer from an anode and a cathode, respectively. Then, thus injected holes and electrons are recombined in the emitting layer, and excitons are formed therein.

The organic EL device contains the emitting layer between the anode and the cathode. Further, the organic EL device has a stacked structure including an organic layer such as a hole-injecting layer, a hole-transporting layer, an electron-injecting layer, and an electron-transporting layer in several cases.

Patent Documents 1 to 5 disclose a material for an organic electroluminescence device composed of anthracene compound.

RELATED ART DOCUMENTS

Patent Documents

[Patent Document 1] WO2010/137285A1
[Patent Document 2] WO2014/141725A1
[Patent Document 3] US2016/0351817A1
[Patent Document 4] US2017/0133600A1
[Patent Document 5] US2018/0198077A1

SUMMARY OF INVENTION

An object of the invention is to provide an organic electroluminescence device having a low driving voltage and a long lifetime, and an electronic apparatus using the same.

According to the invention, the following organic electroluminescence device and electronic apparatus are provided.

1. An organic electroluminescence device comprising:
   a cathode,
   an anode, and
   an organic layer disposed between the cathode and the anode, wherein
   the organic layer comprises an emitting layer and a first layer,
   the first layer is disposed between the cathode and the emitting layer,
   the emitting layer comprises a compound represented by the following formula (1), and
   the first layer comprises a compound represented by the following formula (BE1):

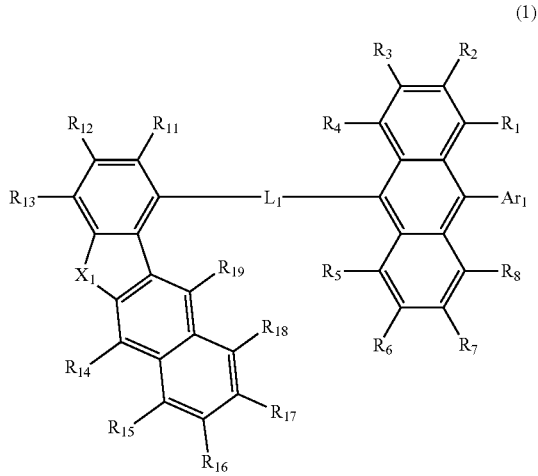

(1)

wherein in the formula (1),
$X_1$ is an oxygen atom or a sulfur atom;
$Ar_1$ is a substituted or unsubstituted aryl group including 6 to 50 ring carbon atoms, or
a substituted or unsubstituted monovalent heterocyclic group including 5 to 50 ring atoms;
$L_1$ is a single bond,
a substituted or unsubstituted arylene group including 6 to 50 ring carbon atoms, or
a substituted or unsubstituted divalent heterocyclic group including 5 to 50 ring atoms;
$R_1$ to $R_8$ and $R_{11}$ to $R_{19}$ are independently
a hydrogen atom, a halogen atom, a cyano group, a nitro group,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
—S—($R_{905}$),
—N($R_{906}$)($R_{907}$),
a substituted or unsubstituted aryl group including 6 to 50 ring carbon atoms, or
a substituted or unsubstituted monovalent heterocyclic group including 5 to 50 ring atoms;
$R_{901}$ to $R_{907}$ are independently
a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted monovalent heterocyclic group including 5 to 50 ring atoms; and
when two or more of each of $R_{901}$ to $R_{907}$ are present, the two or more of each of $R_{901}$ to $R_{907}$ are the same or different;

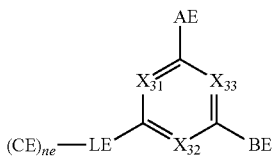

(BE1)

wherein in the formula (BE1), two or more of $X_{31}$ to $X_{33}$ are nitrogen atoms, and the rest which is not a nitrogen atom is CR;

R is a hydrogen atom, a cyano group, a substituted or unsubstituted alkyl group including 1 to 50 carbon atoms, a substituted or unsubstituted cycloalkyl group including 3 to 50 ring carbon atoms, —Si($R_{901}$)($R_{902}$)($R_{903}$),

—O—($R_{904}$), a substituted or unsubstituted aryl group including 6 to 50 ring carbon atoms, or a substituted or unsubstituted monovalent heterocyclic group including 5 to 50 ring atoms;

$R_{901}$ to $R_{904}$ are as defined in the formula (1);

when a plurality of R's are present, the plurality of R's may be the same as or different from each other;

AE is a substituted or unsubstituted aryl group including 6 to 50 ring carbon atoms, or a substituted or unsubstituted monovalent heterocyclic group including 5 to 50 ring atoms;

BE is a substituted or unsubstituted aryl group including 6 to 50 ring carbon atoms, or a substituted or unsubstituted monovalent heterocyclic group including 5 to 50 ring atoms;

LE is a single bond, a substituted or unsubstituted (nE+1)-valent aromatic hydrocarbon ring group including 6 to 50 ring carbon atoms, or a substituted or unsubstituted (nE+1)-valent heterocyclic group including 5 to 50 ring atoms; the aromatic hydrocarbon ring group may have a structure in which two or more different aromatic hydrocarbon rings are bonded;

CE's are independently a substituted or unsubstituted aryl group including 6 to 50 ring carbon atoms, or a substituted or unsubstituted monovalent heterocyclic group including 5 to 50 ring atoms;

nE is an integer of 1 to 3; and when nE is 2 or more, LE is not a single bond.

2. An electronic apparatus wherein the organic electroluminescence device according to 1 is provided.

According to the invention, it is possible to provide an organic electroluminescence device having a low driving voltage and a long lifetime, and an electronic apparatus using the same.

MODE FOR CARRYING OUT THE INVENTION

Definition

Figure 1:
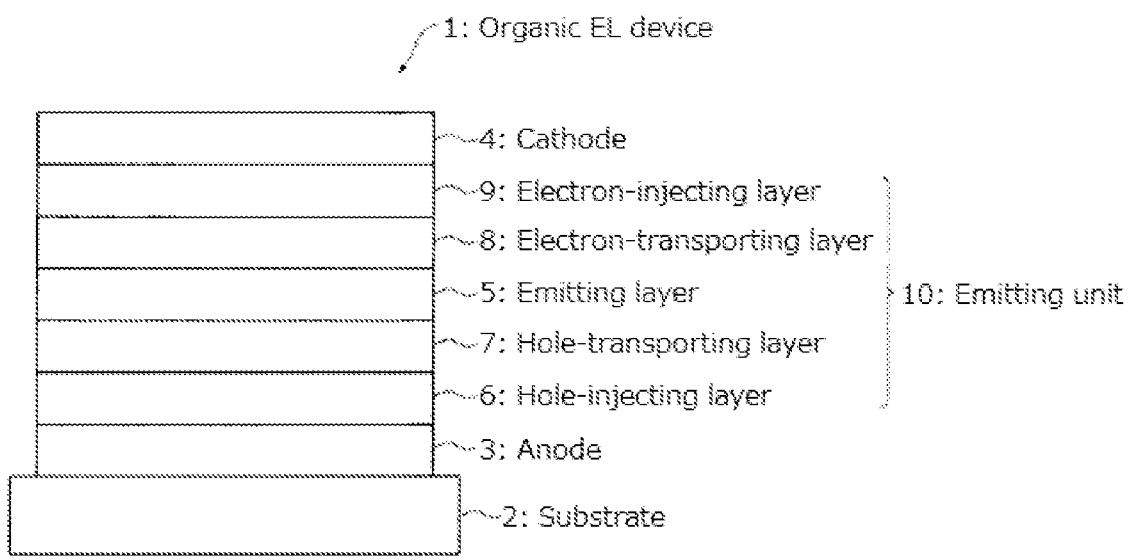
FIG. 1 is a diagram showing a schematic configuration of an embodiment of an organic EL device according to an aspect of the invention.

In this specification, a hydrogen atom includes its isotopes different in the number of neutrons, namely, a protium, a deuterium and a tritium.

In this specification, at a bondable position in a chemical formula where a symbol such as "R", or "D" representing a deuterium atom is not indicated, a hydrogen atom, that is, a protium atom, a deuterium atom or a tritium atom is bonded.

In this specification, the number of ring carbon atoms represents the number of carbon atoms forming a subject ring itself among the carbon atoms of a compound having a structure in which atoms are bonded in a ring form (for example, a monocyclic compound, a fused ring compound, a cross-linked compound, a carbocyclic compound, or a heterocyclic compound). When the subject ring is substituted by a substituent, the carbon contained in the substituent is not included in the number of ring carbon atoms. The same shall apply to "the number of ring carbon atoms" described below, unless otherwise specified. For example, a benzene ring has 6 ring carbon atoms, a naphthalene ring includes 10 ring carbon atoms, a pyridine ring includes 5 ring carbon atoms, and a furan ring includes 4 ring carbon atoms. Further, for example, a 9,9-diphenylfluorenyl group includes 13 ring carbon atoms, and a 9,9'-spirobifluorenyl group includes 25 ring carbon atoms.

When a benzene ring is substituted by, for example, an alkyl group as a substituent, the number of carbon atoms of the alkyl group is not included in the number of ring carbon atoms of the benzene ring. Therefore, the number of ring carbon atoms of the benzene ring substituted by the alkyl group is 6. When a naphthalene ring is substituted by, for example, an alkyl group as a substituent, the number of carbon atoms of the alkyl group is not included in the number of ring carbon atoms of the naphthalene ring. Therefore, the number of ring carbon atoms of the naphthalene ring substituted by the alkyl group is 10.

In this specification, the number of ring atoms represents the number of atoms forming a subject ring itself among the atoms of a compound having a structure in which atoms are bonded in a ring form (for example, the structure includes a monocyclic ring, a fused ring and a ring assembly) (for example, a monocyclic compound, a fused ring compound, a cross-linked compound, a carbocyclic compound and a heterocyclic compound). The number of ring atoms does not include atoms which do not form the ring (for example, a hydrogen atom which terminates a bond of the atoms forming the ring), or atoms contained in a substituent when the ring is substituted by the substituent. The same shall apply to "the number of ring atoms" described below, unless otherwise specified. For example, the number of atoms of a pyridine ring is 6, the number of atoms of a quinazoline ring is 10, and the number of a furan ring is 5. For example, hydrogen atoms bonded to a pyridine ring and atoms constituting a substituent substituted on the pyridine ring are not included in the number of ring atoms of the pyridine ring. Therefore, the number of ring atoms of a pyridine ring with which a hydrogen atom or a substituent is bonded is 6. For example, hydrogen atoms and atoms constituting a substituent which are bonded with a quinazoline ring is not included in the number of ring atoms of the quinazoline ring. Therefore, the number of ring atoms of a quinazoline ring with which a hydrogen atom or a substituent is bonded is 10.

In this specification, "XX to YY carbon atoms" in the expression "a substituted or unsubstituted ZZ group including XX to YY carbon atoms" represents the number of carbon atoms in the case where the ZZ group is unsubstituted by a substituent, and does not include the number of carbon atoms of a substituent in the case where the ZZ group is substituted by the substituent. Here, "YY" is larger than "XX", and "XX" means an integer of 1 or more and "YY" means an integer of 2 or more.

In this specification, "XX to YY atoms" in the expression "a substituted or unsubstituted ZZ group including XX to YY atoms" represents the number of atoms in the case where the ZZ group is unsubstituted by a substituent, and does not include the number of atoms of a substituent in the case where the ZZ group is substituted by the substituent. Here, "YY" is larger than "XX", and "XX" means an integer of 1 or more and "YY" means an integer of 2 or more.

In this specification, the unsubstituted ZZ group represents the case where the "substituted or unsubstituted ZZ group" is a "ZZ group unsubstituted by a substituent", and the substituted ZZ group represents the case where the "substituted or unsubstituted ZZ group" is a "ZZ group substituted by a substituent".

In this specification, a term "unsubstituted" in the case of "a substituted or unsubstituted ZZ group" means that hydrogen atoms in the ZZ group are not substituted by a substituent. Hydrogen atoms in a term "unsubstituted ZZ group" are a protium atom, a deuterium atom, or a tritium atom.

In this specification, a term "substituted" in the case of "a substituted or unsubstituted ZZ group" means that one or more hydrogen atoms in the ZZ group are substituted by a substituent. Similarly, a term "substituted" in the case of "a BB group substituted by an AA group" means that one or more hydrogen atoms in the BB group are substituted by the AA group.

"Substituent as Described in this Specification"

Hereinafter, the substituent described in this specification will be explained.

The number of ring carbon atoms of the "unsubstituted aryl group" described in this specification is 6 to 50, preferably 6 to 30, and more preferably 6 to 18, unless otherwise specified.

The number of ring atoms of the "unsubstituted heterocyclic group" described in this specification is 5 to 50, preferably 5 to 30, and more preferably 5 to 18, unless otherwise specified.

The number of carbon atoms of the "unsubstituted alkyl group" described in this specification is 1 to 50, preferably 1 to 20, and more preferably 1 to 6, unless otherwise specified.

The number of carbon atoms of the "unsubstituted alkenyl group" described in this specification is 2 to 50, preferably 2 to 20, and more preferably 2 to 6, unless otherwise specified.

The number of carbon atoms of the "unsubstituted alkynyl group" described in this specification is 2 to 50, preferably 2 to 20, and more preferably 2 to 6, unless otherwise specified.

The number of ring carbon atoms of the "unsubstituted cycloalkyl group" described in this specification is 3 to 50, preferably 3 to 20, and more preferably 3 to 6, unless otherwise specified.

The number of ring carbon atoms of the "unsubstituted arylene group" described in this specification is 6 to 50, preferably 6 to 30, and more preferably 6 to 18, unless otherwise specified.

The number of ring atoms of the "unsubstituted divalent heterocyclic group" described in this specification is 5 to 50, preferably 5 to 30, and more preferably 5 to 18, unless otherwise specified.

The number of carbon atoms of the "unsubstituted alkylene group" described in this specification is 1 to 50, preferably 1 to 20, and more preferably 1 to 6, unless otherwise specified.

"Substituted or Unsubstituted Aryl Group"

Specific examples of the "substituted or unsubstituted aryl group" described in this specification (specific example group G1) include the following unsubstituted aryl groups (specific example group G1A), substituted aryl groups (specific example group G1B), and the like. (Here, the unsubstituted aryl group refers to the case where the "substituted or unsubstituted aryl group" is an "aryl group unsubstituted by a substituent", and the substituted aryl group refers to the case where the "substituted or unsubstituted aryl group" is an "aryl group substituted by a substituent"). In this specification, in the case where simply referred as an "aryl group", it includes both a "unsubstituted aryl group" and a "substituted aryl group."

The "substituted aryl group" means a group in which one or more hydrogen atoms of the "unsubstituted aryl group" are substituted by a substituent. Specific examples of the "substituted aryl group" include, for example, groups in which one or more hydrogen atoms of the "unsubstituted aryl group" of the following specific example group G1A are substituted by a substituent, the substituted aryl groups of the following specific example group G1B, and the like. It should be noted that the examples of the "unsubstituted aryl group" and the examples of the "substituted aryl group" enumerated in this specification are mere examples, and the "substituted aryl group" described in this specification also includes a group in which a hydrogen atom bonded with a carbon atom of the aryl group itself in the "substituted aryl group" of the following specific group G1B is further substituted by a substituent, and a group in which a hydrogen atom of a substituent in the "substituted aryl group" of the following specific group G1B is further substituted by a substituent.

Unsubstituted Aryl Group (Specific Example Group G1A):
a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group,
a benzanthryl group,
a phenanthryl group,
a benzophenanthryl group,
a phenalenyl group,
a pyrenyl group, a chrysenyl group,
a benzochrysenyl group,
a triphenylenyl group,
a benzotriphenylenyl group,
a tetracenyl group,
a pentacenyl group,
a fluorenyl group,
a 9,9'-spirobifluorenyl group,
a benzofluorenyl group,
a dibenzofluorenyl group,
a fluoranthenyl group,
a benzofluoranthenyl group,
a perylenyl group, and
a monovalent aryl group derived by removing one hydrogen atom from the ring structures represented by any of the following general formulas (TEMP-1) to (TEMP-15).

(TEMP-1)

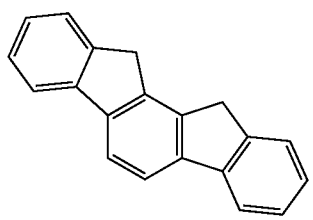

(TEMP-2)

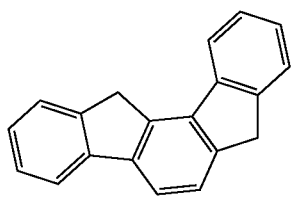

(TEMP-3)

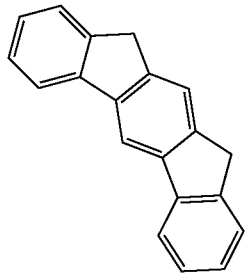

(TEMP-4)

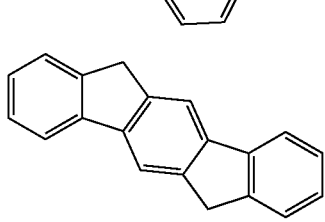

(TEMP-5)

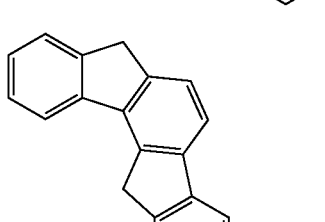

(TEMP-6)

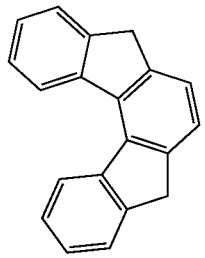

(TEMP-7)

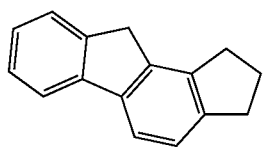

(TEMP-8)

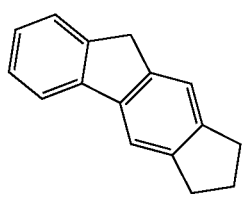

(TEMP-9)

(TEMP-10)

(TEMP-11)

(TEMP-12)

(TEMP-13)

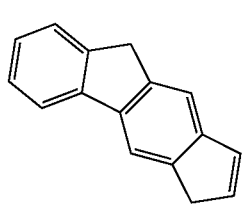

-continued

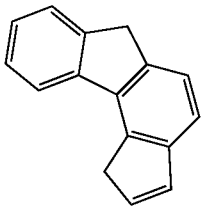

(TEMP-14)

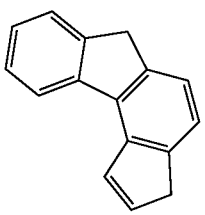

(TEMP-15)

Substituted Aryl Group (Specific Example Group G1B):
an o-tolyl group,
a m-tolyl group,
a p-tolyl group,
a p-xylyl group,
a m-xylyl group,
an o-xylyl group,
a p-isopropylphenyl group,
a m-isopropylphenyl group,
an o-isopropylphenyl group,
a p-t-butylphenyl group,
a m-t-butylphenyl group,
an o-t-butylphenyl group,
a 3,4,5-trimethylphenyl group,
a 9,9-dimethylfluorenyl group,
a 9,9-diphenylfluorenyl group,
a 9,9-bis(4-methylphenyl)fluorenyl group,
a 9,9-bis(4-isopropylphenyl)fluorenyl group,
a 9,9-bis(4-t-butylphenyl)fluorenyl group,
a cyanophenyl group,
a triphenylsilylphenyl group,
a trimethylsilylphenyl group,
a phenylnaphthyl group,
a naphthylphenyl group, and
a group in which one or more hydrogen atoms of a monovalent group derived from the ring structures represented by any of the general formulas (TEMP-1) to (TEMP-15) are substituted by a substituent.

"Substituted or Unsubstituted Heterocyclic Group"

The "heterocyclic group" described in this specification is a ring group having at least one hetero atom in the ring atom. Specific examples of the hetero atom include a nitrogen atom, an oxygen atom, a sulfur atom, a silicon atom, a phosphorus atom, and a boron atom.

The "heterocyclic group" in this specification is a monocyclic group or a fused ring group.

The "heterocyclic group" in this specification is an aromatic heterocyclic group or a non-aromatic heterocyclic group.

Specific examples of the "substituted or unsubstituted heterocyclic group" (specific example group G2) described in this specification include the following unsubstituted heterocyclic group (specific example group G2A), the following substituted heterocyclic group (specific example group G2B), and the like. (Here, the unsubstituted heterocyclic group refers to the case where the "substituted or unsubstituted heterocyclic group" is a "heterocyclic group unsubstituted by a substituent", and the substituted heterocyclic group refers to the case where the "substituted or unsubstituted heterocyclic group" is a "heterocyclic group substituted by a substituent"). In this specification, in the case where simply referred as a "heterocyclic group", it includes both the "unsubstituted heterocyclic group" and the "substituted heterocyclic group."

The "substituted heterocyclic group" means a group in which one or more hydrogen atom of the "unsubstituted heterocydic group" are substituted by a substituent. Specific examples of the "substituted heterocyclic group" include a group in which a hydrogen atom of "unsubstituted heterocydic group" of the following specific example group G2A is substituted by a substituent, the substituted heterocyclic groups of the following specific example group G2B, and the like. It should be noted that the examples of the "unsubstituted heterocyclic group" and the examples of the "substituted heterocyclic group" enumerated in this specification are mere examples, and the "substituted heterocyclic group" described in this specification includes groups in which hydrogen atom bonded with a ring atom of the heterocyclic group itself in the "substituted heterocyclic group" of the specific example group G2B is further substituted by a substituent, and a group in which hydrogen atom of a substituent in the "substituted heterocyclic group" of the specific example group G2B is further substituted by a substituent.

Specific example group G2A includes, for example, the following unsubstituted heterocyclic group containing a nitrogen atom (specific example group G2A1), the following unsubstituted heterocyclic group containing an oxygen atom (specific example group G2A2), the following unsubstituted heterocydic group containing a sulfur atom (specific example group G2A3), and the monovalent heterocyclic group derived by removing one hydrogen atom from the ring structures represented by any of the following general formulas (TEMP-16) to (TEMP-33) (specific example group G2A4).

Specific example group G2B includes, for example, the following substituted heterocydic group containing a nitrogen atom (specific example group G2B1), the following substituted heterocyclic group containing an oxygen atom (specific example group G2B2), the following substituted heterocydic group containing a sulfur atom (specific example group G2B3), and the following group in which one or more hydrogen atoms of the monovalent heterocyclic group derived from the ring structures represented by any of the following general formulas (TEMP-16) to (TEMP-33) are substituted by a substituent (specific example group G2B4).

Unsubstituted Heterocyclic Group Containing a Nitrogen Atom (Specific Example Group G2A1):
a pyrrolyl group,
an imidazolyl group,
a pyrazolyl group,
a triazolyl group,
a tetrazolyl group,
an oxazolyl group,
an isoxazolyl group,
an oxadiazolyl group,
a thiazolyl group,
an isothiazolyl group,
a thiadiazolyl group,
a pyridyl group,
a pyridazinyl group,
a pyrimidinyl group,
a pyrazinyl group, a triazinyl group,
an indolyl group,
an isoindolyl group,
an indolizinyl group,
a quinolizinyl group,
a quinolyl group,
an isoquinolyl group,
a cinnolyl group,
a phthalazinyl group,
a quinazolinyl group,
a quinoxalinyl group,
a benzimidazolyl group,
an indazolyl group,
a phenanthrolinyl group,
a phenanthridinyl group,
an acridinyl group,
a phenazinyl group,
a carbazolyl group,
a benzocarbazolyl group,
a morpholino group,
a phenoxazinyl group,
a phenothiazinyl group,
an azacarbazolyl group, and
a diazacarbazolyl group.

Unsubstituted Heterocyclic Group Containing an Oxygen Atom (Specific Example Group G2A2):
  a furyl group,
  an oxazolyl group,
  an isoxazolyl group,
  an oxadiazolyl group,
  a xanthenyl group,
  a benzofuranyl group,
  an isobenzofuranyl group,
  a dibenzofuranyl group,
  a naphthobenzofuranyl group,
  a benzoxazolyl group,
  a benzisoxazolyl group,
  a phenoxazinyl group,
  a morpholino group,
  a dinaphthofuranyl group,
  an azadibenzofuranyl group,
  a diazadibenzofuranyl group,
  an azanaphthobenzofuranyl group, and
  a diazanaphthobenzofuranyl group.

Unsubstituted Heterocyclic Group Containing a Sulfur Atom (Specific Example Group G2A3):
  a thienyl group,
  a thiazolyl group,
  an isothiazolyl group,
  a thiadiazolyl group,
  a benzothiophenyl group (benzothienyl group),
  an isobenzothiophenyl group (isobenzothienyl group),
  a dibenzothiophenyl group (dibenzothienyl group),
  a naphthobenzothiophenyl group (naphthobenzothienyl group),
  a benzothiazolyl group,
  a benzisothiazolyl group,
  a phenothiazinyl group,
  a dinaphthothiophenyl group (dinaphthothienyl group),
  an azadibenzothiophenyl group (azadibenzothienyl group),
  a diazadibenzothiophenyl group (diazadibenzothienyl group),
  an azanaphthobenzothiophenyl group (azanaphthobenzothienyl group), and
  a diazanaphthobenzothiophenyl group (diazanaphthobenzothienyl group).

Monovalent Heterocyclic Group Derived by Removing One Hydrogen Atom from the Ring Structures Represented by any of the Following General Formulas (TEMP-16) to (TEMP-33) (Specific Example Group G2A4):

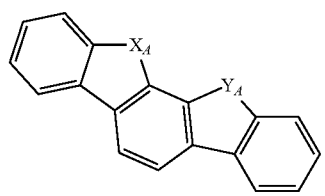
(TEMP-16)

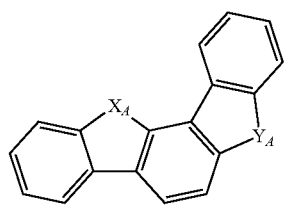
(TEMP-17)

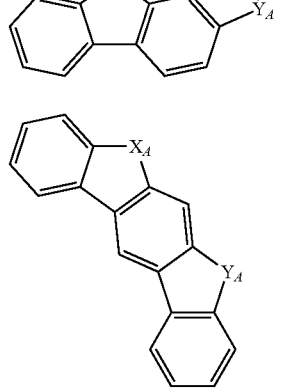
(TEMP-18)

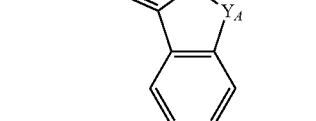
(TEMP-19)

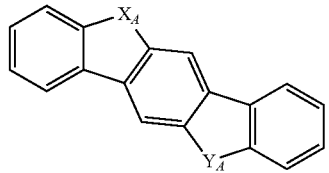
(TEMP-20)

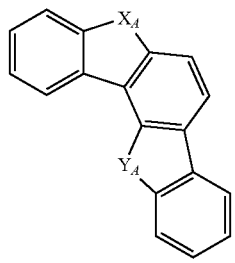
(TEMP-21)

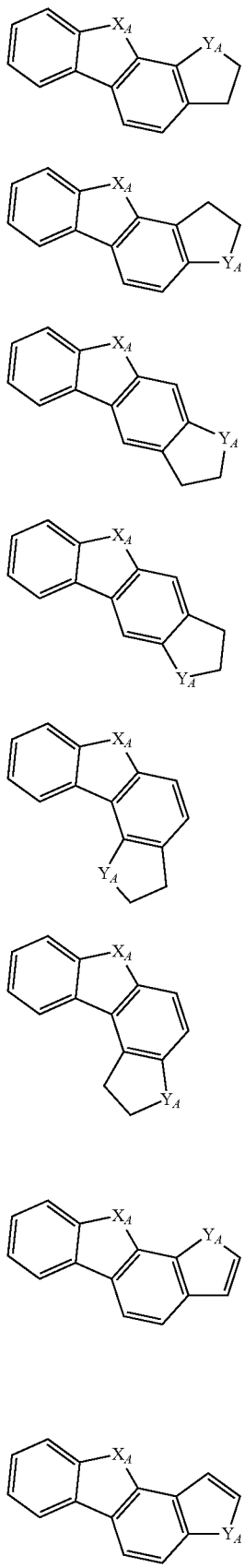

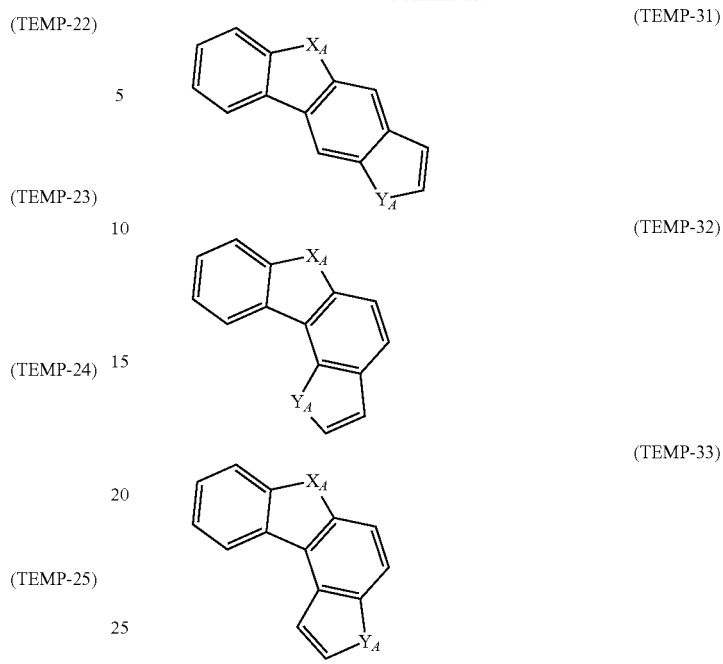

In the general formulas (TEMP-16) to (TEMP-33), $X_A$ and $Y_A$ are independently an oxygen atom, a sulfur atom, NH, or $CH_2$. Provided that at least one of $X_A$ and $Y_A$ is an oxygen atom, a sulfur atom, or NH.

In the general formulas (TEMP-16) to (TEMP-33), when at least one of $X_A$ and $Y_A$ is NH or $CH_2$, the monovalent heterocyclic group derived from the ring structures represented by any of the general formulas (TEMP-16) to (TEMP-33) includes a monovalent group derived by removing one hydrogen atom from these NH or $CH_2$.

Substituted Heterocyclic Group Containing a Nitrogen Atom (Specific Example Group G2B1):
 a (9-phenyl)carbazolyl group,
 a (9-biphenylyl)carbazolyl group,
 a (9-phenyl)phenylcarbazolyl group,
 a (9-naphthyl)carbazolyl group,
 a diphenylcarbazol-9-yl group,
 a phenylcarbazol-9-yl group,
 a methylbenzimidazolyl group,
 an ethylbenzimidazolyl group,
 a phenyltriazinyl group,
 a biphenylyltriazinyl group,
 a diphenyltriazinyl group,
 a phenylquinazolinyl group, and
 a biphenylylquinazolinyl group.

Substituted Heterocyclic Group Containing an Oxygen Atom (Specific Example Group G2B2):
 a phenyldibenzofuranyl group,
 a methyldibenzofuranyl group,
 a t-butyldibenzofuranyl group, and
 a monovalent residue of spiro[9H-xanthene-9,9'-[9H]fluorene].

Substituted Heterocyclic Group Containing a Sulfur Atom (Specific Example Group G2B3):
 a phenyldibenzothiophenyl group,
 a methyldibenzothiophenyl group,
 a t-butyldibenzothiophenyl group, and
 a monovalent residue of spiro[9H-thioxanthene-9,9'-[9H]fluorene].

Group in which One or More Hydrogen Atoms of the Monovalent Heterocyclic Group Derived from the Ring Structures Represented by any of the Following General Formulas (TEMP-16) to (TEMP-33) are Substituted by a Substituent (Specific Example Group G2B4):

The "one or more hydrogen atoms of the monovalent heterocyclic group" means one or more hydrogen atoms selected from hydrogen atoms bonded with ring carbon atoms of the monovalent heterocyclic group, a hydrogen atom bonded with a nitrogen atom when at least one of $X_A$ and $Y_A$ is NH, and hydrogen atoms of a methylene group when one of $X_A$ and $Y_A$ is $CH_2$.

"Substituted or Unsubstituted Alkyl Group"

Specific examples of the "substituted or unsubstituted alkyl group" (specific example group G3) described in this specification include the following unsubstituted alkyl groups (specific example group G3A) and the following substituted alkyl groups (specific example group G3B). (Here, the unsubstituted alkyl group refers to the case where the "substituted or unsubstituted alkyl group" is an "alkyl group unsubstituted by a substituent", and the substituted alkyl group refers to the case where the "substituted or unsubstituted alkyl group" is an "alkyl group substituted by a substituent"). In this specification, in the case where simply referred as an "alkyl group" includes both the "unsubstituted alkyl group" and the "substituted alkyl group."

The "substituted alkyl group" means a group in which one or more hydrogen atoms in the "unsubstituted alkyl group" are substituted by a substituent. Specific examples of the "substituted alkyl group" include groups in which one or more hydrogen atoms in the following "unsubstituted alkyl group" (specific example group G3A) are substituted by a substituent, the following substituted alkyl group (specific example group G3B), and the like. In this specification, the alkyl group in the "unsubstituted alkyl group" means a linear alkyl group. Thus, the "unsubstituted alkyl group" includes a straight-chain "unsubstituted alkyl group" and a branched-chain "unsubstituted alkyl group". It should be noted that the examples of the "unsubstituted alkyl group" and the examples of the "substituted alkyl group" enumerated in this specification are mere examples, and the "substituted alkyl group" described in this specification includes a group in which hydrogen atom of the alkyl group itself in the "substituted alkyl group" of the specific example group G3B is further substituted by a substituent, and a group in which hydrogen atom of a substituent in the "substituted alkyl group" of the specific example group G3B is further substituted by a substituent.

Unsubstituted Alkyl Group (Specific Example Group G3A):
  a methyl group,
  an ethyl group,
  a n-propyl group,
  an isopropyl group,
  a n-butyl group,
  an isobutyl group,
  a s-butyl group, and
  a t-butyl group.

Substituted Alkyl Group (Specific Example Group G3B):
  a heptafluoropropyl group (including isomers),
  a pentafluoroethyl group,
  a 2,2,2-trifluoroethyl group, and
  a trifluoromethyl group.

"Substituted or Unsubstituted Alkenyl Group"

Specific examples of the "substituted or unsubstituted alkenyl group" described in this specification (specific example group G4) include the following unsubstituted alkenyl group (specific example group G4A), the following substituted alkenyl group (specific example group G4B), and the like. (Here, the unsubstituted alkenyl group refers to the case where the "substituted or unsubstituted alkenyl group" is a "alkenyl group unsubstituted by a substituent", and the "substituted alkenyl group" refers to the case where the "substituted or unsubstituted alkenyl group" is a "alkenyl group substituted by a substituent."). In this specification, in the case where simply referred as an "alkenyl group" includes both the "unsubstituted alkenyl group" and the "substituted alkenyl group."

The "substituted alkenyl group" means a group in which one or more hydrogen atoms in the "unsubstituted alkenyl group" are substituted by a substituent. Specific examples of the "substituted alkenyl group" include a group in which the following "unsubstituted alkenyl group" (specific example group G4A) has a substituent, the following substituted alkenyl group (specific example group G4B), and the like. It should be noted that the examples of the "unsubstituted alkenyl group" and the examples of the "substituted alkenyl group" enumerated in this specification are mere examples, and the "substituted alkenyl group" described in this specification includes a group in which a hydrogen atom of the alkenyl group itself in the "substituted alkenyl group" of the specific example group G4B is further substituted by a substituent, and a group in which a hydrogen atom of a substituent in the "substituted alkenyl group" of the specific example group G4B is further substituted by a substituent.

Unsubstituted Alkenyl Group (Specific Example Group G4A):
  a vinyl group,
  an allyl group,
  a 1-butenyl group,
  a 2-butenyl group, and
  a 3-butenyl group.

Substituted Alkenyl Group (Specific Example Group G4B):
  a 1,3-butanedienyl group,
  a 1-methylvinyl group,
  a 1-methylallyl group,
  a 1,1-dimethylallyl group,
  a 2-methylally group, and
  a 1,2-dimethylallyl group.

"Substituted or Unsubstituted Alkynyl Group"

Specific examples of the "substituted or unsubstituted alkynyl group" described in this specification (specific example group G5) include the following unsubstituted alkynyl group (specific example group G5A) and the like. (Here, the unsubstituted alkynyl group refers to the case where the "substituted or unsubstituted alkynyl group" is an "alkynyl group unsubstituted by a substituent"). In this specification, in the case where simply referred as an "alkynyl group" includes both the "unsubstituted alkynyl group" and the "substituted alkynyl group."

The "substituted alkynyl group" means a group in which one or more hydrogen atoms in the "unsubstituted alkynyl group" are substituted by a substituent. Specific examples of the "substituted alkynyl group" include a group in which one or more hydrogen atoms in the following "unsubstituted alkynyl group" (specific example group G5A) are substituted by a substituent, and the like.

Unsubstituted Alkynyl Group (Specific Example Group G5A):
  an ethynyl group.

"Substituted or Unsubstituted Cycloalkyl Group"

Specific examples of the "substituted or unsubstituted cycloalkyl group" described in this specification (specific example group G6) include the following unsubstituted cycloalkyl group (specific example group G6A), the following substituted cycloalkyl group (specific example group G6B), and the like. (Here, the unsubstituted cycloalkyl group refers to the case where the "substituted or unsubstituted cycloalkyl group" is a "cycloalkyl group unsubstituted by a substituent", and the substituted cycloalkyl group refers to the case where the "substituted or unsubstituted cycloalkyl group" is a "cycloalkyl group substituted by a substituent"). In this specification, in the case where simply referred to as a "cycloalkyl group" includes both the "unsubstituted cycloalkyl group" and the "substituted cycloalkyl group."

The "substituted cycloalkyl group" means a group in which one or more hydrogen atoms in the "unsubstituted cycloalkyl group" are substituted by a substituent. Specific examples of the "substituted cycloalkyl group" include a group in which one or more hydrogen atoms in the following "unsubstituted cycloalkyl group" (specific example group G6A) are substituted by a substituent, and examples of the following substituted cycloalkyl group (specific example group G6B), and the like. It should be noted that the examples of the "unsubstituted cycloalkyl group" and the examples of the "substituted cycloalkyl group" enumerated in this specification are mere examples, and the "substituted cycloalkyl group" in this specification includes a group in which one or more hydrogen atoms bonded with the carbon atom of the cycloalkyl group itself in the "substituted cycloalkyl group" of the specific example group G6B are substituted by a substituent, and a group in which a hydrogen atom of a substituent in the "substituted cycloalkyl group" of specific example group G6B is further substituted by a substituent.

Unsubstituted Cycloalkyl Group (Specific Example Group G6A):
  a cyclopropyl group,
  a cyclobutyl group,
  a cyclopentyl group,
  a cyclohexyl group,
  a 1-adamantyl group,
  a 2-adamantyl group,
  a 1-norbornyl group, and
  a 2-norbornyl group.

Substituted Cycloalkyl Group (Specific Example Group G6B):
  a 4-methylcyclohexyl group.

"Group Represented by —Si ($R_{901}$)($R_{902}$)($R_{903}$)"

Specific examples of the group represented by —Si($R_{901}$)($R_{902}$)($R_{903}$) described in this specification (specific example group G7) include:
  —Si(G1)(G1)(G1),
  —Si(G1)(G2)(G2),
  —Si(G1)(G1)(G2),
  —Si(G2)(G2)(G2),
  —Si(G3)(G3)(G3), and
  —Si(G6)(G6)(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

Plural G1's in —Si(G1)(G1)(G1) are the same or different.

Plural G2's in —Si(G1)(G2)(G2) are the same or different.

Plural G1's in —Si(G1)(G1)(G2) are the same or different.

Plural G2's in —Si(G2)(G2)(G2) are be the same or different.

Plural G3's in —Si(G3)(G3)(G3) are the same or different.

Plural G6's in —Si(G6)(G6)(G6) are be the same or different.

"Group Represented by —O—($R_{904}$)"

Specific examples of the group represented by —O—($R_{904}$) in this specification (specific example group G8) include:
  —O(G1),
  —O(G2),
  —O(G3), and
  —O(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

"Group Represented by —S—($R_{905}$)"

Specific examples of the group represented by —S—($R_{906}$) in this specification (specific example group G9) include:
  —S(G1),
  —S(G2),
  —S(G3), and
  —S(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

"Group Represented by —N($R^{906}$)($R_{907}$)"

Specific examples of the group represented by —N($R_{906}$)($R_{907}$) in this specification (specific example group G10) include:
  —N(G1)(G1),
  —N(G2)(G2),
  —N(G1)(G2),
  —N(G3)(G3), and
  —N(G6)(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

Plural G1's in —N(G1)(G1) are the same or different.
Plural G2's in —N(G2)(G2) are the same or different.
Plural G3's in —N(G3)(G3) are the same or different.
Plural G6's in —N(G6)(G6) are the same or different.

"Halogen Atom"

Specific examples of the "halogen atom" described in this specification (specific example group G11) include a fluorine atom, a chlorine atom, a bromine atom, an iodine atom, and the like.

"Substituted or Unsubstituted Fluoroalkyl Group"

The "substituted or unsubstituted fluoroalkyl group" described in this specification is a group in which at least one hydrogen atom bonded with a carbon atom constituting the alkyl group in the "substituted or unsubstituted alkyl group" is substituted by a fluorine atom, and includes a group in which all hydrogen atoms bonded with a carbon atom constituting the alkyl group in the "substituted or unsubstituted alkyl group" are substituted by a fluorine atom (a perfluoro group). The number of carbon atoms of the "unsubstituted fluoroalkyl group" is 1 to 50, preferably 1 to 30, more preferably 1 to 18, unless otherwise specified in this specification. The "substituted fluoroalkyl group" means a group in which one or more hydrogen atoms of the "fluoroalkyl group" are substituted by a substituent. The "substituted fluoroalkyl group" described in this specification also includes a group in which one or more hydrogen atoms bonded with a carbon atom of the alkyl chains in the "substituted fluoroalkyl group" are further substituted by a substituent, and a group in which one or more hydrogen atom of a substituent in the "substituted fluoroalkyl group" are further substituted by a substituent. Specific examples of the "unsubstituted fluoroalkyl group" include a group in which one or more hydrogen atoms in the "alkyl group" (specific group G3) are substituted by a fluorine atom, and the like.

"Substituted or Unsubstituted Haloalkyl Group"

The "substituted or unsubstituted haloalkyl group" described in this specification is a group in which at least one hydrogen atom bonded with a carbon atom constituting the alkyl group in the "substituted or unsubstituted alkyl group" is substituted by a halogen atom, and also includes a group in which all hydrogen atoms bonded with a carbon atom constituting the alkyl group in the "substituted or unsubstituted alkyl group" are substituted by a halogen atom. The number of carbon atoms of the "unsubstituted haloalkyl group" is 1 to 50, preferably 1 to 30, more preferably 1 to 18, unless otherwise specified in this specification. The "substituted haloalkyl group" means a group in which one or more hydrogen atoms of the "haloalkyl group" are substituted by a substituent. The "substituted haloalkyl group" described in this specification also includes a group in which one or more hydrogen atoms bonded with a carbon atom of the alkyl chain in the "substituted haloalkyl group" are further substituted by a substituent, and a group in which one or more hydrogen atoms of a substituent in the "substituted haloalkyl group" are further substituted by a substituent. Specific examples of the "unsubstituted haloalkyl group" include a group in which one or more hydrogen atoms in the "alkyl group" (specific example group G3) are substituted by a halogen atom, and the like. A haloalkyl group is sometimes referred to as an alkyl halide group.

"Substituted or Unsubstituted Alkoxy Group"

Specific examples of the "substituted or unsubstituted alkoxy group" described in this specification include a group represented by —O(G3), wherein G3 is the "substituted or unsubstituted alkyl group" described in the specific example group G3. The number of carbon atoms of the "unsubstituted alkoxy group" is 1 to 50, preferably 1 to 30, more preferably 1 to 18, unless otherwise specified in this specification.

"Substituted or Unsubstituted Alkylthio Group"

Specific examples of the "substituted or unsubstituted alkylthio group" described in this specification include a group represented by —S(G3), wherein G3 is the "substituted or unsubstituted alkyl group" described in the specific example group G3. The number of carbon atoms of the "unsubstituted alkylthio group" is 1 to 50, preferably 1 to 30, more preferably 1 to 18, unless otherwise specified in this specification.

"Substituted or Unsubstituted Aryloxy Group"

Specific examples of the "substituted or unsubstituted aryloxy group" described in this specification include a group represented by —O(G1), wherein G1 is the "substituted or unsubstituted aryl group" described in the specific example group G1. The number of ring carbon atoms of the "unsubstituted aryloxy group" is 6 to 50, preferably 6 to 30, more preferably 6 to 18, unless otherwise specified in this specification.

"Substituted or Unsubstituted Arylthio Group"

Specific examples of the "substituted or unsubstituted arylthio group" described in this specification include a group represented by —S(G1), wherein G1 is a "substituted or unsubstituted aryl group" described in the specific example group G1. The number of ring carbon atoms of the "unsubstituted arylthio group" is 6 to 50, preferably 6 to 30, more preferably 6 to 18, unless otherwise specified in this specification.

"Substituted or Unsubstituted Trialkylsilyl Group"

Specific examples of the "trialkylsilyl group" described in this specification include a group represented by —Si(G3)(G3)(G3), where G3 is the "substituted or unsubstituted alkyl group" described in the specific example group G3. Plural G3's in —Si(G3)(G3)(G3) are the same or different. The number of carbon atoms in each alkyl group of the "trialkylsilyl group" is 1 to 50, preferably 1 to 20, more preferably 1 to 6, unless otherwise specified in this specification.

"Substituted or Unsubstituted Aralkyl Group"

Specific examples of the "substituted or unsubstituted aralkyl group" described in this specification is a group represented by -(G3)-(G1), wherein G3 is the "substituted or unsubstituted alkyl group" described in the specific example group G3, and G1 is the "substituted or unsubstituted aryl group" described in the specific example group G1. Therefore, the "aralkyl group" is a group in which a hydrogen atom of the "alkyl group" is substituted by an "aryl group" as a substituent, and is one form of the "substituted alkyl group." The "unsubstituted aralkyl group" is the "unsubstituted alkyl group" substituted by the "unsubstituted aryl group", and the number of carbon atoms of the "unsubstituted aralkyl group" is 7 to 50, preferably 7 to 30, more preferably 7 to 18, unless otherwise specified in this specification.

Specific examples of the "substituted or unsubstituted aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, and the like.

Unless otherwise specified in this specification, examples of the substituted or unsubstituted aryl group described in this specification preferably include a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, 9,9-dimethylfluorenyl group, 9,9-diphenylfluorenyl group, and the like.

Unless otherwise specified in this specification, examples of the substituted or unsubstituted heterocyclic groups described in this specification preferably include a pyridyl group, a pyrimidinyl group, a triazinyl group, a quinolyl group, an isoquinolyl group, a quinazolinyl group, a benzimidazolyl group, a phenanthrolinyl group, a carbazolyl group (a 1-carbazolyl group, a 2-carbazolyl group, a 3-carbazolyl group, a 4-carbazolyl group, or a 9-carbazolyl group), a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group (a (9-phenyl)carbazol-1-yl group, a (9-phenyl)carbazol-2-yl group, a (9-phenyl)carbazol-3-yl group, or a (9-phenyl)carbazol-4-yl group), a (9-biphenylyl)carbazolyl group, a (9-phenyl)phenylcarbazolyl group, a diphenylcarbazol-9-yl group, a phenylcarbazol-9-yl group, a phenyltriazinyl group, a biphenylyltriazinyl group, a diphenyltriazinyl group, a phenyldibenzofuranyl group, a phenyldibenzothiophenyl group, and the like.

In this specification, the carbazolyl group is specifically any of the following groups, unless otherwise specified in this specification.

(TEMP-Cz1)

(TEMP-Cz2)

(TEMP-Cz3)

(TEMP-Cz4)

(TEMP-Cz5)

In this specification, the (9-phenyl)carbazolyl group is specifically any of the following groups, unless otherwise specified in this specification.

(TEMP-Cz6)

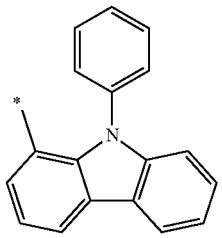

(TEMP-Cz7)

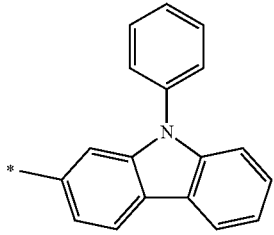

(TEMP-Cz8)

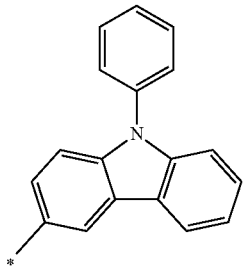

(TEMP-Cz9)

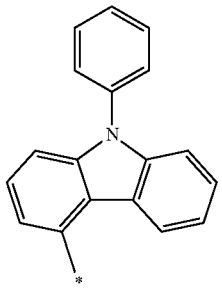

In the general formulas (TEMP-Cz1) to (TEMP-Cz9), * represents a bonding position.

In this specification, the dibenzofuranzoyl group are specifically any of the following groups, unless otherwise specified in this specification.

(TEMP-34)

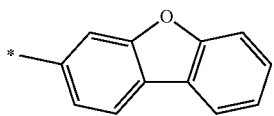
(TEMP-35)

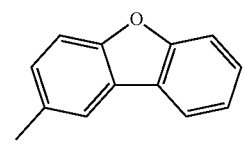
(TEMP-36)

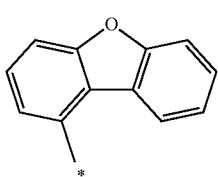
(TEMP-37)

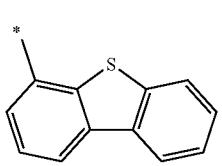
(TEMP-38)

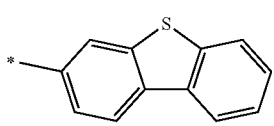
(TEMP-39)

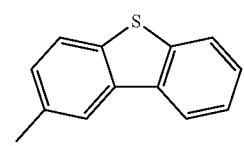
(TEMP-40)

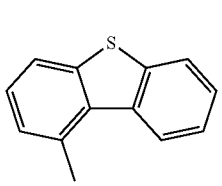
(TEMP-41)

In the general formulas (TEMP-34) to (TEMP-41), * represents a bonding position.

The substituted or unsubstituted alkyl group described in this specification is preferably a methyl group, an ethyl group, a propyl group, an isopropyl group, a n-butyl group, an isobutyl group, a t-butyl group, or the like, unless otherwise specified in this specification.

"Substituted or Unsubstituted Arylene Group"

The "substituted or unsubstituted arylene group" described in this specification is a divalent group derived by removing one hydrogen atom on the aryl ring of the "substituted or unsubstituted aryl group", unless otherwise specified. Specific examples of the "substituted or unsubstituted arylene group" (specific example group G12) include a divalent group derived by removing one hydrogen atom on the aryl ring of the "substituted or unsubstituted aryl group" described in the specific example group G1, and the like.

"Substituted or Unsubstituted Divalent Heterocyclic Group"

The "substituted or unsubstituted divalent heterocyclic group" described in this specification is a divalent group derived by removing one hydrogen atom on the heterocyclic ring of the "substituted or unsubstituted heterocyclic group", unless otherwise specified. Specific examples of the "substituted or unsubstituted divalent heterocyclic group" (specific example group G13) include a divalent group derived by removing one hydrogen atom on the heterocydic ring of the "substituted or unsubstituted heterocyclic group" described in the specific example group G2, and the like.

"Substituted or Unsubstituted Alkylene Group"

The "substituted or unsubstituted alkylene group" described in this specification is a divalent group derived by removing one hydrogen atom on the alkyl chain of the "substituted or unsubstituted alkyl group", unless otherwise specified. Specific examples of the "substituted or unsubstituted alkylene group" (specific example group G14) include a divalent group derived by removing one hydrogen atom on the alkyl chain of the "substituted or unsubstituted alkyl group" described in the specific example group G3, and the like.

The substituted or unsubstituted arylene group described in this specification is preferably any group of the following general formulas (TEMP-42) to (TEMP-68), unless otherwise specified in this specification.

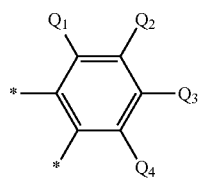
(TEMP-42)

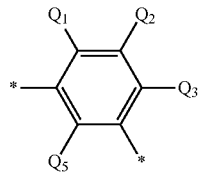
(TEMP-43)

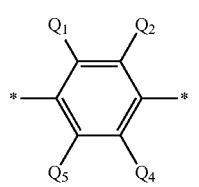
(TEMP-44)

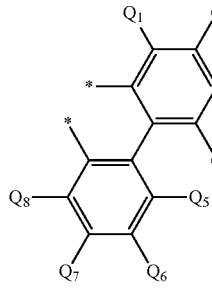
(TEMP-45)

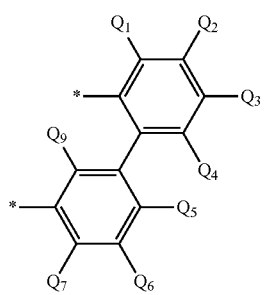
(TEMP-46)
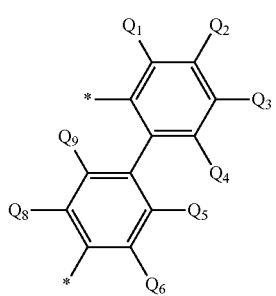
(TEMP-47)
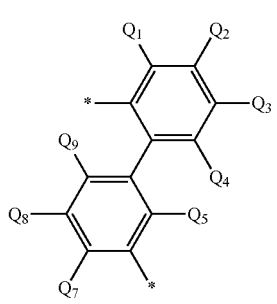
(TEMP-48)
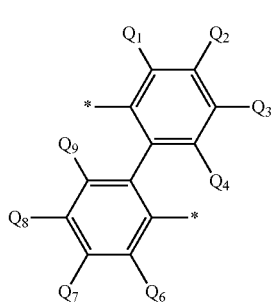
(TEMP-49)
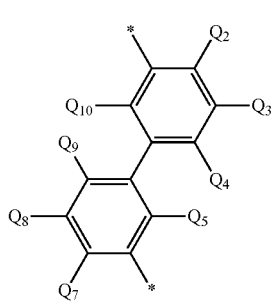
(TEMP-50)
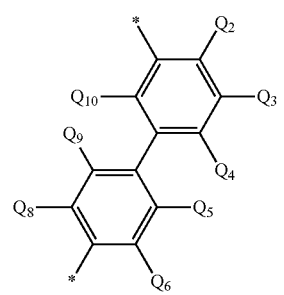
(TEMP-51)
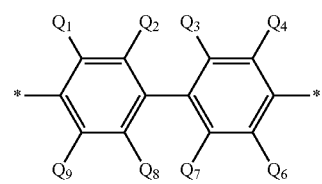
(TEMP-52)
In the general formulas (TEMP-42) to (TEMP-52), $Q_1$ to $Q_{10}$ are independently a hydrogen atom or a substituent.
In the general formulas (TEMP-42) to (TEMP-52), * represents a bonding position.
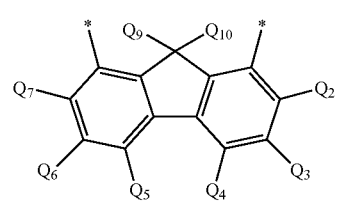
(TEMP-53)
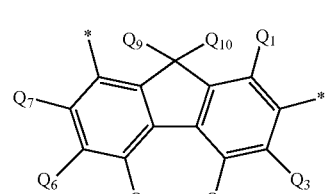
(TEMP-54)
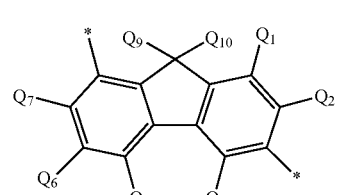
(TEMP-55)
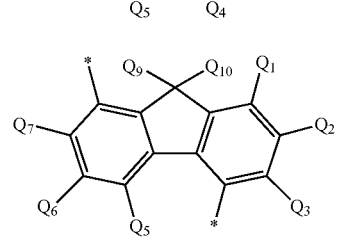
(TEMP-56)

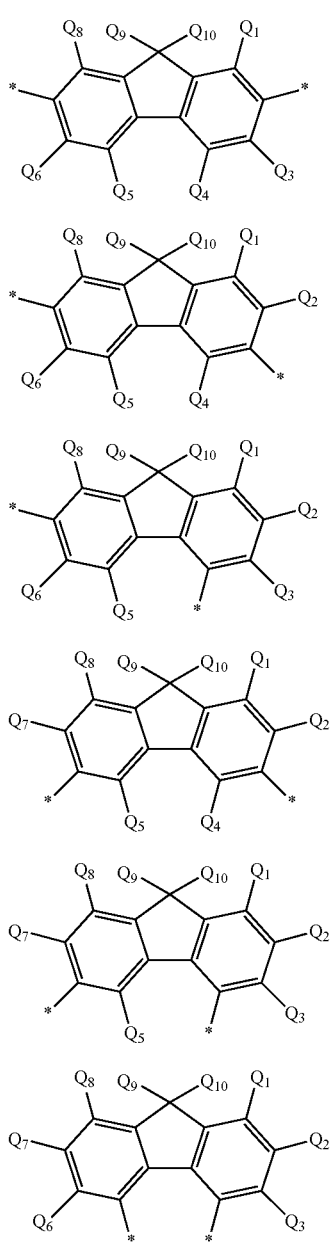

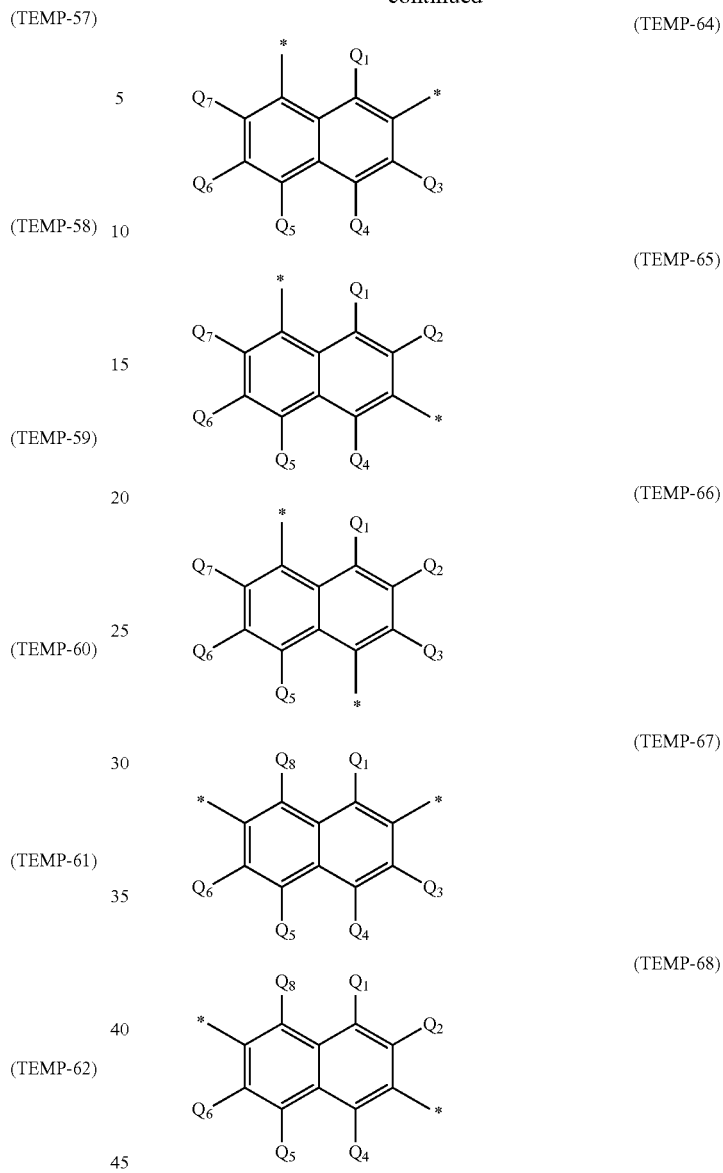

In the general formulas (TEMP-53) to (TEMP-62), $Q_1$ to $Q_{10}$ are independently a hydrogen atom or a substituent.

$Q_9$ and $Q_{10}$ may be bonded with each other via a single bond to form a ring.

In the general formulas (TEMP-53) to (TEMP-62), * represents a bonding position.

In the general formulas (TEMP-63) to (TEMP-68), $Q_1$ to $Q_8$ are independently a hydrogen atom or a substituent.

In the general formulas (TEMP-63) to (TEMP-68), * represents a bonding position.

The substituted or unsubstituted divalent heterocyclic group described in this specification is preferably any group of the following general formulas (TEMP-69) to (TEMP-102), unless otherwise specified in this specification.

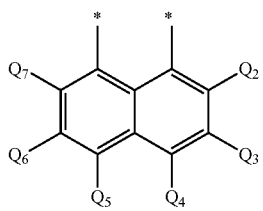

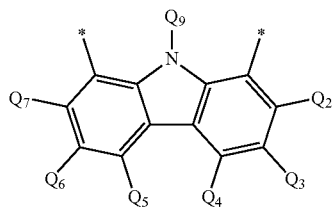

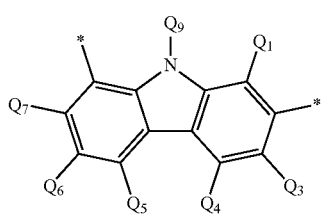
(TEMP-70)
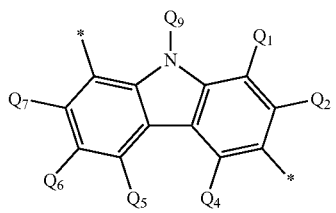
(TEMP-71)
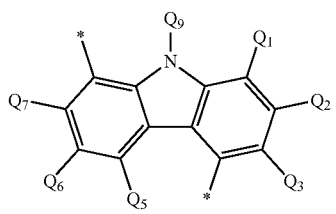
(TEMP-72)
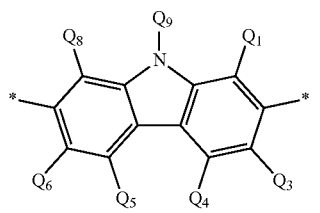
(TEMP-73)
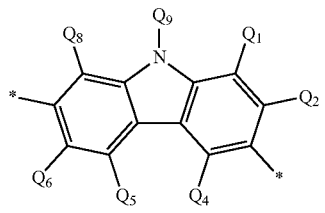
(TEMP-74)
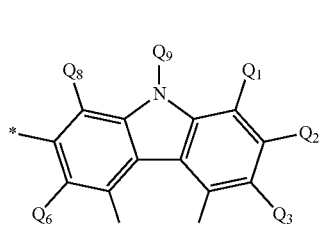
(TEMP-75)
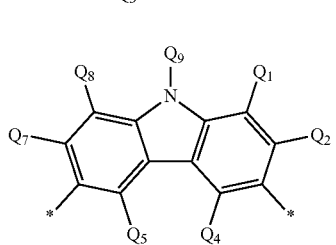
(TEMP-76)
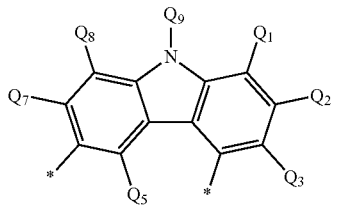
(TEMP-77)
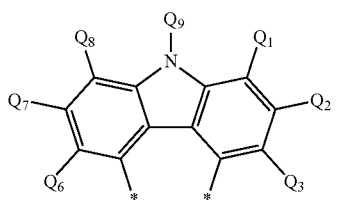
(TEMP-78)
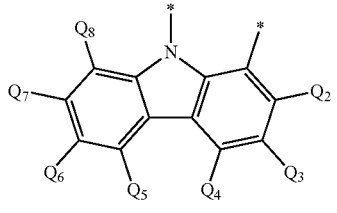
(TEMP-79)
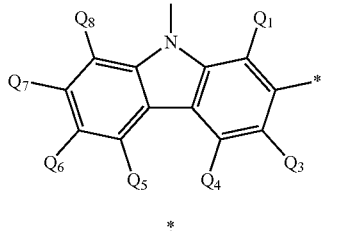
(TEMP-80)
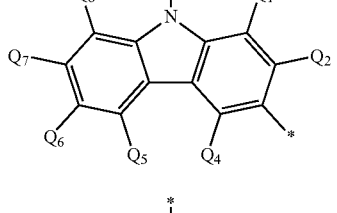
(TEMP-81)
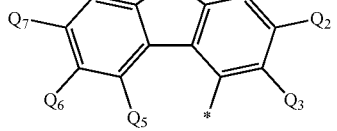
(TEMP-82)
In the general formulas (TEMP-69) to (TEMP-82), $Q_1$ to $Q_9$ are independently a hydrogen atom or a substituent.
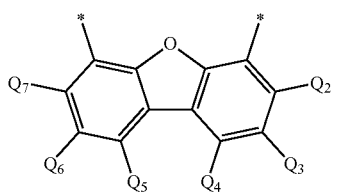
(TEMP-83)

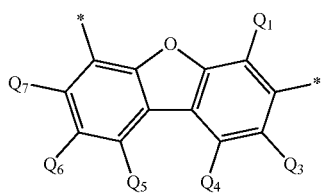
(TEMP-84)
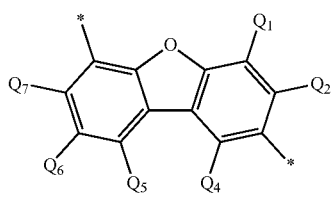
(TEMP-85)
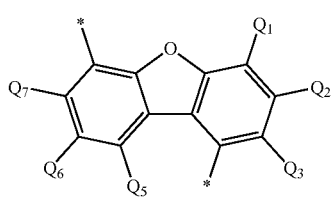
(TEMP-86)
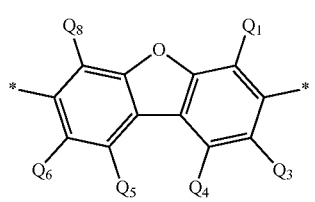
(TEMP-87)
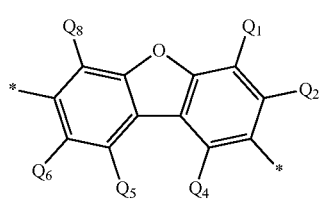
(TEMP-88)
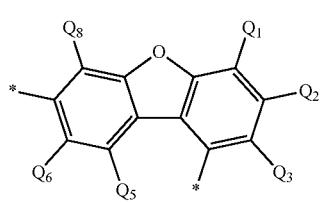
(TEMP-89)
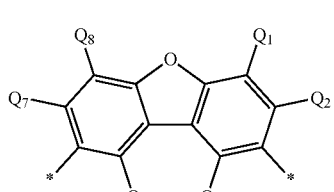
(TEMP-90)
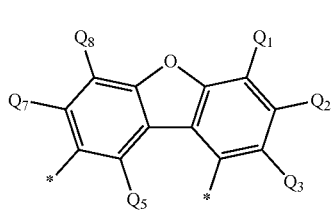
(TEMP-91)
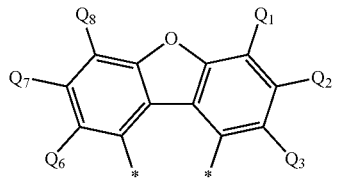
(TEMP-92)
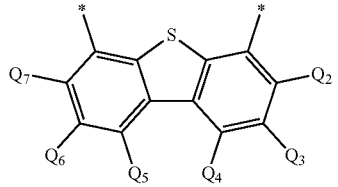
(TEMP-93)
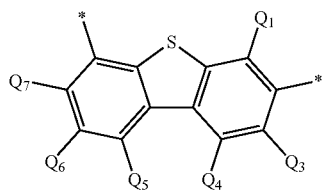
(TEMP-94)
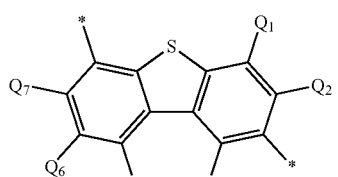
(TEMP-95)
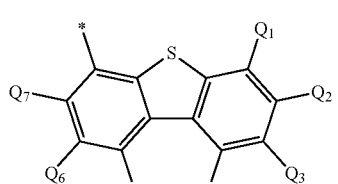
(TEMP-96)
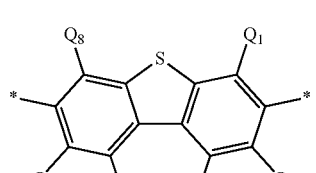
(TEMP-97)
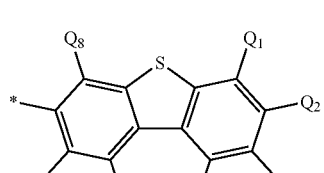
(TEMP-98)
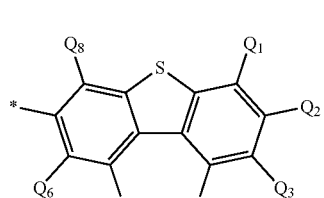
(TEMP-99)

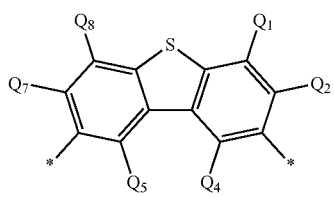

(TEMP-100)

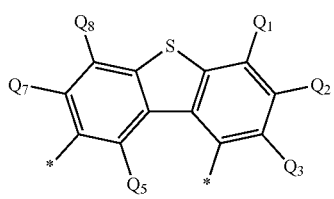

(TEMP-101)

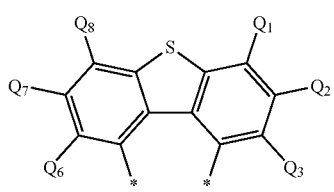

(TEMP-102)

In the general formulas (TEMP-83) to (TEMP-102), $Q_1$ to $Q_8$ are independently a hydrogen atom or a substituent.

The above is the explanation of the "Substituent described in this specification."

"The Case where Bonded with Each Other to Form a Ring"

In this specification, the case where "one or more sets of adjacent two or more form a substituted or unsubstituted monocycle by bonding with each other, form a substituted or unsubstituted fused ring by bonding with each other, or do not bond with each other" means the case where "one or more sets of adjacent two or more form a substituted or unsubstituted monocycle by bonding with each other"; the case where "one or more sets of adjacent two or more form a substituted or unsubstituted fused ring by bonding with each other"; and the case where "one or more sets of adjacent two or more do not bond with each other."

The case where "one or more sets of adjacent two or more form a substituted or unsubstituted monocycle by bonding with each other" and the case where "one or more sets of adjacent two or more form a substituted or unsubstituted fused ring by bonding with each other" in this specification (these cases may be collectively referred to as "the case where forming a ring by bonding with each other") will be described below. The case of an anthracene compound represented by the following general formula (TEMP-103) in which the mother skeleton is an anthracene ring will be described as an example.

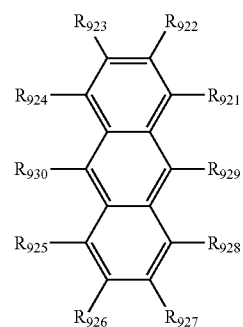

(TEMP-103)

For example, in the case where "one or more sets of adjacent two or more among $R_{921}$ to $R_{930}$ form a ring by bonding with each other", the one set of adjacent two includes a pair of $R_{921}$ and $R_{922}$, a pair of $R_{922}$ and $R_{923}$, a pair of $R_{923}$ and $R_{924}$, a pair of $R_{924}$ and $R_{930}$, a pair of $R_{930}$ and $R_{925}$, a pair of $R_{925}$ and $R_{926}$, a pair of $R_{926}$ and $R_{927}$, a pair of $R_{927}$ and $R_{928}$, a pair of $R_{928}$ and $R_{929}$, and a pair of $R_{929}$ and $R_{921}$.

The "one or more sets" means that two or more sets of the adjacent two or more sets may form a ring at the same time. For example, $R_{921}$ and $R_{922}$ form a ring $Q_A$ by bonding with each other, and at the same, time $R_{925}$ and $R_{926}$ form a ring $Q_B$ by bonding with each other, the anthracene compound represented by the general formula (TEMP-103) is represented by the following general formula (TEMP-104).

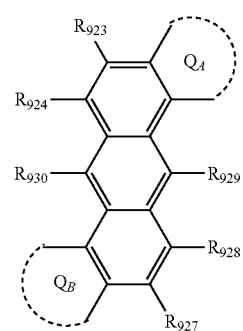

(TEMP-104)

The case where the "set of adjacent two or more" form a ring includes not only the case where the set(pair) of adjacent "two" is bonded with as in the above-mentioned examples, but also the case where the set of adjacent "three or more" are bonded with each other. For example, it means the case where $R_{921}$ and $R_{922}$ form a ring $Q_A$ by bonding with each other, and $R_{922}$ and $R_{923}$ form a ring $Q_C$ by bonding with each other, and adjacent three ($R_{921}$, $R_{922}$ and $R_{923}$) form rings by bonding with each other and together fused to the anthracene mother skeleton. In this case, the anthracene compound represented by the general formula (TEMP-103) is represented by the following general formula (TEMP-105). In the following general formula (TEMP-105), the ring $Q_A$ and the ring $Q_C$ share $R_{922}$.

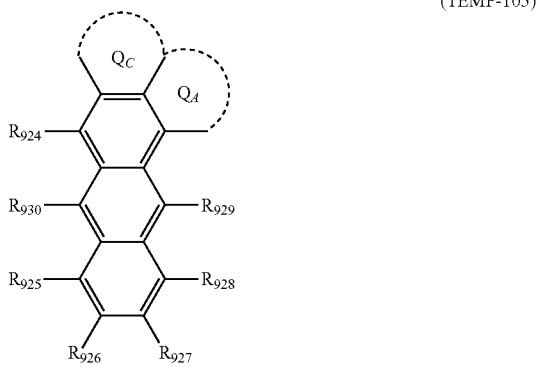

(TEMP-105)

The "monocycle" or "fused ring" formed may be a saturated ring or an unsaturated ring, as a structure of the formed ring alone. Even when the "one pair of adjacent two" forms a "monocycle" or a "fused ring", the "monocycle" or the "fused ring" may forma saturated ring or an unsaturated ring. For example, the ring $Q_A$ and the ring $Q_B$ formed in the general formula (TEMP-104) are independently a "monocycle" or a "fused ring." The ring $Q_A$ and the ring $Q_C$ formed in the general formula (TEMP-105) are "fused ring." The ring $Q_A$ and ring $Q_C$ of the general formula (TEMP-105) are fused ring by fusing the ring $Q_A$ and the ring $Q_C$ together. When the ring $Q_A$ of the general formula (TMEP-104) is a benzene ring, the ring $Q_A$ is a monocycle. When the ring $Q_A$ of the general formula (TMEP-104) is a naphthalene ring, the ring $Q_A$ is a fused ring.

The "unsaturated ring" means an aromatic hydrocarbon ring or an aromatic heterocyclic ring. The "saturated ring" means an aliphatic hydrocarbon ring, or a non-aromatic heterocyclic ring.

Specific examples of the aromatic hydrocarbon ring include a structure in which the group listed as a specific example in the specific example group G1 is terminated by a hydrogen atom.

Specific examples of the aromatic heterocyclic ring include a structure in which the aromatic heterocyclic group listed as a specific example in the example group G2 is terminated by a hydrogen atom.

Specific examples of the aliphatic hydrocarbon ring include a structure in which the group listed as a specific example in the specific example group G6 is terminated by a hydrogen atom.

The term "to form a ring" means forming a ring only with plural atoms of the mother skeleton, or with plural atoms of the mother skeleton and one or more arbitrary elements in addition. For example, the ring $Q_A$ shown in the general formula (TEMP-104), which is formed by bonding $R_{921}$ and $R_{922}$ with each other, is a ring formed from the carbon atom of the anthracene skeleton with which $R_{921}$ is bonded, the carbon atom of the anthracene skeleton with which $R_{922}$ is bonded, and one or more arbitrary elements. For example, in the case where the ring $Q_A$ is formed with $R_{921}$ and $R_{922}$, when a monocyclic unsaturated ring is formed with the carbon atom of the anthracene skeleton with which $R_{921}$ is bonded, the carbon atom of the anthracene skeleton with which $R_{922}$ is bonded, and four carbon atoms, the ring formed with $R_{921}$ and $R_{922}$ is a benzene ring.

Here, the "arbitrary element" is preferably at least one element selected from the group consisting of a carbon element, a nitrogen element, an oxygen element, and a sulfur element, unless otherwise specified in this specification. In the arbitrary element (for example, a carbon element or a nitrogen element), a bond which does not form a ring may be terminated with a hydrogen atom or the like, or may be substituted with "arbitrary substituent" described below. When an arbitrary element other than a carbon element is contained, the ring formed is a heterocyclic ring.

The number of "one or more arbitrary element(s)" constituting a monocycle or a fused ring is preferably 2 or more and 15 or less, more preferably 3 or more and 12 or less, and still more preferably 3 or more and 5 or less, unless otherwise specified in this specification.

The "monocycle" is preferable among the "monocycle" and the "fused ring", unless otherwise specified in this specification.

The "unsaturated ring" is preferable among the "saturated ring" and the "unsaturated ring", unless otherwise specified in this specification.

Unless otherwise specified in this specification, the "monocycle" is preferably a benzene ring.

Unless otherwise specified in this specification, the "unsaturated ring" is preferably a benzene ring.

Unless otherwise specified in this specification, when "one or more sets of adjacent two or more" are "bonded with each other to form a substituted or unsubstituted monocycle" or "bonded with each other to form a substituted or unsubstituted fused ring", this specification, one or more sets of adjacent two or more are preferably bonded with each other to form a substituted or unsubstituted "unsaturated ring" from plural atoms of the mother skeleton and one or more and 15 or less elements which is at least one kind selected from a carbon elements, a nitrogen element, an oxygen element, and a sulfur element.

The substituent in the case where the above-mentioned "monocycle" or "fused ring" has a substituent is, for example, an "arbitrary substituent" described below. Specific examples of the substituent which the above-mentioned "monocycle" or "fused ring" has include the substituent described above in the "Substituent described in this specification" section.

The substituent in the case where the above-mentioned "saturated ring" or "unsaturated ring" has a substituent is, for example, an "arbitrary substituent" described below. Specific examples of the substituent which the above-mentioned "monocycle" or "fused ring" has include the substituent described above in the "Substituent described in this specification" section.

The foregoing describes the case where "one or more sets of adjacent two or more form a substituted or unsubstituted monocycle by bonding with each other" and the case where "one or more sets of adjacent two or more form a substituted or unsubstituted fused ring by bonding with each other" (the case where "forming a ring by bonding with each other").

Substituent in the Case of "Substituted or Unsubstituted"

In one embodiment in this specification, the substituent (in this specification, sometimes referred to as an "arbitrary substituent") in the case of "substituted or unsubstituted" is, for example, a group selected from the group consisting of:
an unsubstituted alkyl group including 1 to 50 carbon atoms,
an unsubstituted alkenyl group including 2 to 50 carbon atoms,
an unsubstituted alkynyl group including 2 to 50 carbon atoms,
an unsubstituted cycloalkyl group including 3 to 50 ring carbon atoms,
—Si($R_{901}$)($R_{902}$)($R_{903}$),
—O—($R_{904}$), —S—(R$_{905}$),
—N(R$_{906}$)(R$_{907}$),
a halogen atom, a cyano group, a nitro group,
an unsubstituted aryl group including 6 to 50 ring carbon atoms, and
an unsubstituted heterocyclic group including 5 to 50 ring atoms,
wherein, R$_{901}$ to R$_{907}$ are independently
a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted heterocyclic group including 5 to 50 ring atoms.

When two or more R$_{901}$'s are present, the two or more R$_{901}$'s may be the same or different.
When two or more R$_{902}$'s are present, the two or more R$_{902}$'s may be the same or different.
When two or more R$_{903}$'s are present, the two or more R$_{903}$'s may be the same or different.
When two or more R$_{904}$'s are present, the two or more R$_{904}$'s may be the same or different.
When two or more R$_{905}$'s are present, the two or more R$_{905}$'s may be the same or different.
When two or more R$_{906}$'s are present, the two or more R$_{906}$'s may be the same or different.
When two or more R$_{907}$'s are present, the two or more R$_{907}$'s may be the same or different.

In one embodiment, the substituent in the case of "substituted or unsubstituted" is a group selected from the group consisting of:
an alkyl group including 1 to 50 carbon atoms,
an aryl group including 6 to 50 ring carbon atoms, and
a heterocyclic group including 5 to 50 ring atoms.

In one embodiment, the substituent in the case of "substituted or unsubstituted" is a group selected from the group consisting of:
an alkyl group including 1 to 18 carbon atoms,
an aryl group including 6 to 18 ring carbon atoms, and
a heterocyclic group including 5 to 18 ring atoms.

Specific examples of each of the arbitrary substituents include specific examples of substituent described in the section "Substituent described in this specification" above.

Unless otherwise specified in this specification, adjacent arbitrary substituents may form a "saturated ring" or an "unsaturated ring", preferably form a substituted or unsubstituted saturated 5-membered ring, a substituted or unsubstituted saturated 6-membered ring, a substituted or unsubstituted unsaturated 5-membered ring, or a substituted or unsubstituted unsaturated 6-membered ring, more preferably form a benzene ring.

Unless otherwise specified in this specification, the arbitrary substituent may further have a substituent. The substituent which the arbitrary substituent further has is the same as that of the above-mentioned arbitrary substituent.

In this specification, the numerical range represented by "AA to BB" means the range including the numerical value AA described on the front side of "AA to BB" as the lower limit and the numerical value BB described on the rear side of "AA to BB" as the upper limit.

[Organic Electroluminescence Device]

The organic electroluminescence device according to one aspect of the invention is characterized in that the organic electroluminescence device contains:
a cathode,
an anode, and
an organic layer disposed between the cathode and the anode, wherein
the organic layer comprises an emitting layer and a first layer,
the first layer is disposed between the cathode and the emitting layer,
the emitting layer comprises a compound represented by the following formula (1),
the first layer comprises a compound represented by the following formula (BE1):

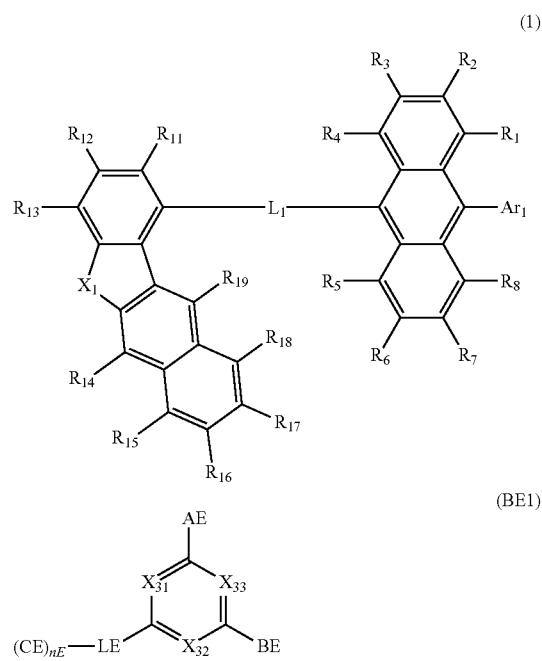

The definitions of substituents and the like of the compounds represented by the formulas (1) and (BE1) are omitted here, as the definitions will be described in detail in the description of each compound below.

An organic EL device having high luminous efficiency and a device life equivalent to that of conventional devices can be obtained by containing a compound represented by the formula (1) in the emitting layer and the first layer disposed between the cathode and the emitting layer contains a compound represented by the formula (BE1).

The schematic configuration of one embodiment of the organic EL device according to an aspect of the invention is shown in FIG. 1.

The organic EL device 1 contains a light-transmitting substrate 2, an anode 3, a cathode 4, and an emitting unit 10 arranged between the anode 3 and the cathode 4.

The emitting unit 10 is configured by stacking a hole-injecting layer 6, a hole-transporting layer 7, an emitting layer 5, an electron-transporting layer 8, and the electron-injecting layer 9 in this order from the anode 3. The organic EL device 1 is a bottom emission type organic EL device in which light is emitted from the substrate 2 side.

The organic EL device according to an aspect of the invention may be a bottom emission type (FIG. 1) in which light is taken out from the substrate side, or a top emission type (FIG. 2) in which light is taken out from the cathode side.

When the top emission type is adopted, the emitting unit portion sandwiched between the anode and the cathode (emitting unit 10 in FIG. 1) can be configured in the same manner as in the bottom emission type.

<Compound Represented by the Formula (1)>

The emitting layer of the organic EL device according to one aspect of the invention contains a compound represented by the following formula (1).

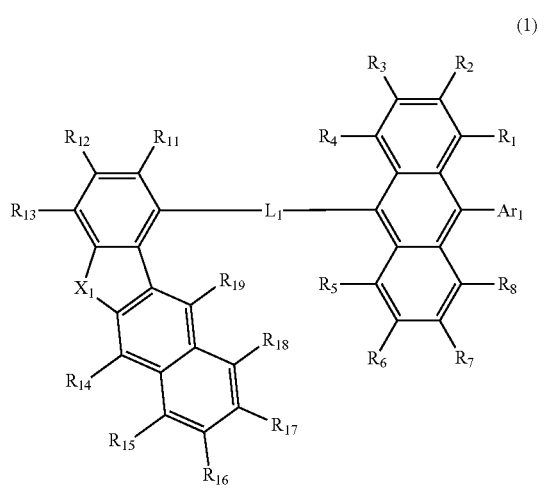

(1)

In the formula (1), $X_1$ is an oxygen atom or a sulfur atom;

$Ar_1$ is a substituted or unsubstituted aryl group including 6 to 50 ring carbon atoms, or
a substituted or unsubstituted monovalent heterocyclic group including 5 to 50 ring atoms;

$L_1$ is a single bond,
a substituted or unsubstituted arylene group including 6 to 50 ring carbon atoms, or
a substituted or unsubstituted divalent heterocyclic group including 5 to 50 ring atoms;

$R_1$ to $R_8$ and $R_{11}$ to $R_{19}$ are independently
a hydrogen atom, a halogen atom, a cyano group, a nitro group,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
—S—($R_{905}$),
—N($R_{606}$)($R_{907}$),
a substituted or unsubstituted aryl group including 6 to 50 ring carbon atoms, or
a substituted or unsubstituted monovalent heterocyclic group including 5 to 50 ring atoms;

$R_{901}$ to $R_{907}$ are independently
a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted monovalent heterocyclic group including 5 to 50 ring atoms; when two or more of each of $R_{901}$ to $R_{907}$ are present, the two or more of each of $R_{901}$ to $R_{907}$ are the same or different.

In one embodiment, the compound represented by the formula (1) is a compound represented by the following formula (1-1).

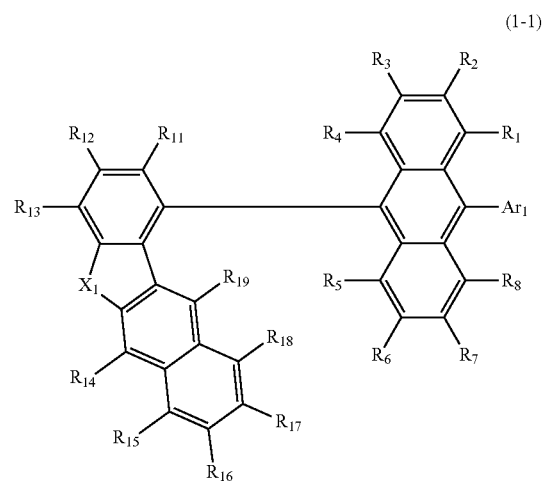

(1-1)

In the formula (1-1), $X_1$, $Ar_1$, $R_1$ to $R_8$, and $R_{11}$ to $R_{19}$ are as defined in the formula (1).

In one embodiment, the compound represented by the formula (1) is a compound represented by the following formula (1-2).

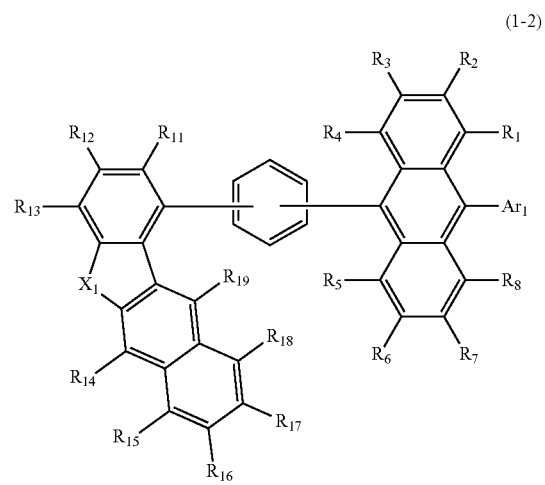

(1-2)

In the formula (1-2), $X_1$, $Ar_1$, $R_1$ to $R_8$, and $R_{11}$ to $R^{19}$ are as defined in the formula (1).

In one embodiment, $L^1$ is
a single bond, or
a substituted or unsubstituted arylene group including 6 to 14 ring carbon atoms.

In one embodiment, An is a substituted or unsubstituted aryl group including 6 to 50 ring carbon atoms.

In one embodiment, An is selected from the group represented by the following formulas (a1) to (a4).

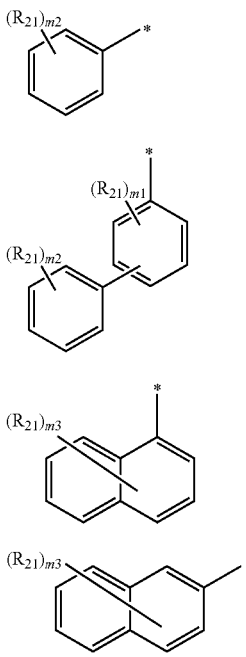

In the formulas (a1) to (a4), "*" is bonded to a carbon atom of the anthracene skeleton;

$R_{21}$ is
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms;
$R_{901}$ to $R_{907}$ are as defined in the formula (1);
m1 is an integer of 0 to 4;
m2 is an integer of 0 to 5;
m3 is an integer of 0 to 7;
when each of m1 to m3 is 2 or more, a plurality of $R_{21}$'s may be the same as or different from each other;
when each of m1 to m3 is 2 or more, a plurality of adjacent $R_{21}$'s form a substituted or unsubstituted, saturated or unsaturated ring by bonding with each other, or do not form a substituted or unsubstituted saturated or unsaturated ring.

In one embodiment, An is selected from the group consisting of
a substituted or unsubstituted carbazolyl group,
a substituted or unsubstituted dibenzothiophenyl group,
a substituted or unsubstituted dibenzofuranyl group,
a substituted or unsubstituted dibenzofuranyl group,
a substituted or unsubstituted naphthobenzothiophenyl group, and
a substituted or unsubstituted naphthobenzofuranyl group.

In one embodiment, $R_1$ to $R_8$ and $R_{11}$ to $R_{19}$ are hydrogen atoms,
$L_1$ is a single bond, an unsubstituted arylene group including 6 to 50 ring carbon atoms, or an unsubstituted divalent heterocyclic group including 5 to 50 ring atoms;
$Ar_1$ is an unsubstituted aryl group including 6 to 50 ring carbon atoms, or an unsubstituted monovalent heterocyclic group including 5 to 50 ring atoms.

In one embodiment, $X_1$ is an oxygen atom.

Specific examples of the compound represented by the formula (1) are described below, but are not limited to these specific example compounds. In the following examples, "D" represents a deuterium atom.

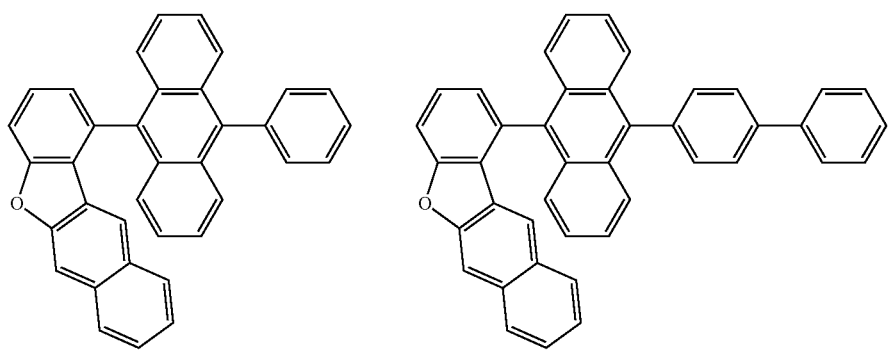

-continued
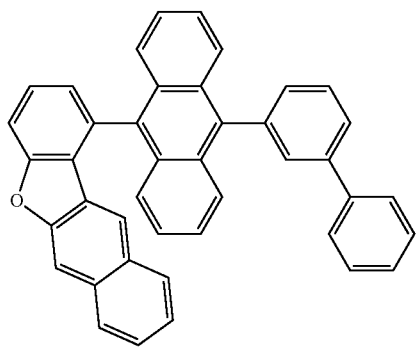
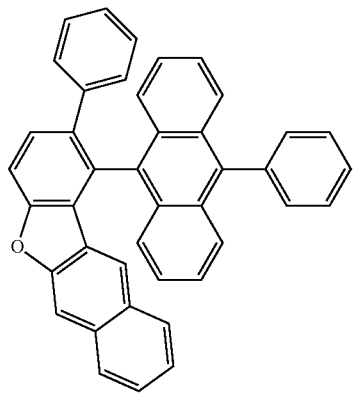
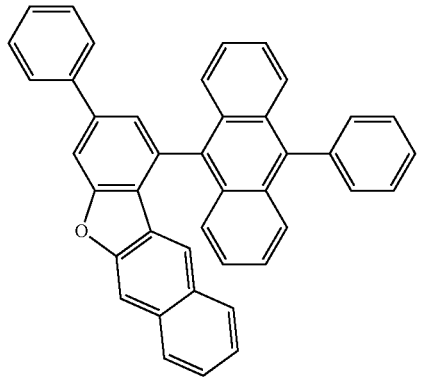
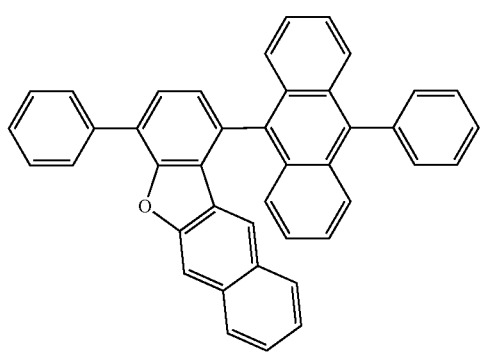
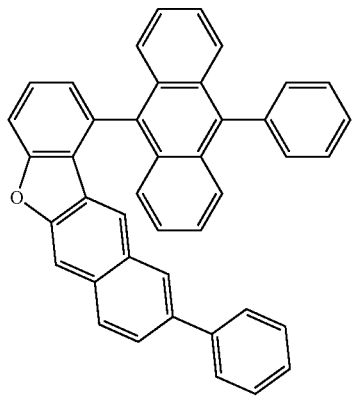
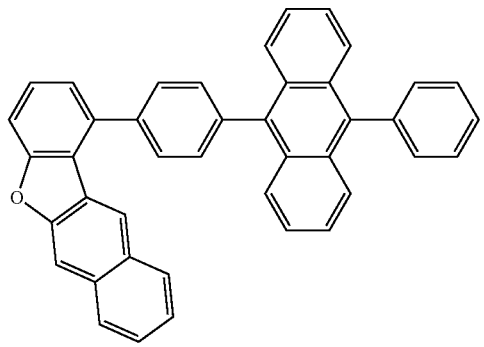
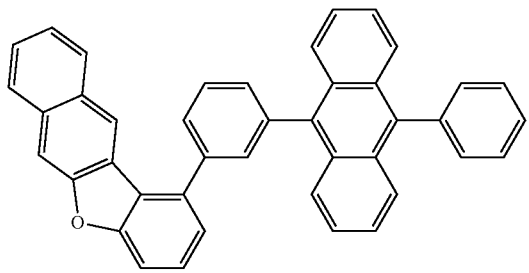
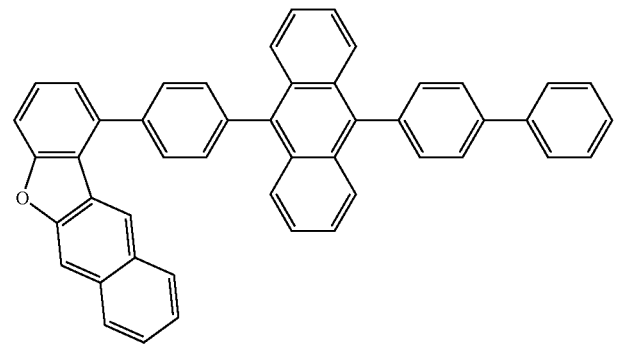

-continued
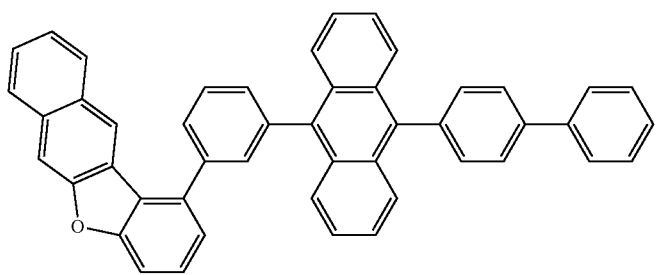
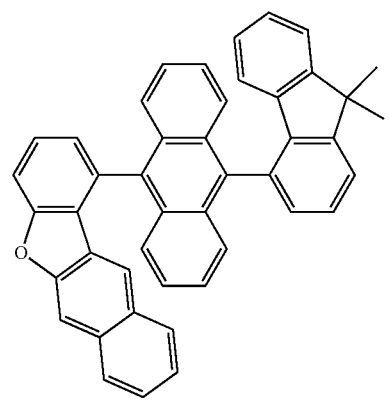
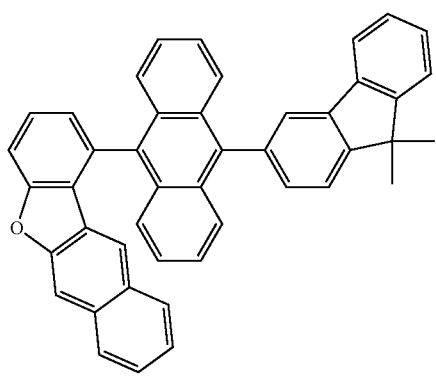
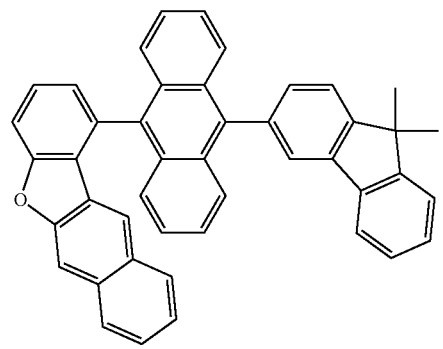
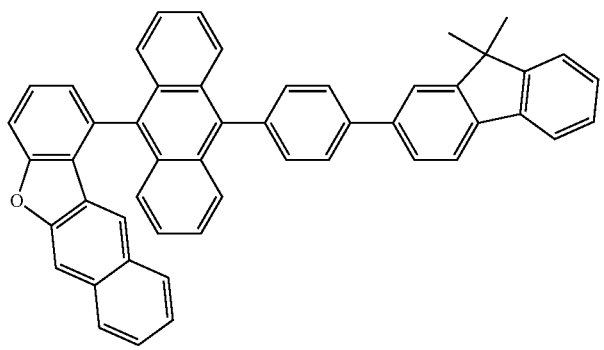
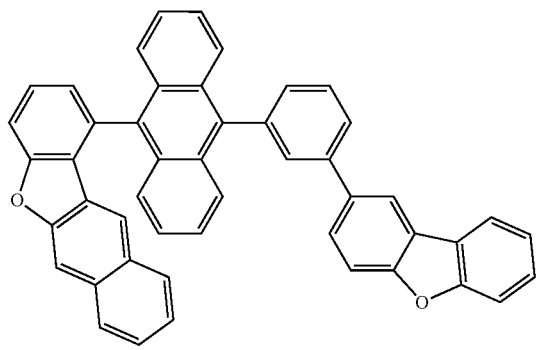
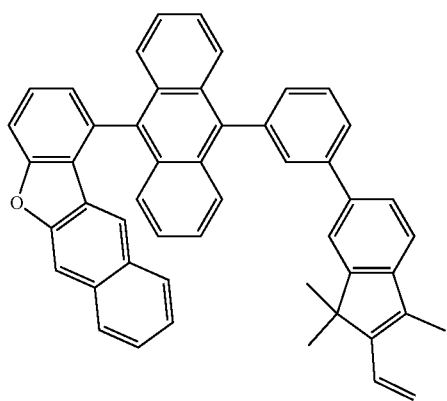

-continued
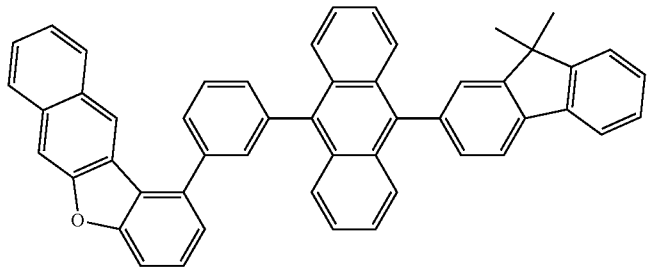
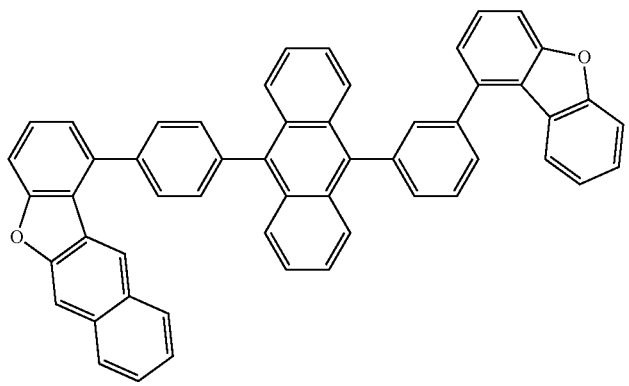
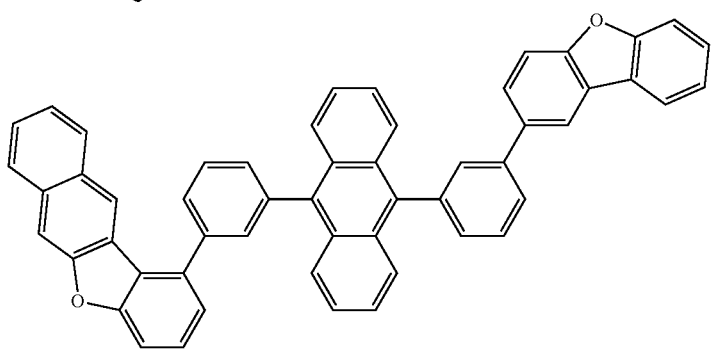
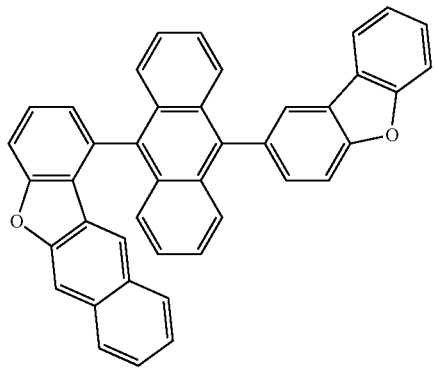
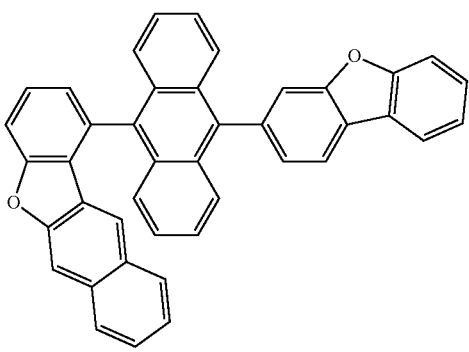
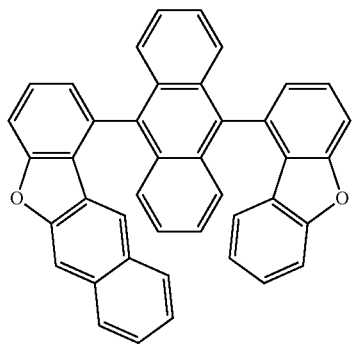
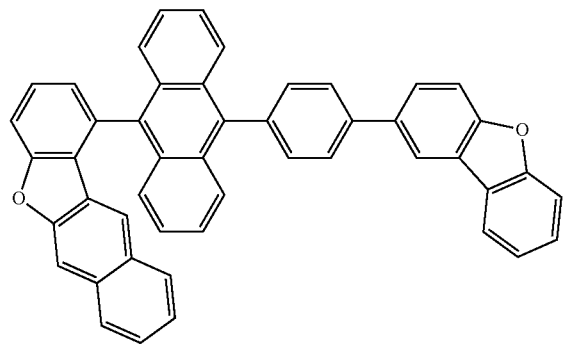

-continued
49
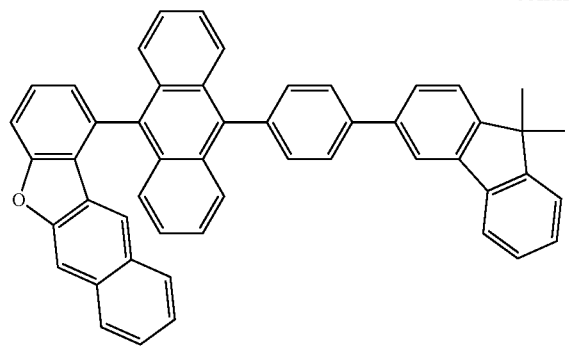
50
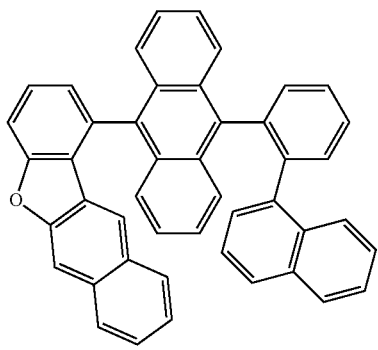
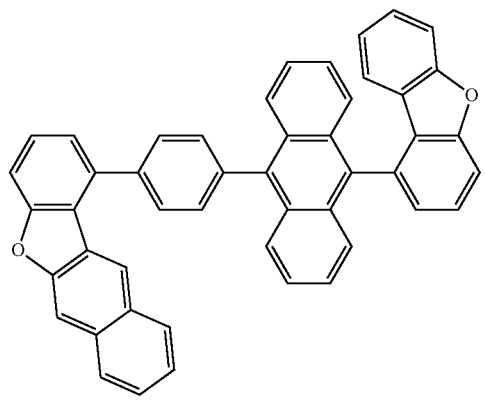
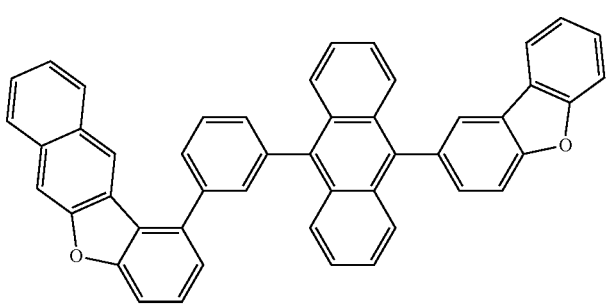
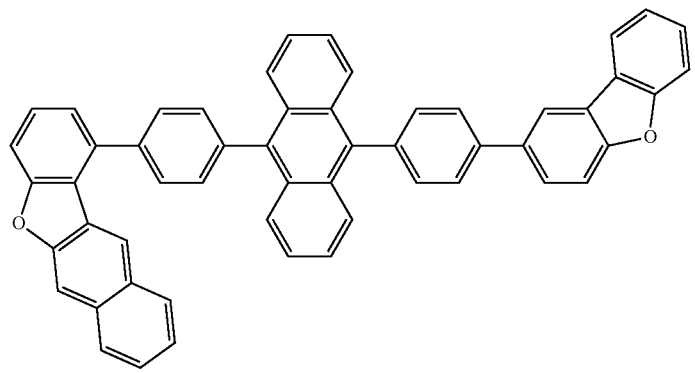
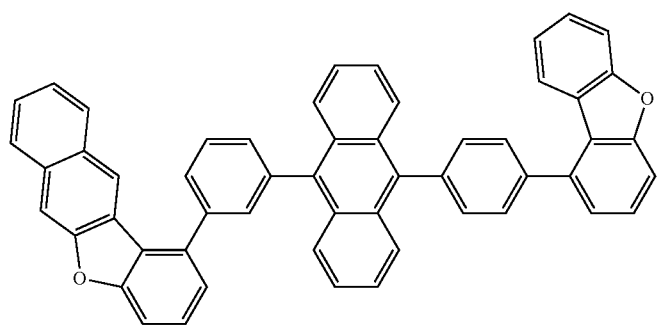

-continued
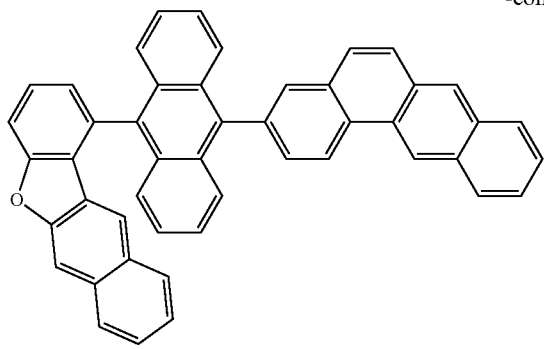
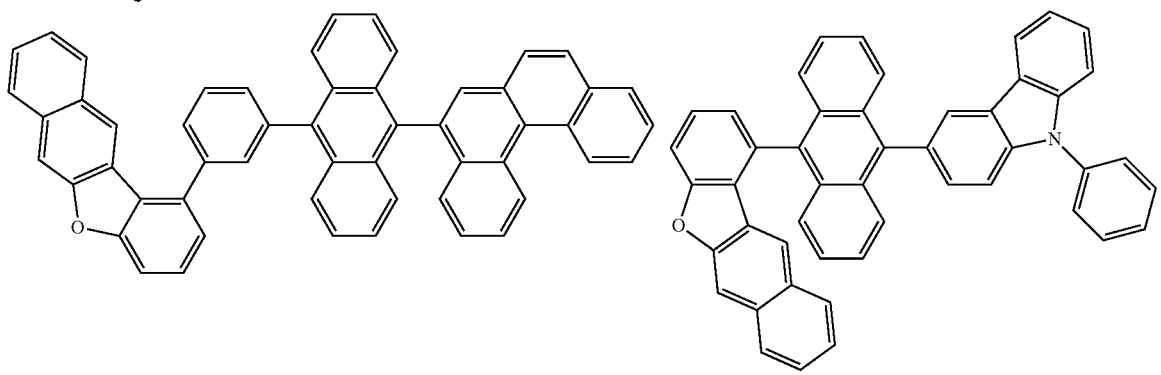
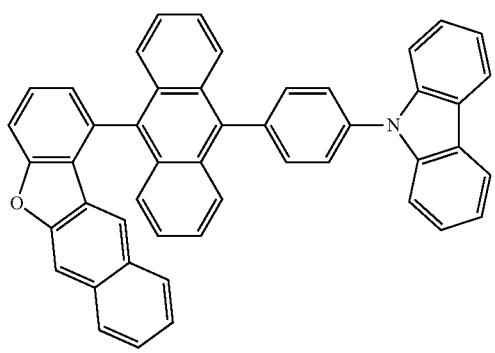
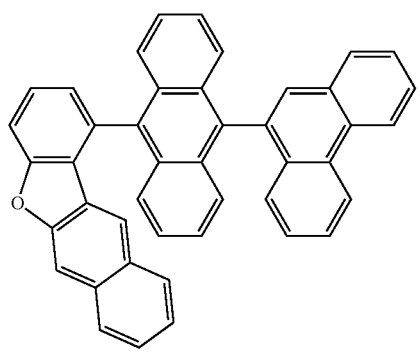
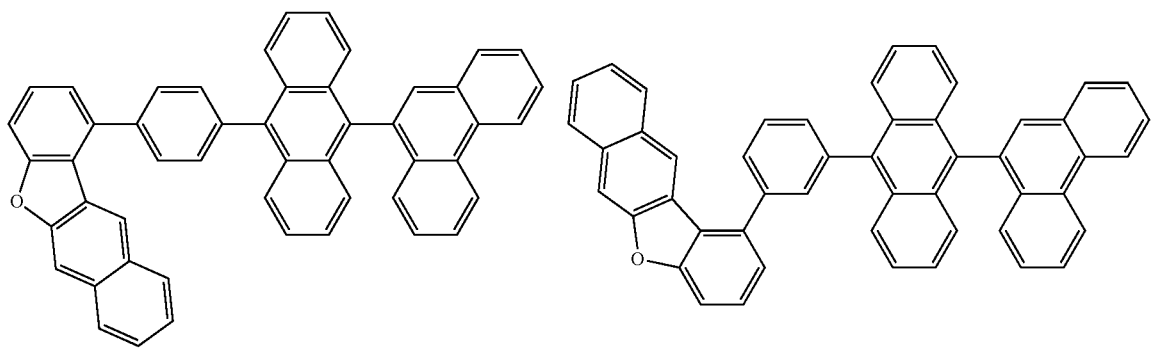

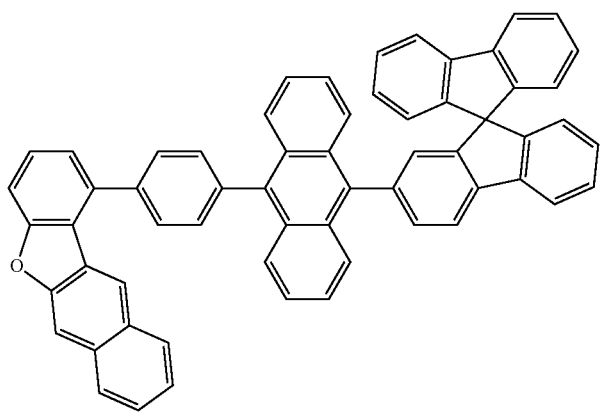
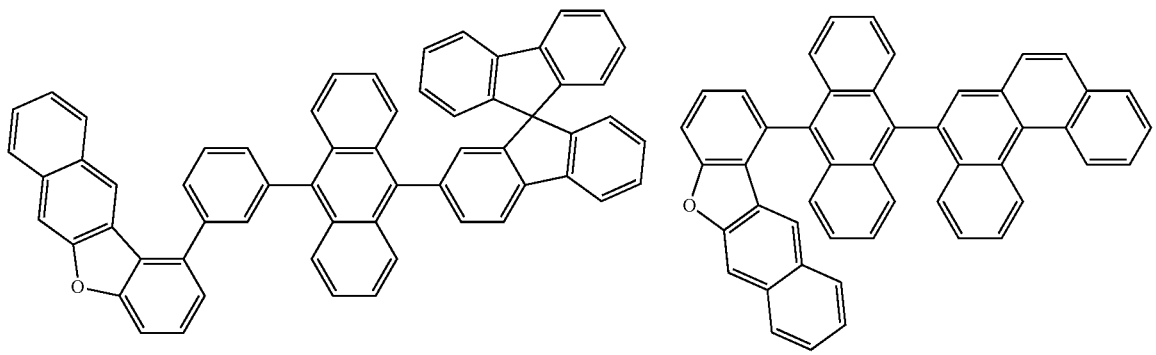
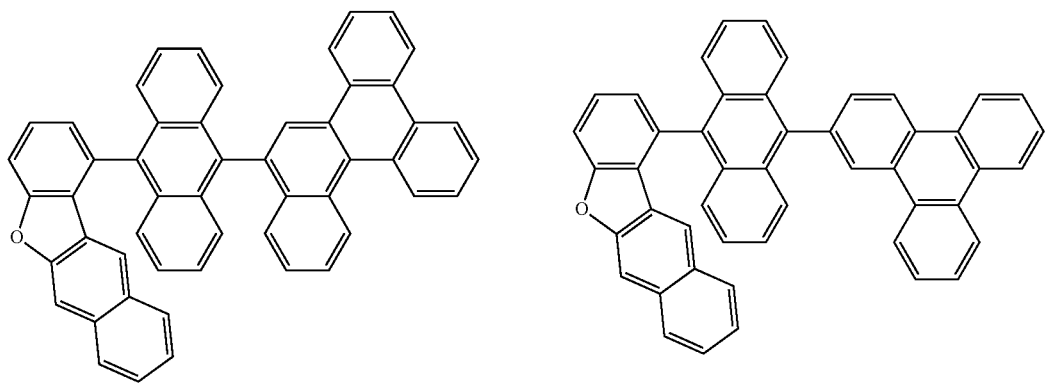
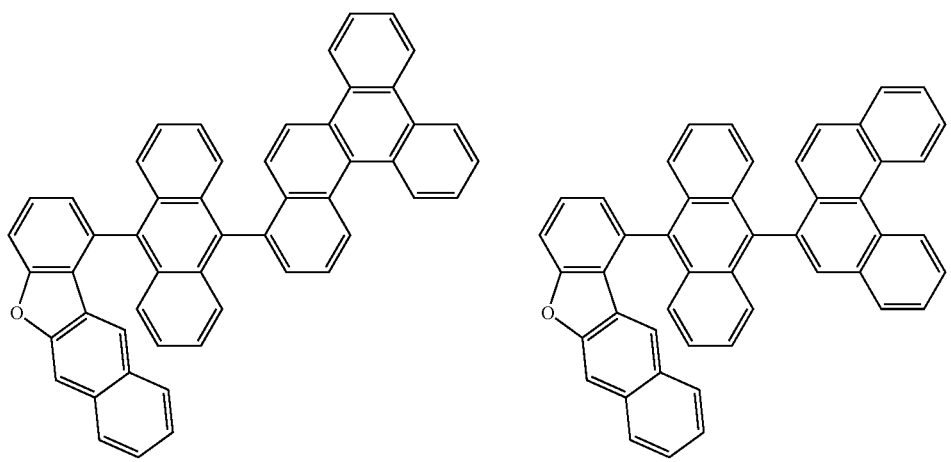

-continued
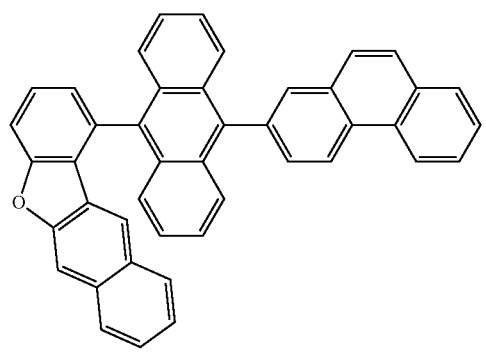
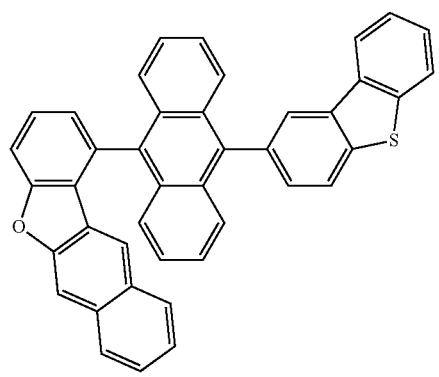
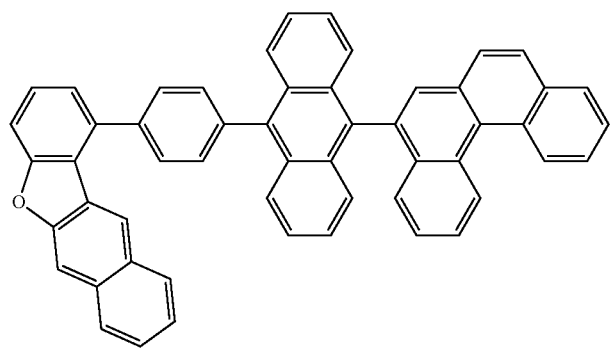
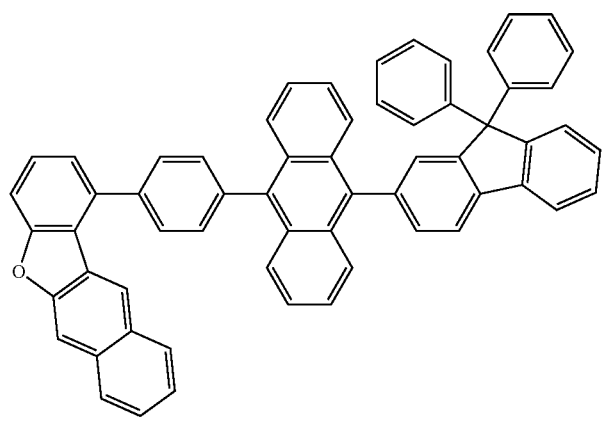
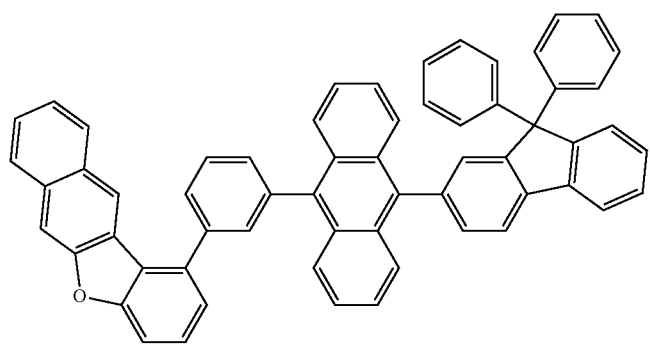

-continued
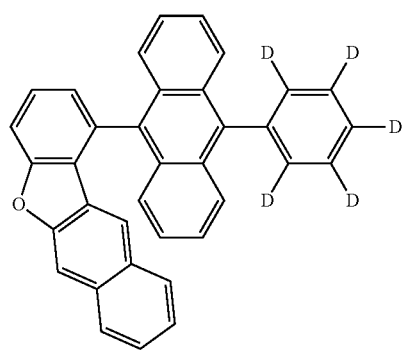
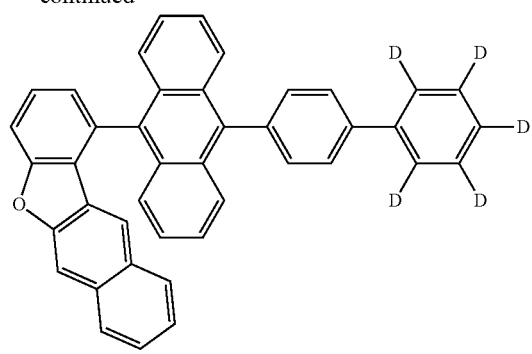
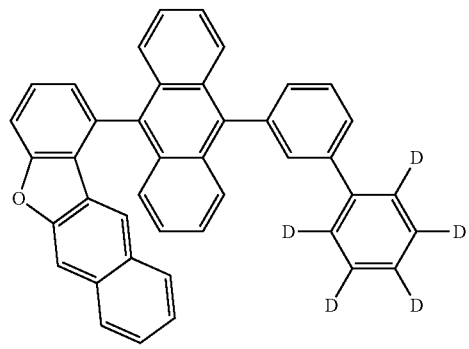
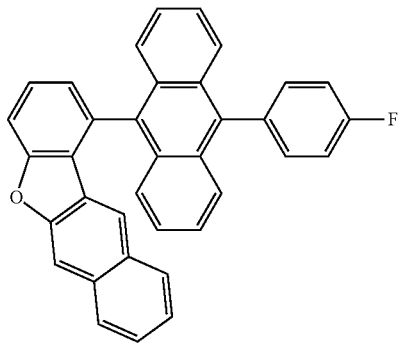
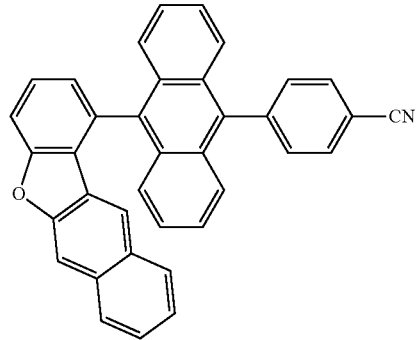
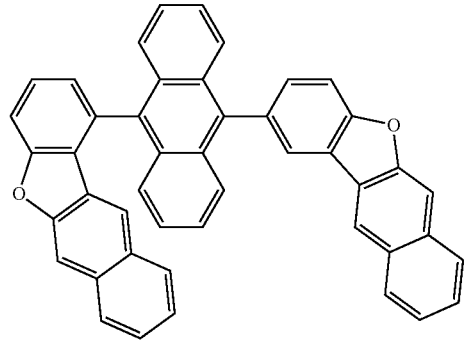
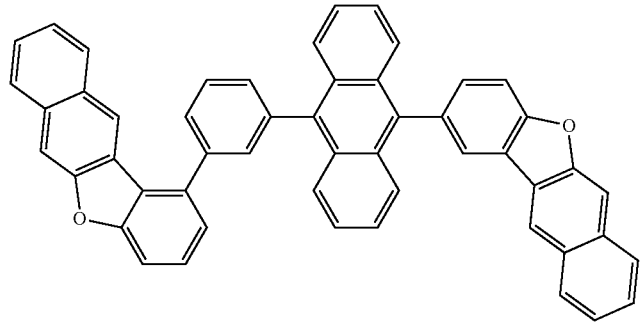
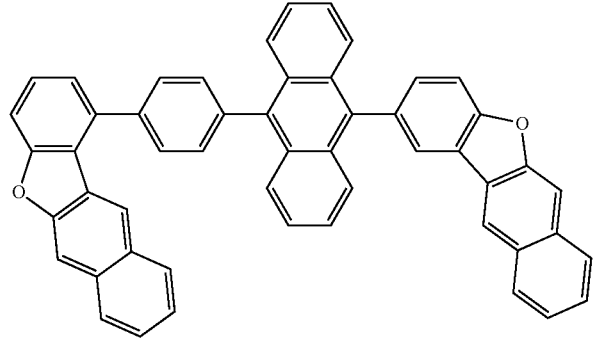

-continued
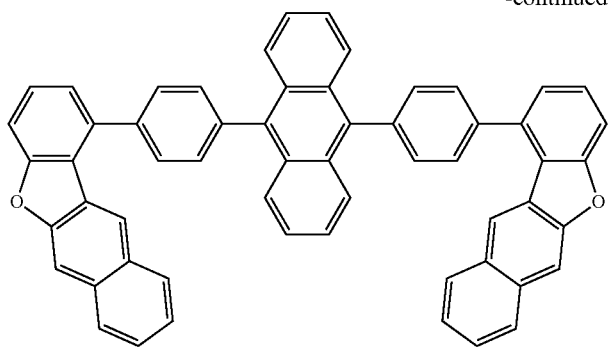
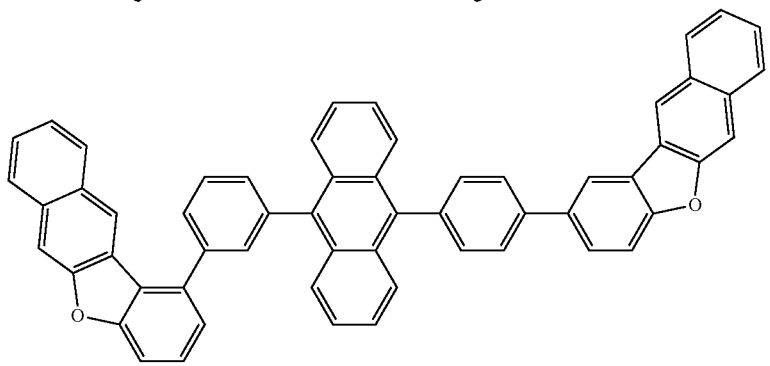
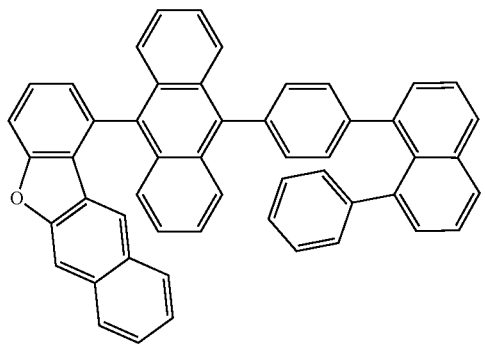
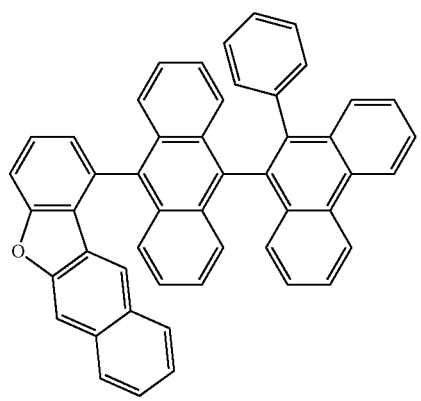
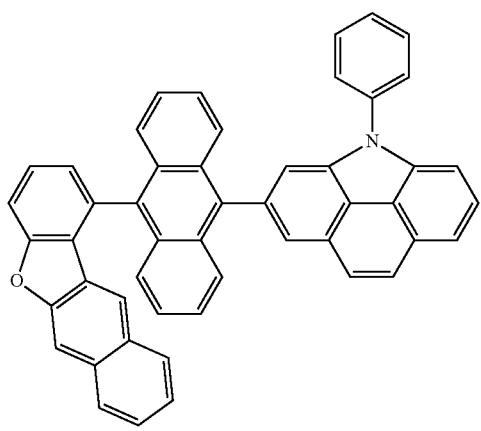
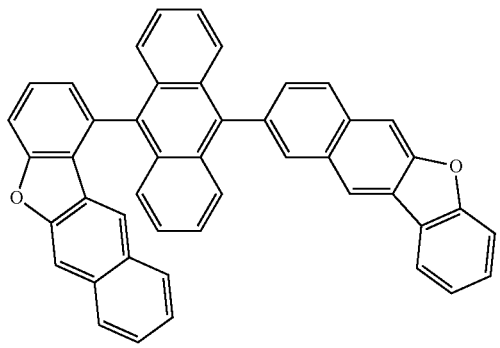

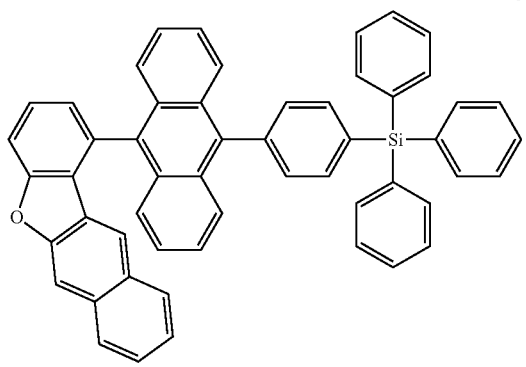
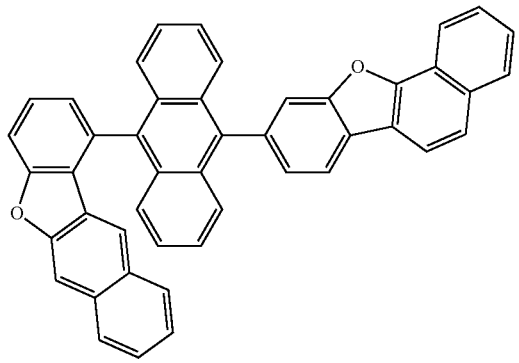
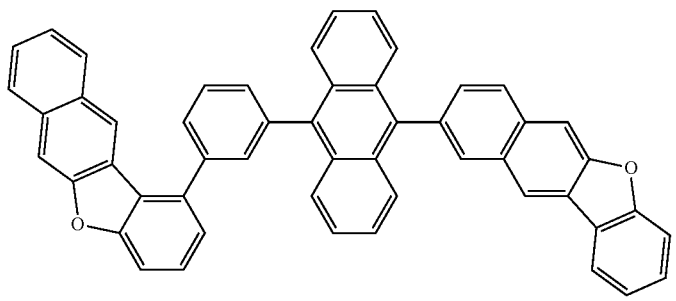
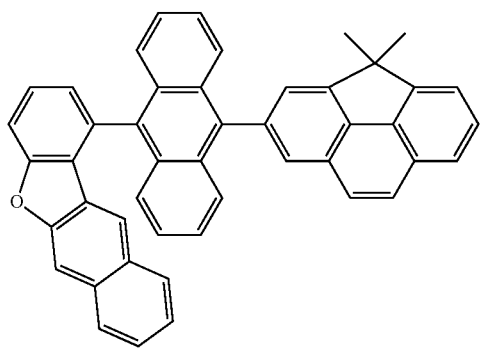
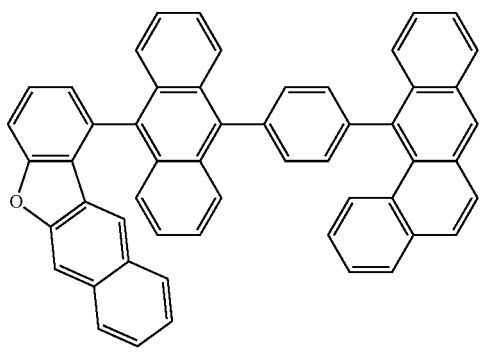
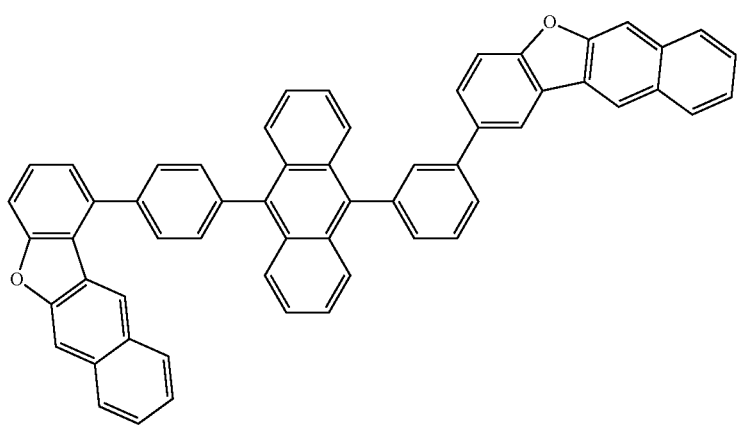

-continued
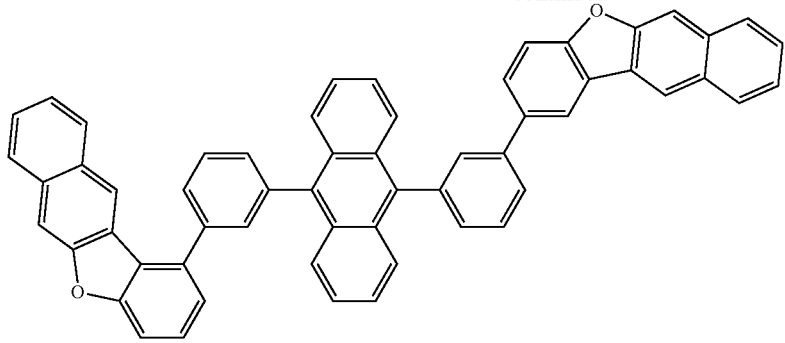
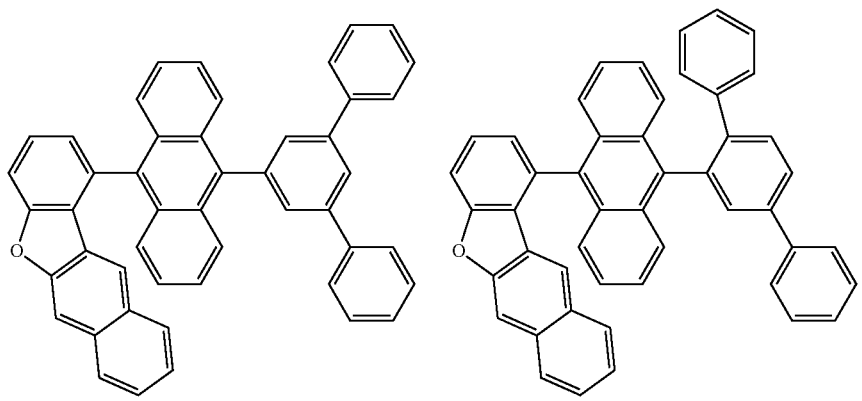
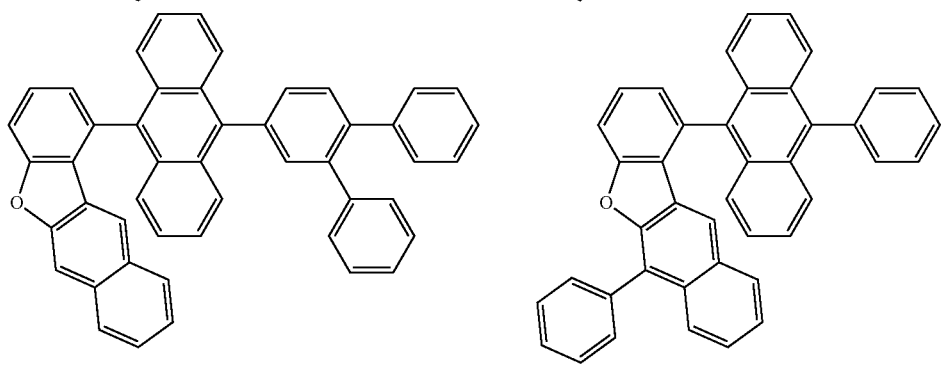
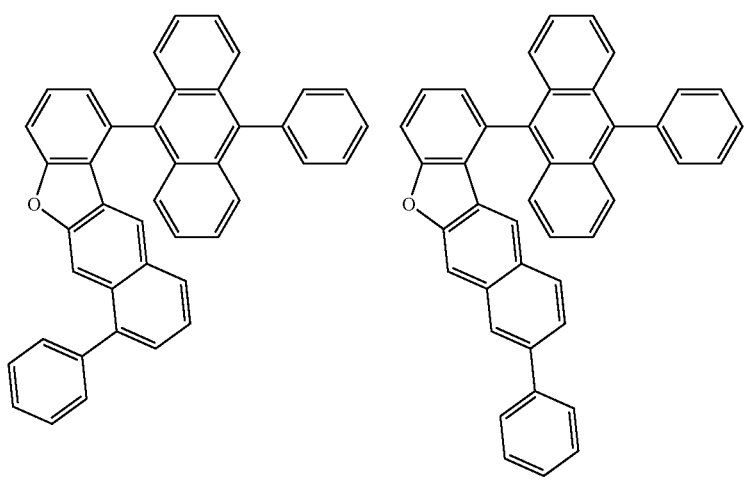

-continued
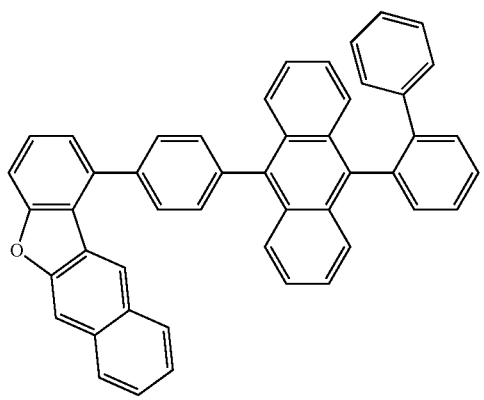 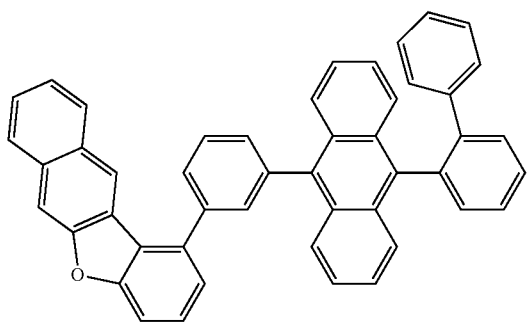
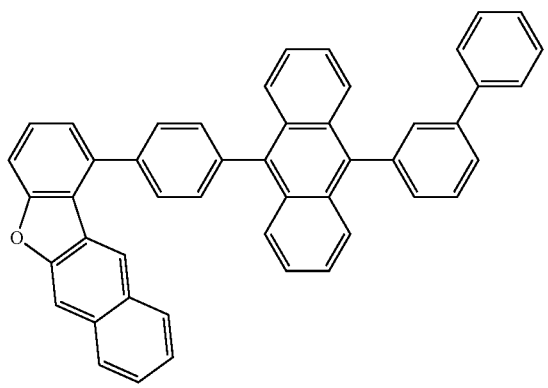 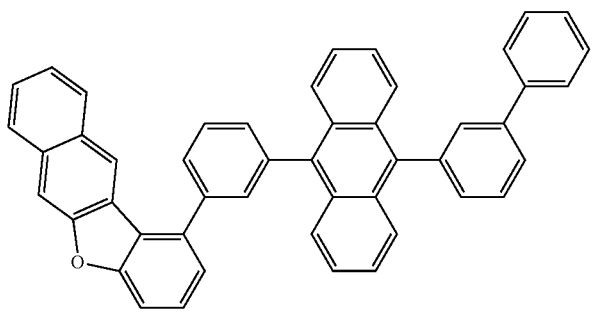
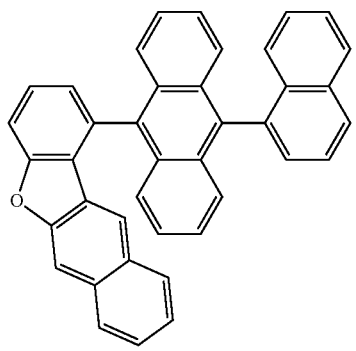 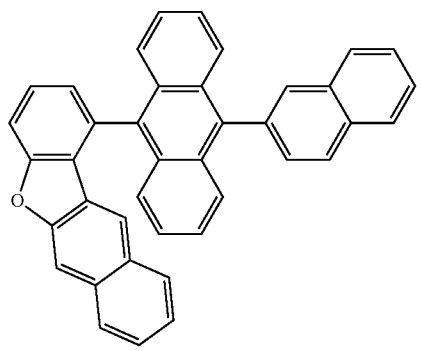
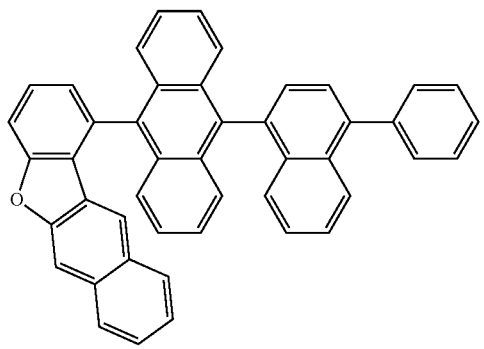 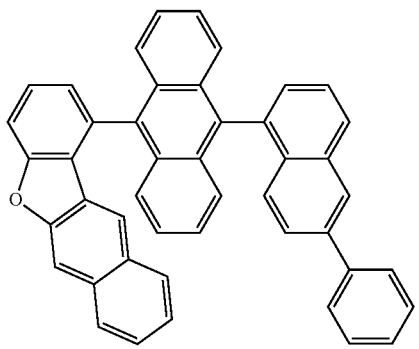

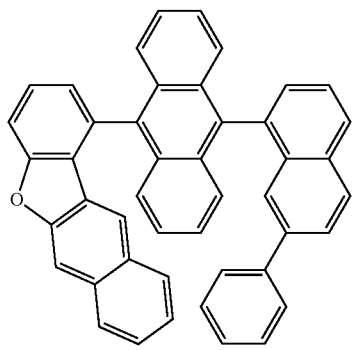
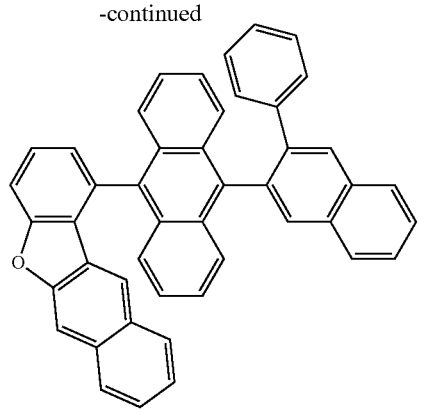
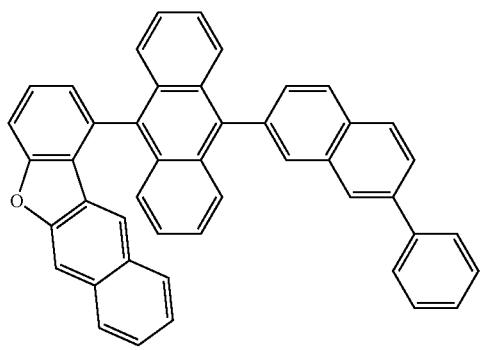
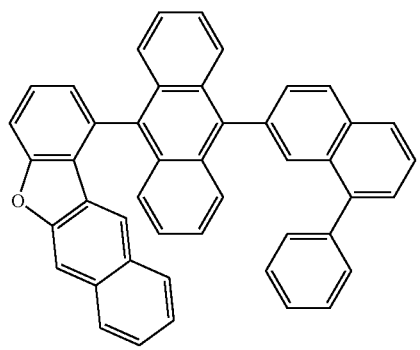
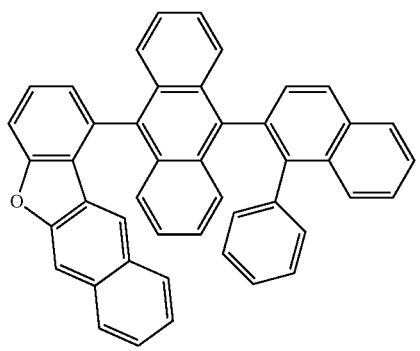
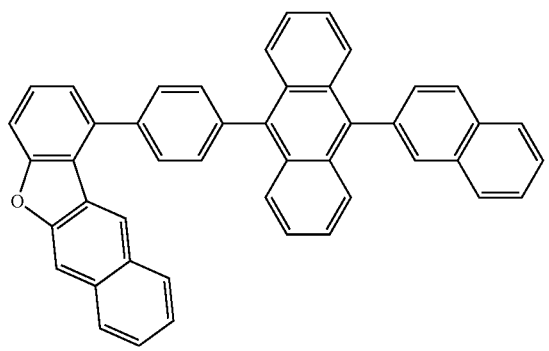
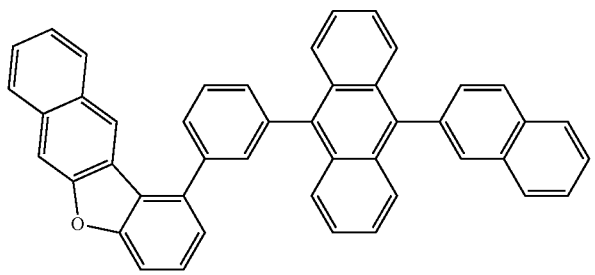

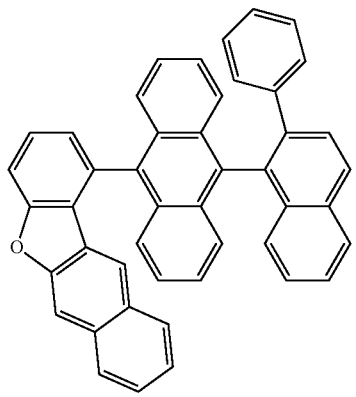
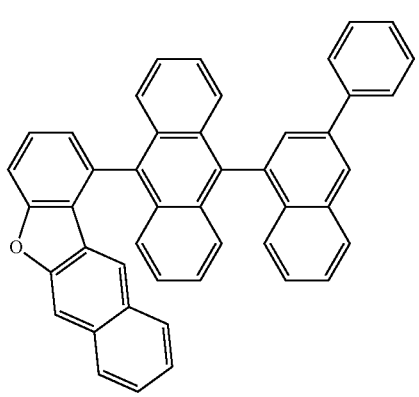
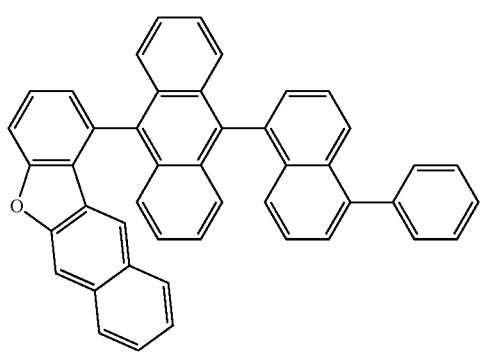
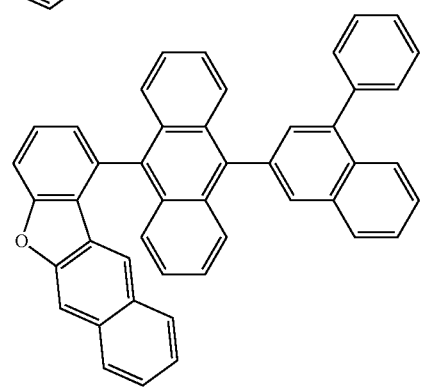
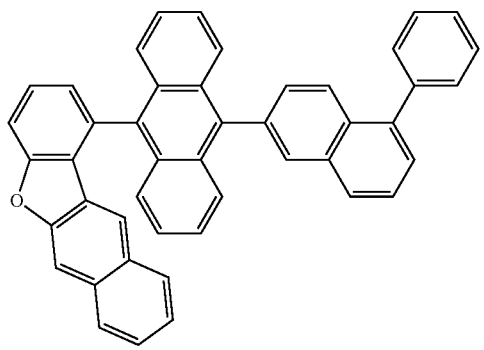
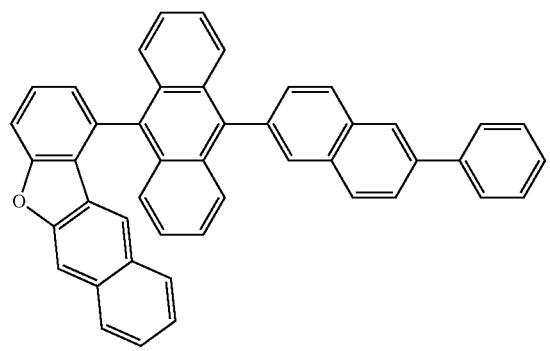
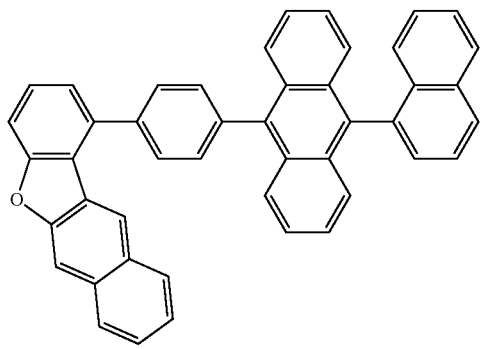
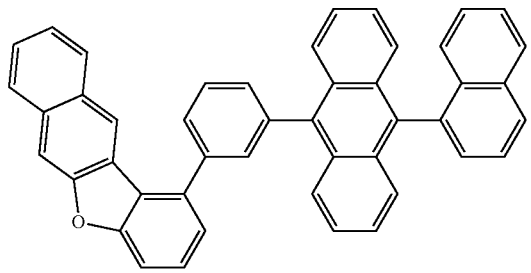

-continued
| 71 | 72 |
|---|---|
| 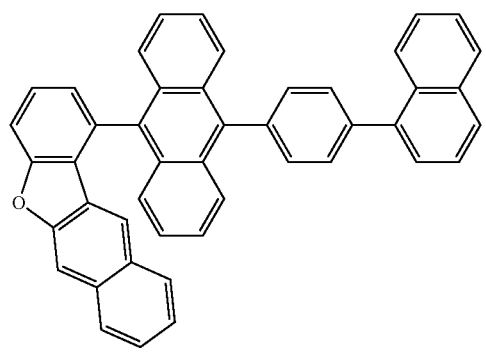 | 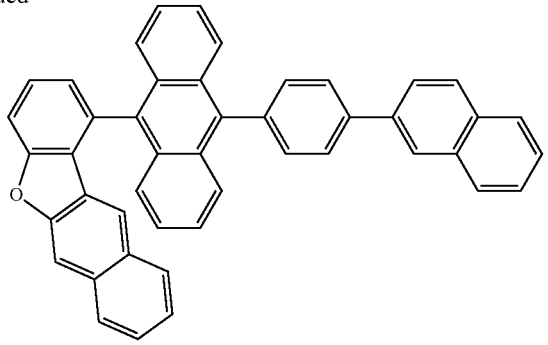 |
| 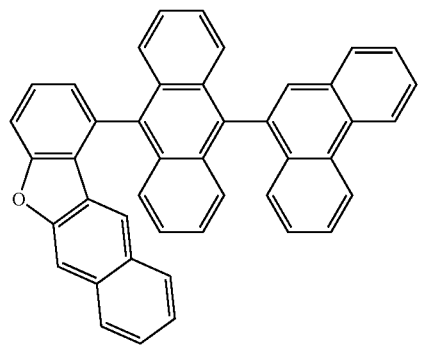 | 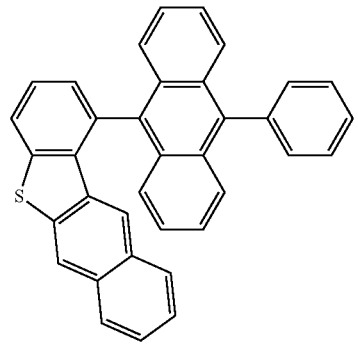 |
| 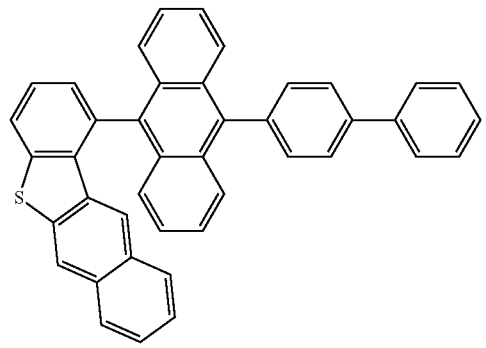 | 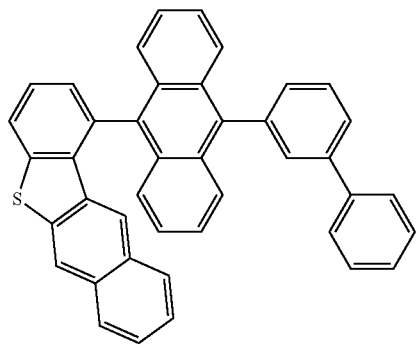 |
| 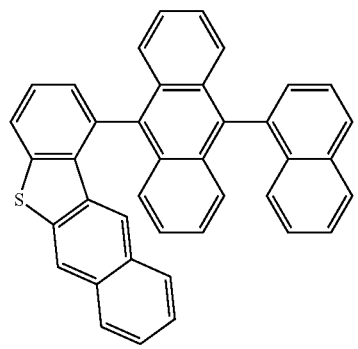 | 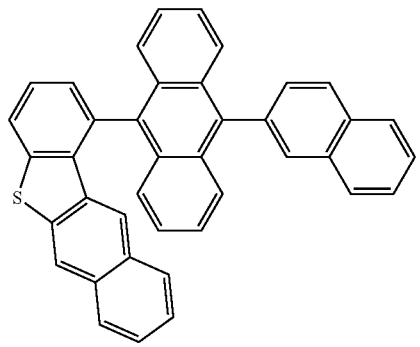 |

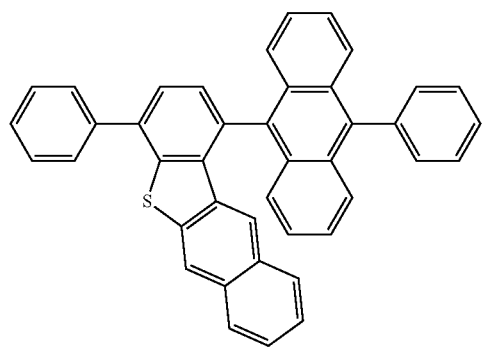
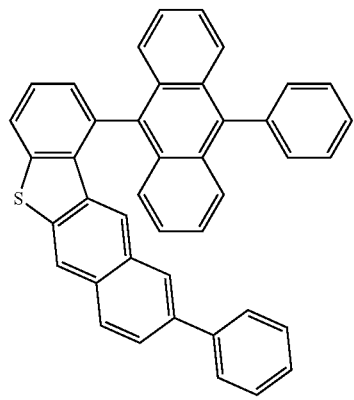
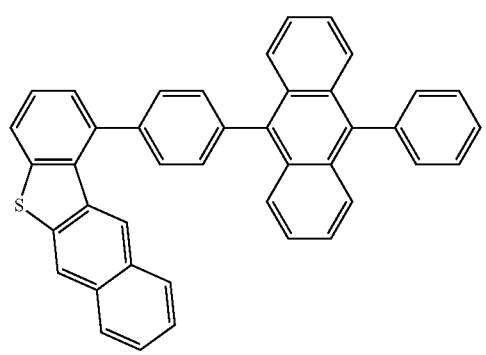
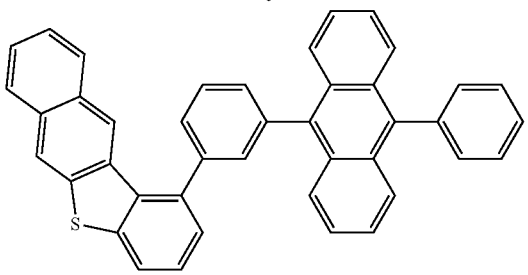
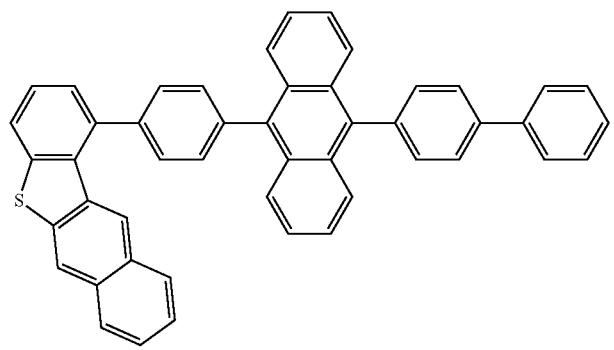
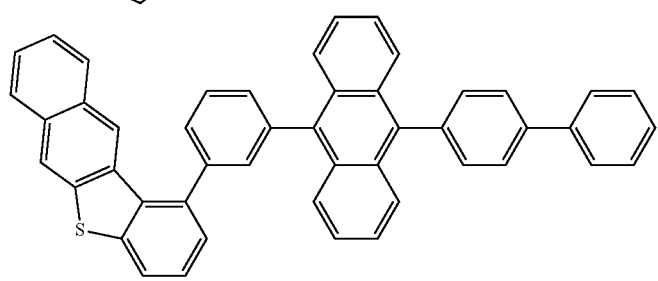
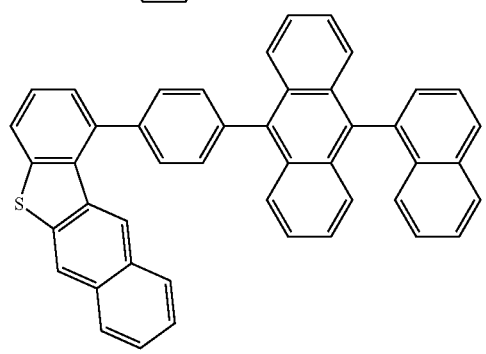
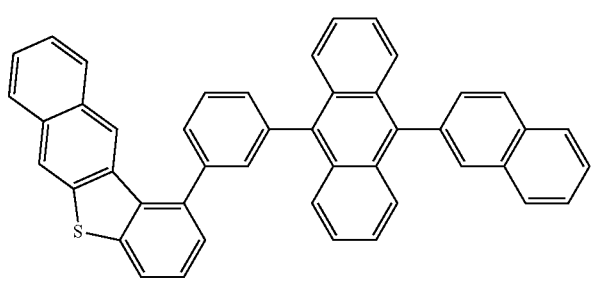

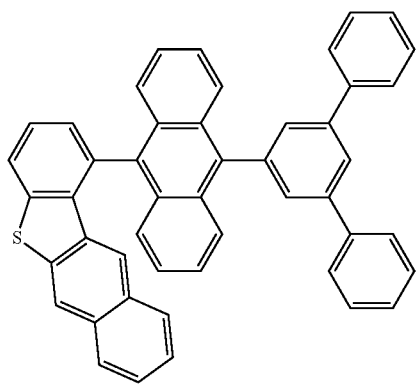 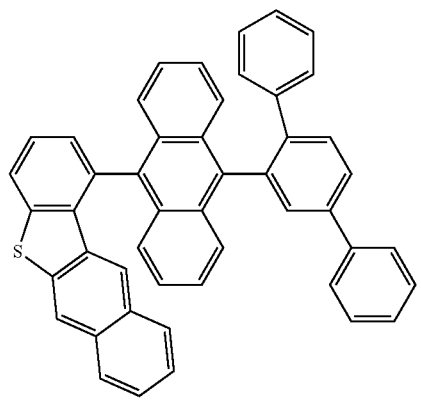
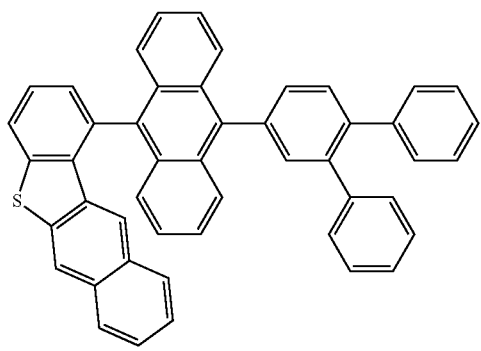 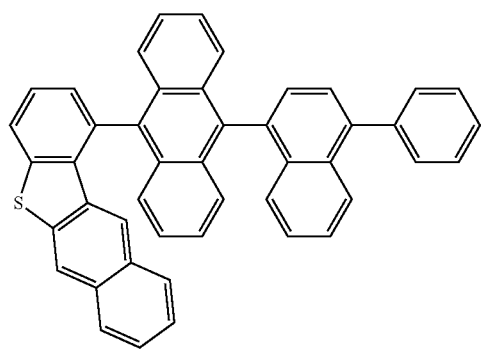
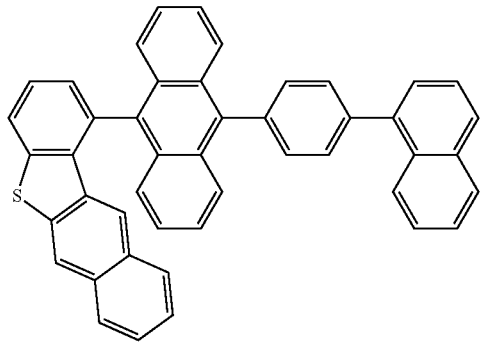 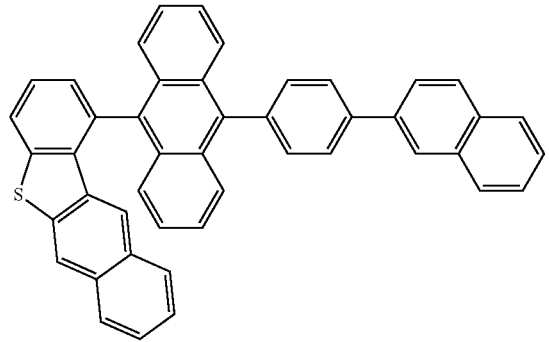
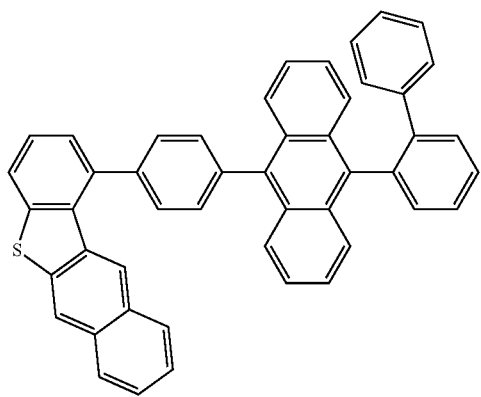 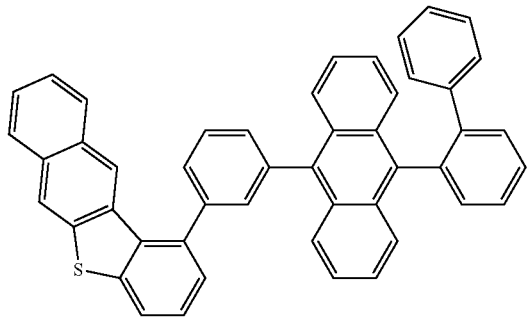

-continued
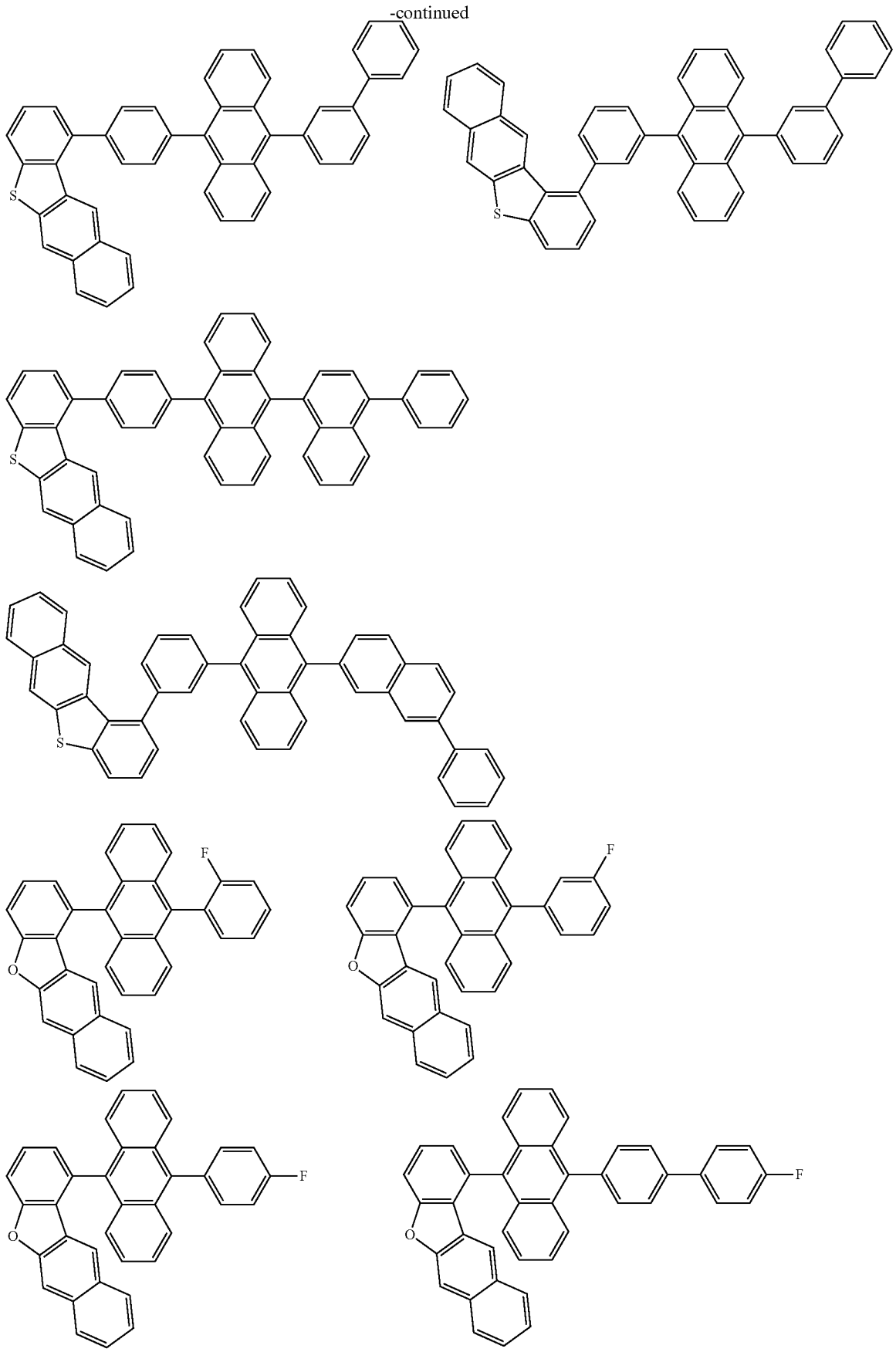

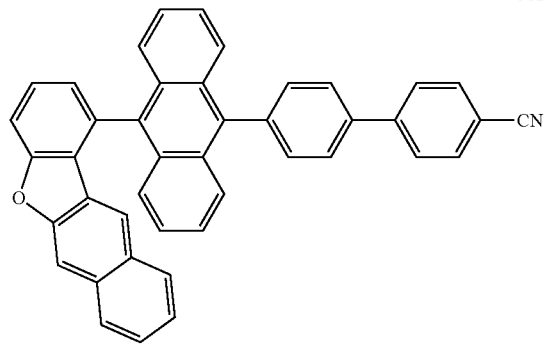
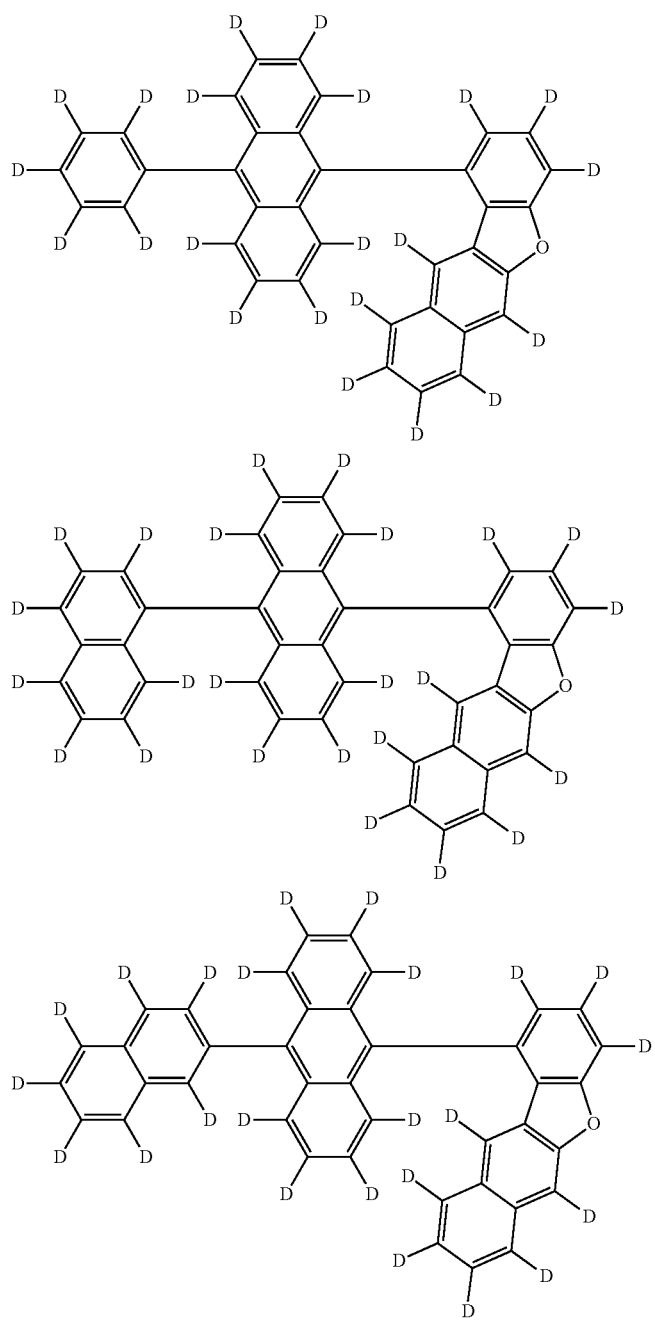

-continued
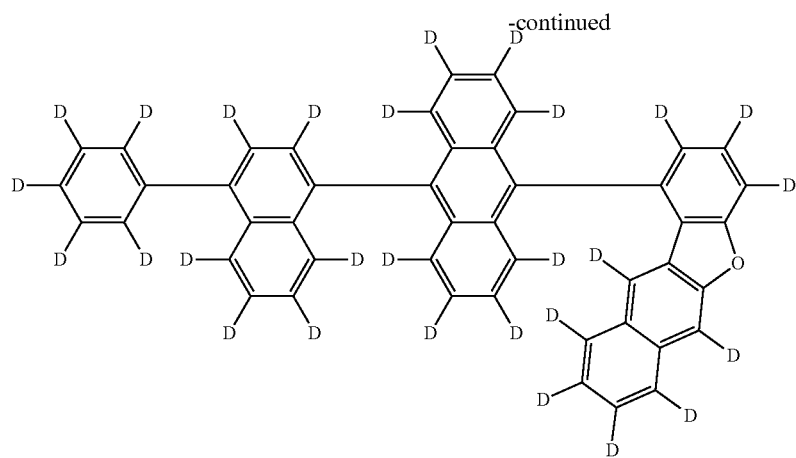
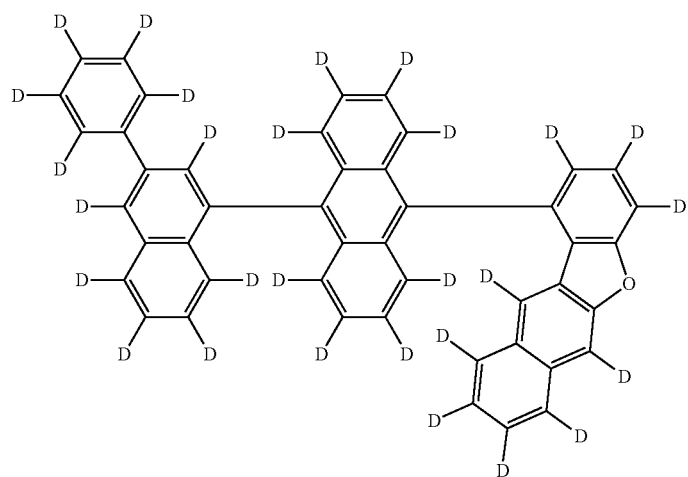
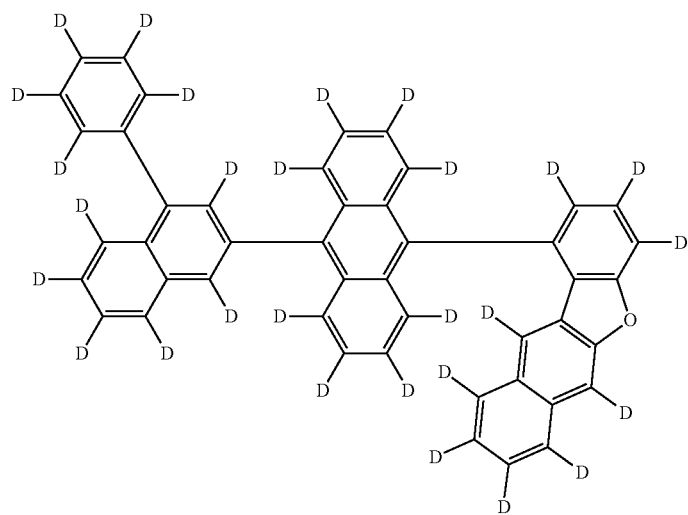

-continued
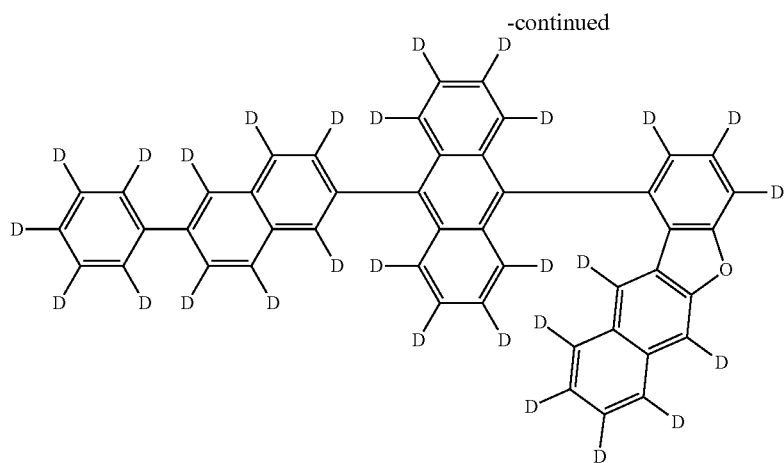
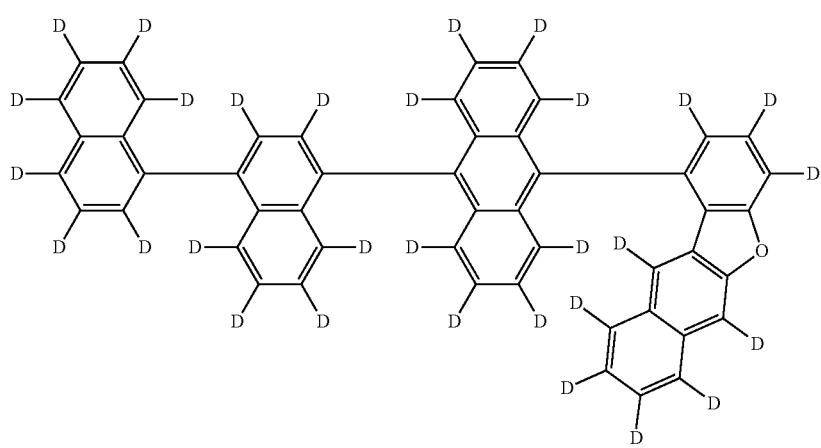
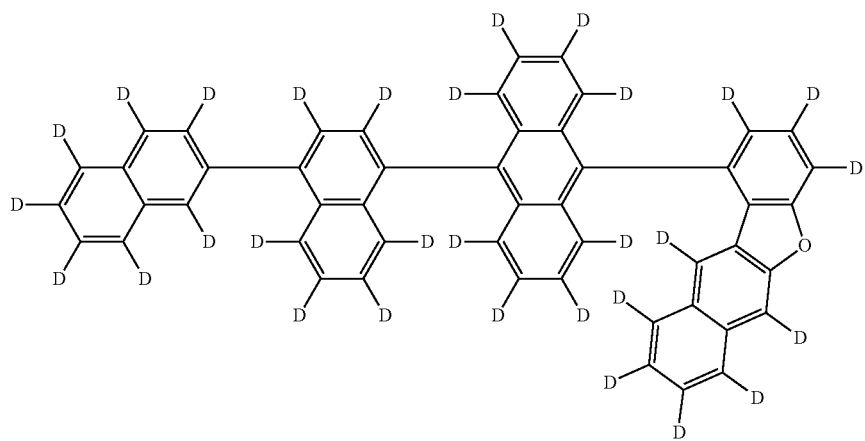

-continued
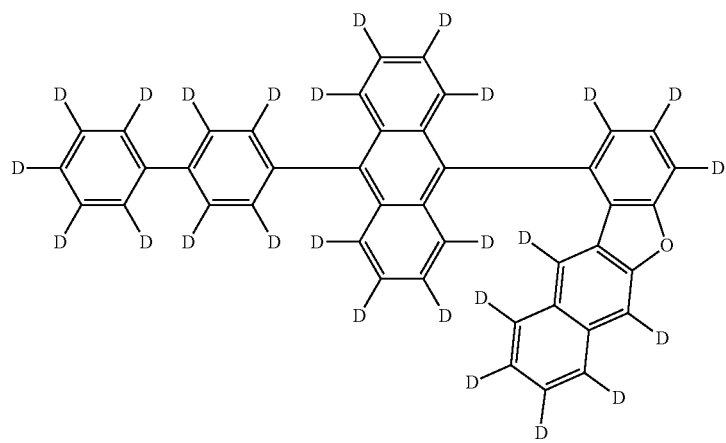
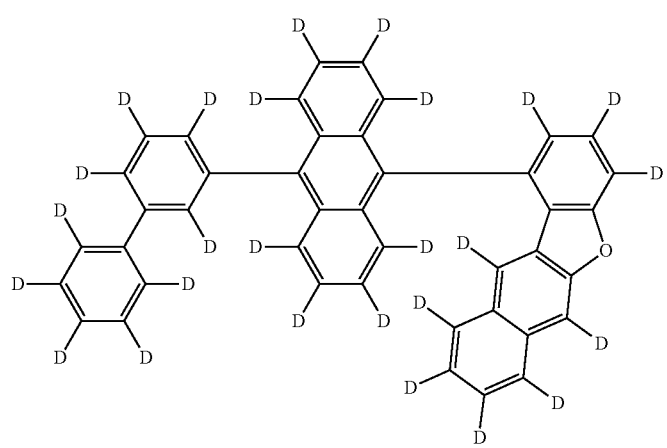
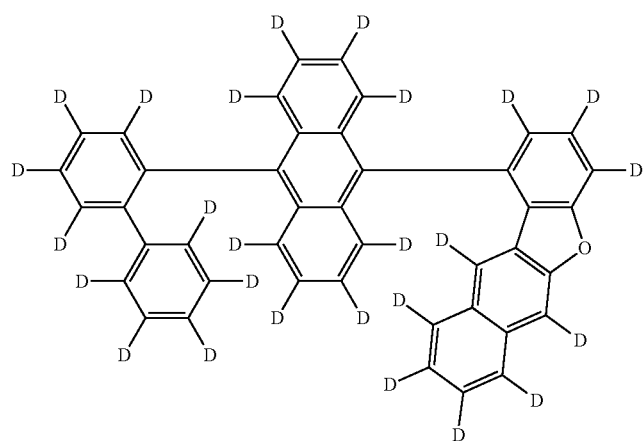

-continued
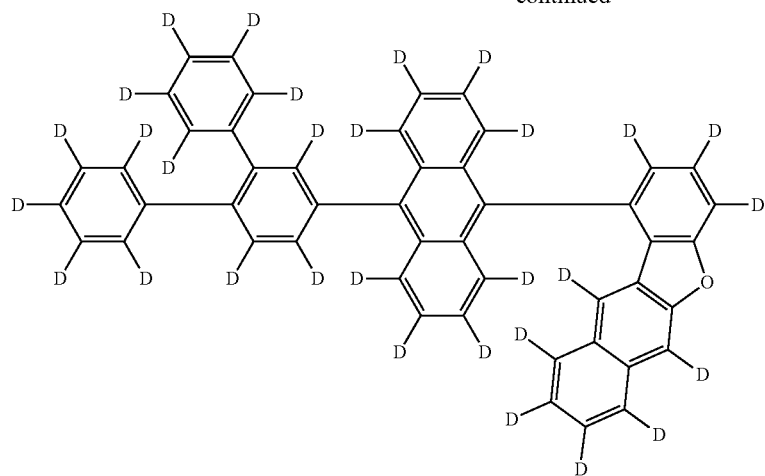
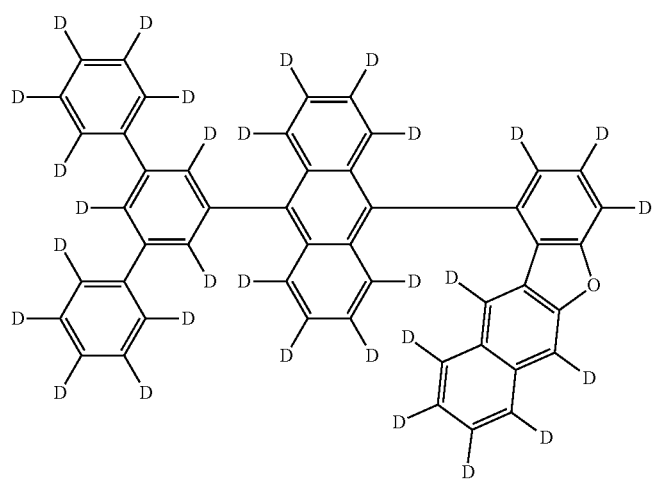
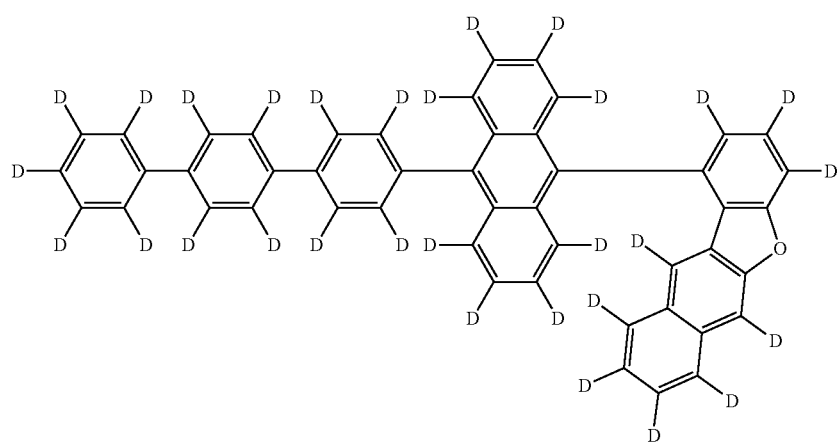

-continued
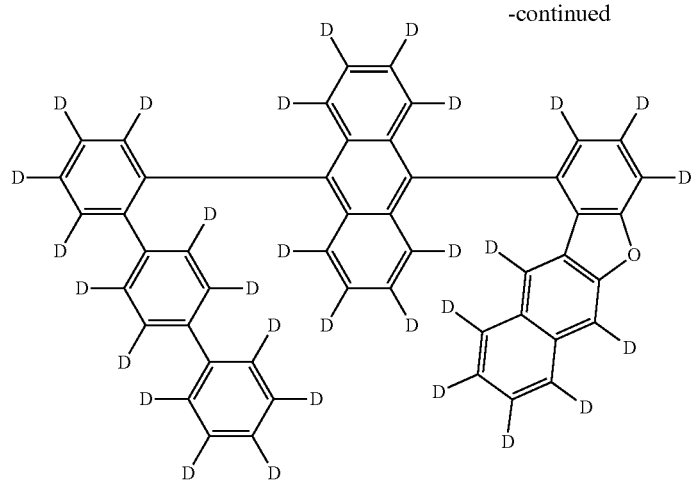
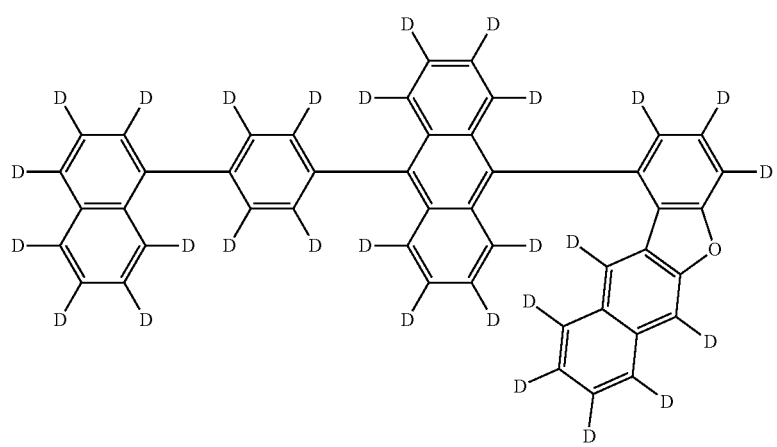
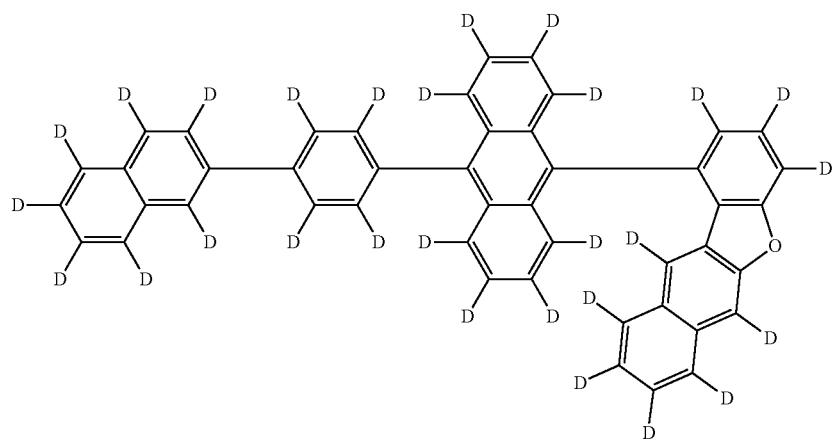

-continued
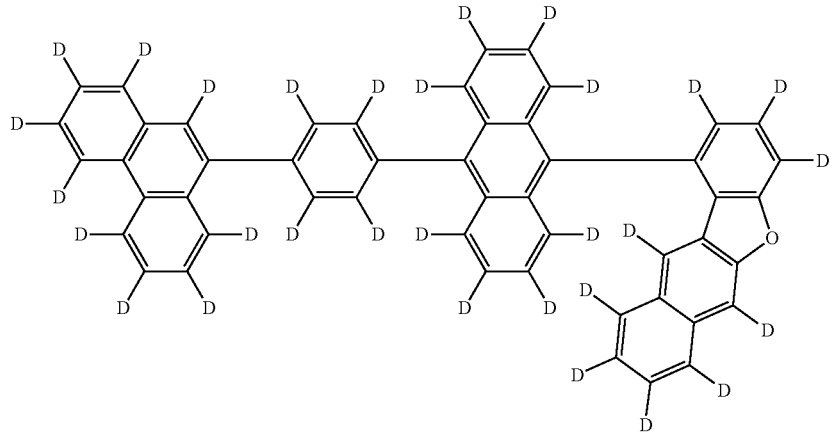
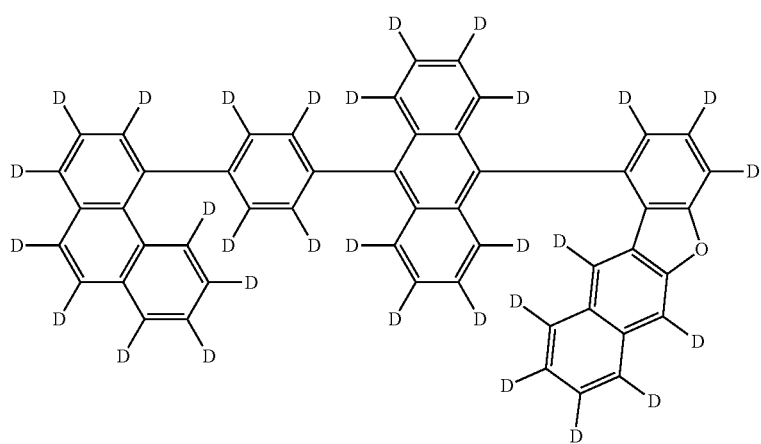
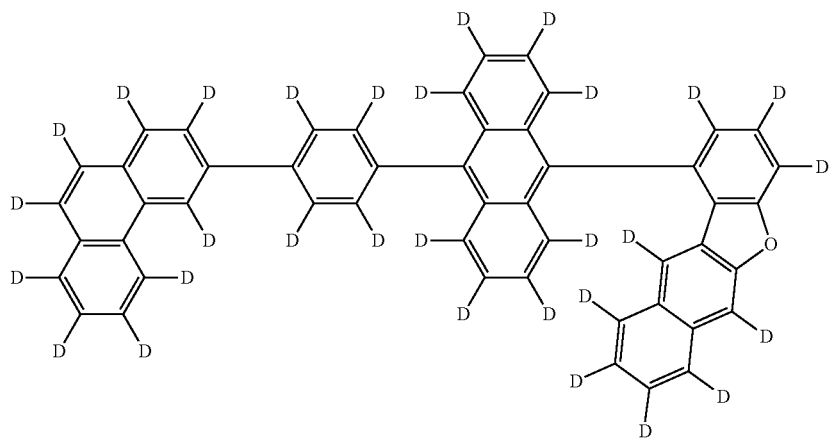

-continued
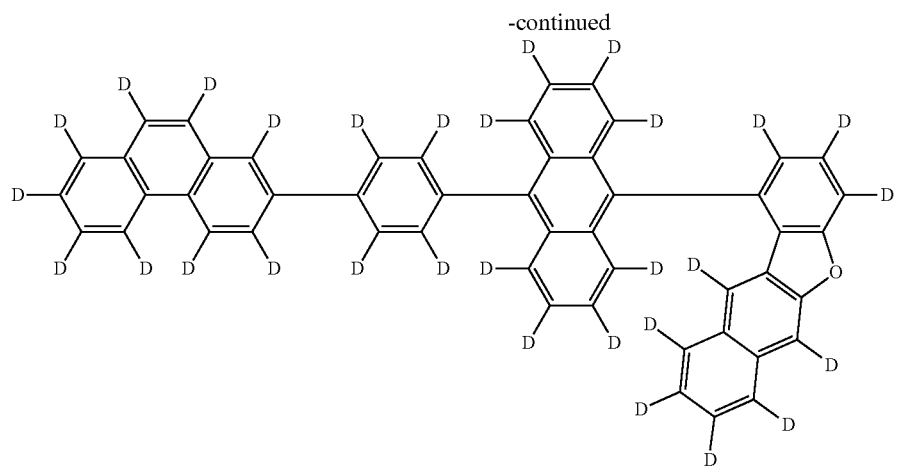
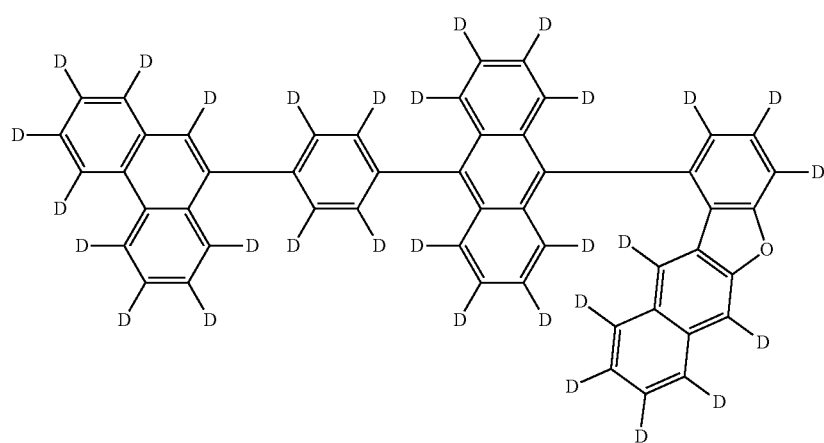
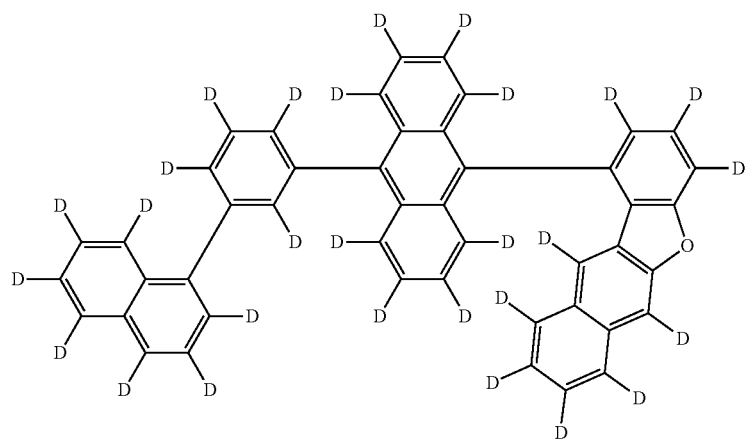

-continued
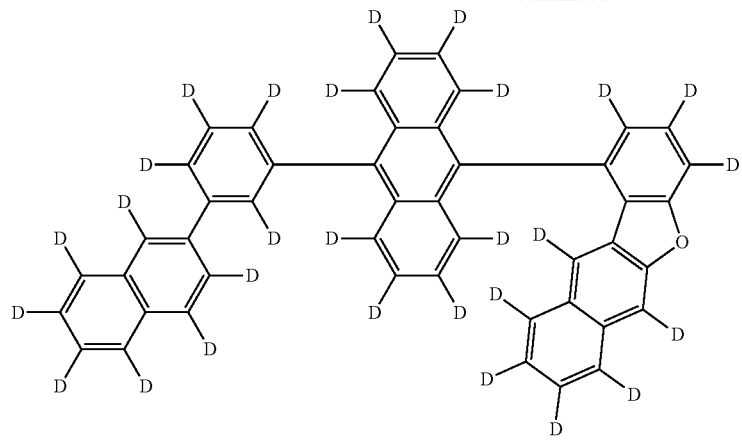
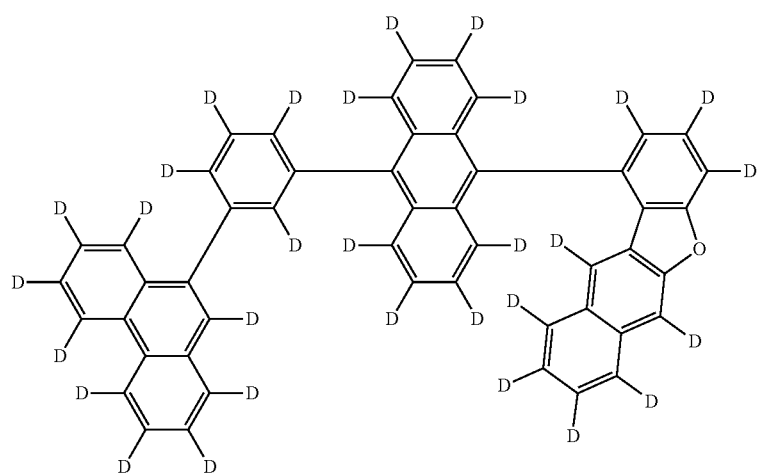
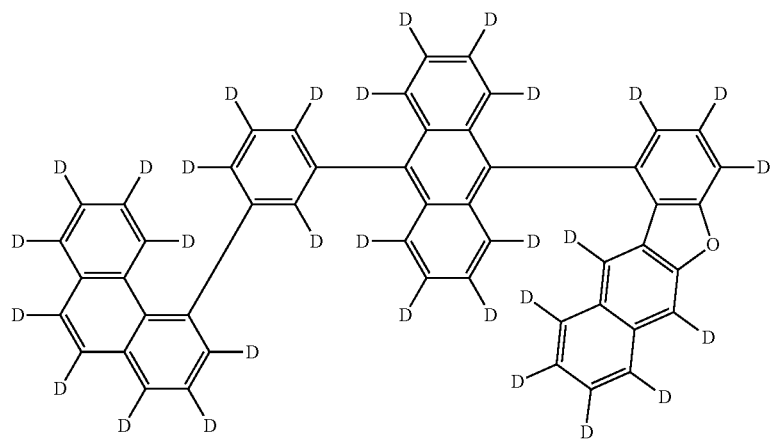

-continued
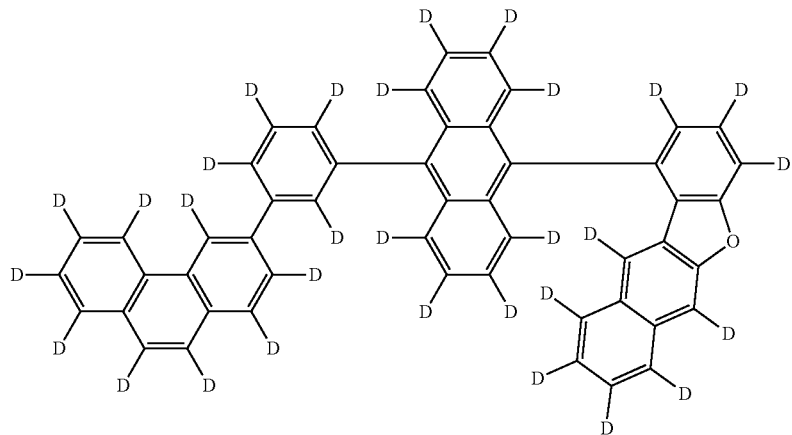
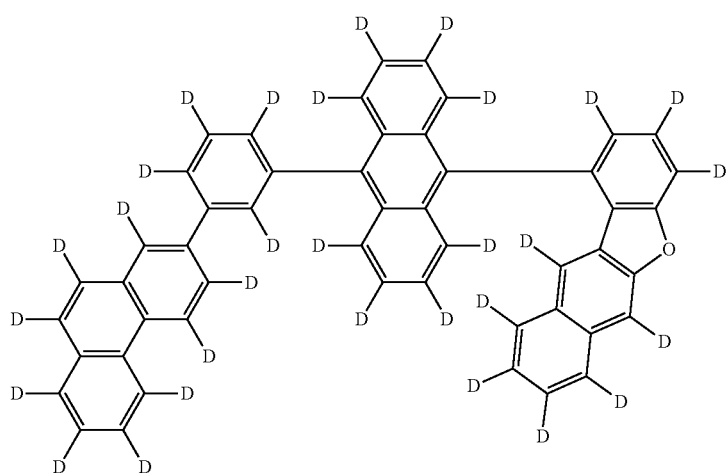
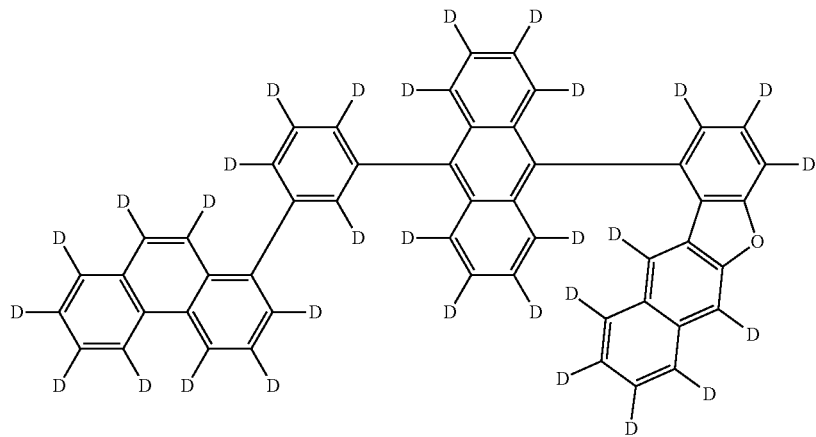

-continued
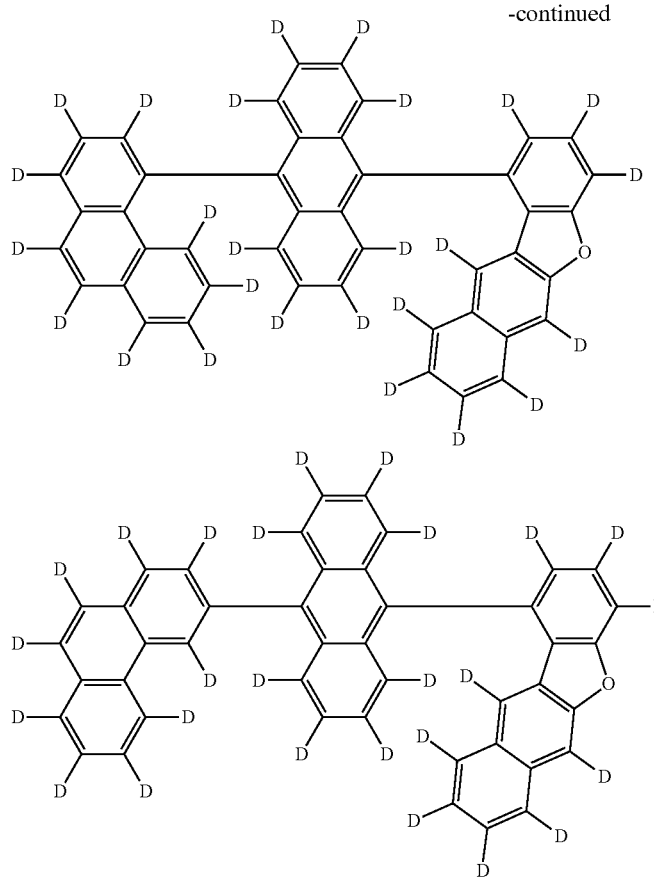
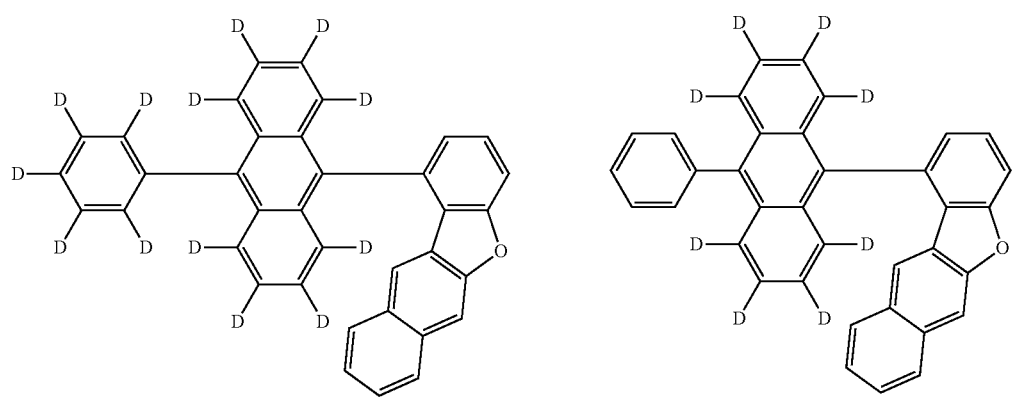
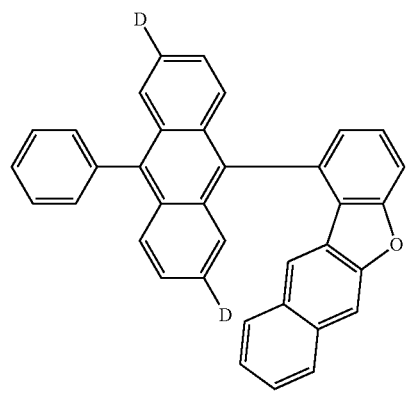
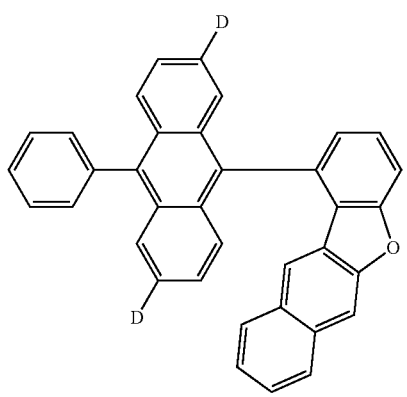

-continued
| 101 | 102 |
|---|---|
| 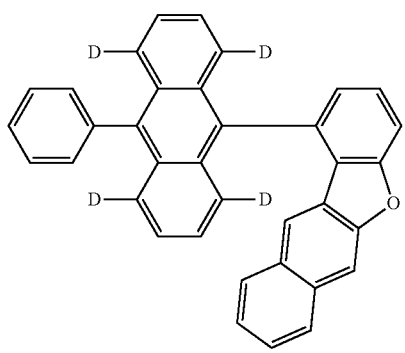 | 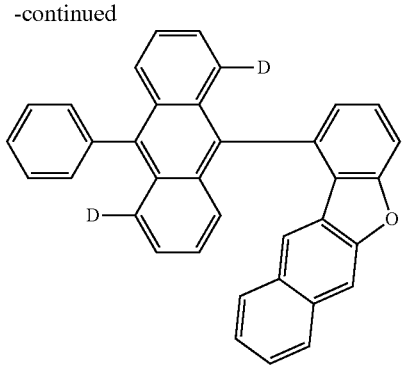 |
| 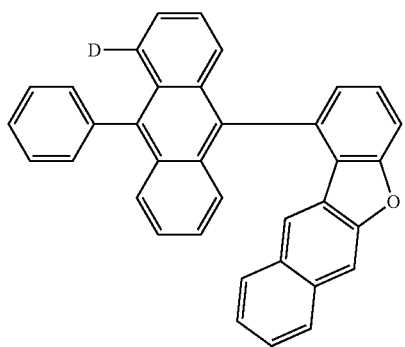 | 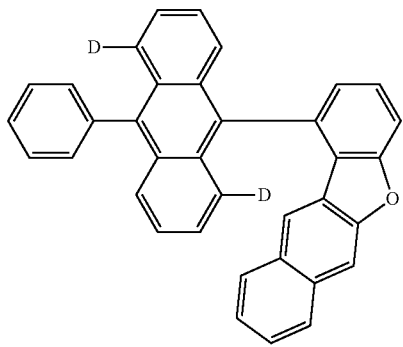 |
| 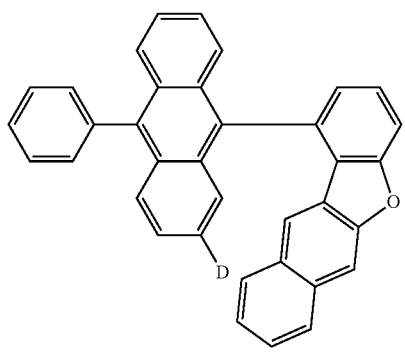 | 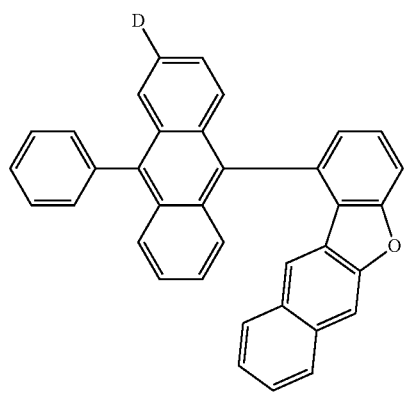 |
| 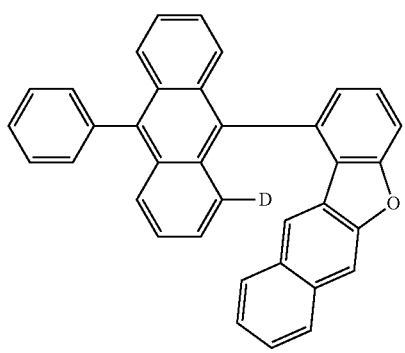 | 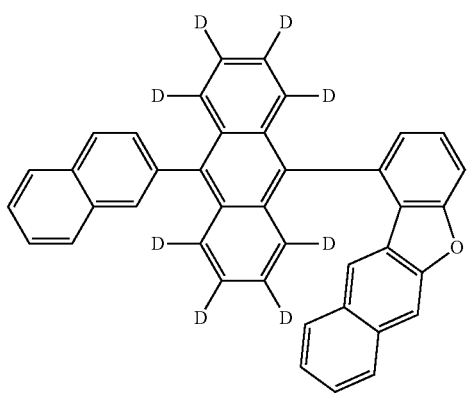 |

-continued
103
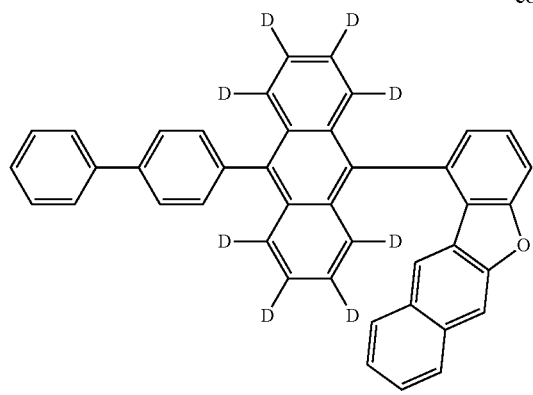
104
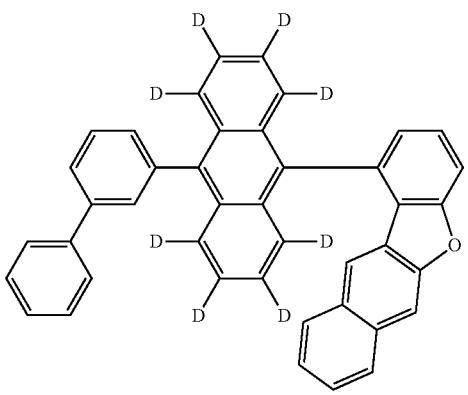
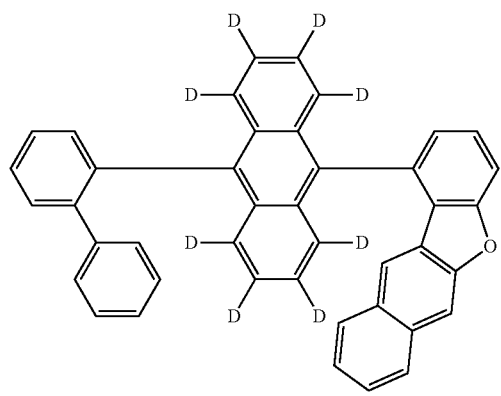
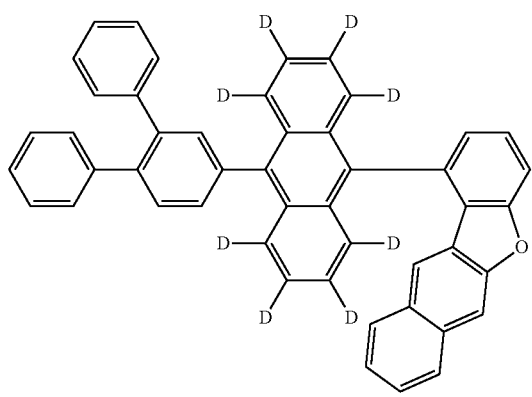
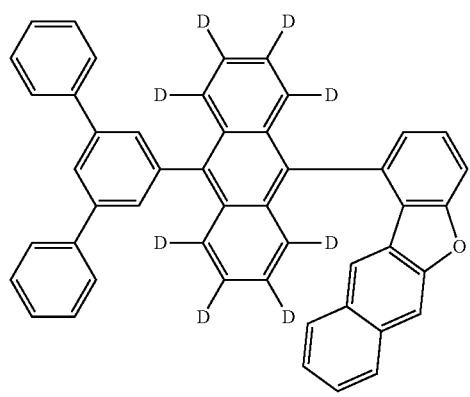
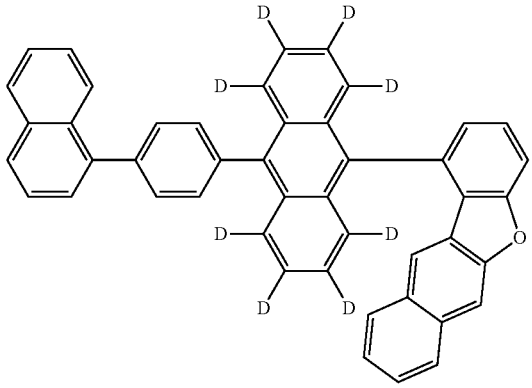
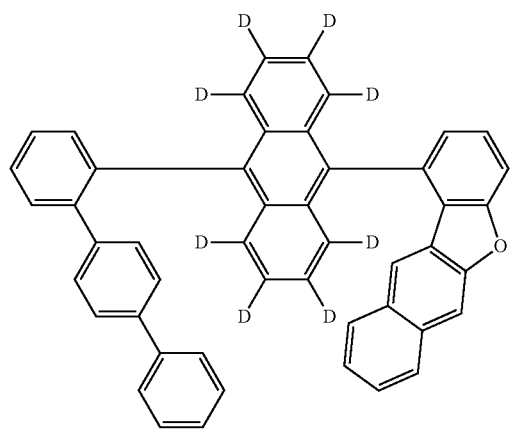

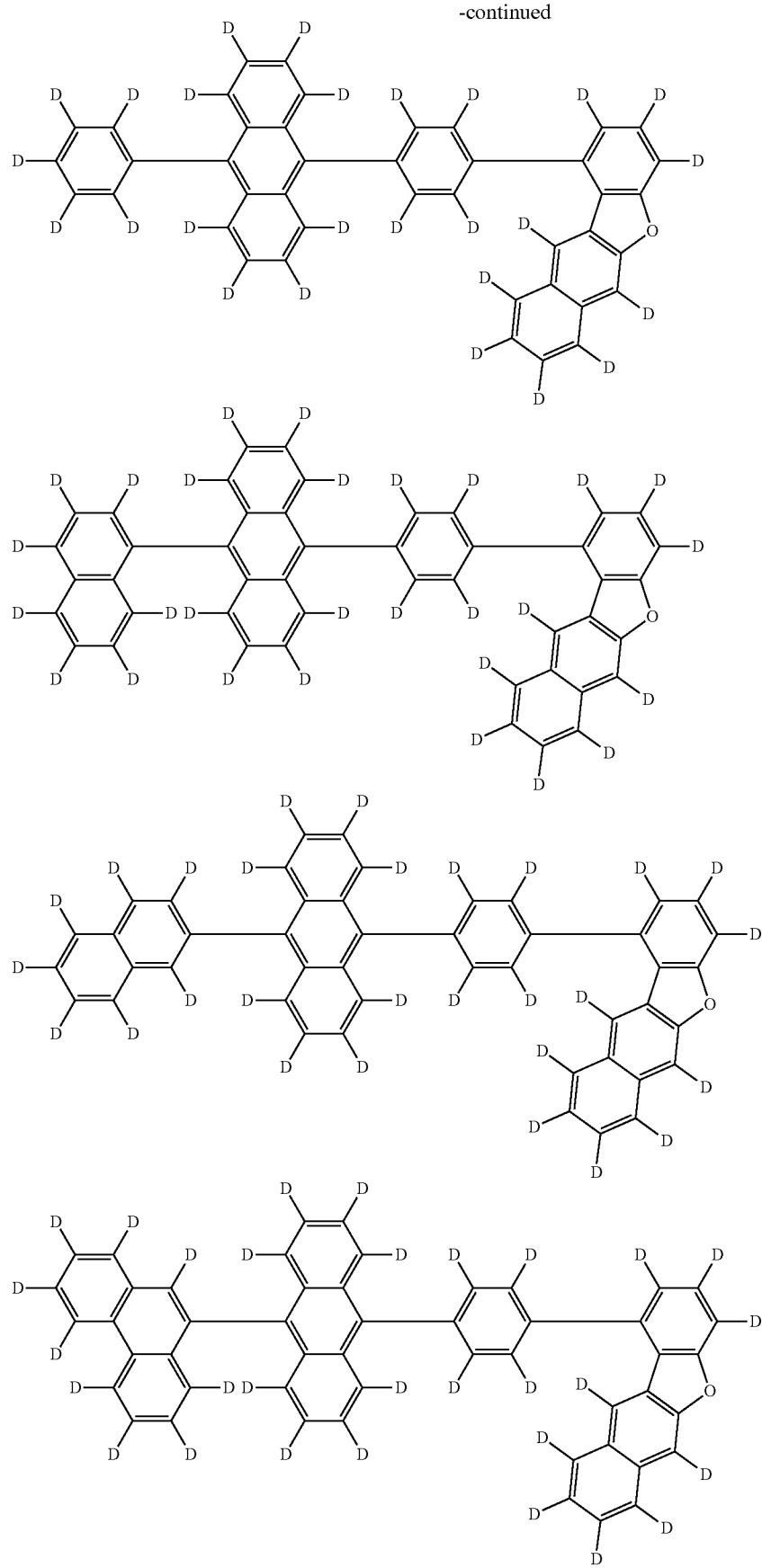

-continued
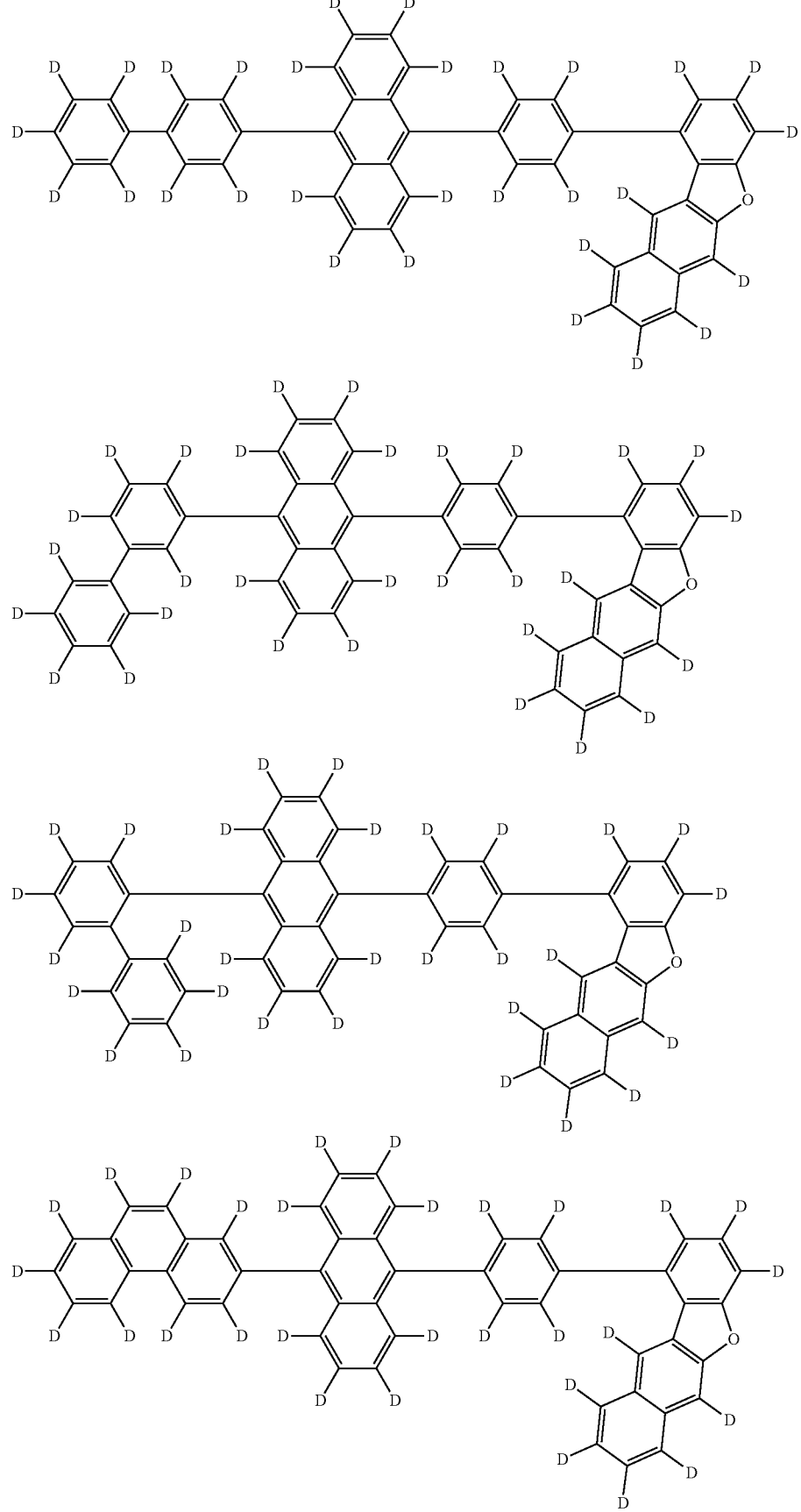

109
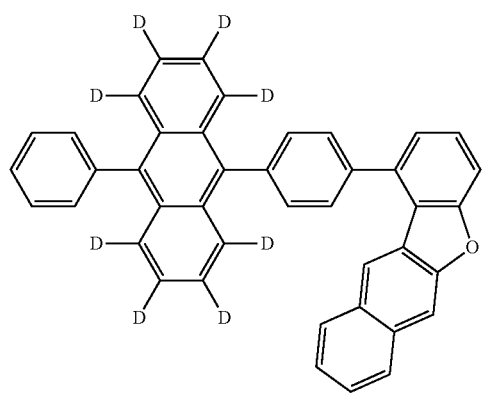
110
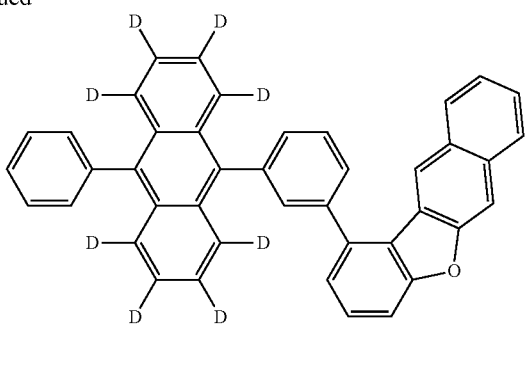
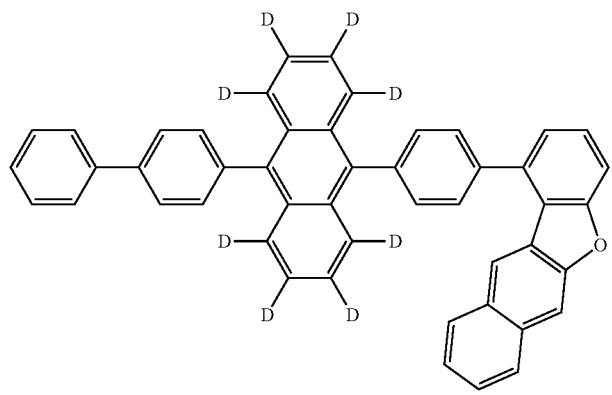
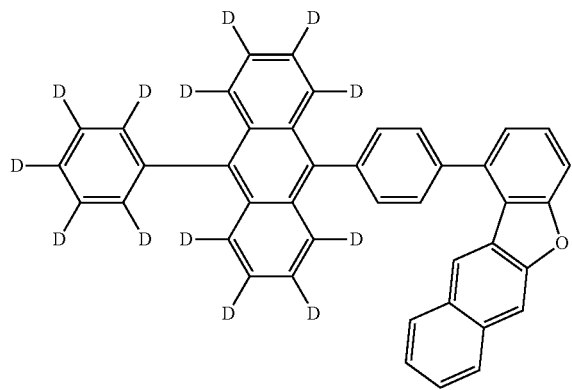
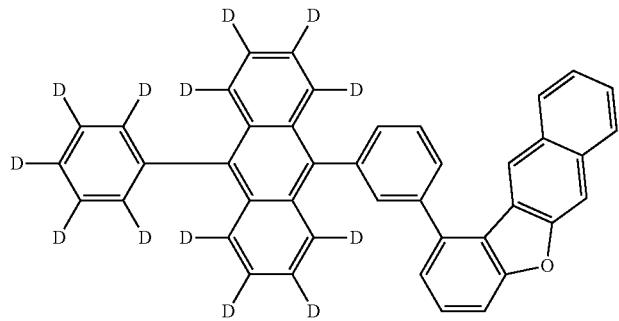

The compound represented by the formula (1) can be synthesized in accordance with the synthetic methods described in Synthesis Examples by using known alternative reactions or raw materials tailored to the target compound.

<Compound Represented by the Formula (BE1)>

The first layer of the organic EL device according to one aspect of the invention contains a compound represented by the following formula (BE1).

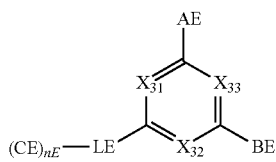
(BE1)

In the formula (BE1), two or more of $X_{31}$ to $X_{33}$ are nitrogen atoms, and the rest which is not a nitrogen atom is CR;

R is a hydrogen atom, a cyano group, a substituted or unsubstituted alkyl group including 1 to 50 carbon atoms, a substituted or unsubstituted cycloalkyl group including 3 to 50 ring carbon atoms, —Si($R_{901}$)($R_{902}$)($R_{903}$),

—O—($R_{904}$), a substituted or unsubstituted aryl group including 6 to 50 ring carbon atoms, or a substituted or unsubstituted monovalent heterocyclic group including 5 to 50 ring atoms;

$R_{901}$ to $R_{904}$ are as defined in the formula (1);

when a plurality of R's are present, the plurality of R's may be the same as or different from each other;

AE is a substituted or unsubstituted aryl group including 6 to 50 ring carbon atoms, or a substituted or unsubstituted monovalent heterocyclic group including 5 to 50 ring atoms;

BE is a substituted or unsubstituted aryl group including 6 to 50 ring carbon atoms, or a substituted or unsubstituted monovalent heterocyclic group including 5 to 50 ring atoms;

LE is a single bond, a substituted or unsubstituted (nE+1)-valent aromatic hydrocarbon ring group including 6 to 50 ring carbon atoms, or a substituted or unsubstituted (nE+1)-valent heterocyclic group including 5 to 50 ring atoms; the aromatic hydrocarbon ring group may have a structure in which two or more different aromatic hydrocarbon rings are bonded;

CE's are independently a substituted or unsubstituted aryl group including 6 to 50 ring carbon atoms, or a substituted or unsubstituted monovalent heterocyclic group including 5 to 50 ring atoms;

nE is an integer of 1 to 3; and when nE is 2 or more, LE is not a single bond.

In one embodiment, the compound represented by the formula (BE1) is a compound represented by the following formula (BE10).

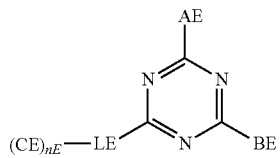
(BE10)

In the formula (BE10),

AE, BE, LE, CE, and nE are as defined in the formula (BE1).

In one embodiment, the compound represented by the formula (BE10) is a compound represented by the following formula (BE11) or formula (BE12).

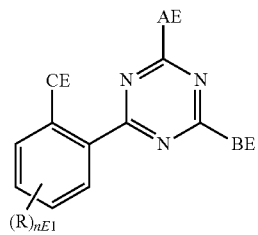
(BE11)

In the formula (BE11),

AE, BE, and CE are as defined in the formula (BE1);

when a plurality of R's are present, one or more sets of adjacent two or more among the plurality of R's are bonded with each other to form a substituted or unsubstituted and saturated or unsaturated ring, or do not form the substituted or unsubstituted and saturated or unsaturated ring;

R which does not form the substituted or unsubstituted, saturated or unsaturated ring is a cyano group, a substituted or unsubstituted alkyl group including 1 to 50 carbon atoms, a substituted or unsubstituted cycloalkyl group including 3 to 50 ring carbon atoms, —Si($R_{901}$)($R_{902}$)($R_{903}$),

—O—($R_{904}$), a substituted or unsubstituted aryl group including 6 to 50 ring carbon atoms, or a substituted or unsubstituted monovalent heterocyclic group including 5 to 50 ring atoms;

$R_{901}$ to $R_{904}$ are as defined in the formula (1);

nE1 is an integer of 0 to 4;

when a plurality of R's are present, the plurality of R's may be the same as or different from each other.

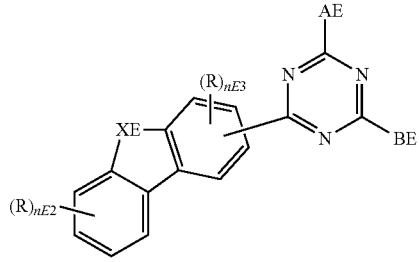
(BE12)

In the formula (BE12),

AE and BE are as defined in the formula (BE1);

XE is $CR_{51}R_{52}$, $NR_{53}$, an oxygen atom, or a sulfur atom;

when XE is $CR_{51}R_{52}$, $R_{51}$ and $R_{52}$ form a substituted or unsubstituted, saturated or unsaturated ring by bonding with each other, or do not form a substituted or unsubstituted, saturated or unsaturated ring;

when a plurality of R's are present, one or more sets of adjacent two or more among the plurality of R's are bonded with each other to form a substituted or unsubstituted, saturated or unsaturated ring, or do not form the substituted or unsubstituted, saturated or unsaturated ring;

$R_{53}$, and R's, $R_{51}$, and $R_{52}$ which do not form the substituted or unsubstituted, saturated or unsaturated ring, are independently a hydrogen atom, a cyano group, a substituted or unsubstituted alkyl group including 1 to 50 carbon atoms, a substituted or unsubstituted cycloalkyl group including 3 to 50 ring carbon atoms, —$Si(R_{901})(R_{902})(R_{903})$,

—$O—(R_{904})$, a substituted or unsubstituted aryl group including 6 to 50 ring carbon atoms, or a substituted or unsubstituted monovalent heterocyclic group including 5 to 50 ring atoms;

$R_{901}$ to $R_{904}$ are as defined in the formula (1);

nE2 is an integer of 0 to 4, and nE3 is an integer of 0 to 3; and when a plurality of R's are present, the plurality of R's may be the same as or different from each other.

In one embodiment, the compound represented by the formula (BE12) is a compound represented by the following formula (BE12-1).

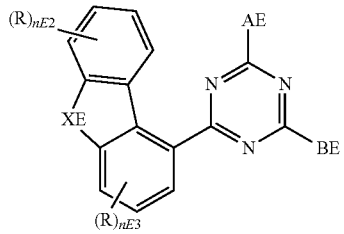

(BE12-1)

In the formula (BE12-1),

AE, BE, XE, R, nE2, and nE3 are as defined in the formula (BE12).

In one embodiment, the compound represented by the formula (BE10) is a compound represented by the following formula (BE13).

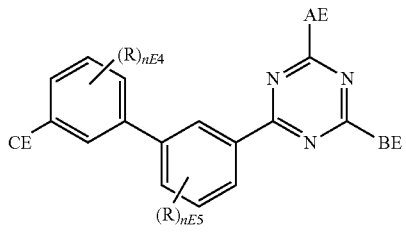

(BE13)

In the formula (BE13),

AE, BE, and CE are as defined in the formula (BE1);

when a plurality of R's are present, one or more sets of adjacent two or more among the plurality of R's are bonded with each other to form a substituted or unsubstituted, saturated or unsaturated ring, or do not form the substituted or unsubstituted, saturated or unsaturated ring;

R's which do not form the substituted or unsubstituted, saturated or unsaturated ring is a cyano group, a substituted or unsubstituted alkyl group including 1 to 50 carbon atoms, a substituted or unsubstituted cycloalkyl group including 3 to 50 ring carbon atoms, —$Si(R_{901})(R_{902})(R_{903})$,

—$O—(R_{904})$, a substituted or unsubstituted aryl group including 6 to 50 ring carbon atoms, or a substituted or unsubstituted monovalent heterocyclic group including 5 to 50 ring atoms;

$R_{901}$ to $R_{904}$ are as defined in the formula (1);

nE4 and nE5 are independently an integer of 0 to 4; and when a plurality of R's are present, the plurality of R's may be the same as or different from each other.

In one embodiment, CE is a substituted or unsubstituted aryl group including 14 to 24 ring carbon atoms, or a substituted or unsubstituted monovalent heterocyclic group including 13 to 35 ring atoms.

In one embodiment, the compound represented by the formula (BE1) is a compound represented by the following formula (BE14).

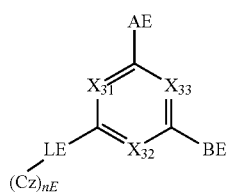

(BE14)

In the formula (BE14), $X_{31}$ to $X_{33}$, AE, BE, LE, and nE are as defined in the formula (BE1);

Cz is a group represented by any one of the following formulas (Cz1), (Cz2), and (Cz3).

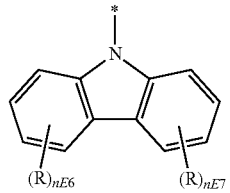

(Cz1)

-continued (Cz2)

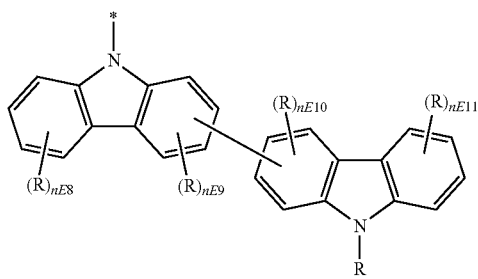

(Cz3)

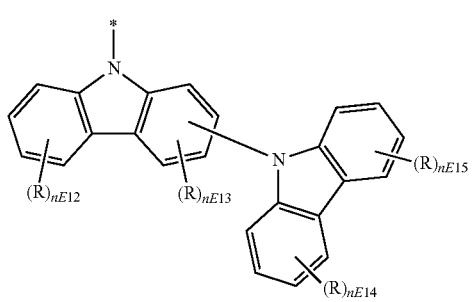

In the formulas (Cz1), (Cz2), and (Cz3),
when a plurality of R's are present, one or more sets of adjacent two or more among the plurality of R's are bonded with each other to form a substituted or unsubstituted, saturated or unsaturated ring, or do not form the substituted or unsubstituted, saturated or unsaturated ring;

R which does not form the substituted or unsubstituted, saturated or unsaturated ring is a cyano group, a substituted or unsubstituted alkyl group including 1 to 50 carbon atoms, a substituted or unsubstituted cycloalkyl group including 3 to 50 ring carbon atoms, —Si($R_{901}$)($R_{902}$)($R_{903}$),

—O—($R_{904}$), a substituted or unsubstituted aryl group including 6 to 50 ring carbon atoms, or a substituted or unsubstituted monovalent heterocyclic group including 5 to 50 ring atoms;

$R_{901}$ to $R_{904}$ are as defined in the formula (1);

nE6 and nE7 are independently an integer of 0 to 4;

nE8 and nE11 are independently an integer of 0 to 4, and nE9 and nE10 are independently an integer of 0 to 3;

nE12, nE14, and nE15 are independently an integer of 0 to 4, and nE13 is an integer of 0 to 3;

when a plurality of R's are present, the plurality of R's may be the same as or different from each other; and "*" is bonded to LE.

In one embodiment, the compound represented by the formula (BE10) is a compound represented by the following formula (BE15).

(BE15)

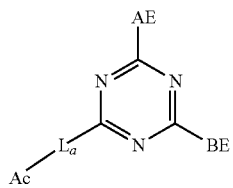

In the formula (BE15),

AE and BE are as defined in the formula (BE1);

$L_a$ is a single bond, a substituted or unsubstituted divalent aromatic hydrocarbon ring group including 6 to 18 ring carbon atoms, or a substituted or unsubstituted divalent heterocyclic group including 5 to 13 ring atoms; the aromatic hydrocarbon ring group may have a structure in which two or more different aromatic hydrocarbon rings are bonded;

Ac is a group represented by any one of the following formulas (Ac1), (Ac2), and (Ac3).

(Ac1)

(Ac2)

(Ac3)

*—D—(CN)$_{nE16}$

In the formula (Ac1), one to five of $XE_1$ to $XE_6$ are nitrogen atoms, the rest of which are not nitrogen atoms are CR's, and one of R's is bonded to $L_a$;

R which is not bonded to $L_a$ is a hydrogen atom, a cyano group, a substituted or unsubstituted alkyl group including 1 to 50 carbon atoms, a substituted or unsubstituted cycloalkyl group including 3 to 50 ring carbon atoms, —Si($R_{901}$)($R_{902}$)($R_{903}$),

—O—($R_{904}$), a substituted or unsubstituted aryl group including 6 to 50 ring carbon atoms, or a substituted or unsubstituted monovalent heterocyclic group including 5 to 50 ring atoms;

$R_{901}$ to $R_{904}$ are as defined in the formula (1);

when a plurality of R's are present, the plurality of R's may be the same as or different from each other.

In the formula (Ac2), one to seven of $XE_{21}$ to $XE_{28}$ are nitrogen atoms, the rest of which is not nitrogen atoms are CR's, and one of R's is bonded to $L_a$;

when a plurality of R's are present, one or more sets of adjacent two or more of the plurality of R's form a substituted or unsubstituted, saturated or unsaturated ring by bonding with each other, or do not form a substituted or unsubstituted, saturated or unsaturated ring;

R which is not bonded to $L_a$ and does not form the substituted or unsubstituted, saturated or unsaturated ring is
a hydrogen atom,
a cyano group,
a substituted or unsubstituted alkyl group including 1 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
a substituted or unsubstituted aryl group including 6 to 50 ring carbon atoms, or
a substituted or unsubstituted monovalent heterocyclic group including 5 to 50 ring atoms;

$R_{901}$ to $R_{904}$ are as defined in the formula (1);
when a plurality of R's are present, the plurality of R's may be the same as or different from each other.

In the formula (Ac3),
D is an aryl group including 6 to 18 ring carbon atoms substituted by nE16 cyano groups, or a monovalent heterocyclic group including 5 to 13 ring atoms substituted by nE16 cyano groups; provided that D may have a substituent other than cyano group;
nE16 represents the number of cyano groups which are substituted for D and is an integer of 1 to 9;
"*" is bonded to $L_a$.

In one embodiment, the compound represented by the formula (BE15) is a compound represented by the following formula (BE16).

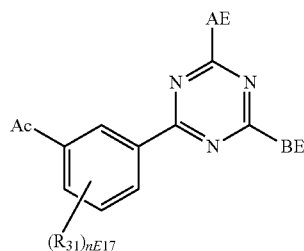

(BE16)

In the formula (BE16),
AE, BE, and Ac are as defined in the formula (BE15);
nE17 is an integer of 0 to 4;
when a plurality of $R_{31}$'s are present, one or more sets of adjacent two or more among the plurality of $R_{31}$'s are bonded with each other to form a substituted or unsubstituted, saturated or unsaturated ring, or do not form the substituted or unsubstituted, saturated or unsaturated ring;
$R_{31}$ which does not form the substituted or unsubstituted, saturated or unsaturated ring is a cyano group,
a substituted or unsubstituted alkyl group including 1 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
a substituted or unsubstituted aryl group including 6 to 50 ring carbon atoms, or
a substituted or unsubstituted monovalent heterocyclic group including 5 to 50 ring atoms;

$R_{901}$ to $R_{904}$ are as defined in the formula (1); and
when a plurality of R's are present, the plurality of R's may be the same as or different from each other.

In one embodiment, LE or $L_a$ is an aromatic hydrocarbon ring group represented by any one of the following formulas (1) to (L4).

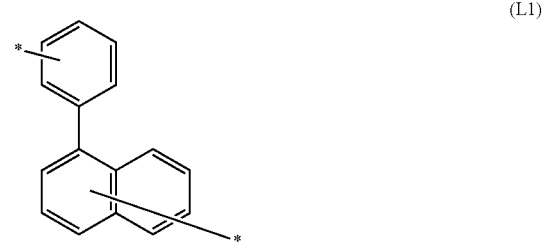

(L1)

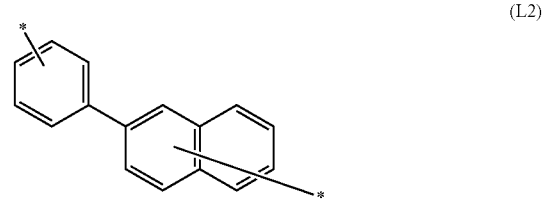

(L2)

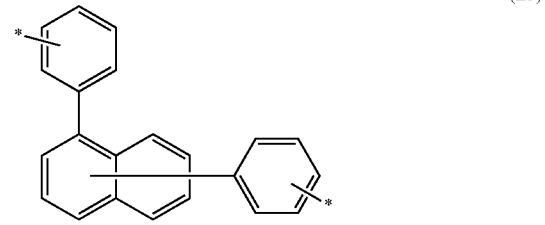

(L3)

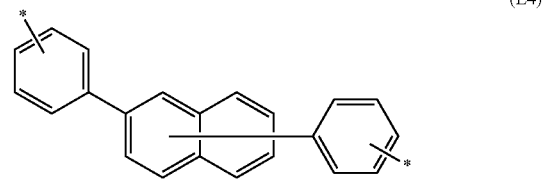

(L4)

In the formulas (1) to (L4), one of the two s is bonded to a nitrogen-containing 6-membered ring and the other is bonded to $(C)_{nE}$, $(CZ)_{nE}$, or Ac. When nE is an integer of 1 to 3, one to three "*"s bonded to $(C)_{nE}$ or $(CZ)_{nE}$ are present, respectively.

In one embodiment, LE or $L_a$ is an aromatic hydrocarbon ring group represented by the following formula (L5).

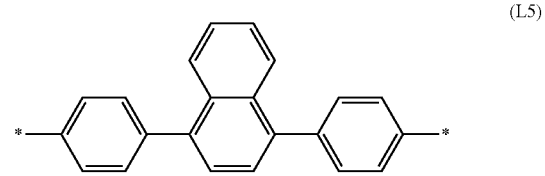 [SMILES: *c1ccc(-c2ccc(-c3ccc(*)cc3)c3ccccc23)cc1]

(L5)

In the formula (L5), one of the two s is bonded to a nitrogen-containing 6-membered ring and the other is bonded to $(C)_{nE}$, $(CZ)_{nE}$, or Ac. When nE is an integer of 1 to 3, one to three "*"s bonded to $(C)_{nE}$ or $(Cz)_{nE}$ are present, respectively.

In one embodiment, LE is a single bond or a substituted or unsubstituted (nE+1)-valent aromatic hydrocarbon ring group including 6 to 12 ring carbon atoms.

In one embodiment, LE or La is a single bond.

In one embodiment, AE is a substituted or unsubstituted aryl group including 6 to 12 ring carbon atoms.

In one embodiment, AE is a substituted or unsubstituted phenyl group, a substituted or unsubstituted biphenyl group, or a substituted or unsubstituted naphthyl group.

In one embodiment, AE is an unsubstituted phenyl group, an unsubstituted biphenyl group, or an unsubstituted naphthyl group.

In one embodiment, BE is a substituted or unsubstituted aryl group including 6 to 12 ring carbon atoms.

In one embodiment, BE is a substituted or unsubstituted phenyl group, a substituted or unsubstituted biphenyl group, or a substituted or unsubstituted naphthyl group.

In one embodiment, BE is an unsubstituted phenyl group, an unsubstituted biphenyl group, or an unsubstituted naphthyl group.

In one embodiment, the first layer is directly adjacent to the emitting layer.

Specific examples of the compound represented by the formula (BE1) are described below, but are not limited to these specific example compounds.

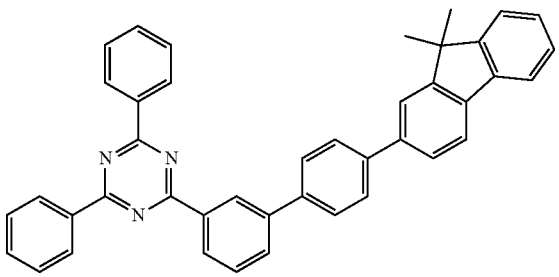

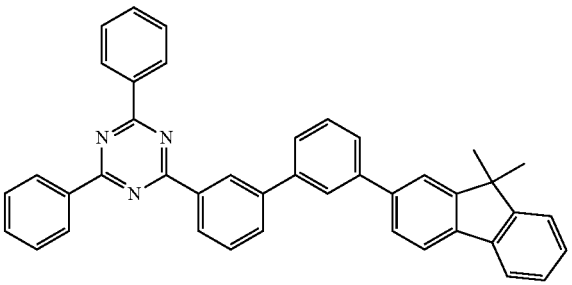

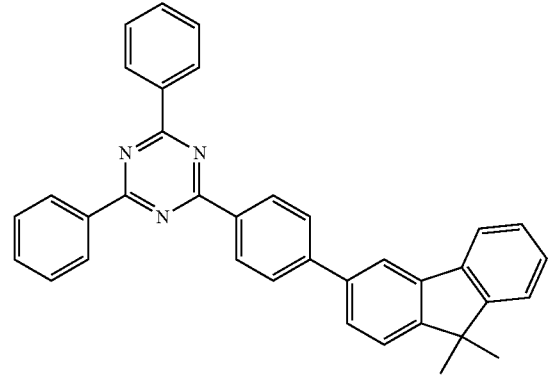

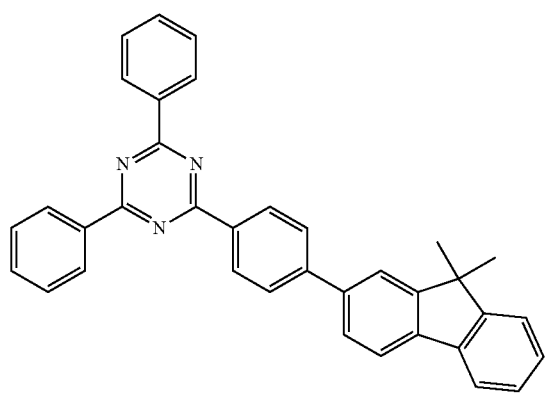

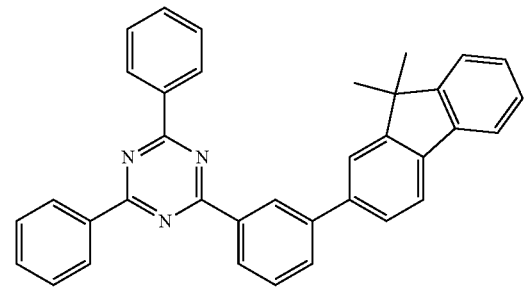

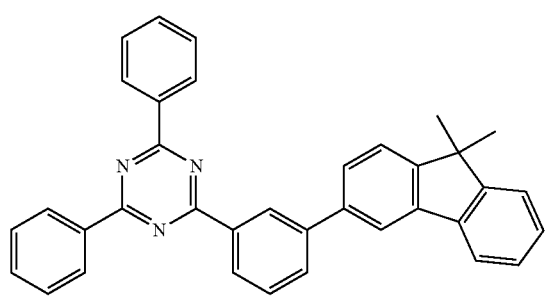

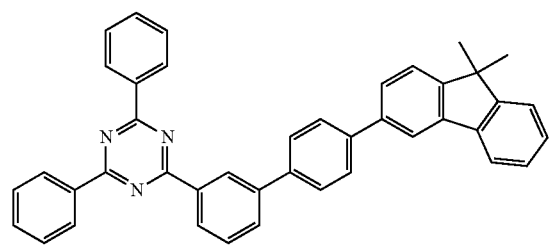

121
-continued
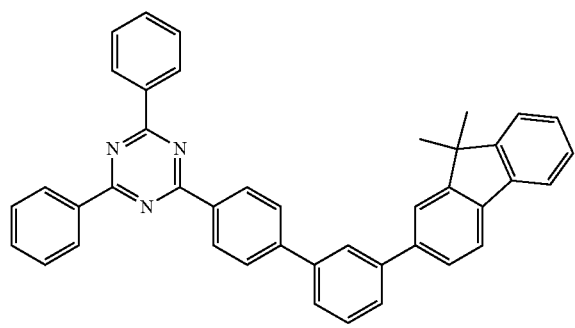
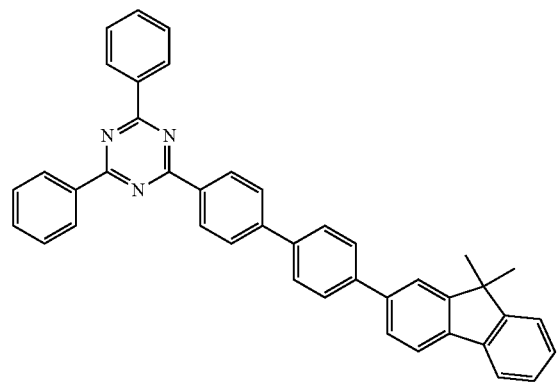
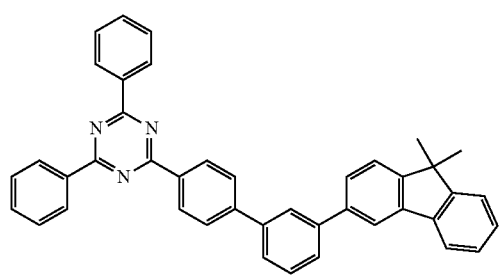
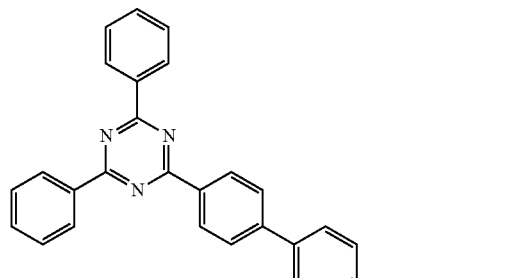
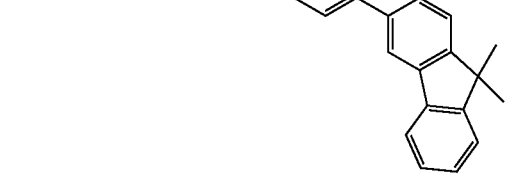
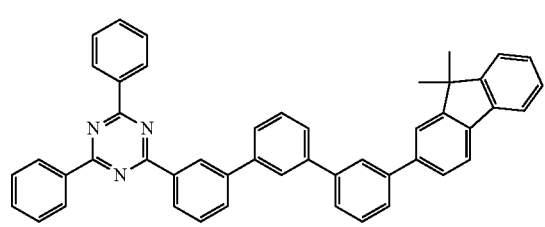
122
-continued
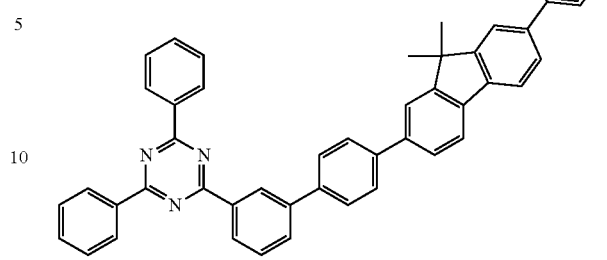
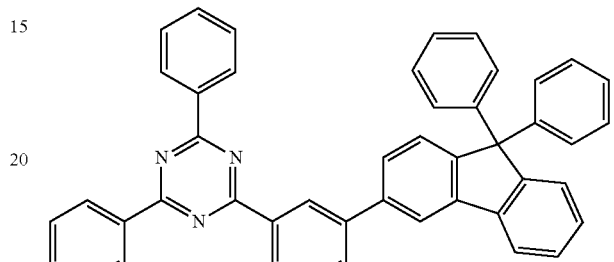
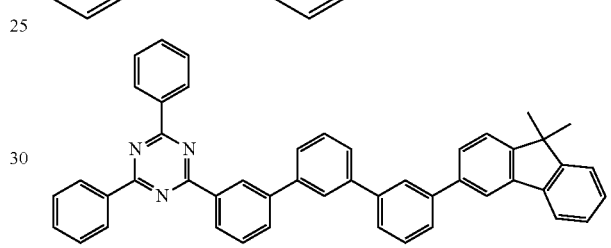
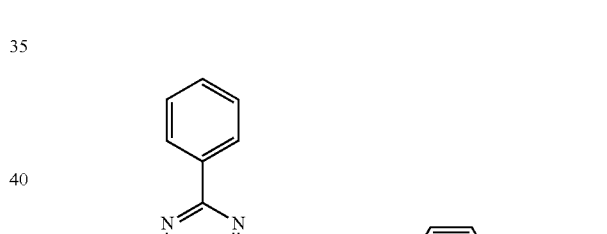
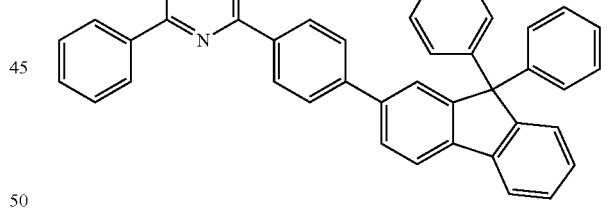
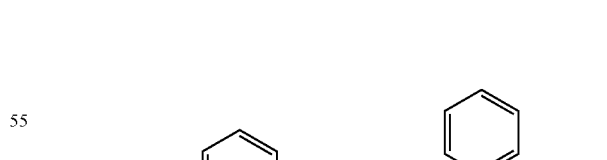
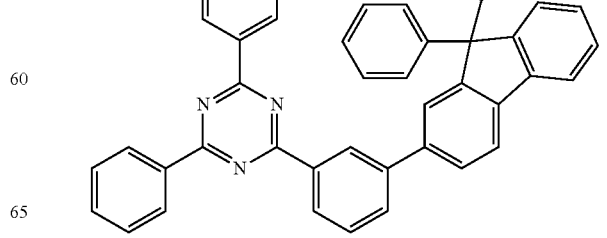

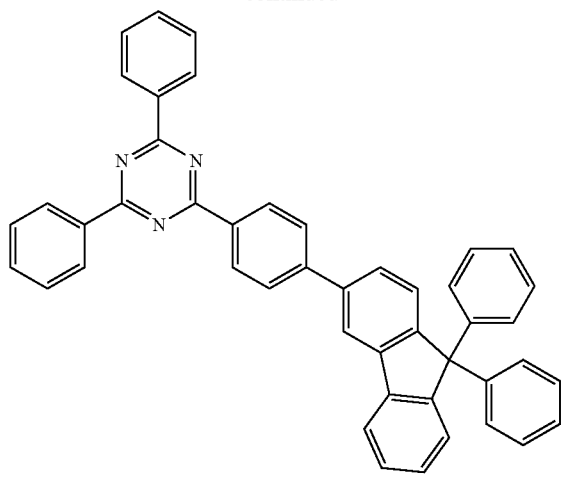
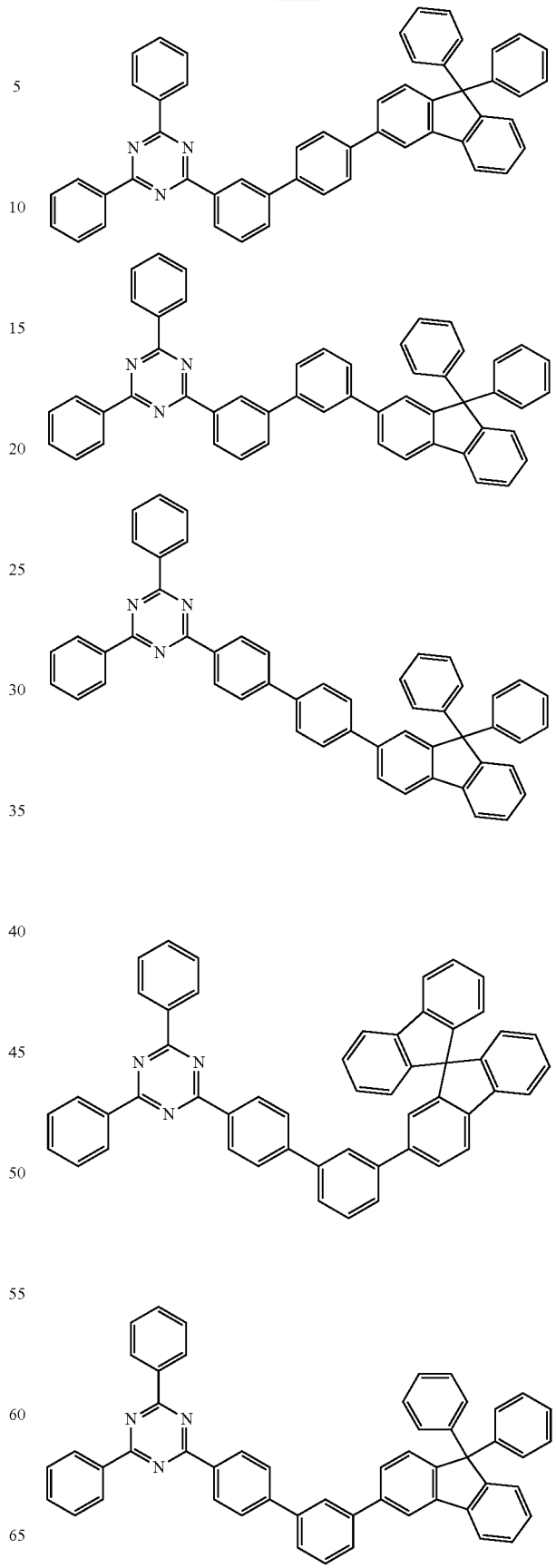

125
-continued
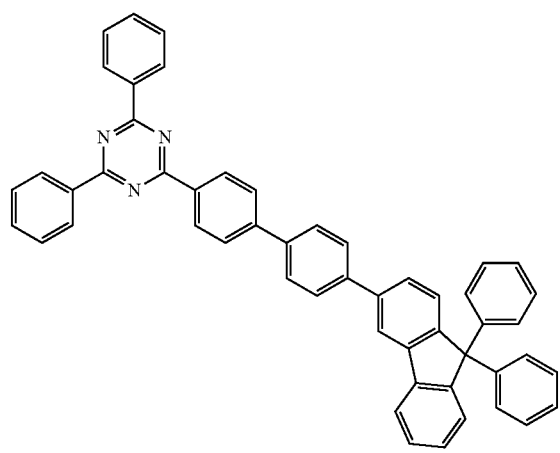
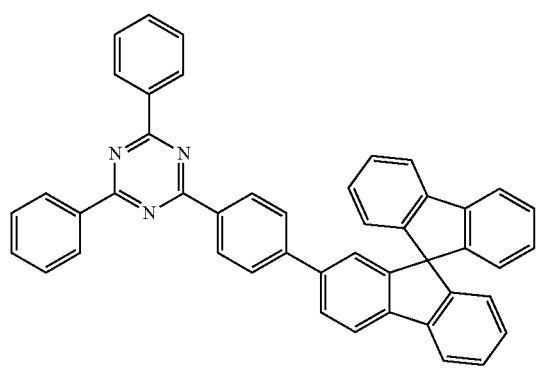
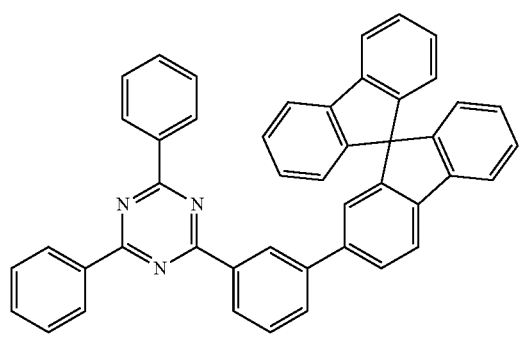
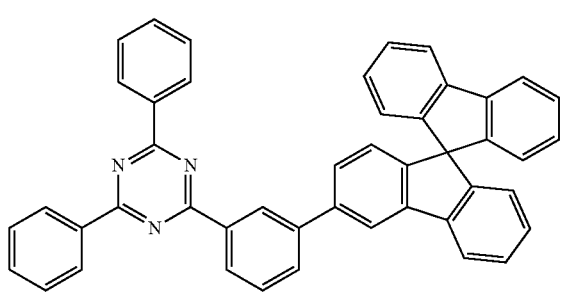
126
-continued
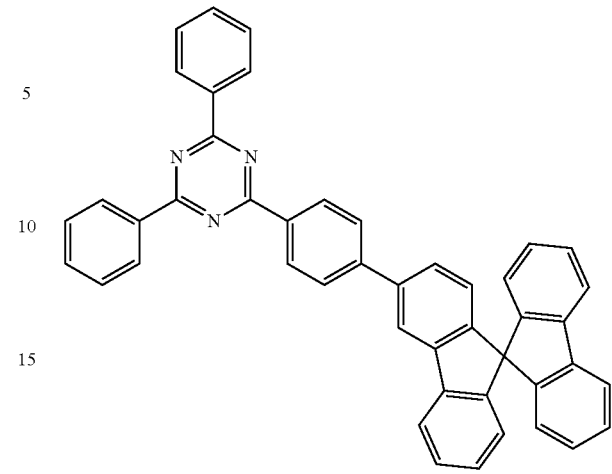
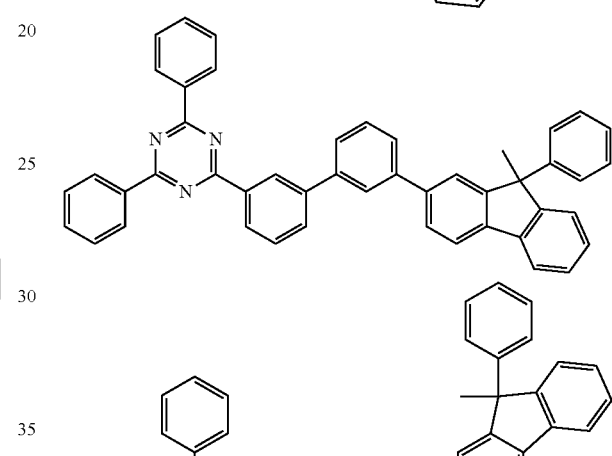
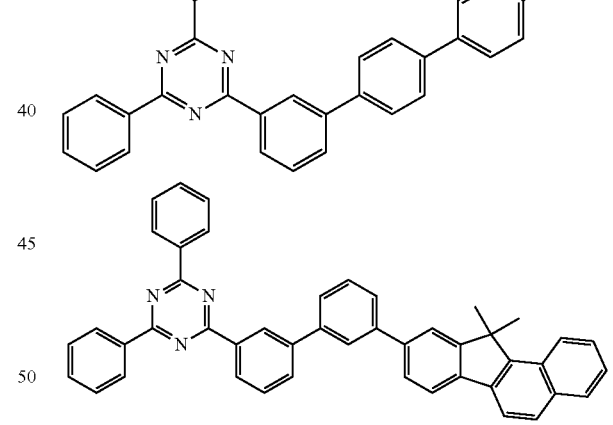
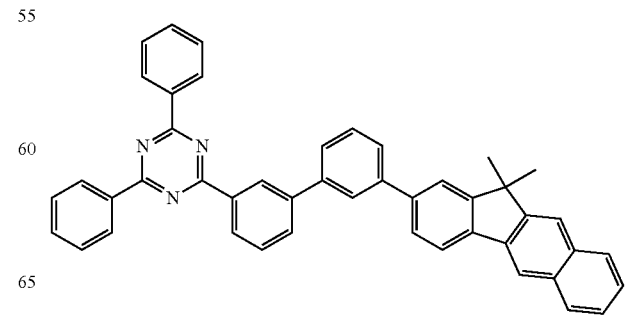

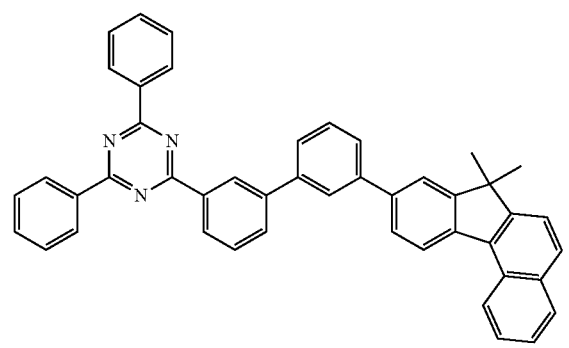
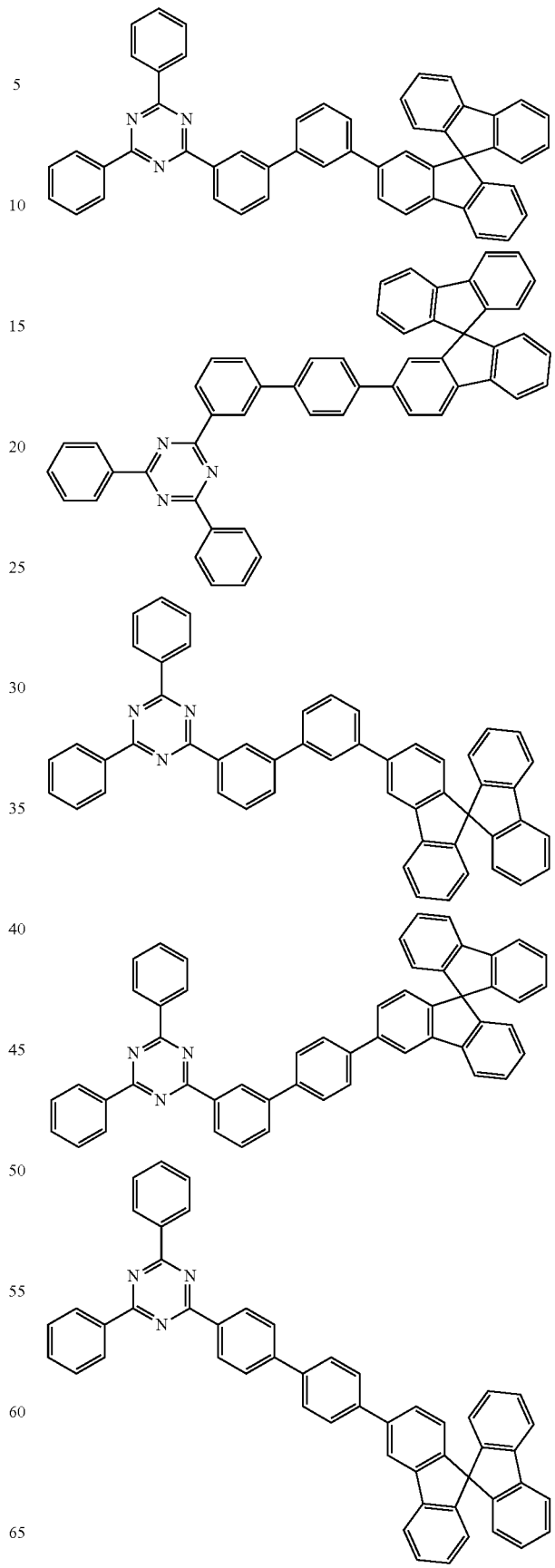

129
-continued
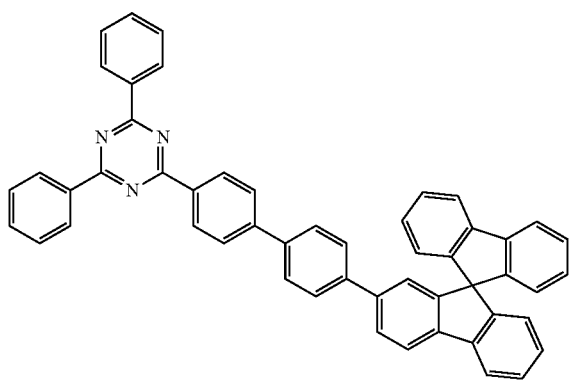
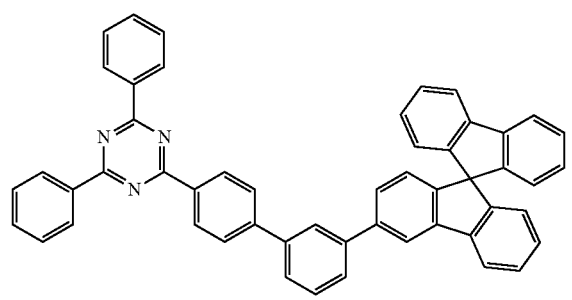
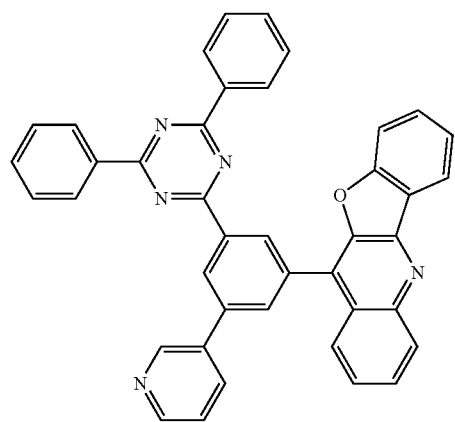
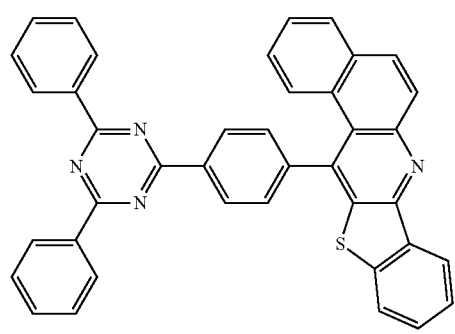
130
-continued
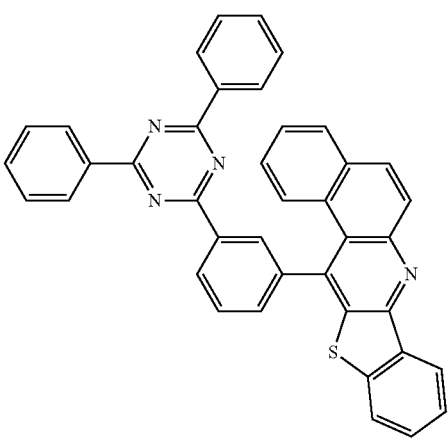
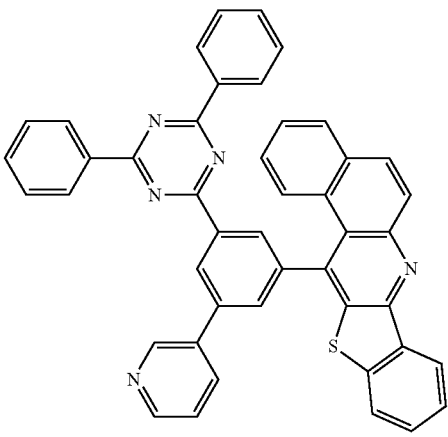
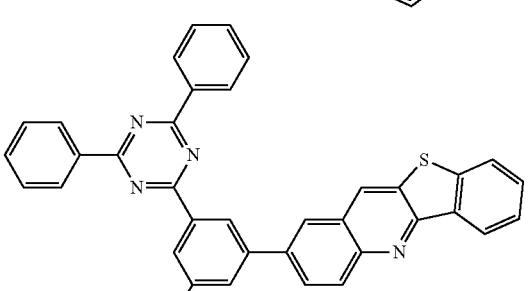
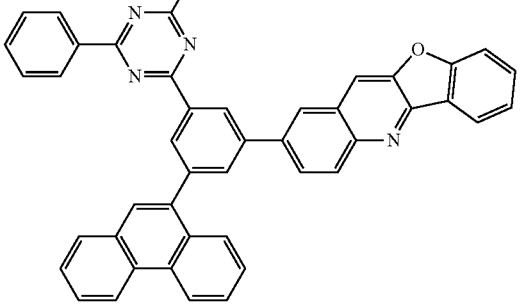

131
-continued
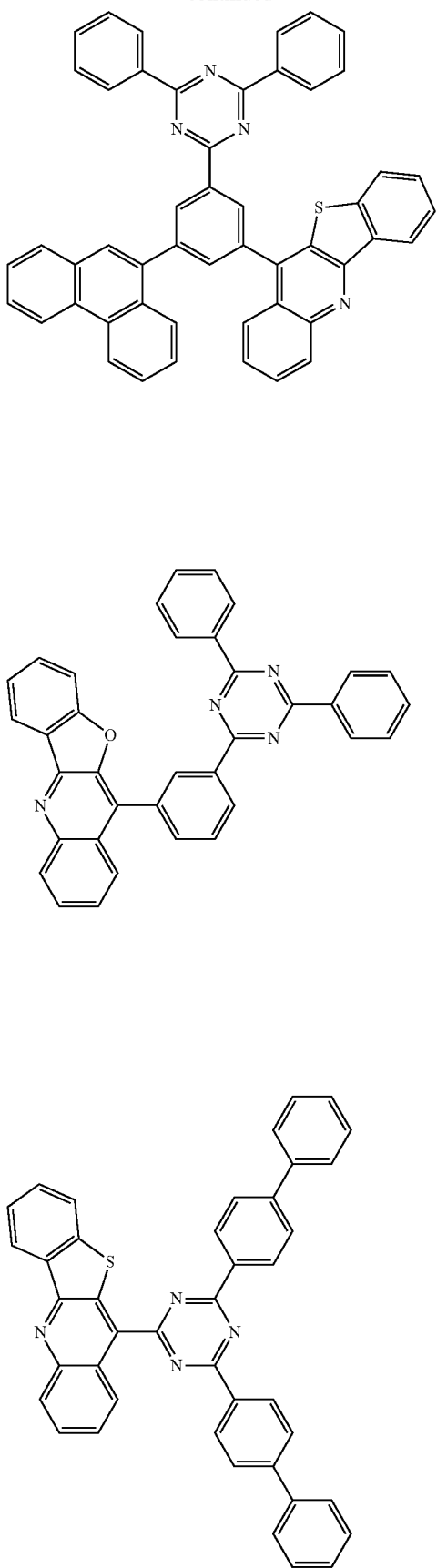
132
-continued
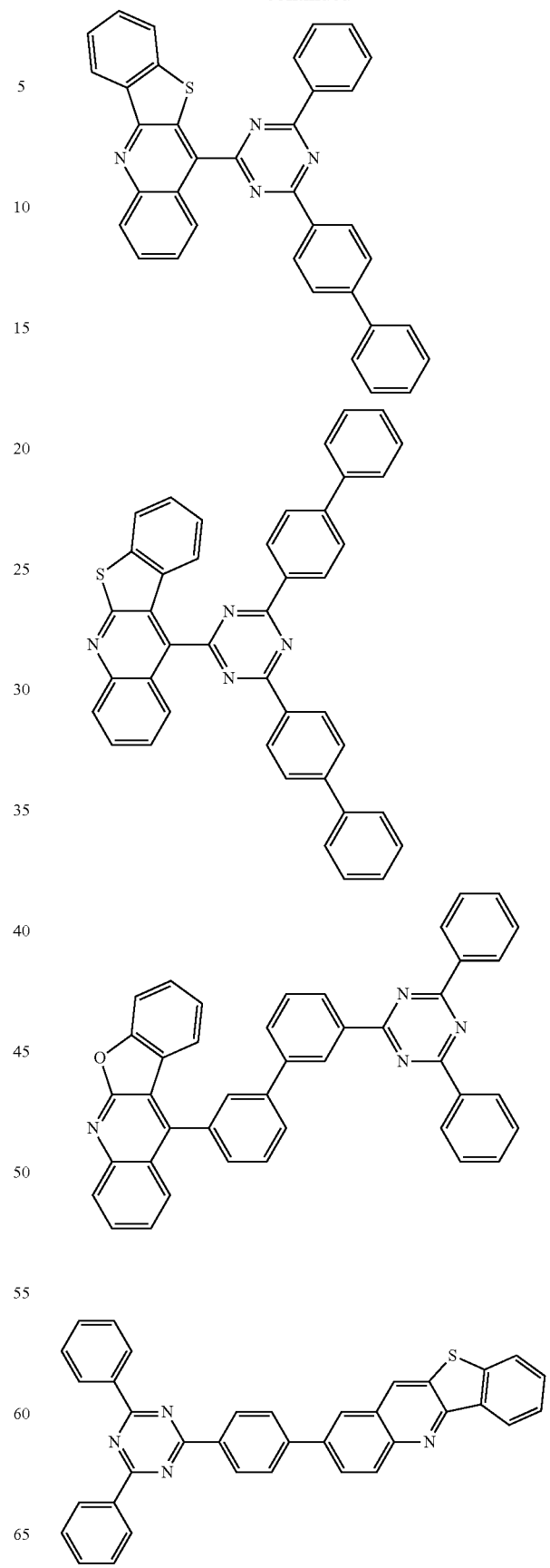

133
-continued
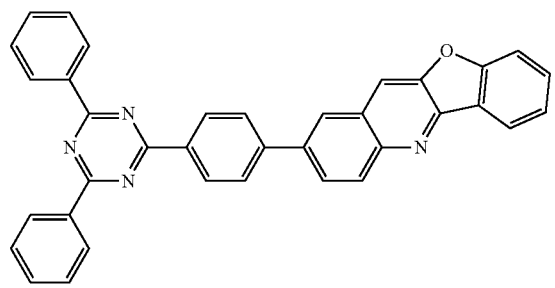
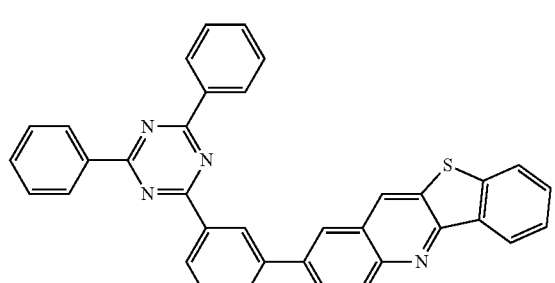
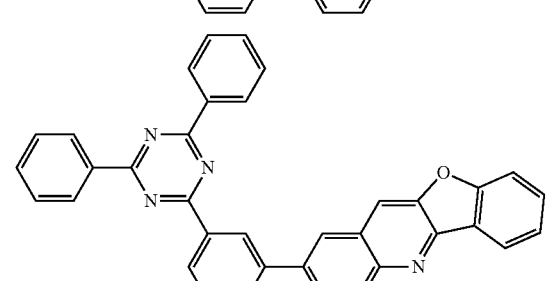
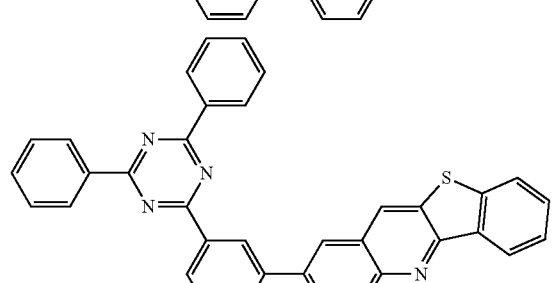
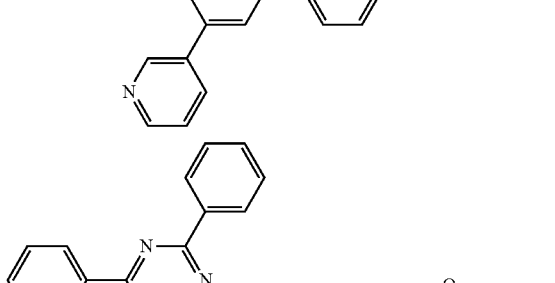
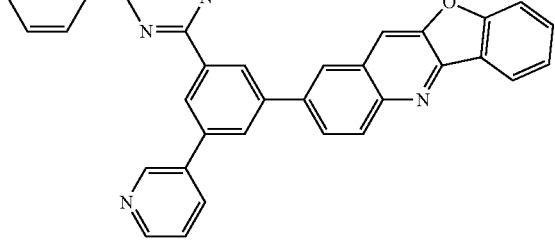
134
-continued
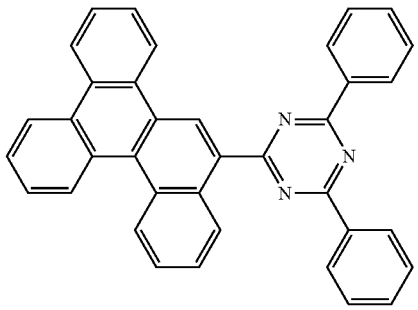
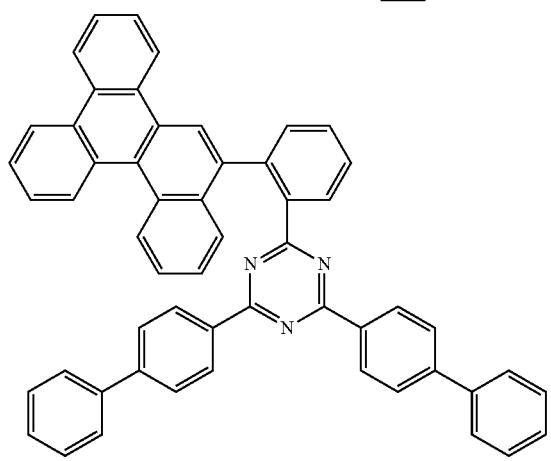
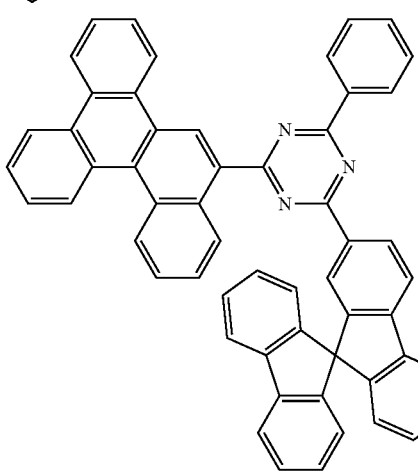
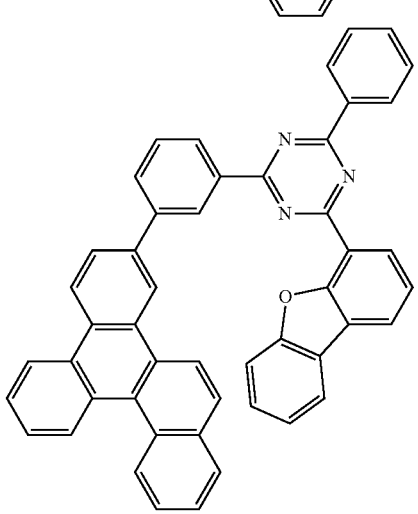

135
-continued
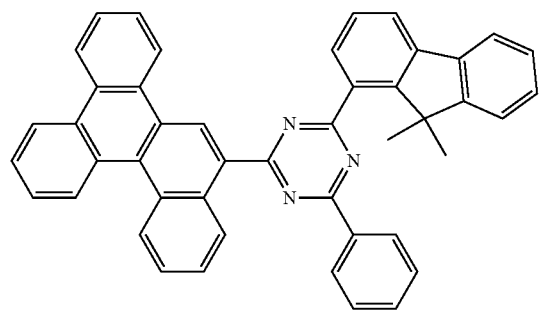
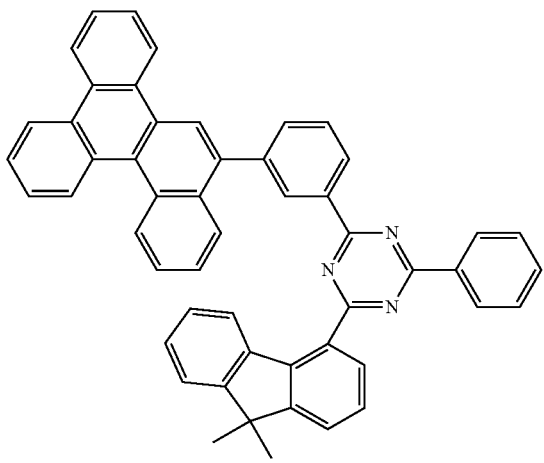
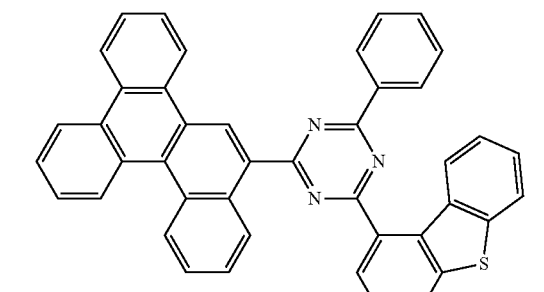
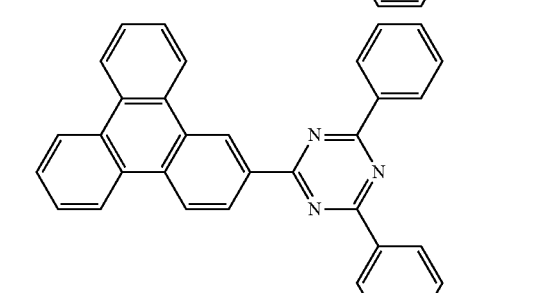
136
-continued
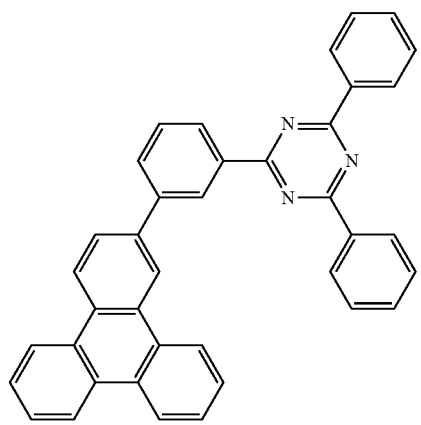
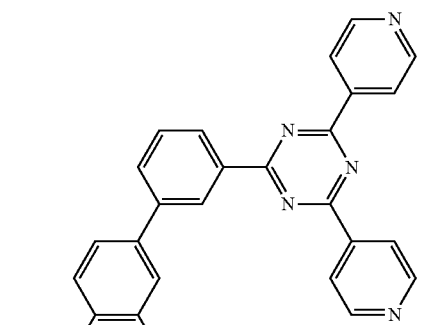
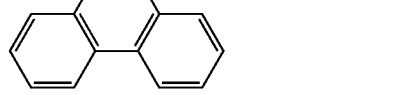
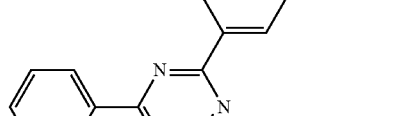
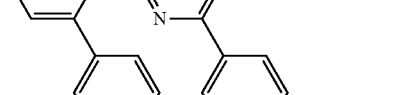
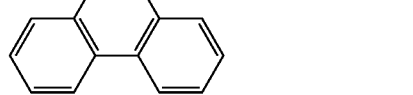
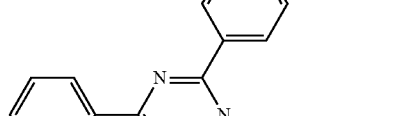
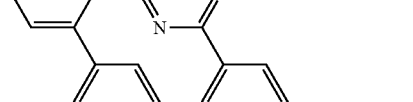
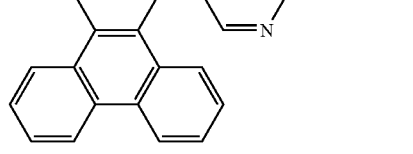

137
-continued
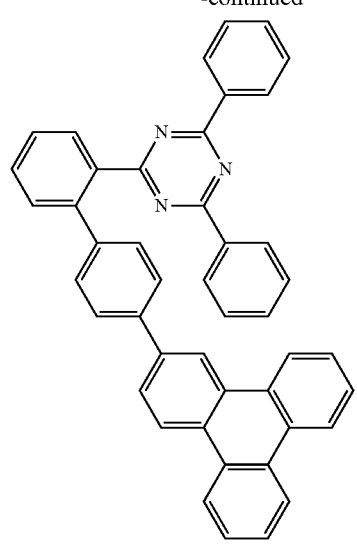
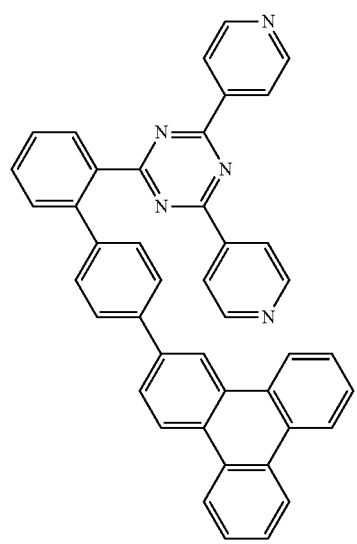
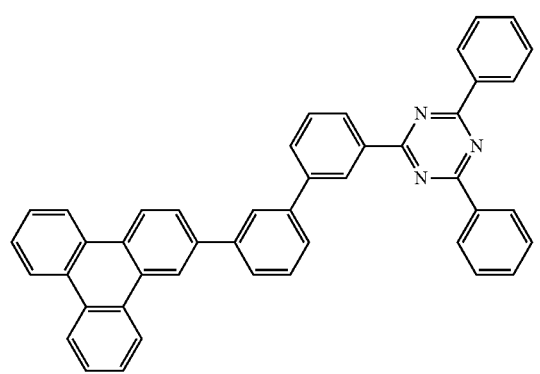
138
-continued
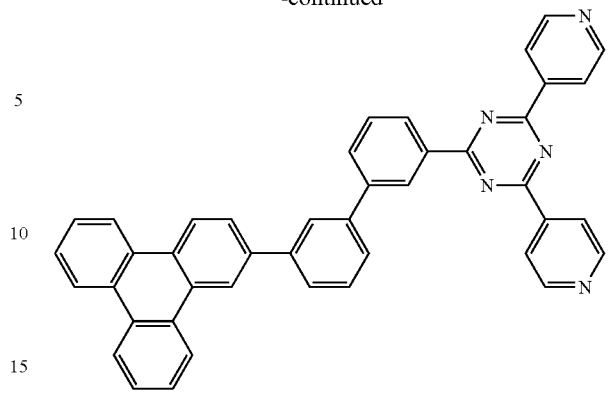
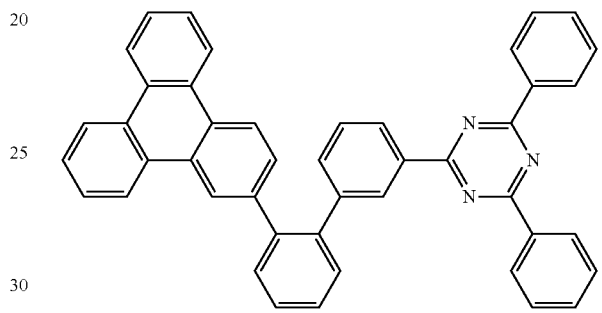
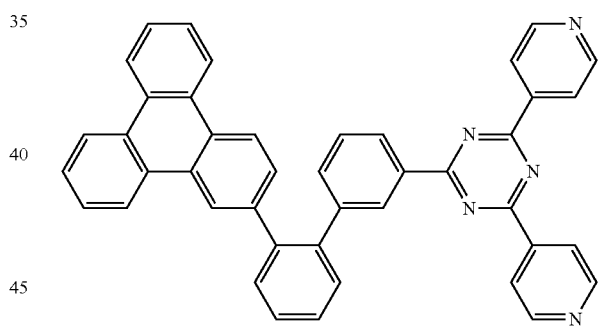
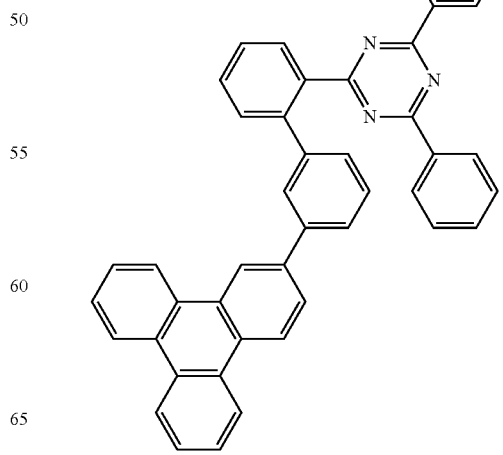

-continued
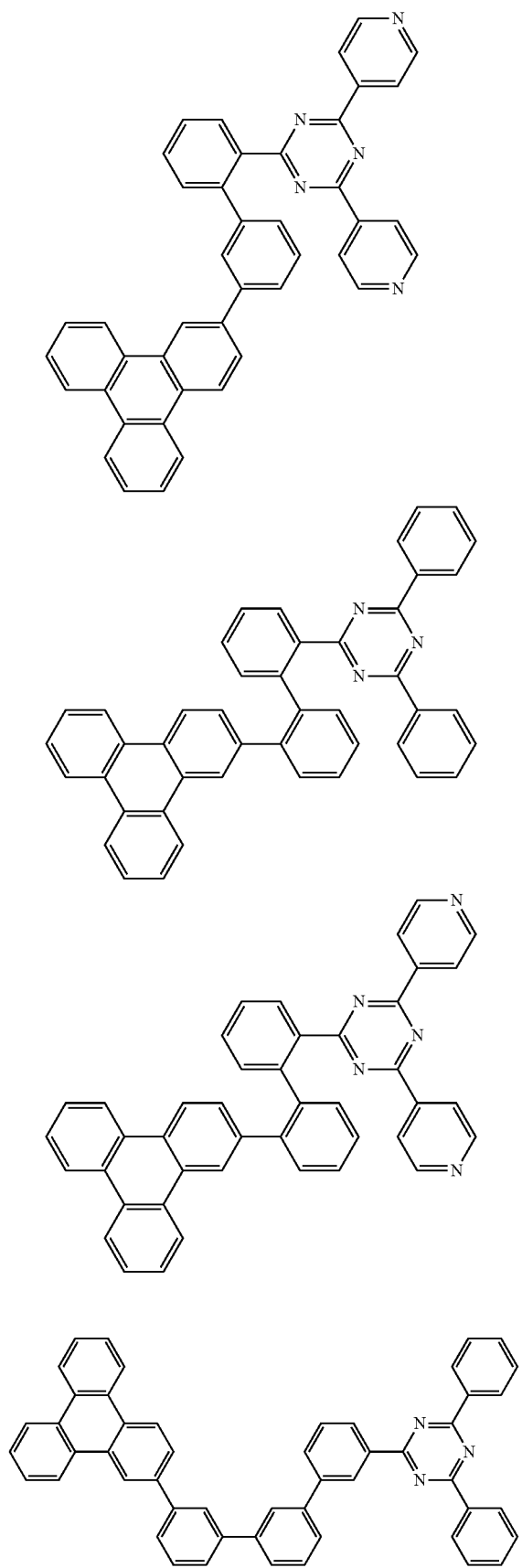
-continued
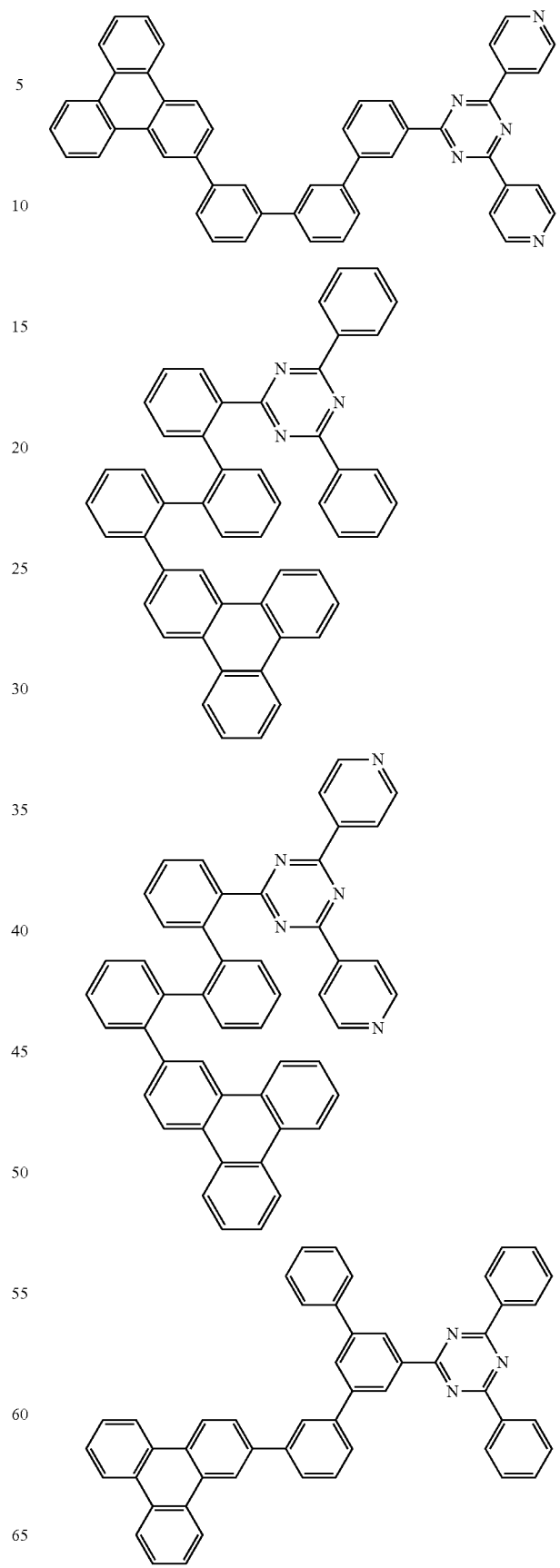

141
-continued
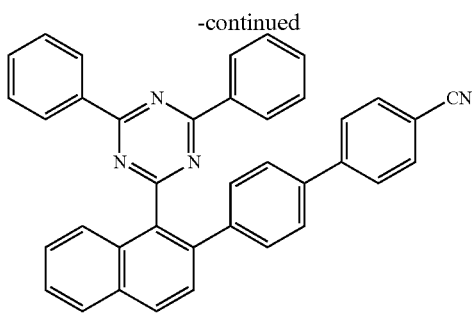
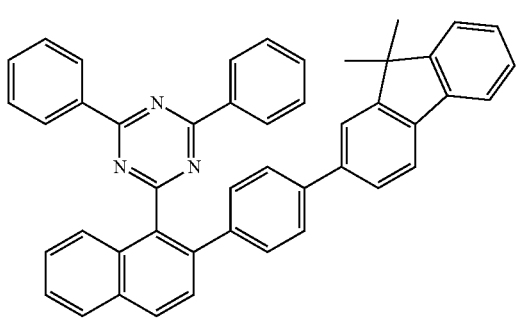
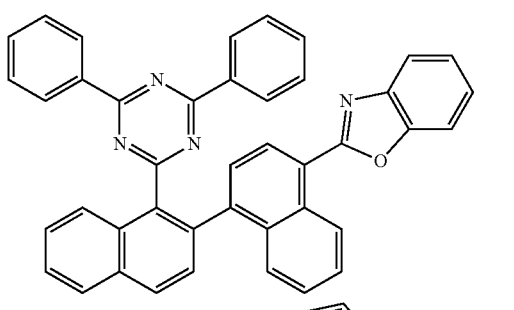
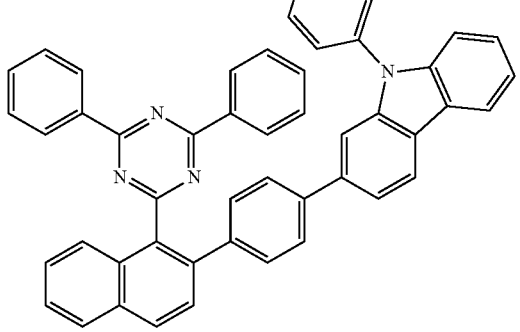
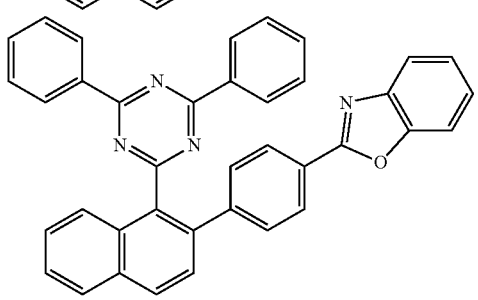
142
-continued
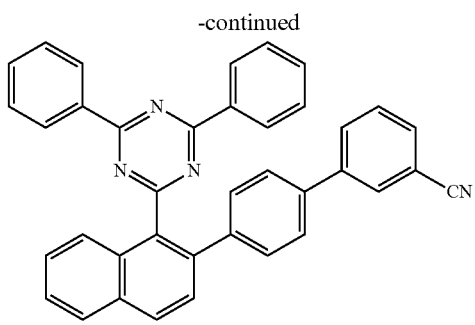
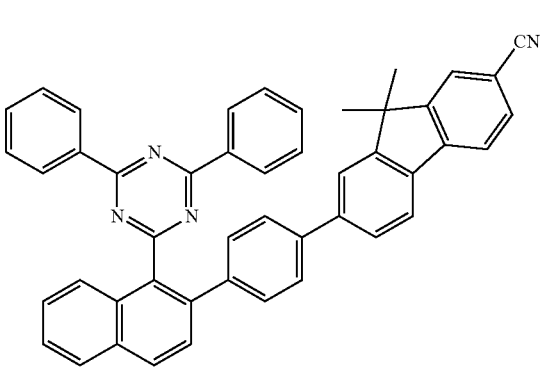
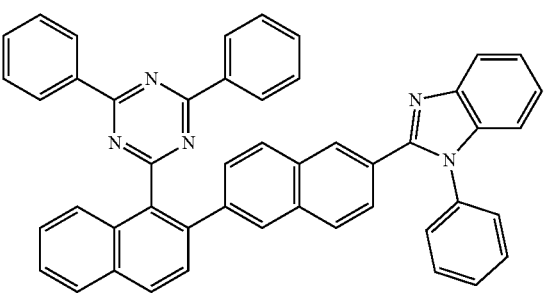
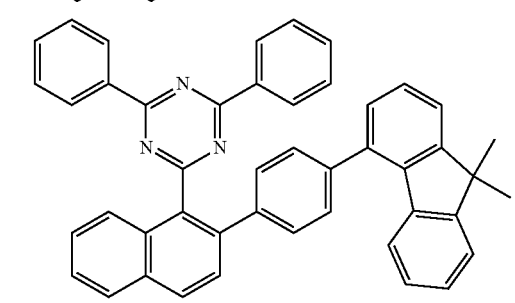
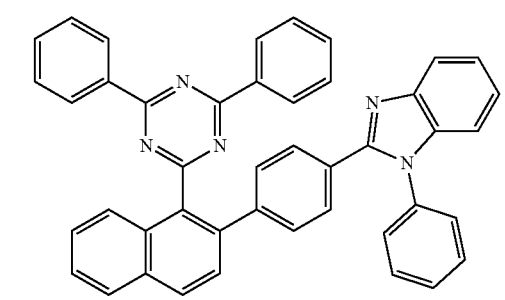

143
-continued
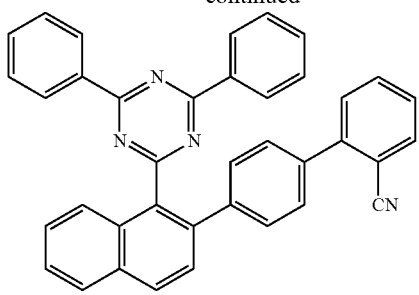
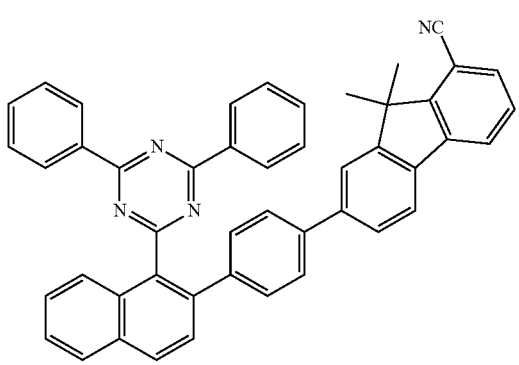
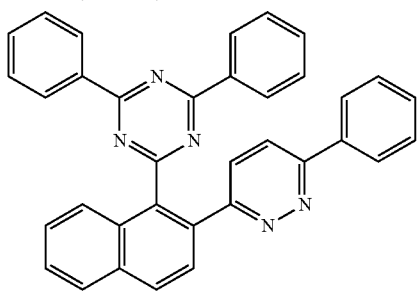
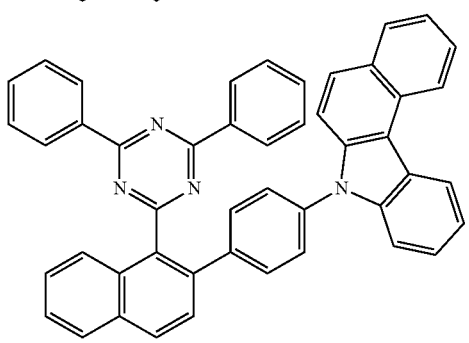
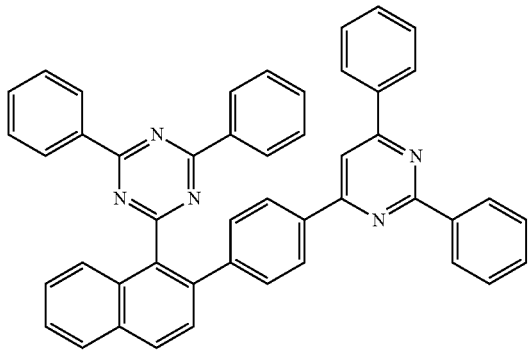
144
-continued
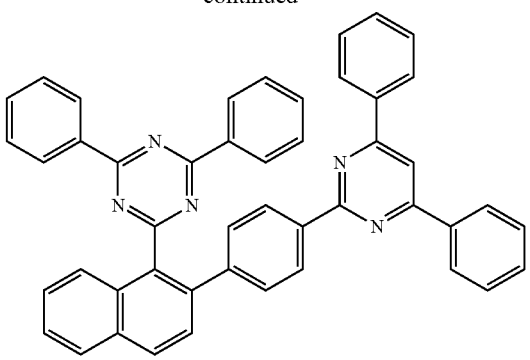
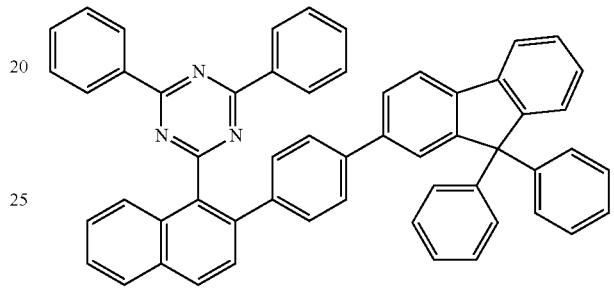
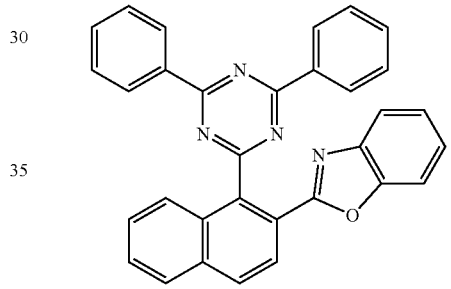
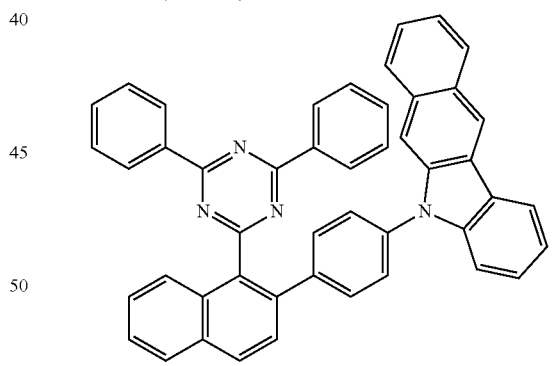
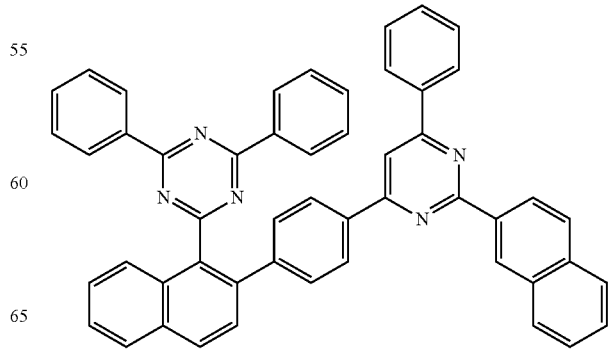

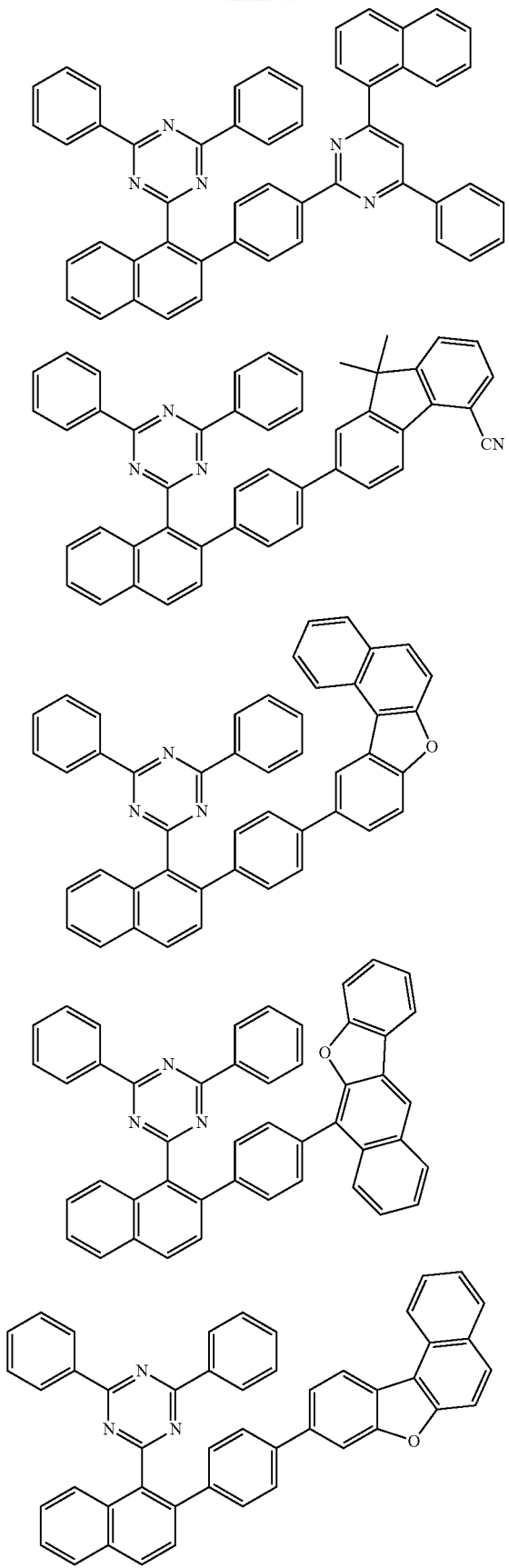
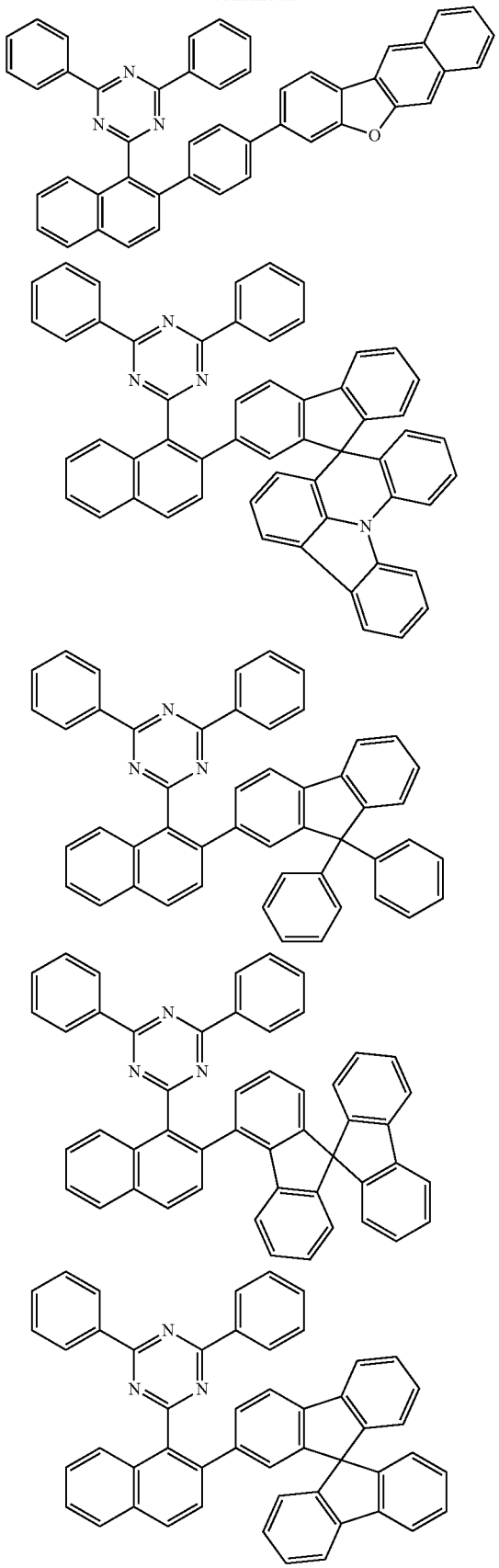

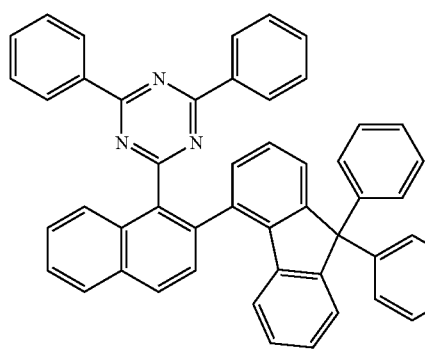
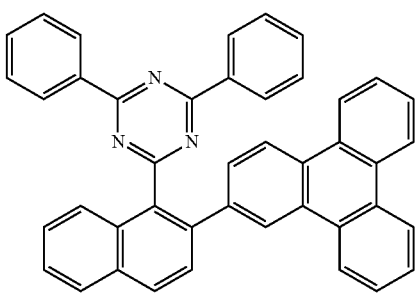
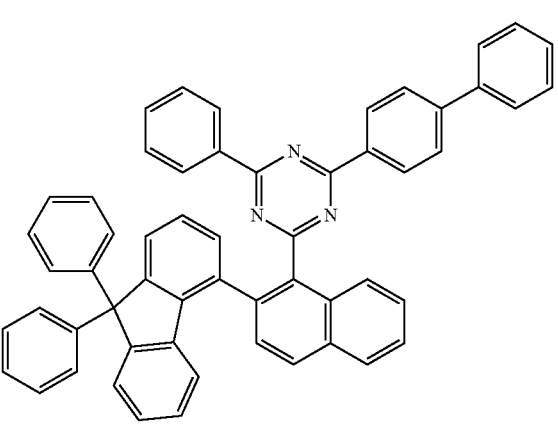
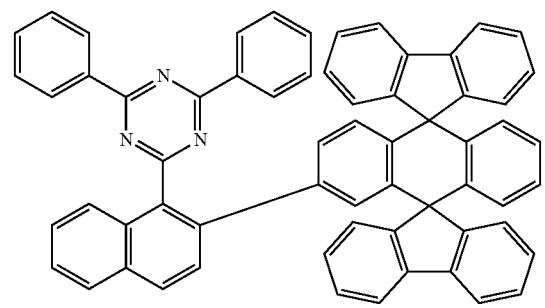
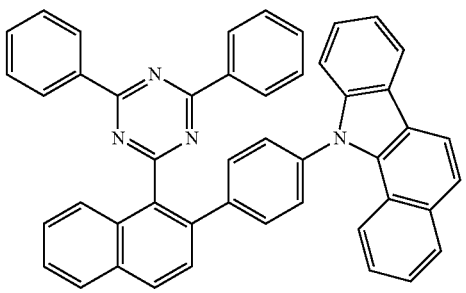
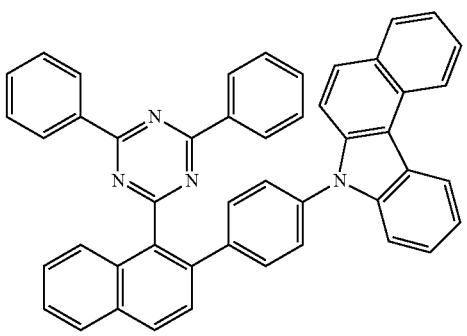

149
-continued
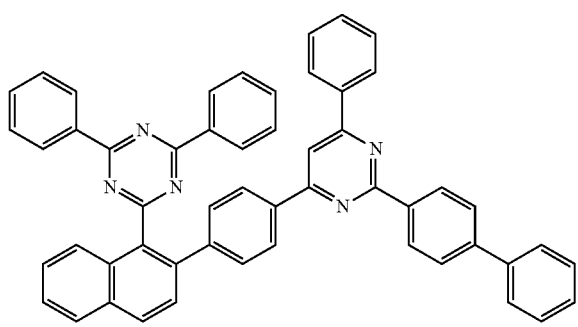
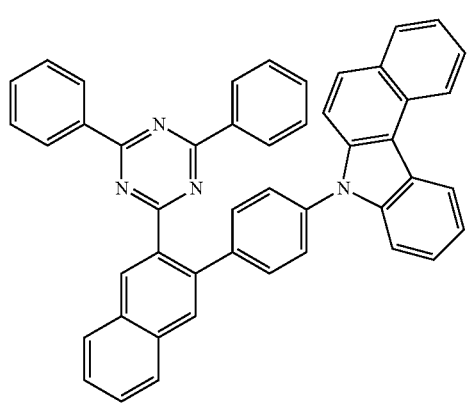
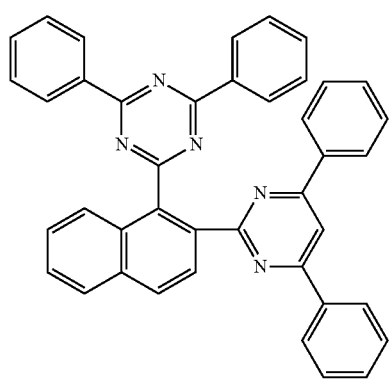
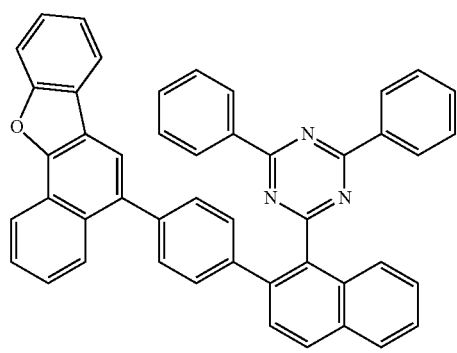
150
-continued
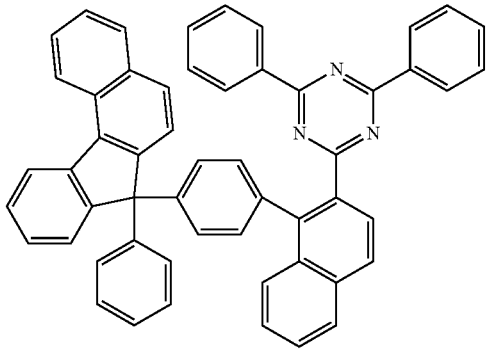
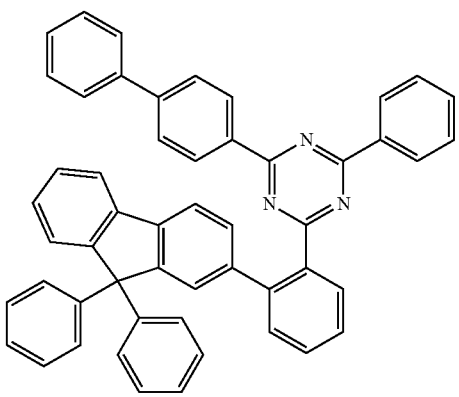
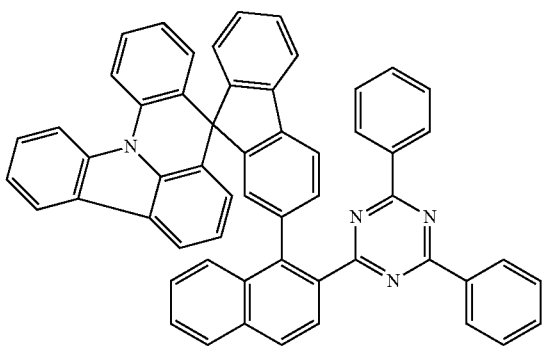
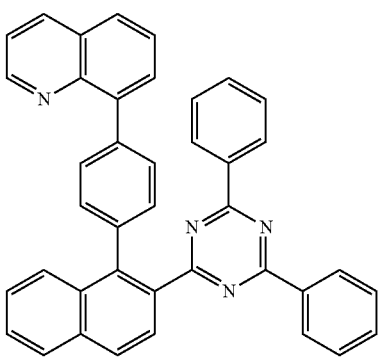

151
-continued
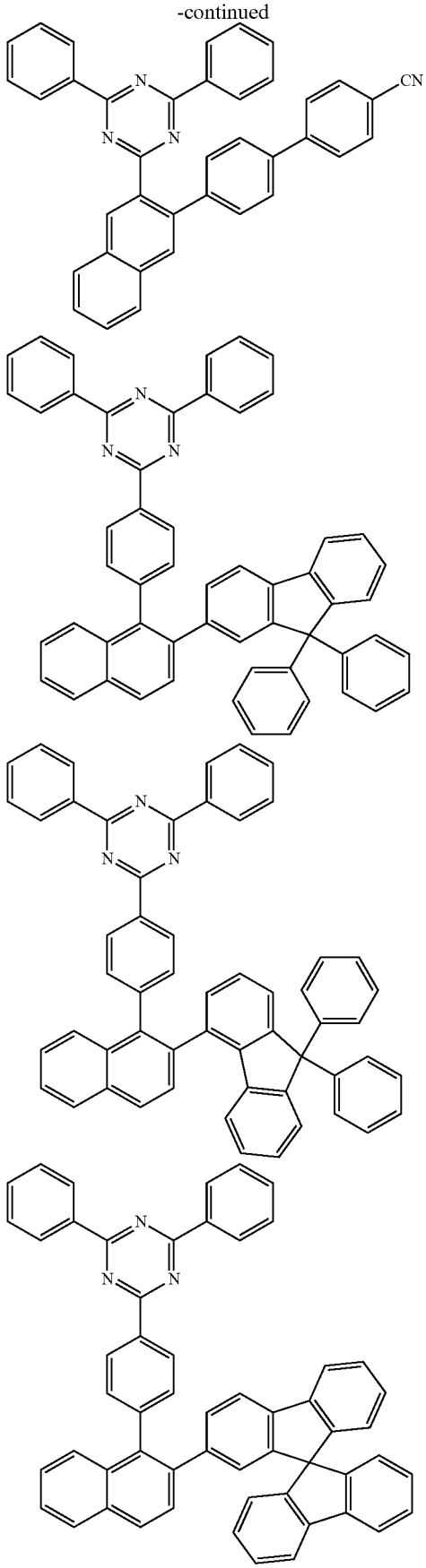
152
-continued
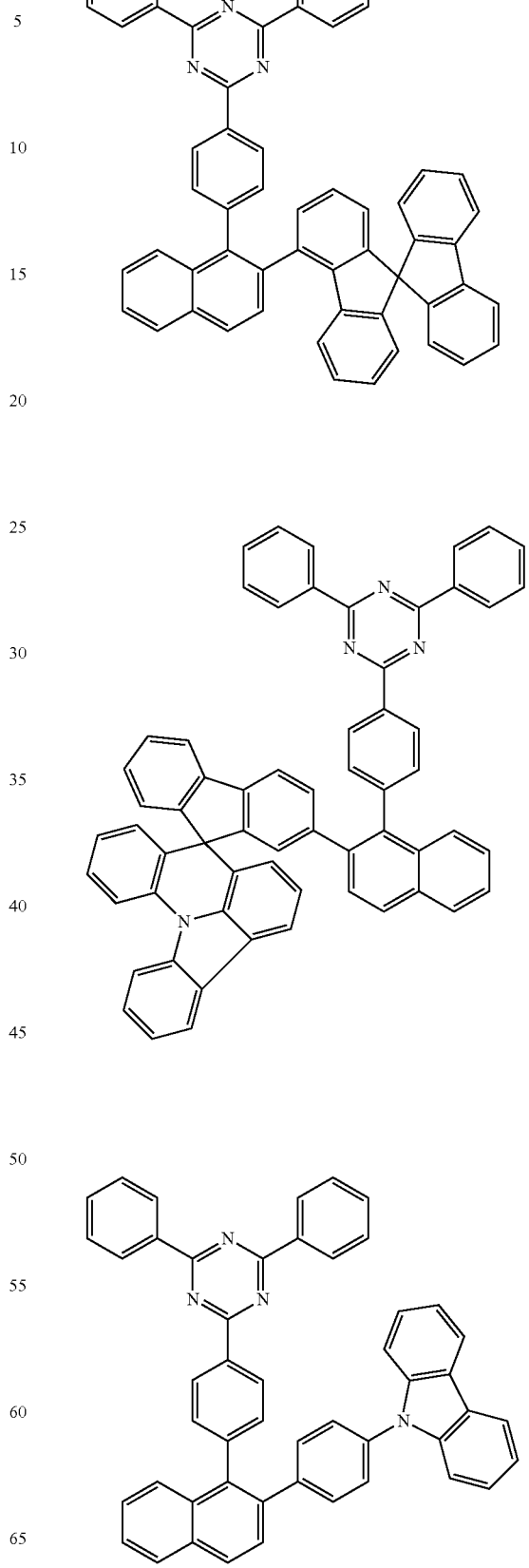

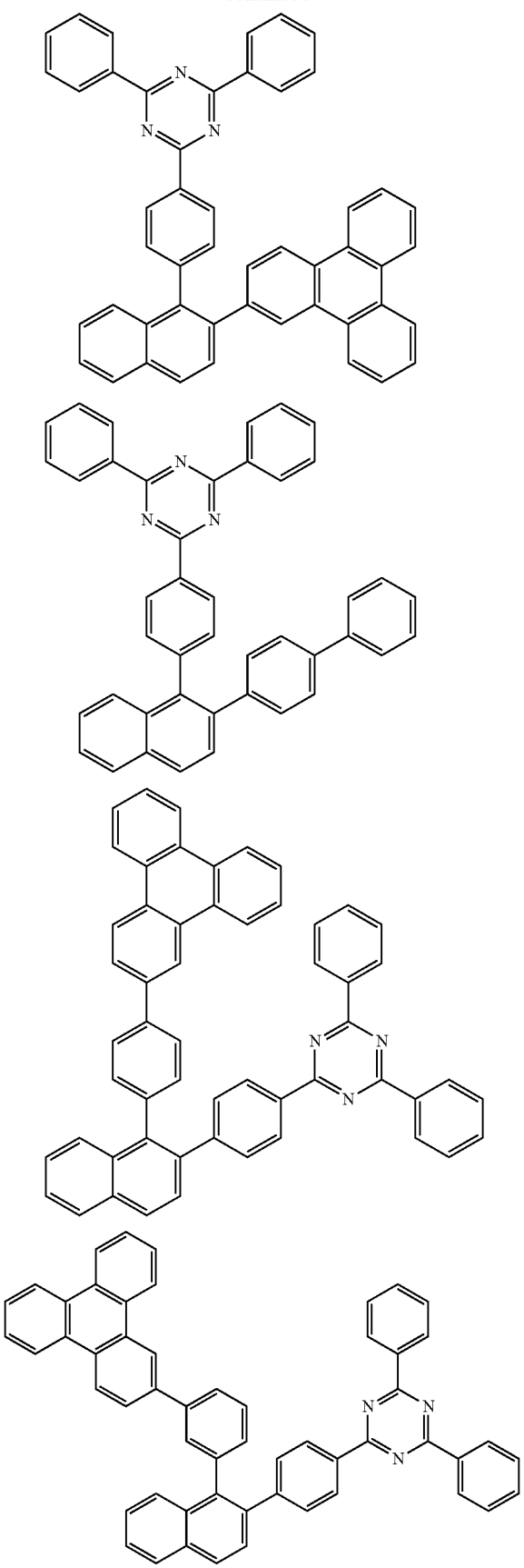
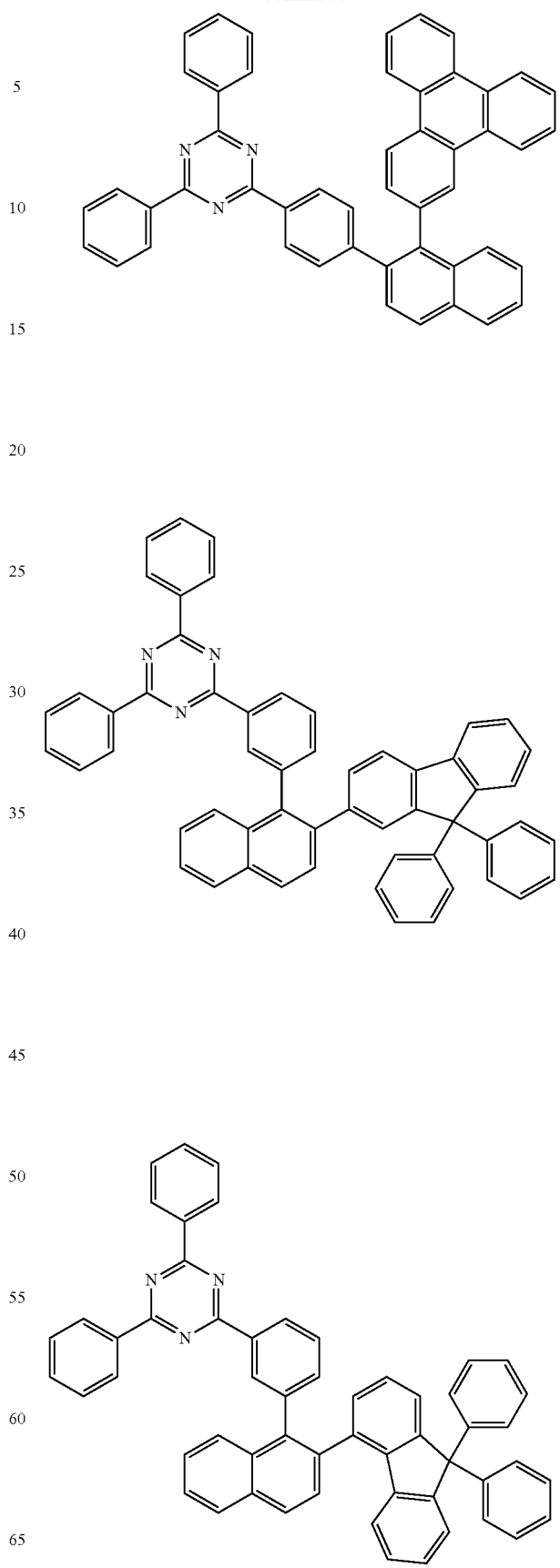

155
-continued
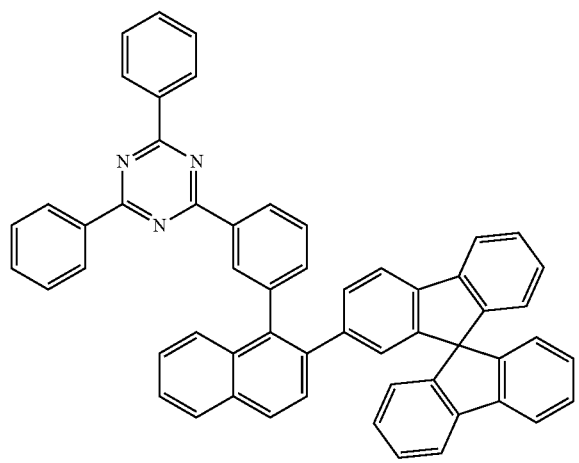
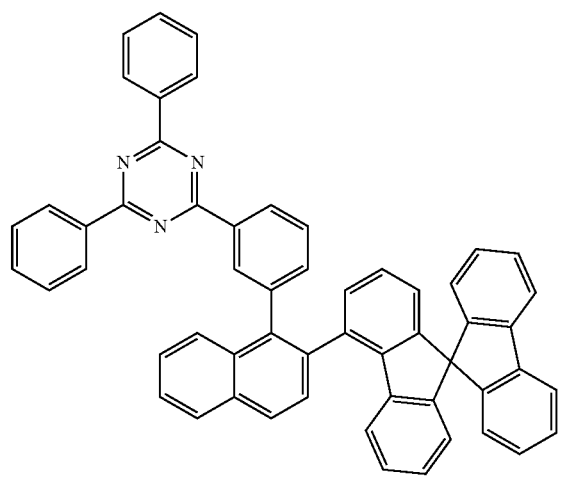
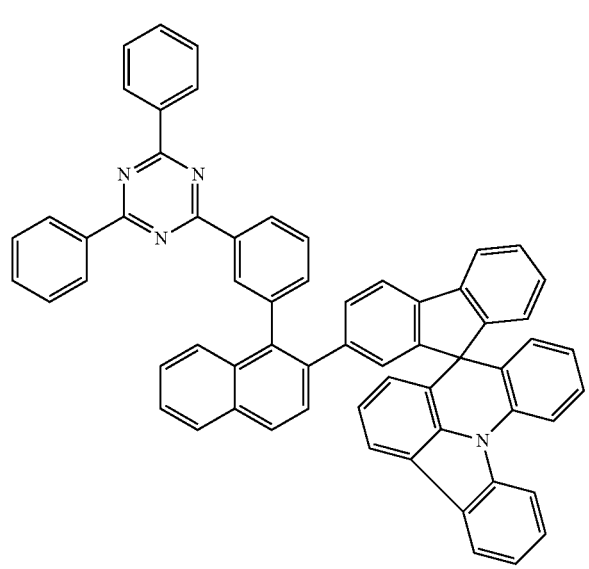
156
-continued
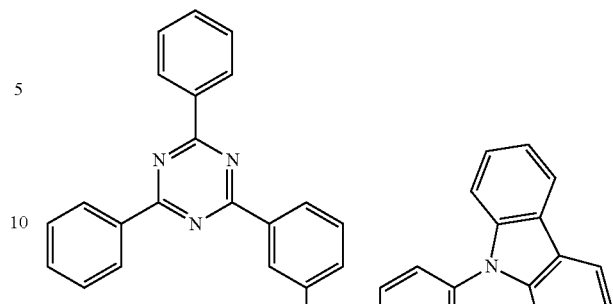
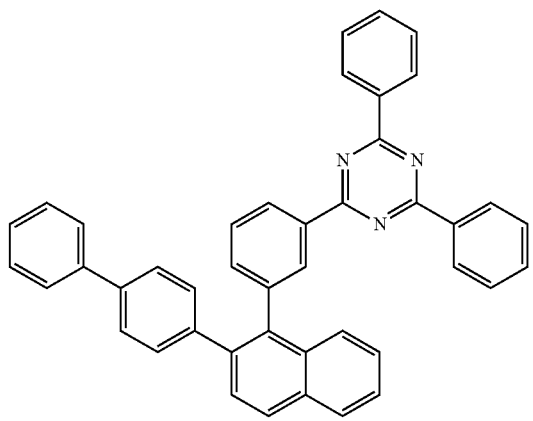
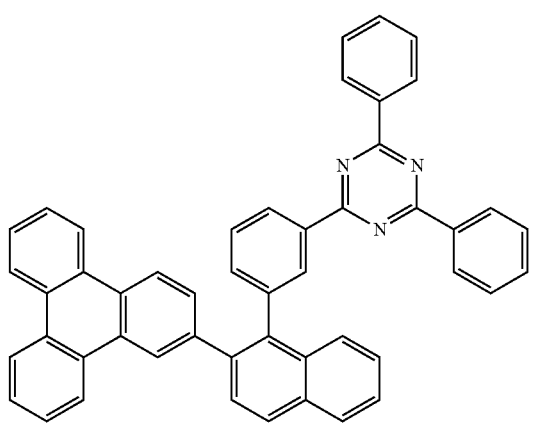

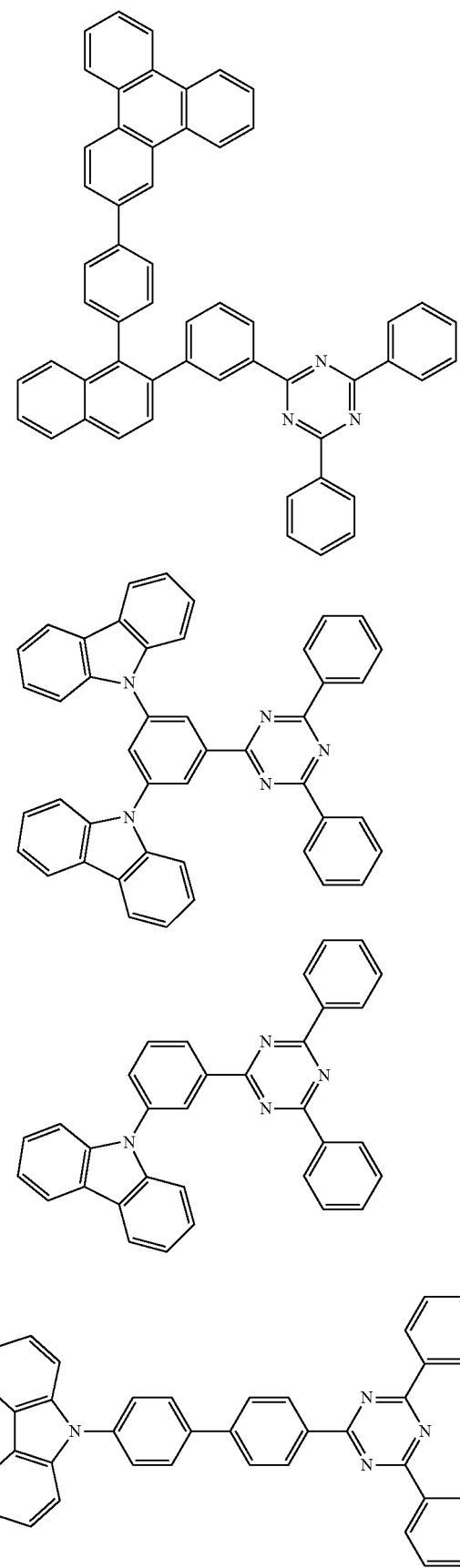
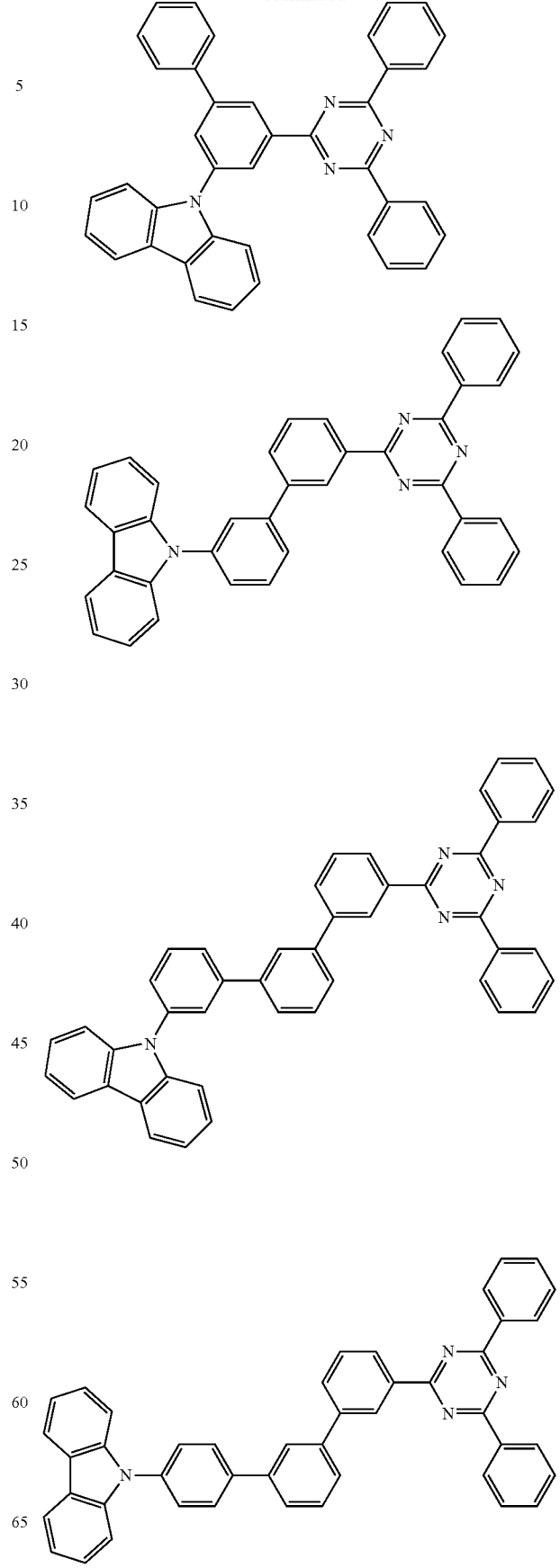

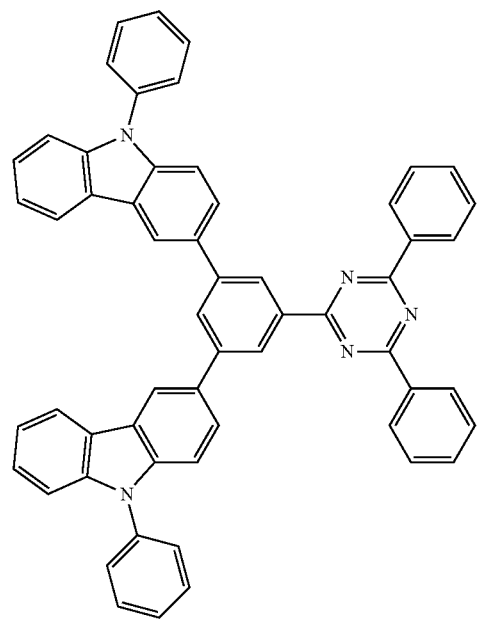
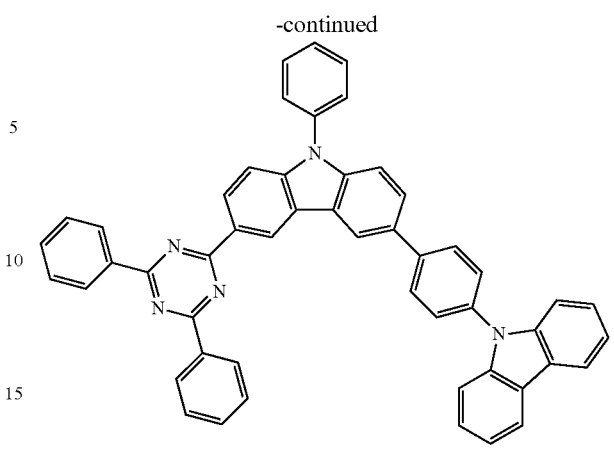
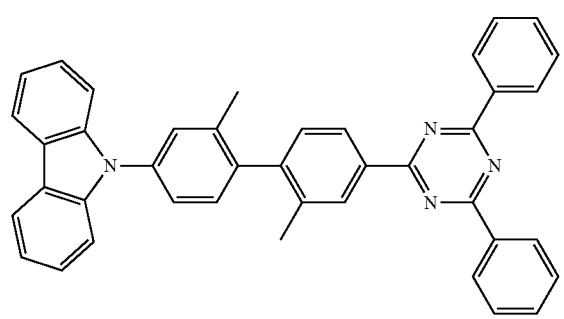
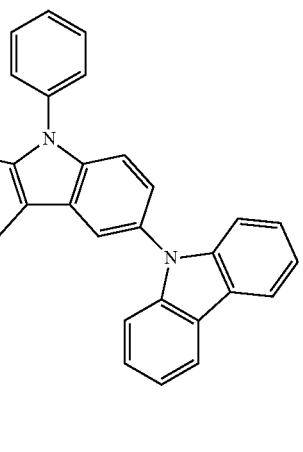
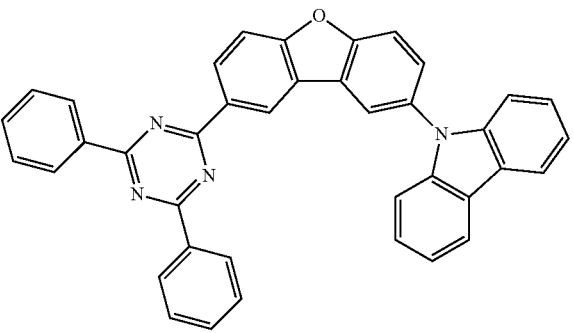
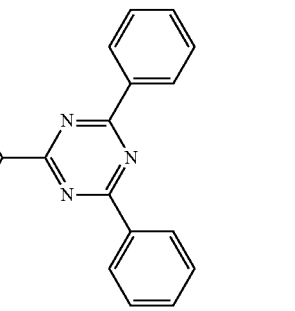
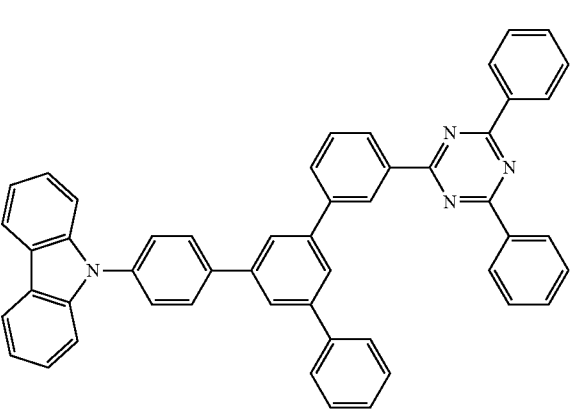
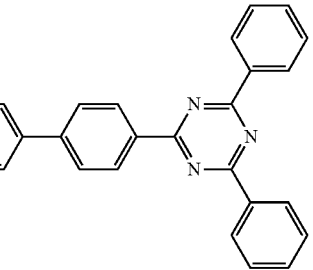

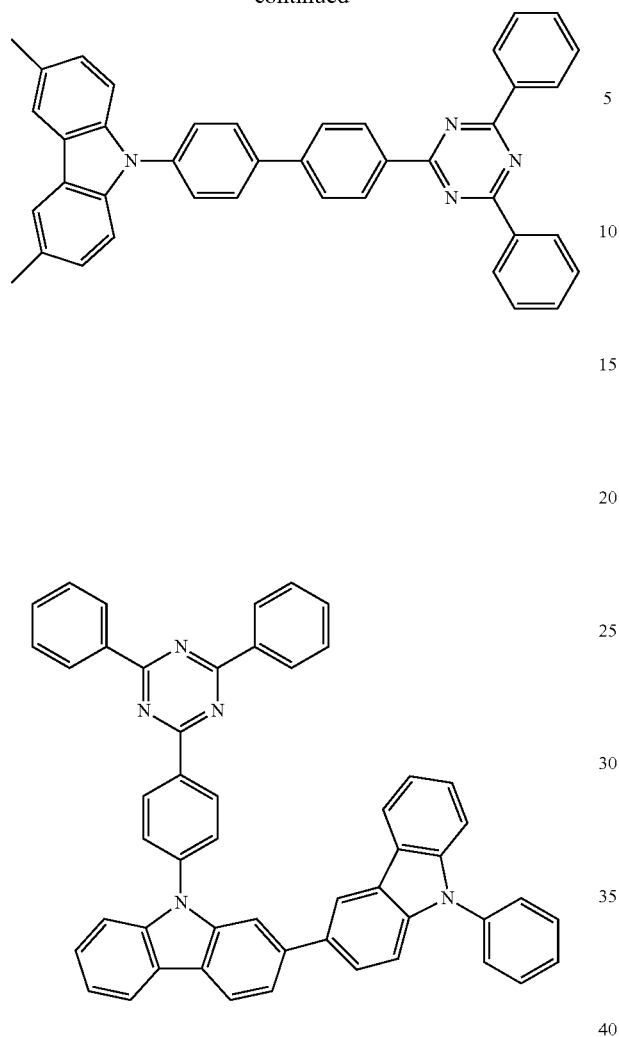
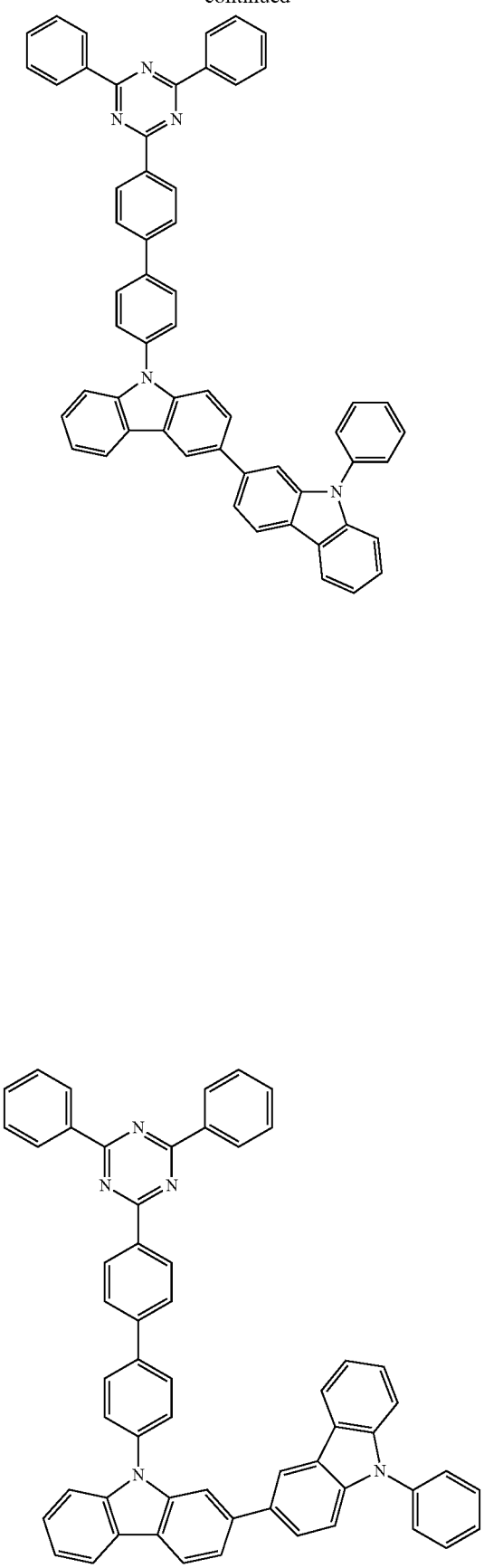

163
-continued
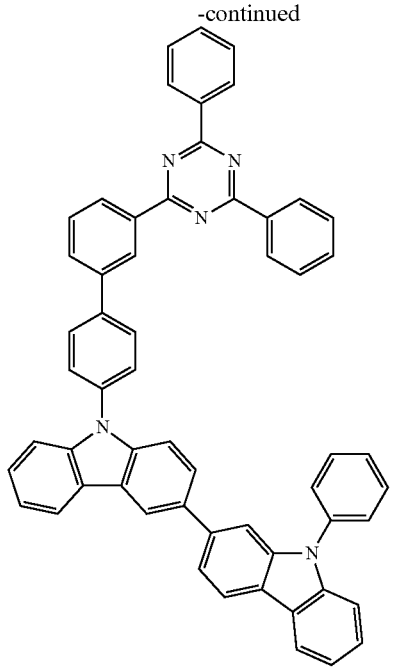
164
-continued
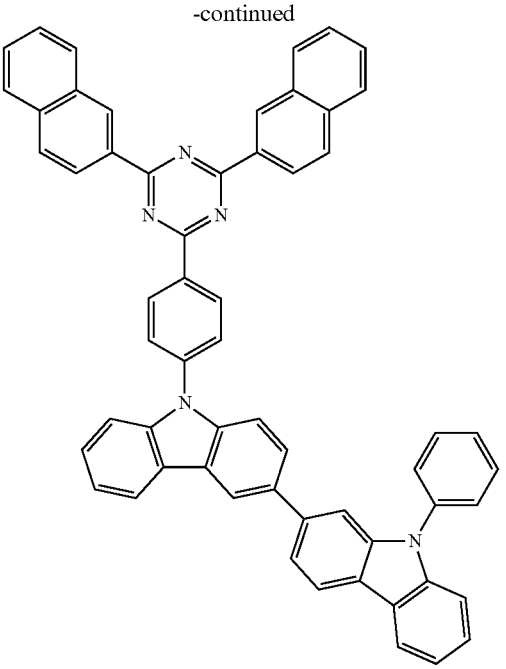
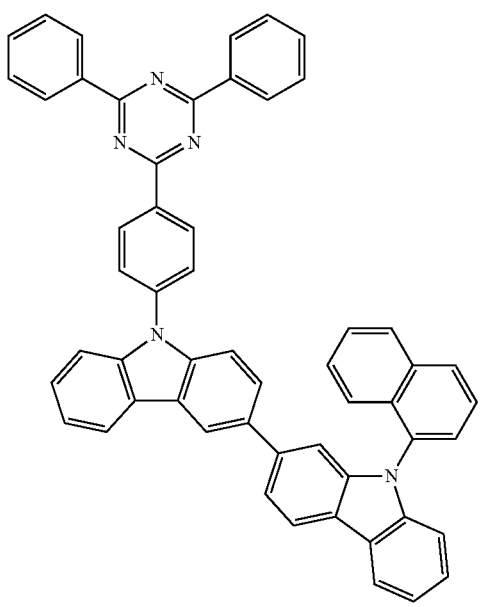

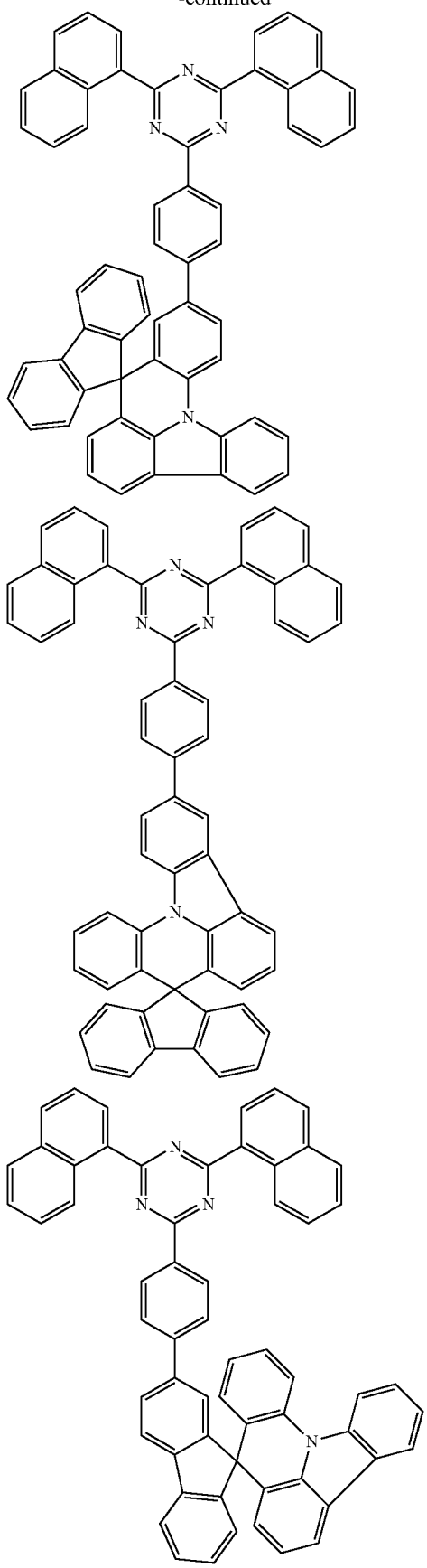
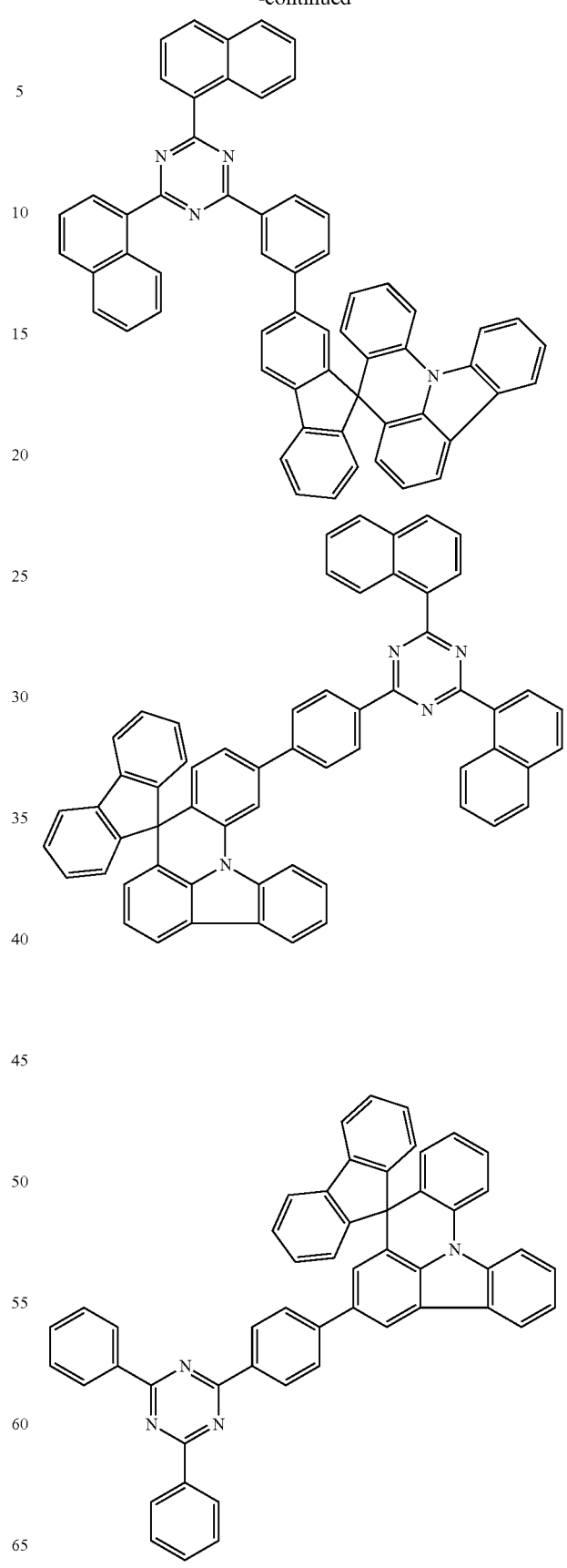

167
-continued
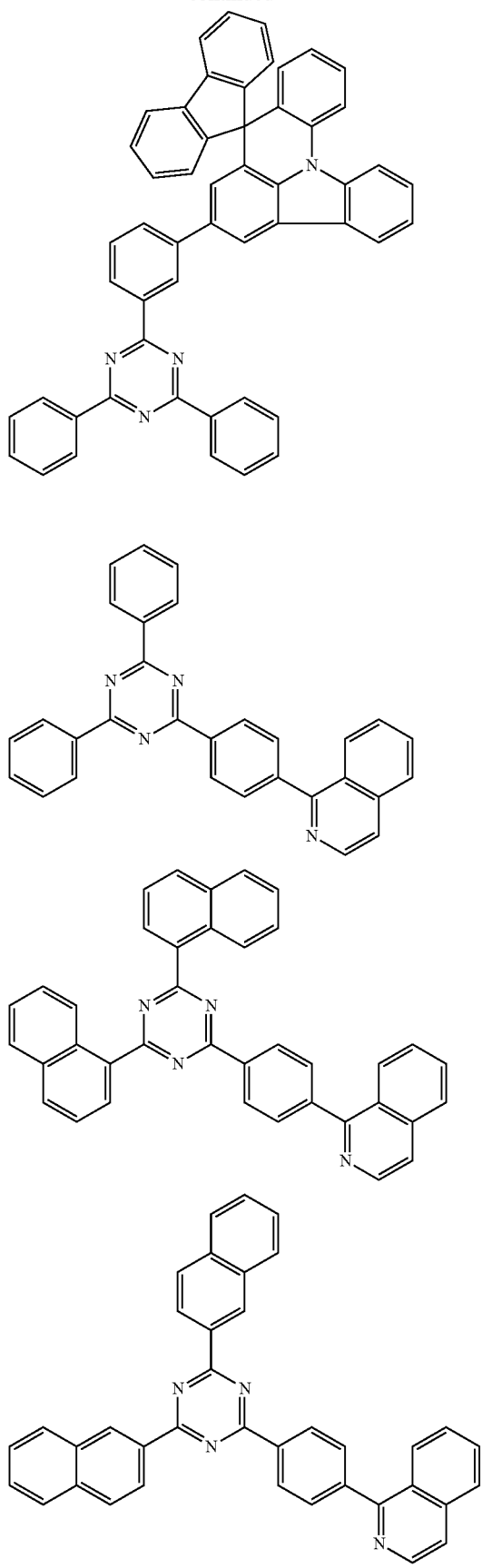
168
-continued
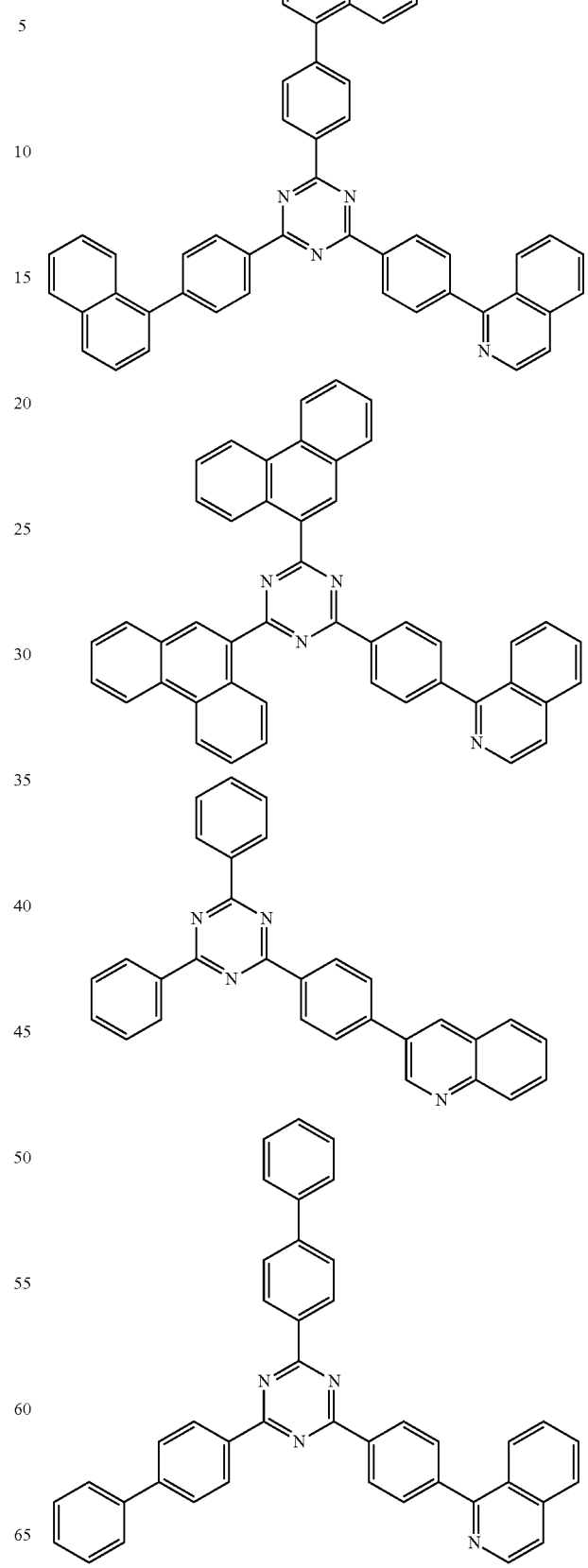

-continued
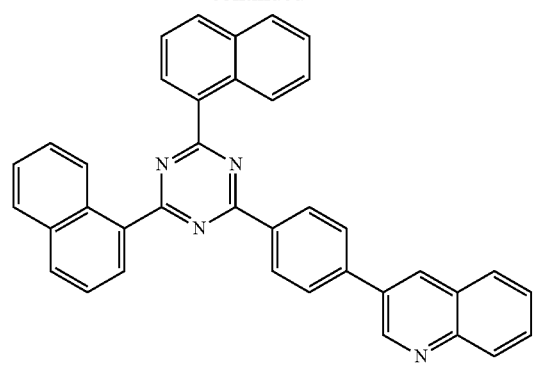
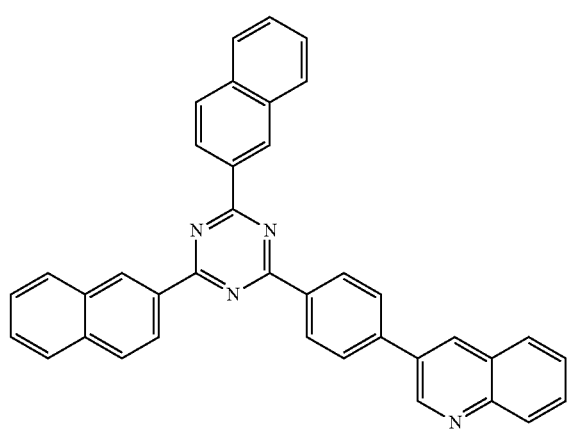
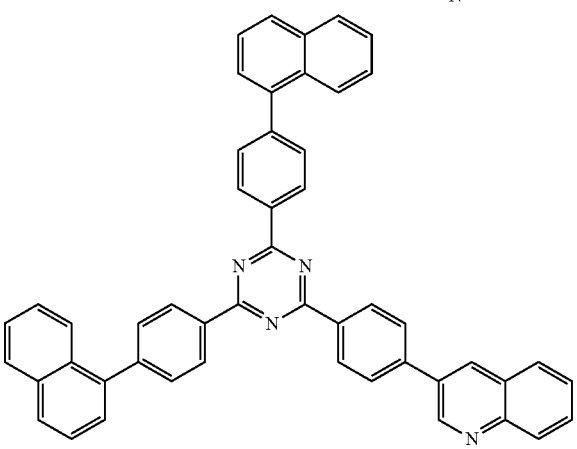
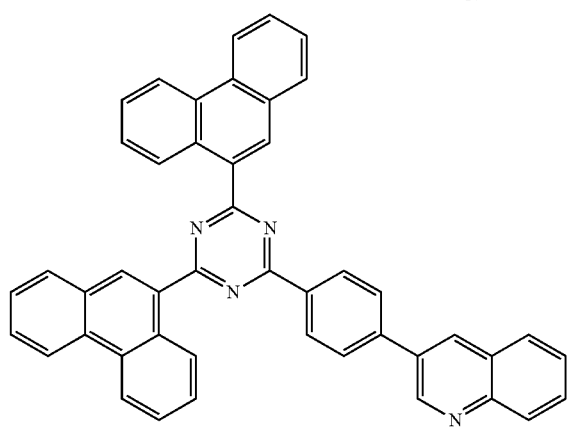
-continued
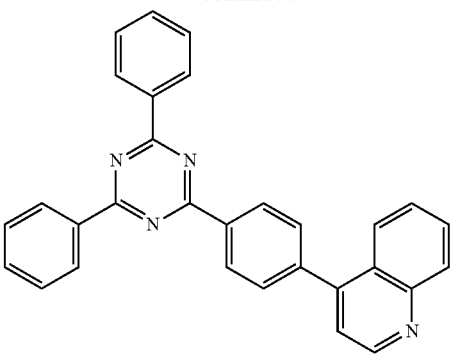
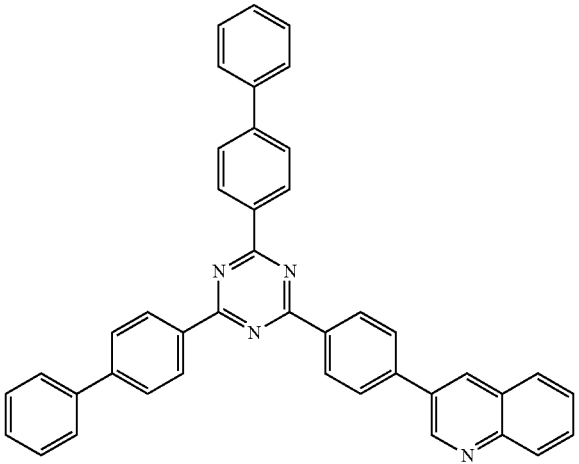
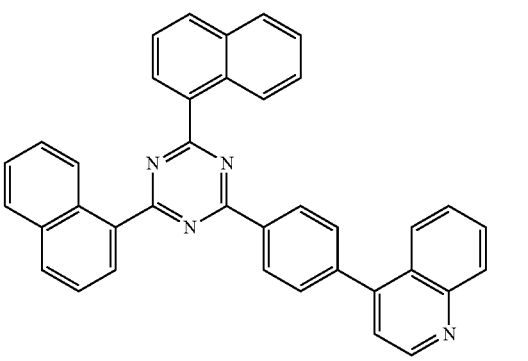
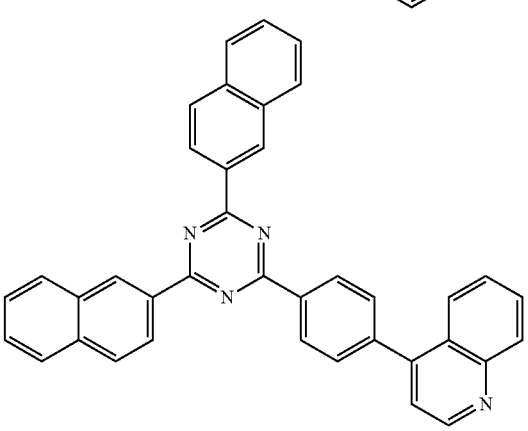

171
-continued
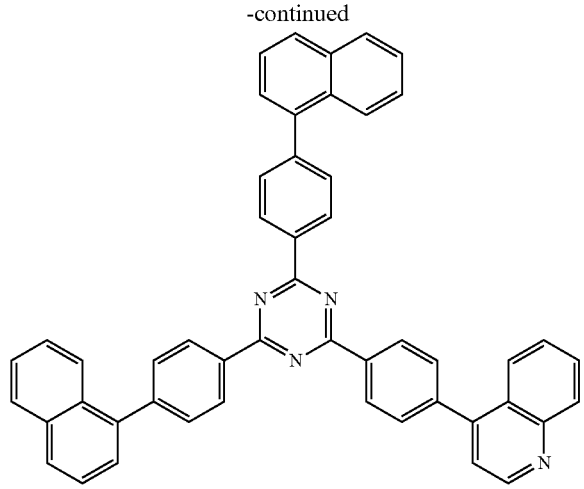
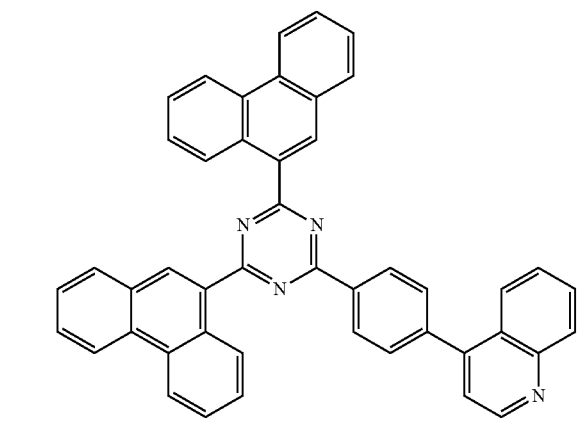
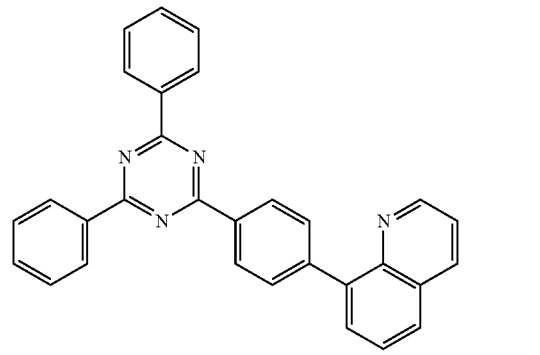
172
-continued
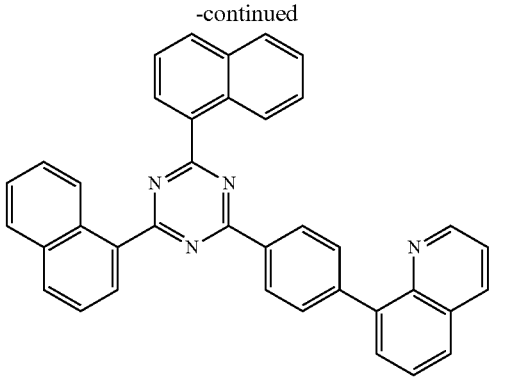
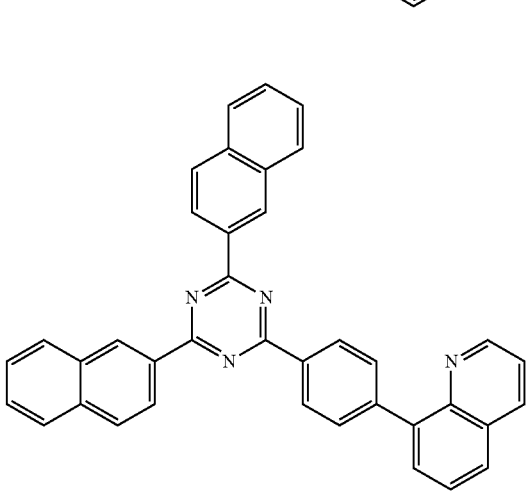

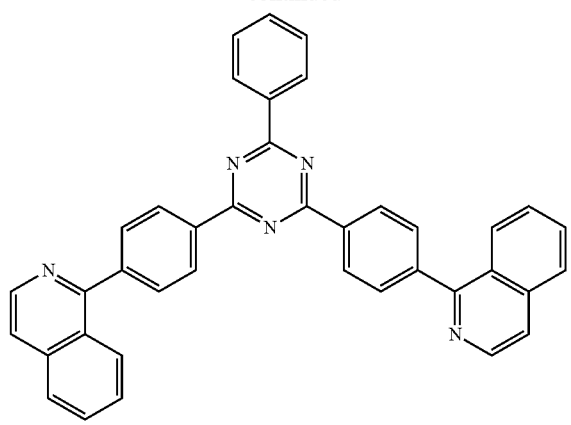
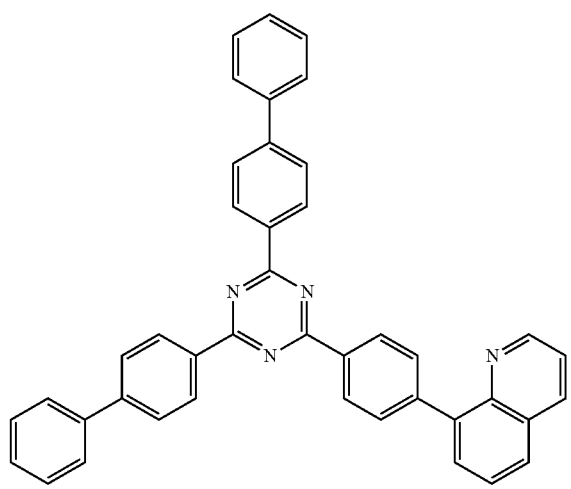
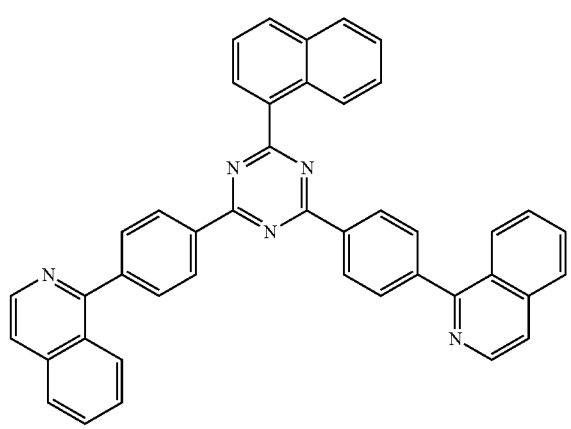
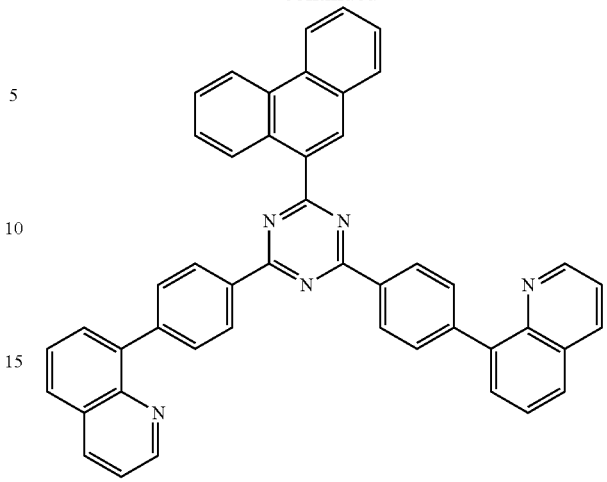
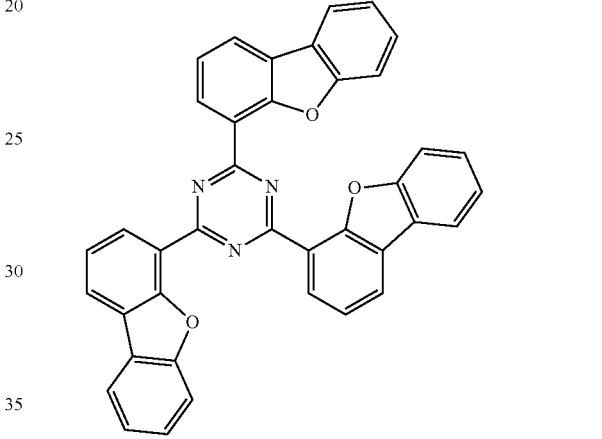
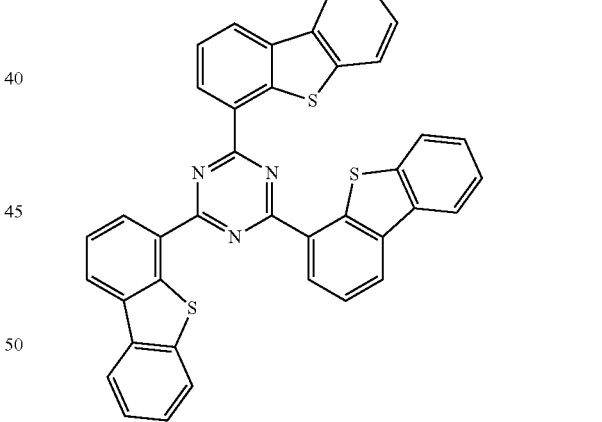
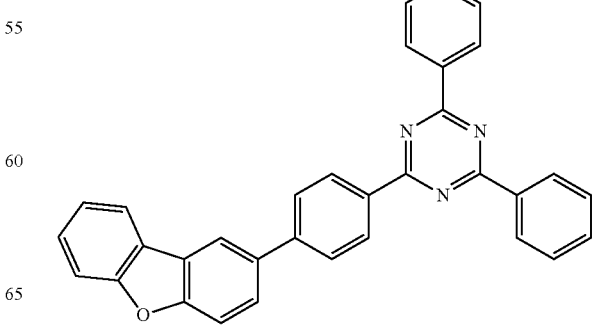

175
-continued
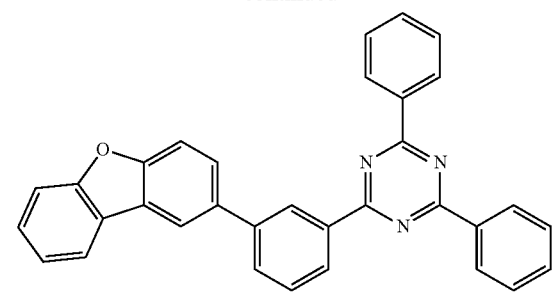
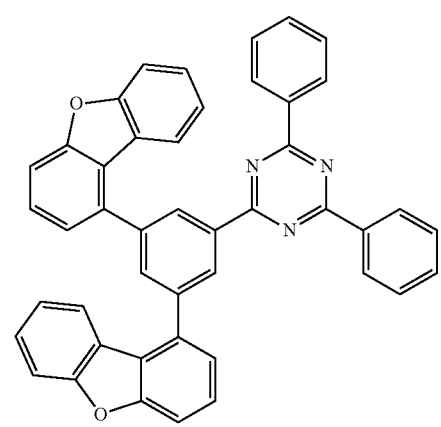
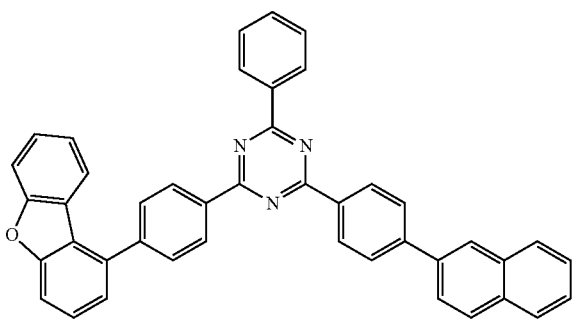
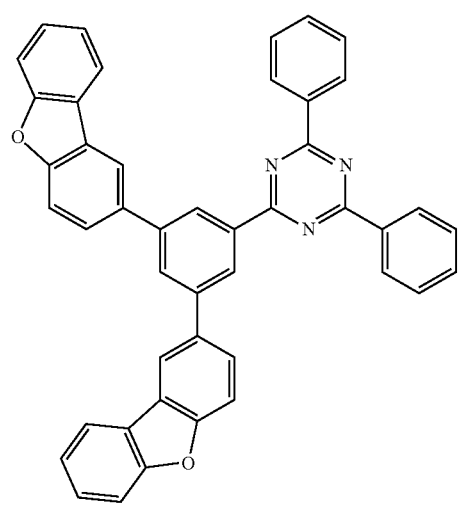
176
-continued
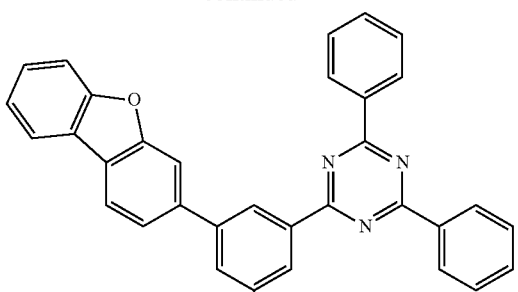
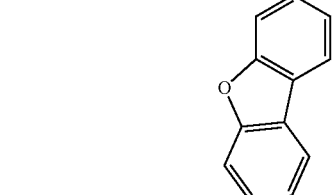
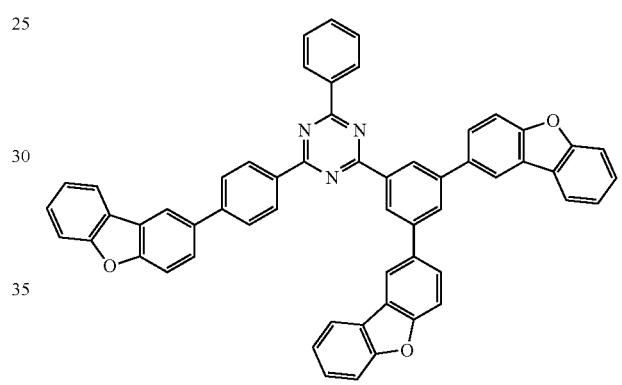
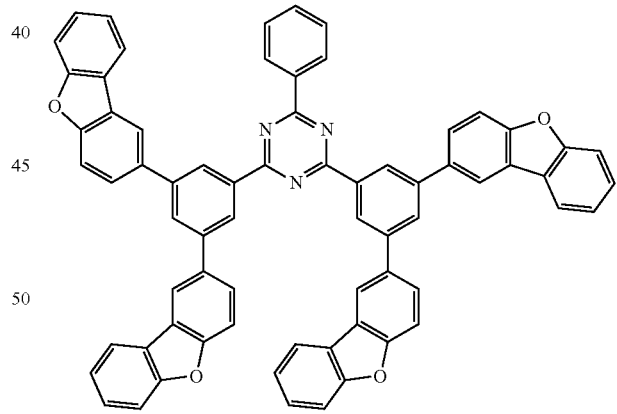
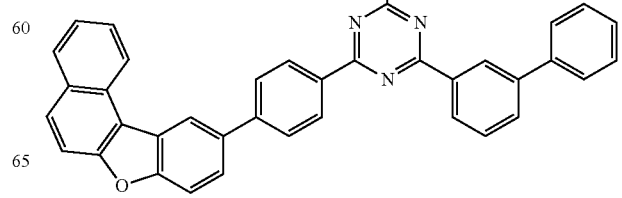

177
-continued
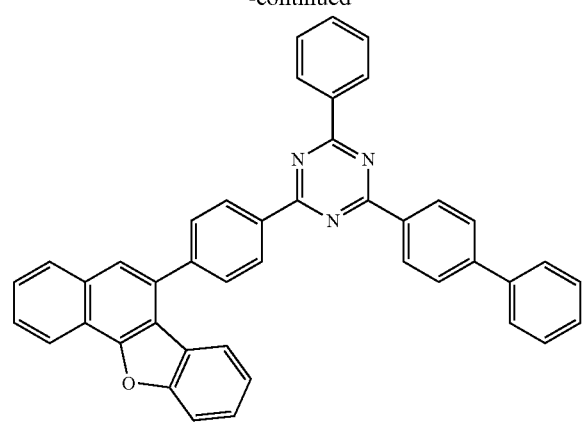
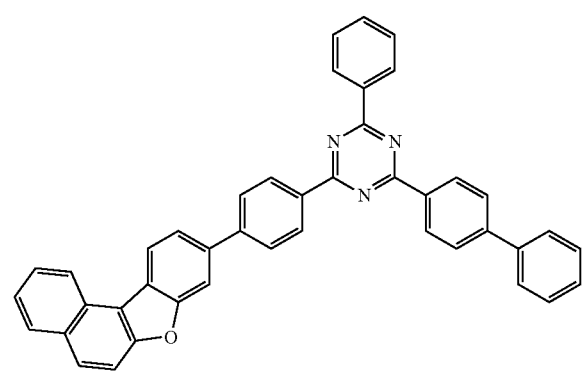
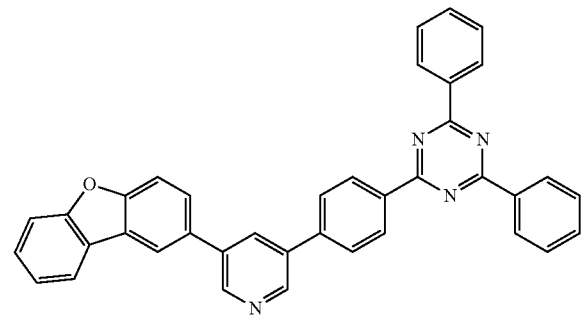
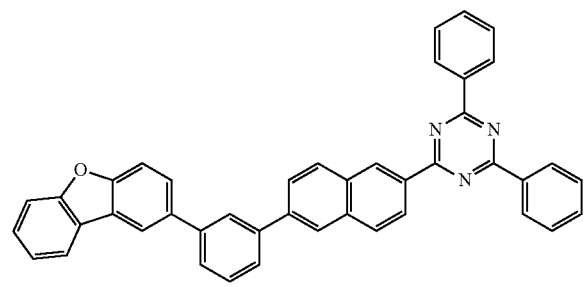
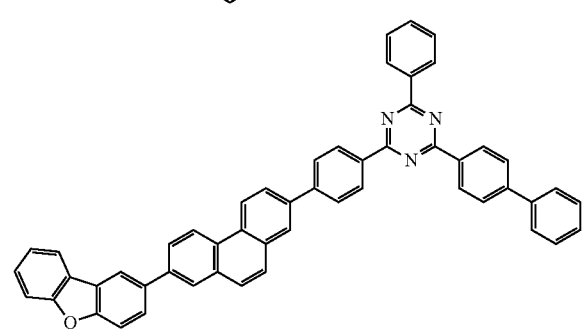
178
-continued
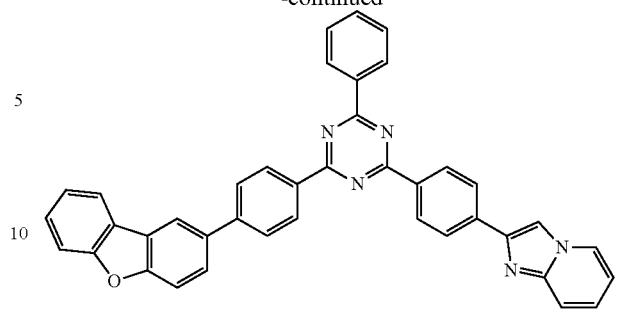
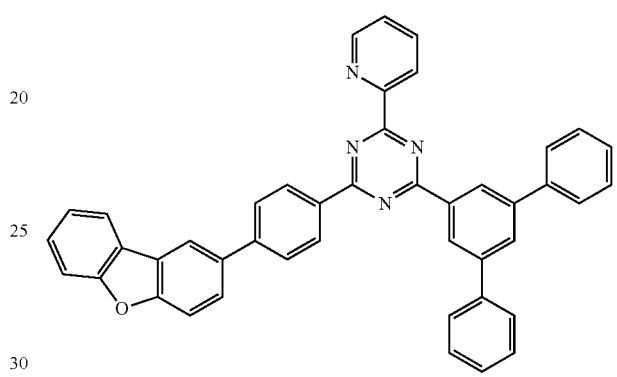
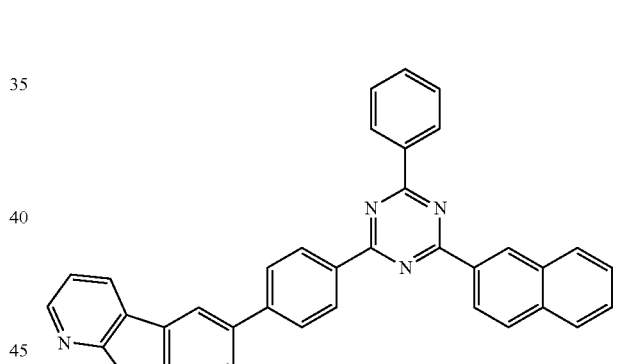
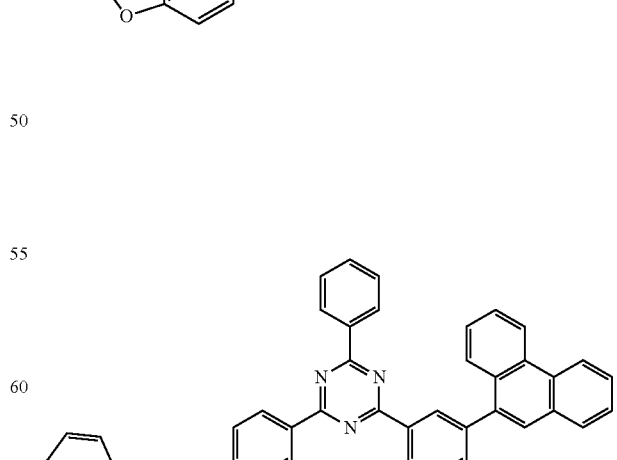

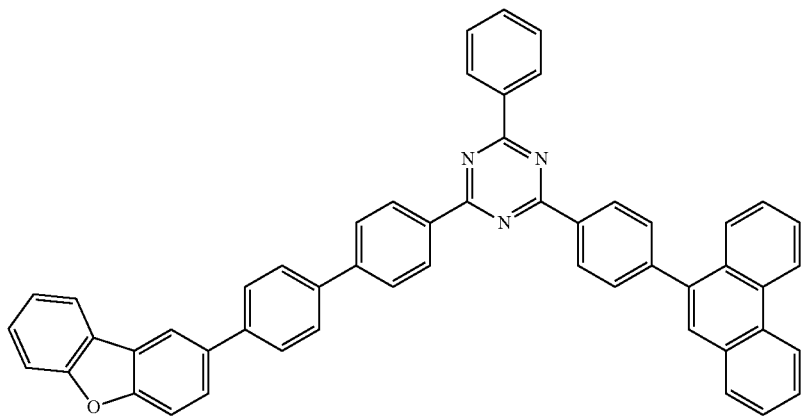
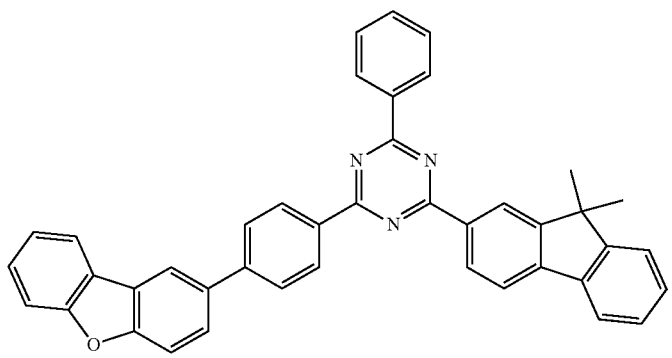
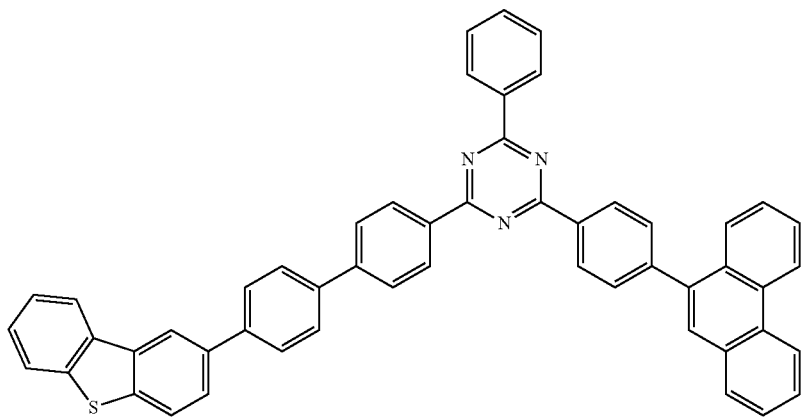
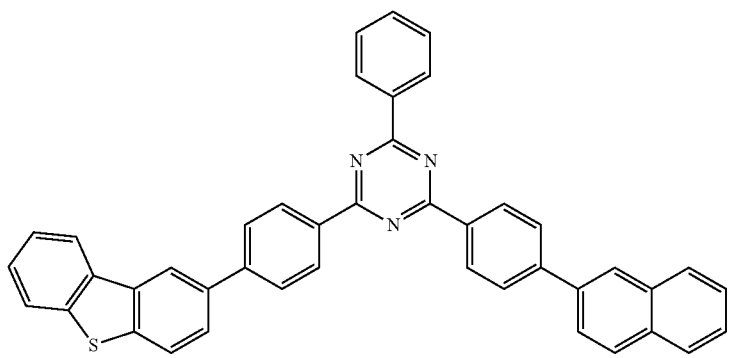

-continued
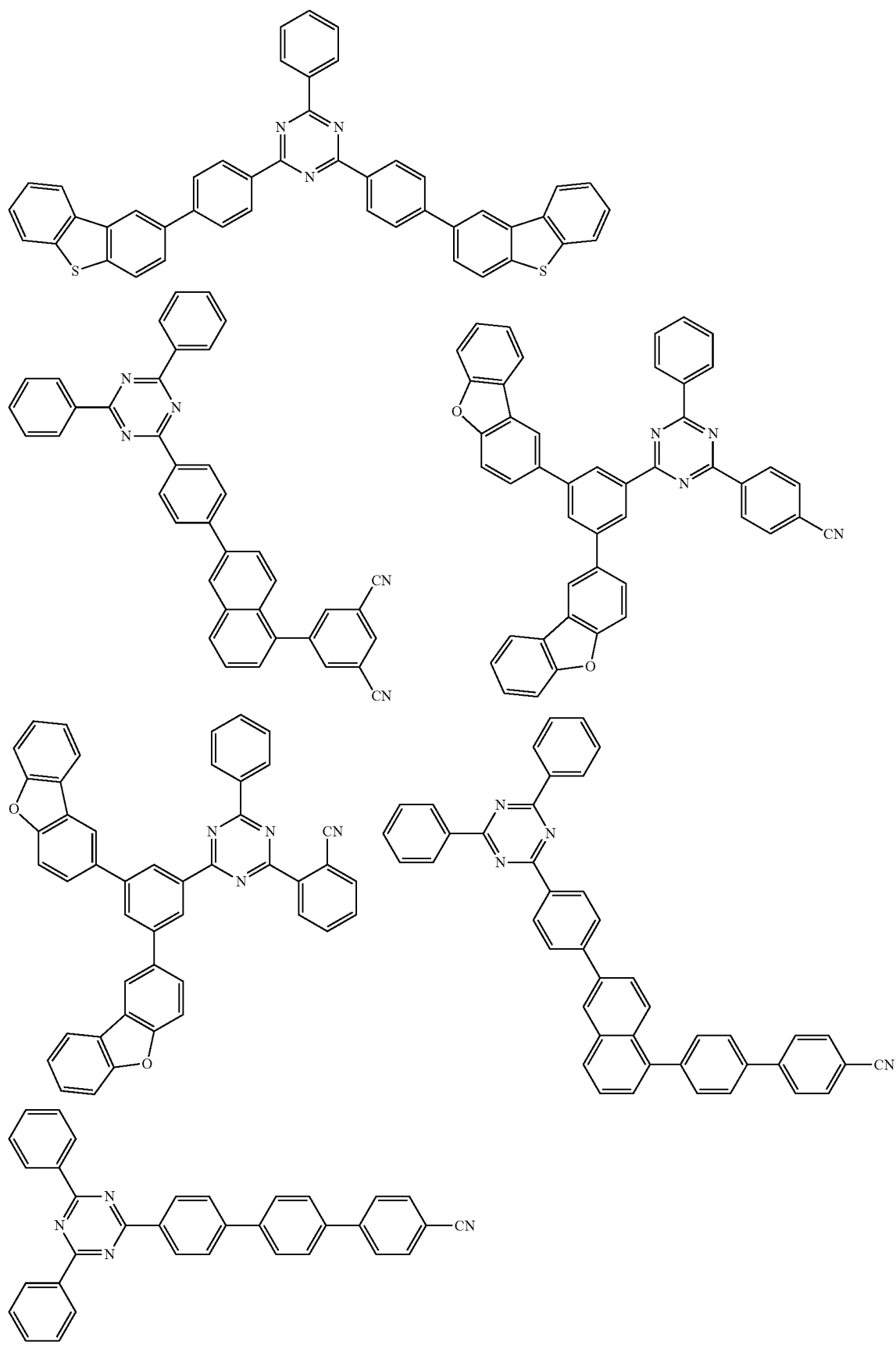

-continued
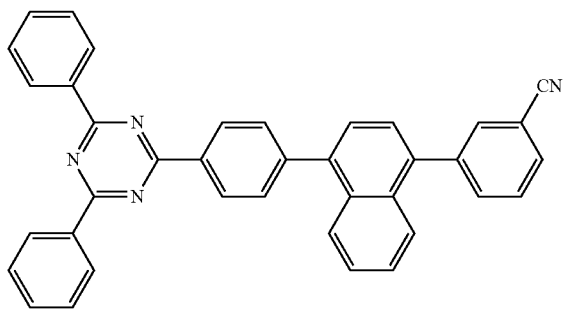
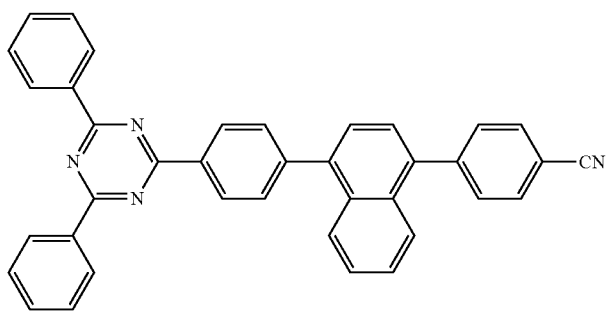
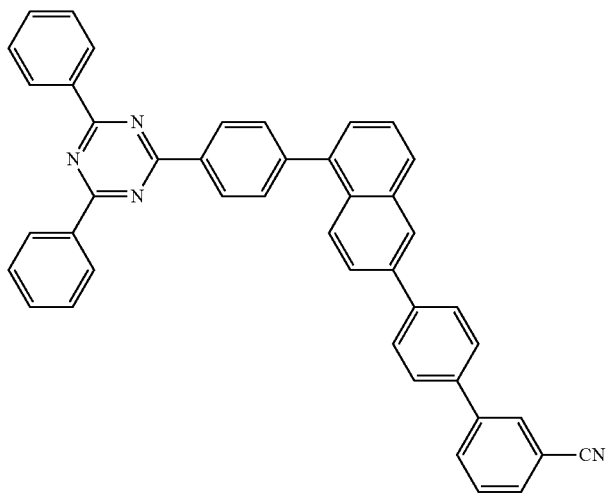
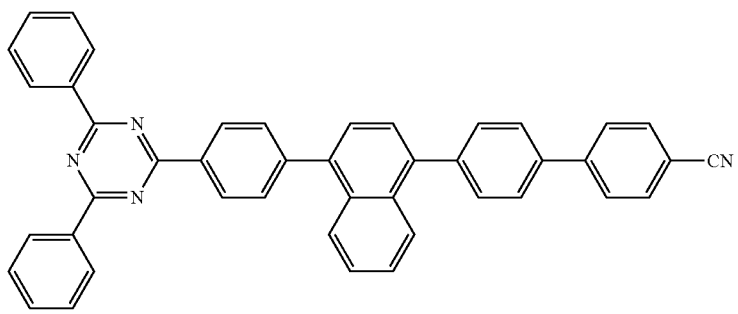

185
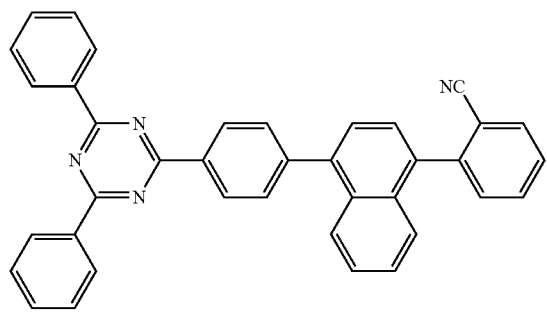
186 -continued
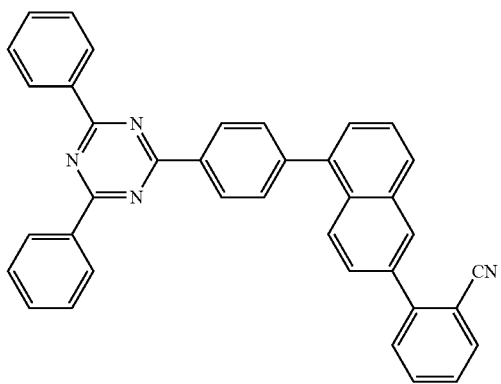
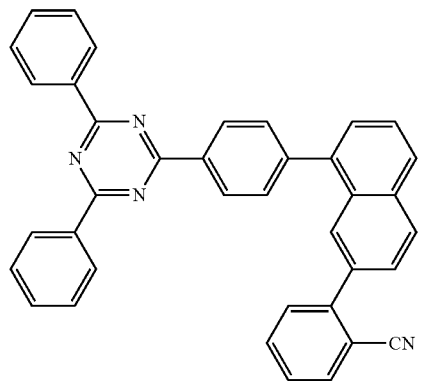
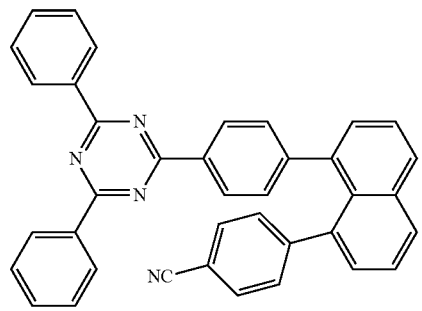
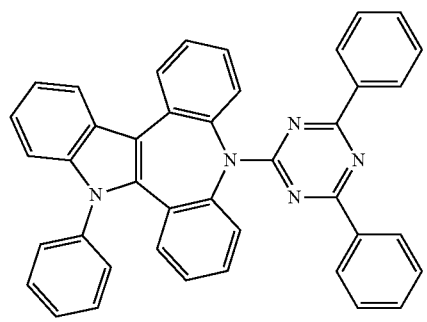
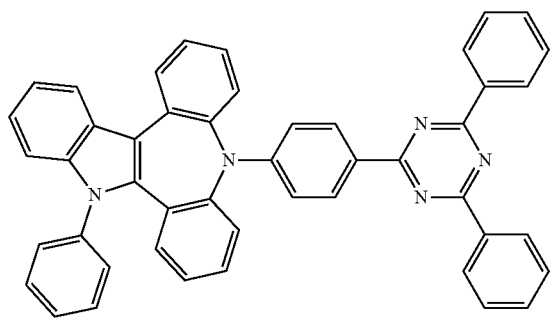
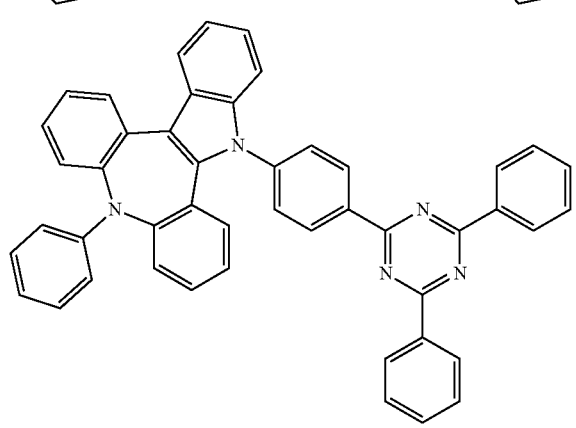

-continued
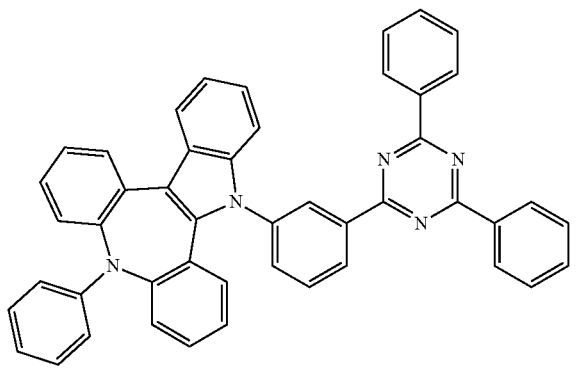
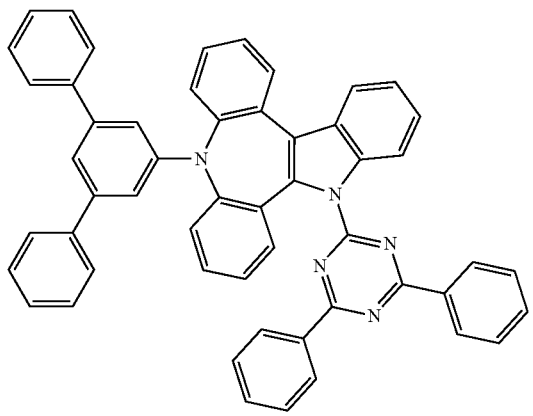
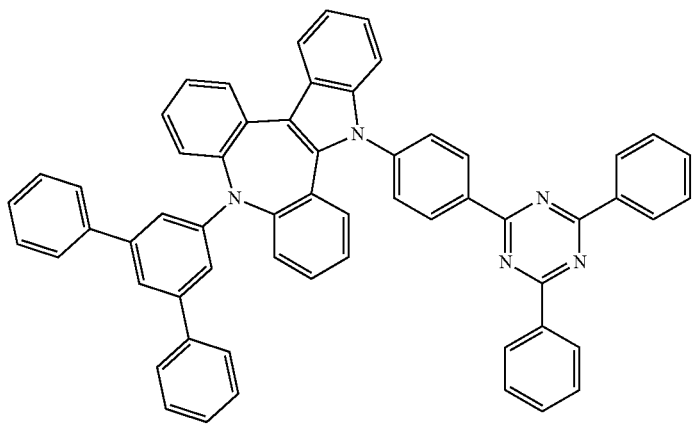
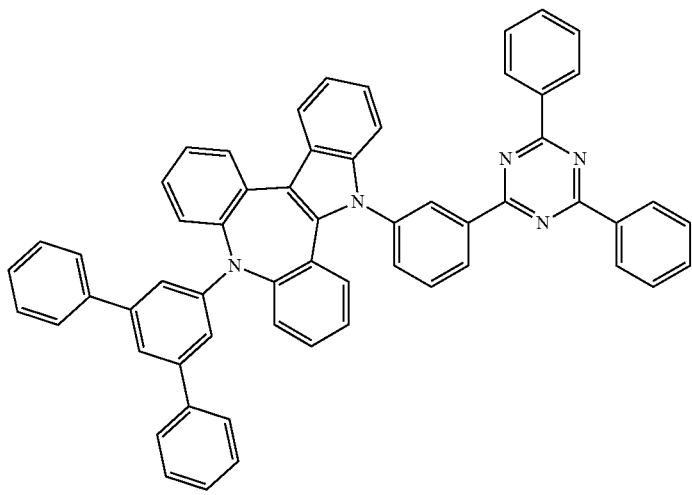

189 190
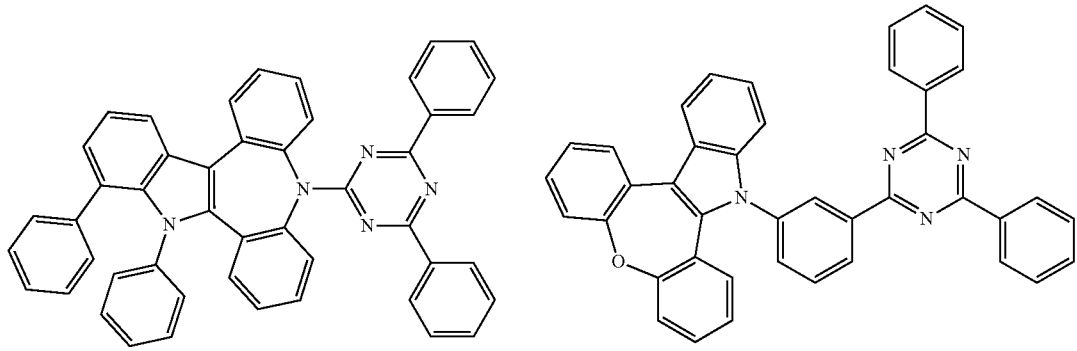
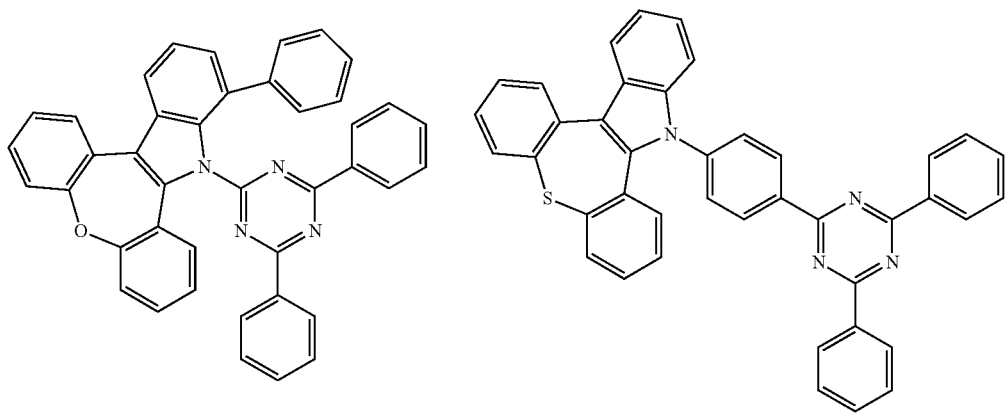
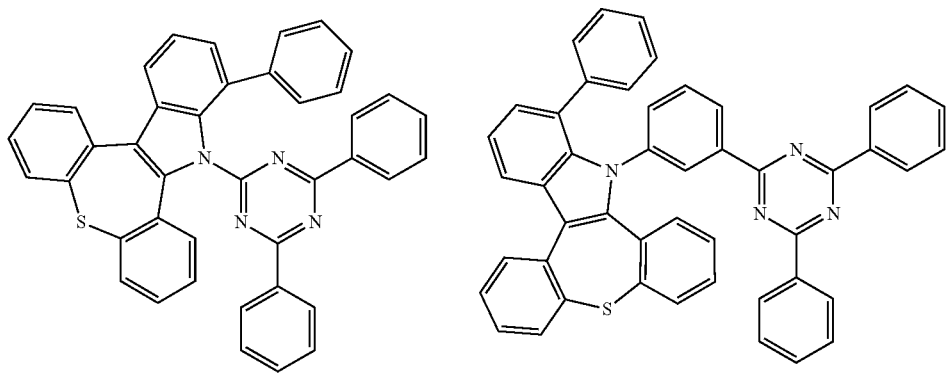
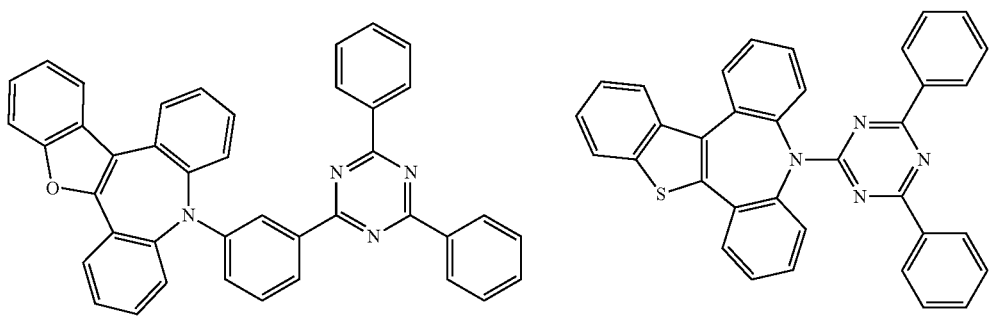

191 192
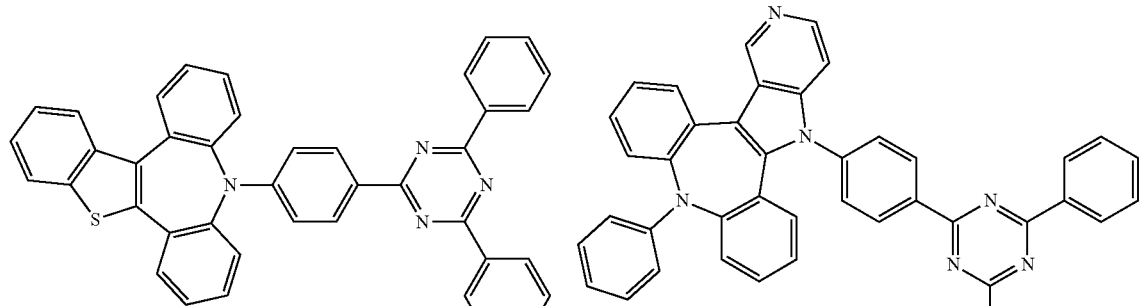
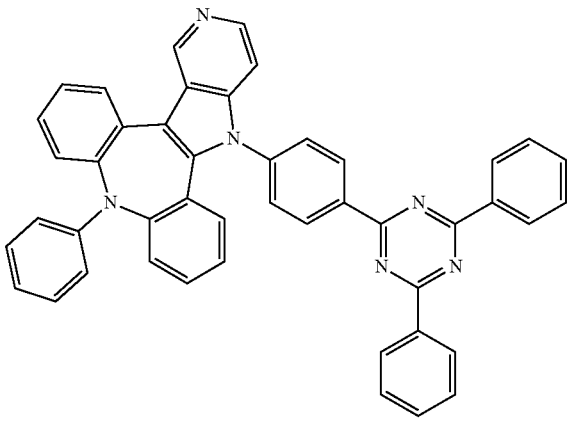
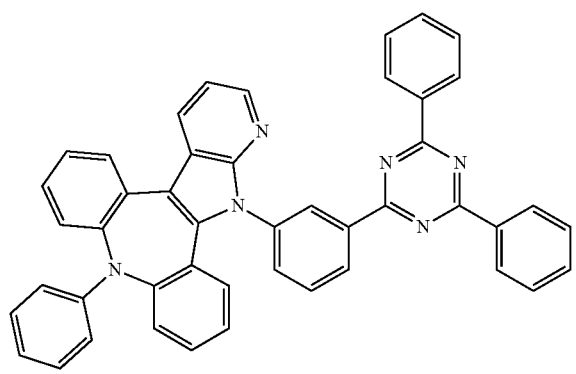
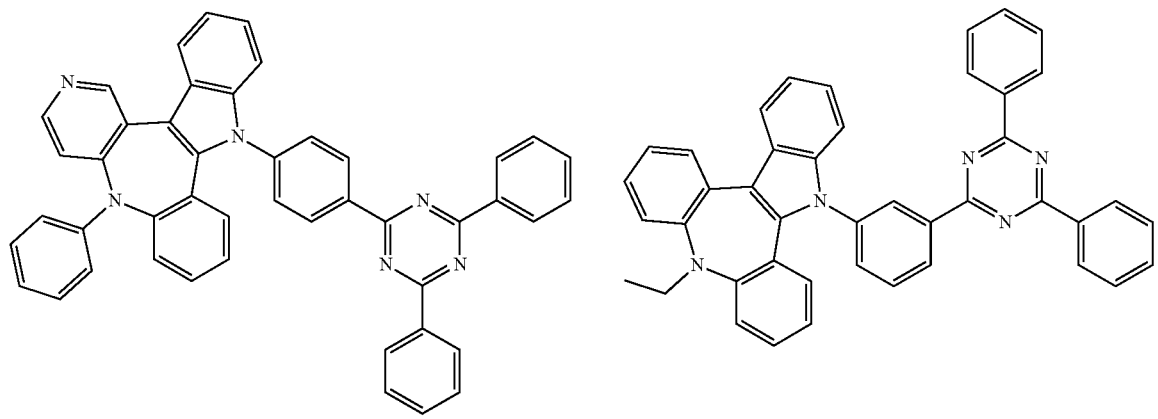
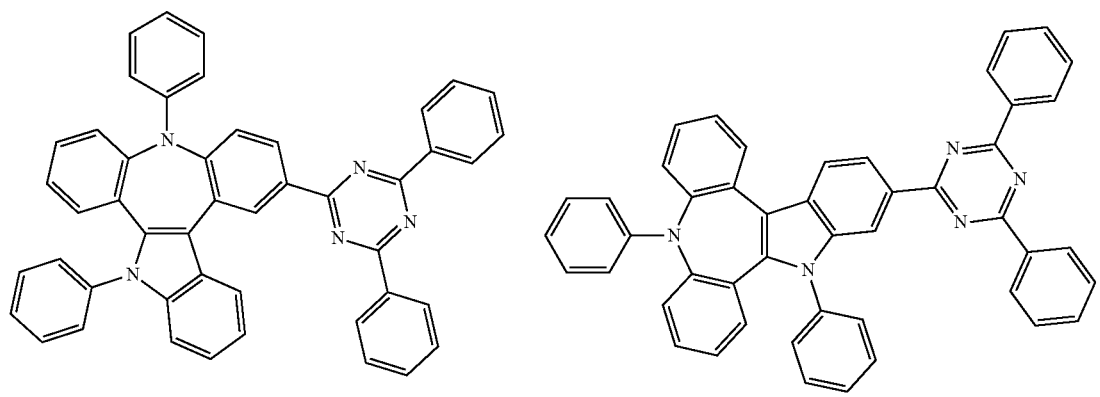

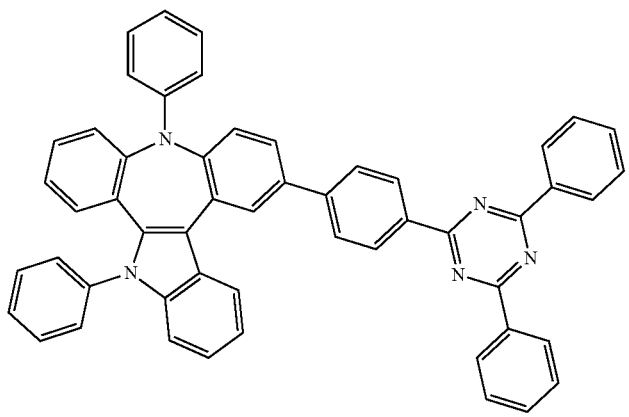
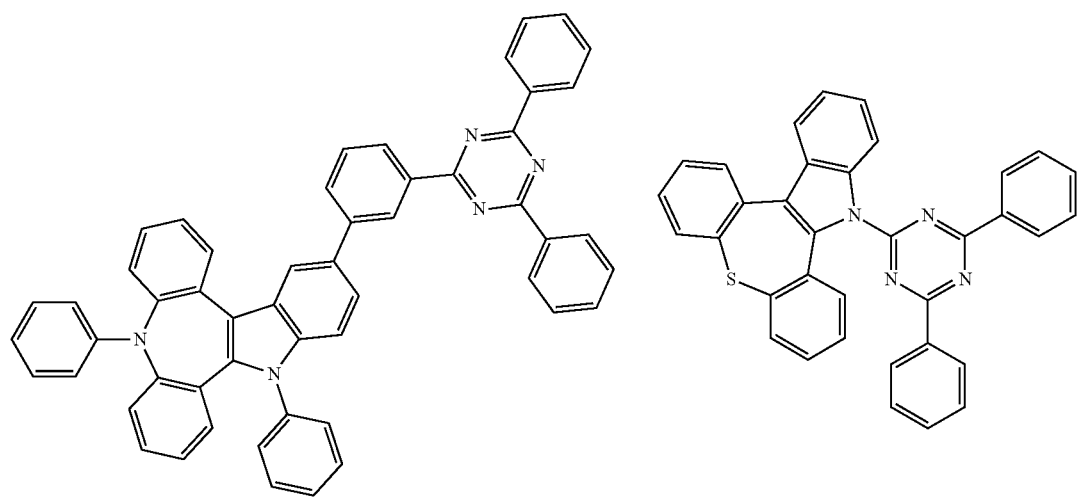
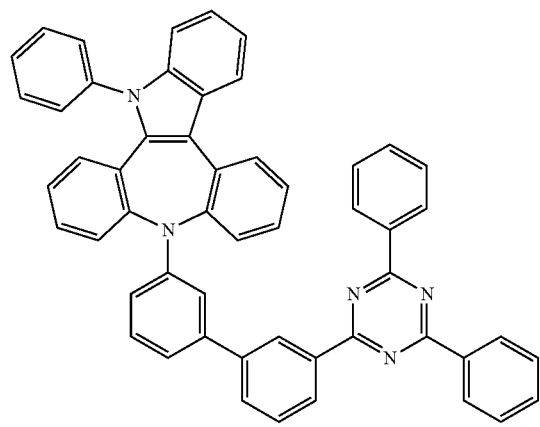

-continued
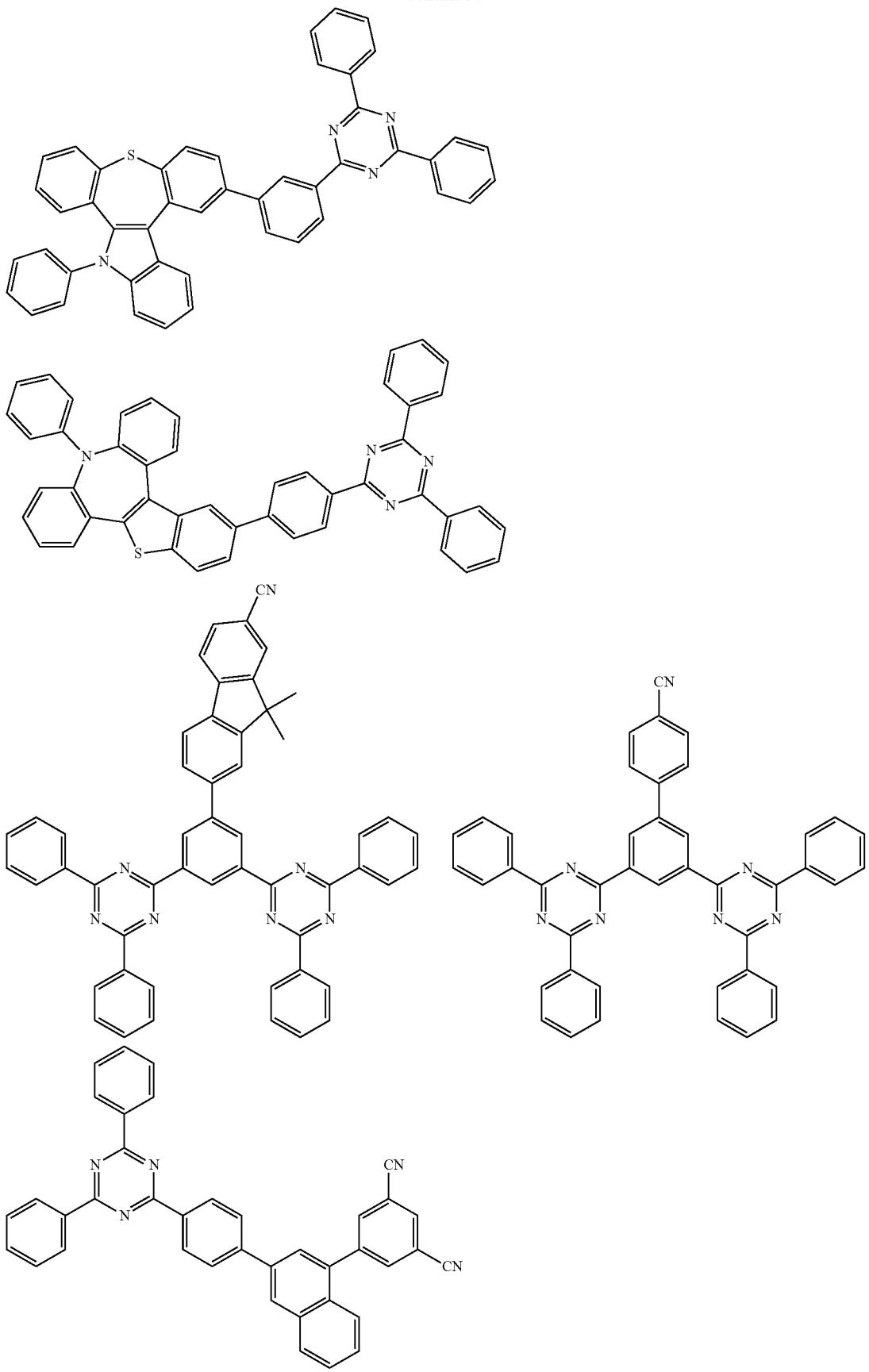

-continued
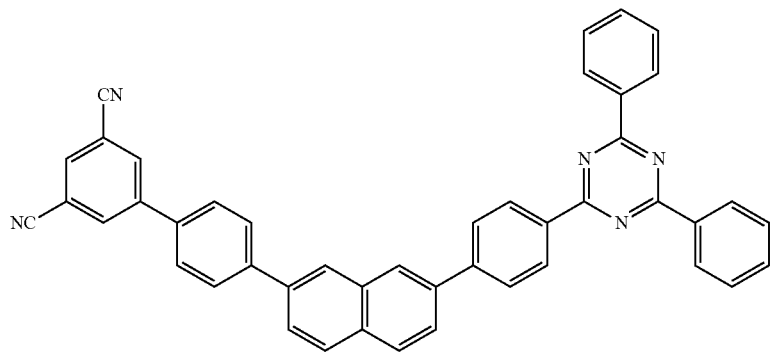
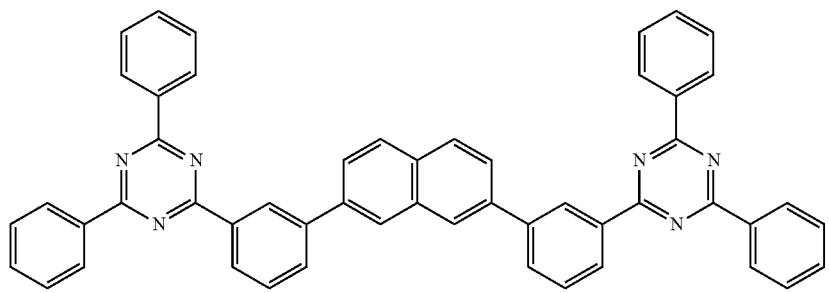
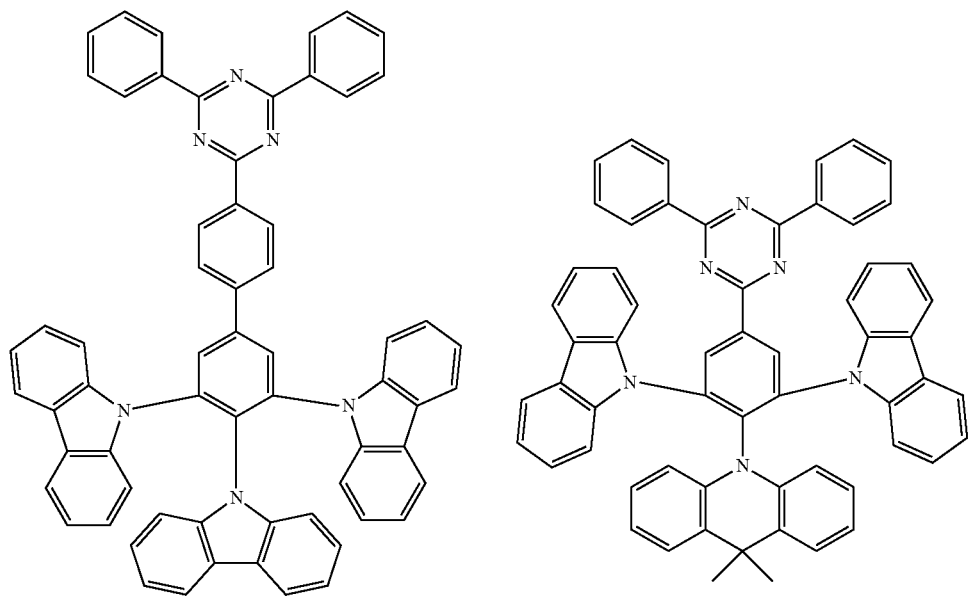

199
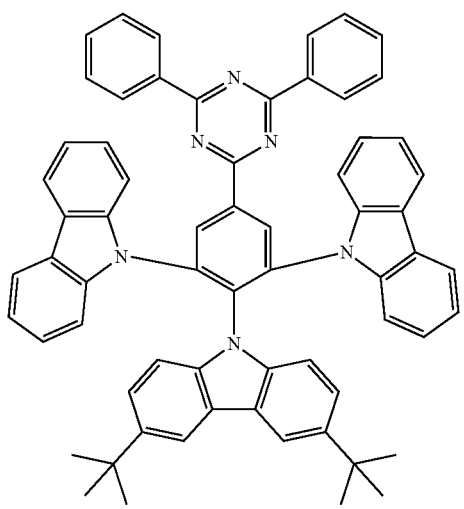
200
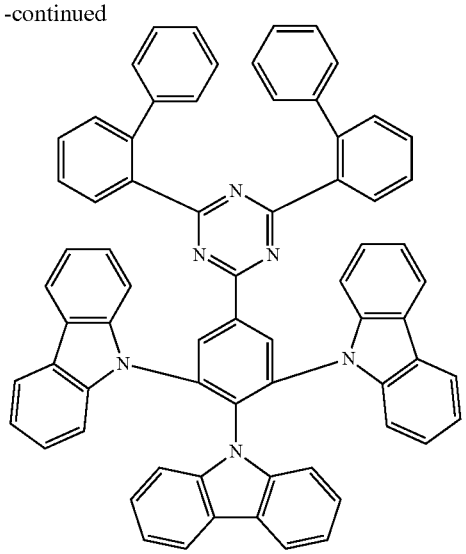
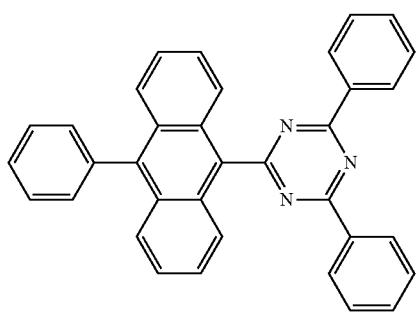
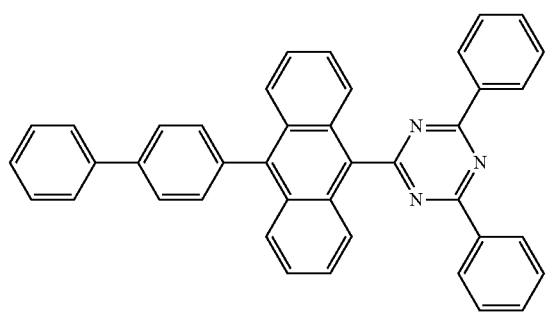
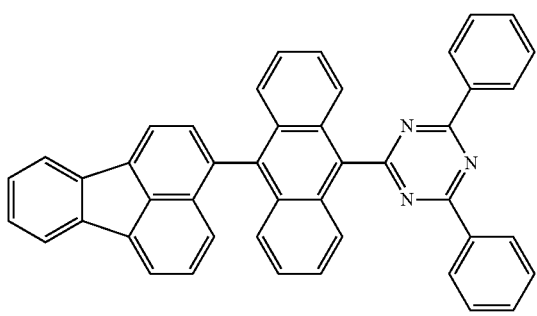
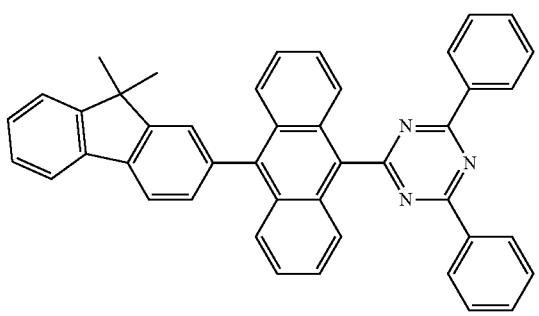
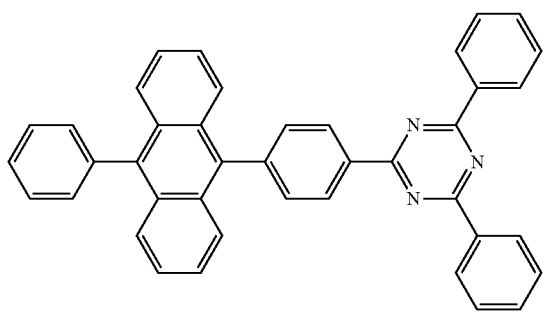

201
-continued
202
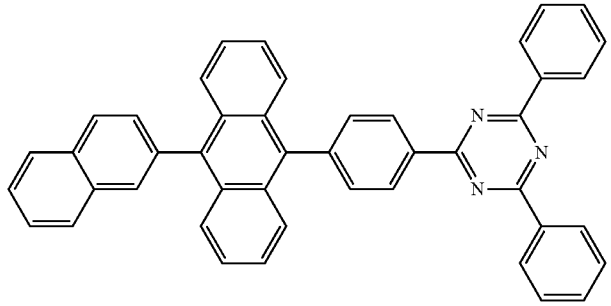
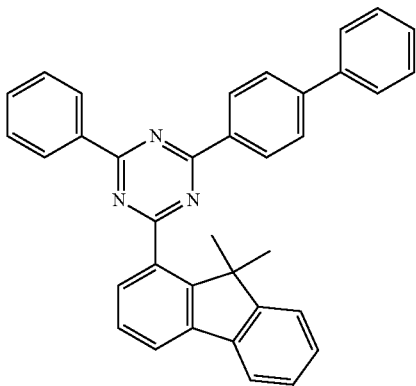
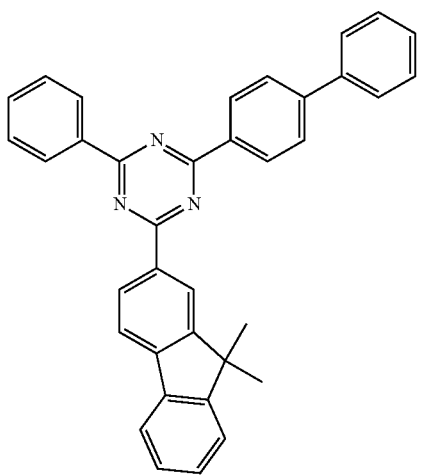
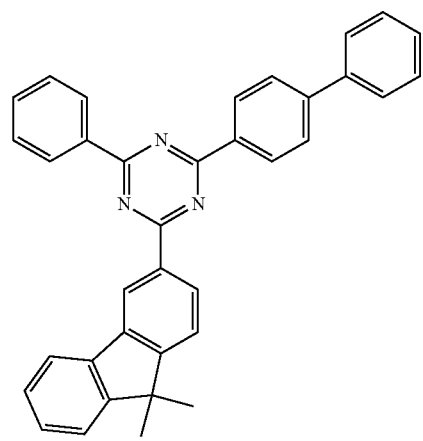
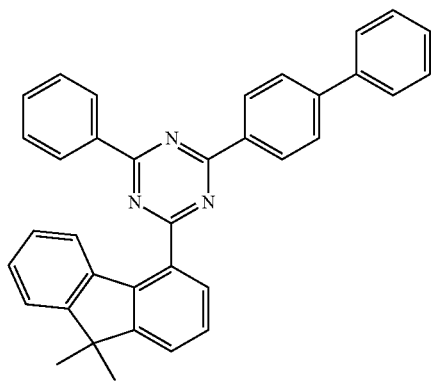
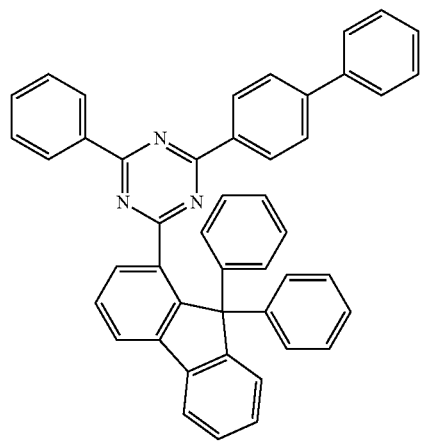

203
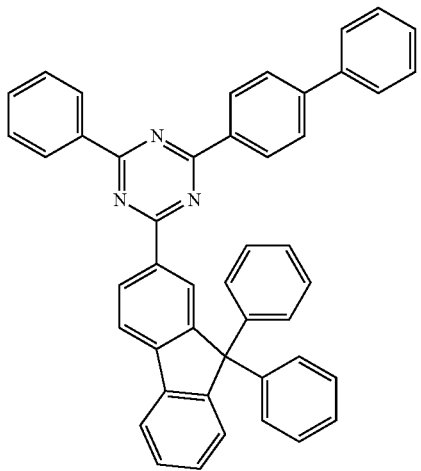
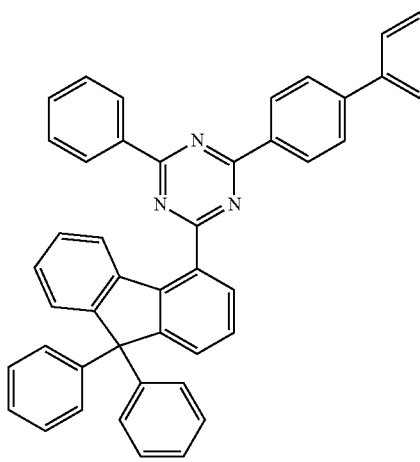
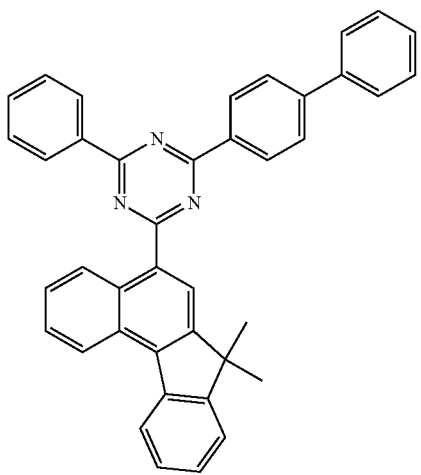
204
-continued
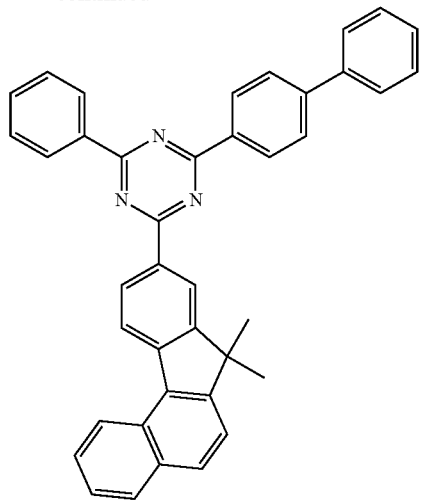
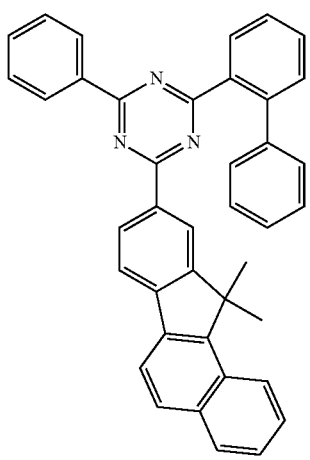
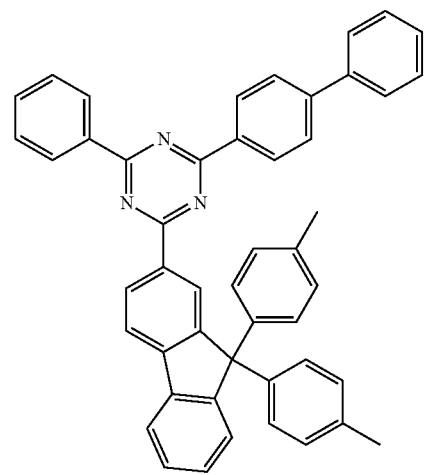

205
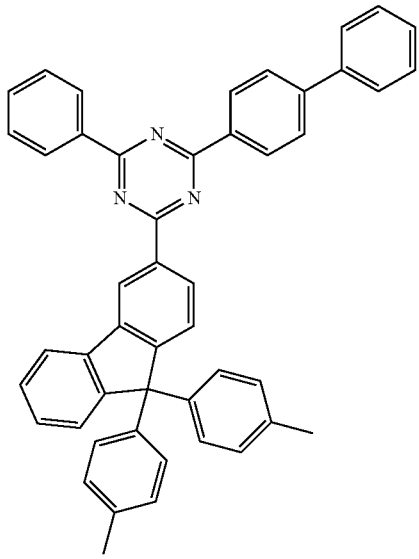
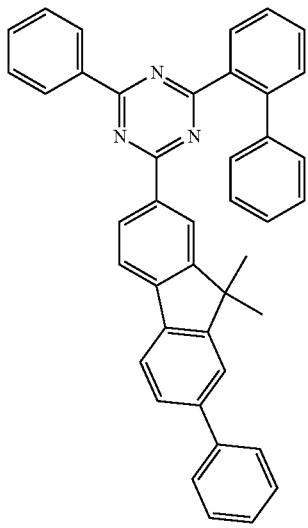
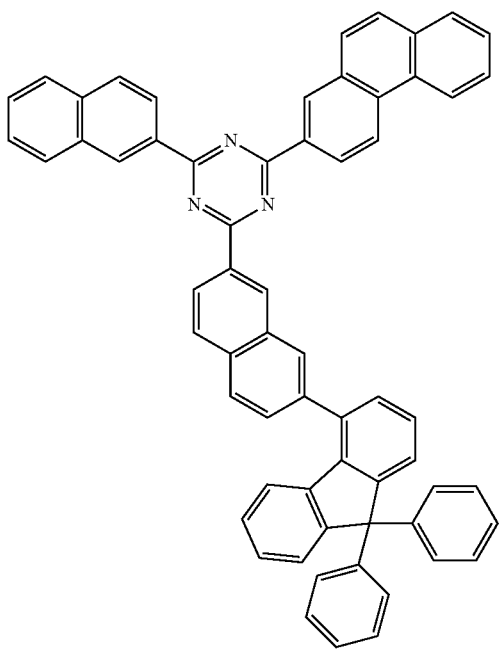
206
-continued
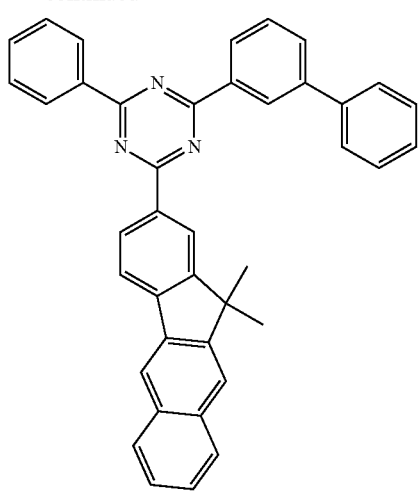
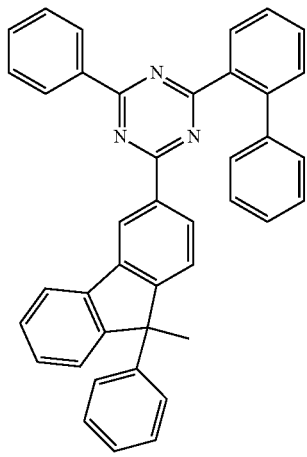
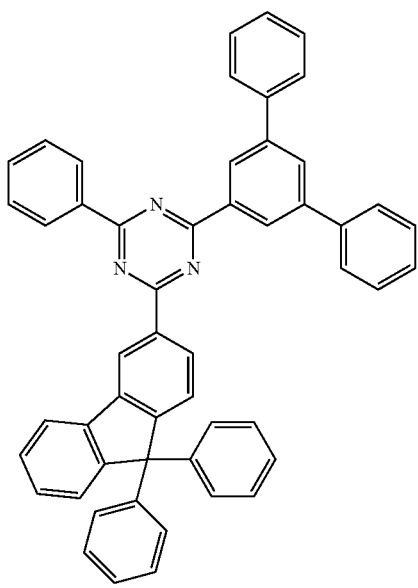

207 208
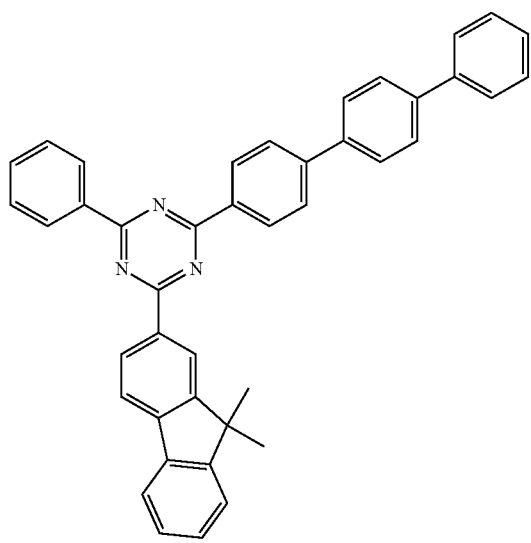
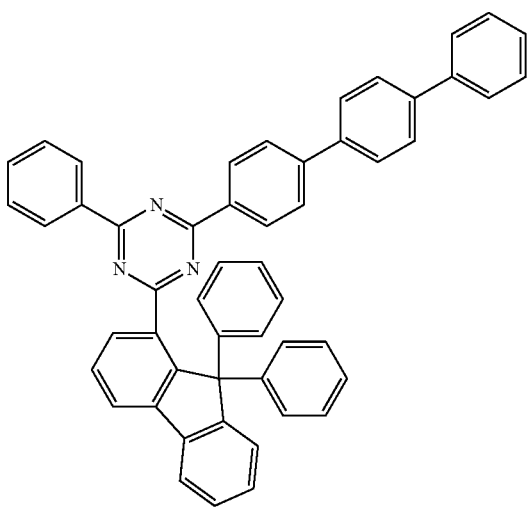
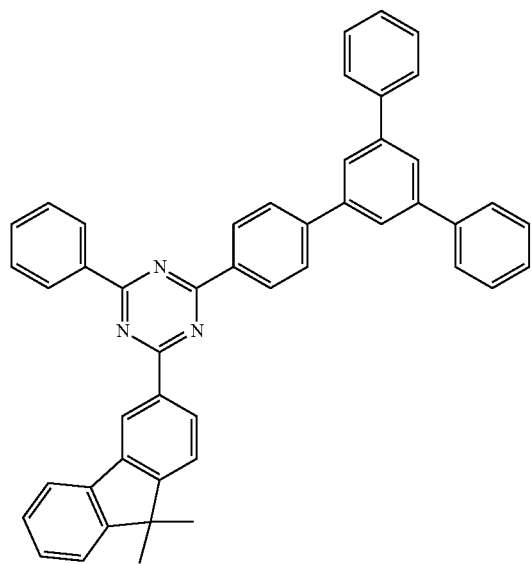
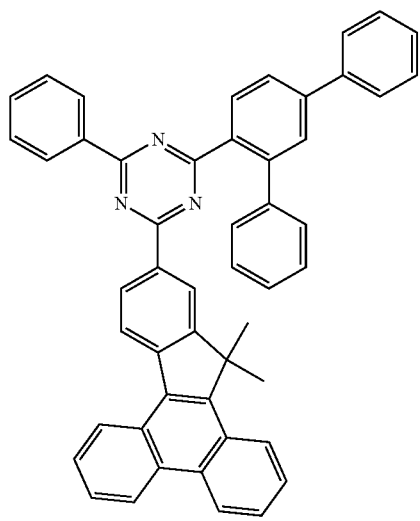

209
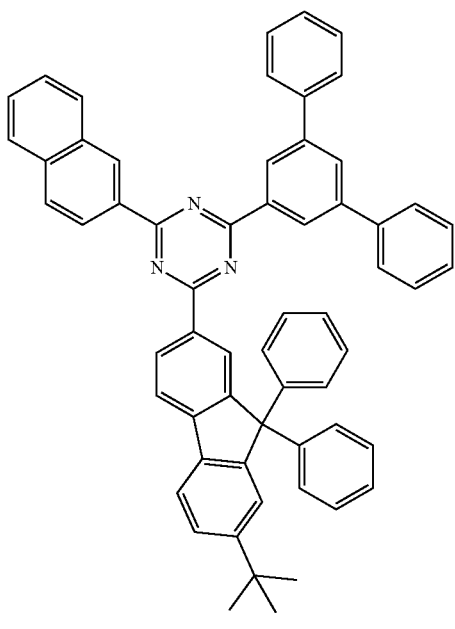
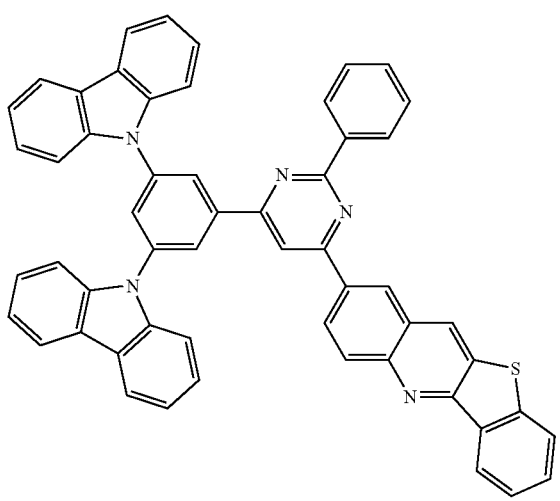
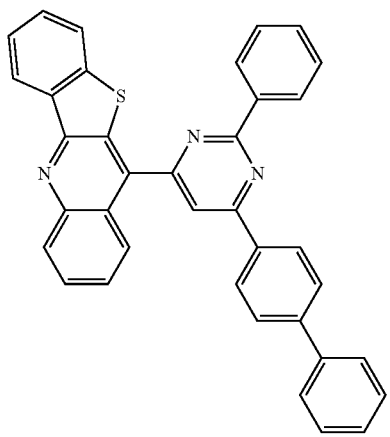
210
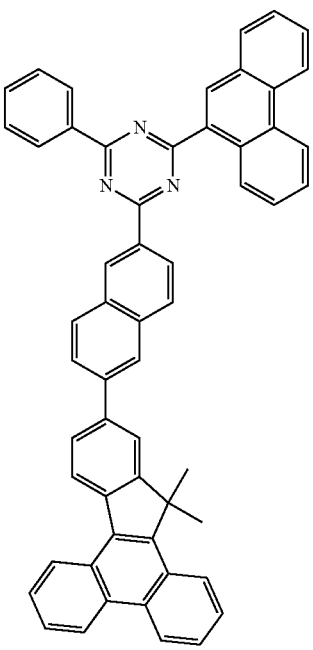
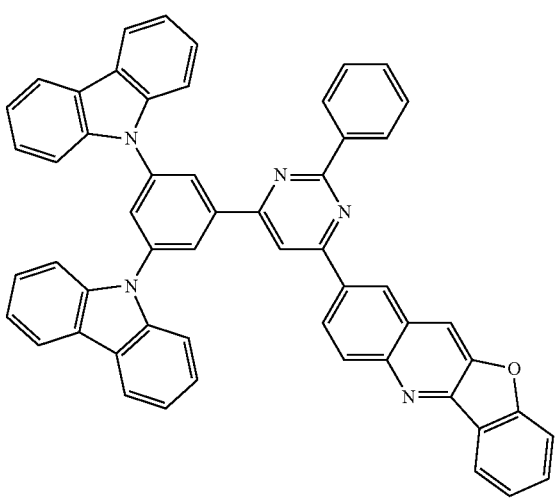
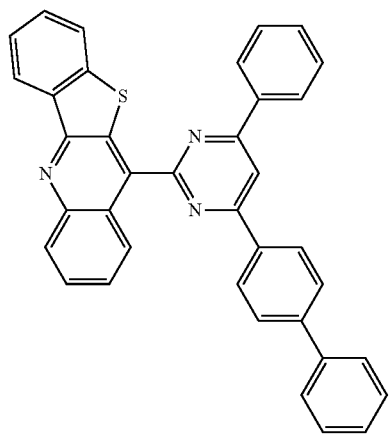

211
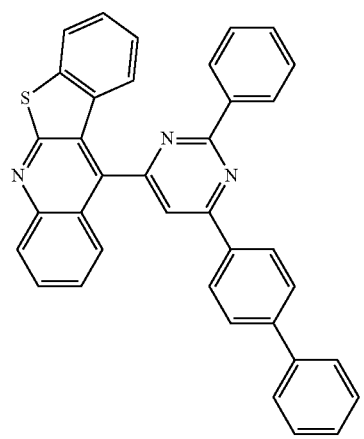
212
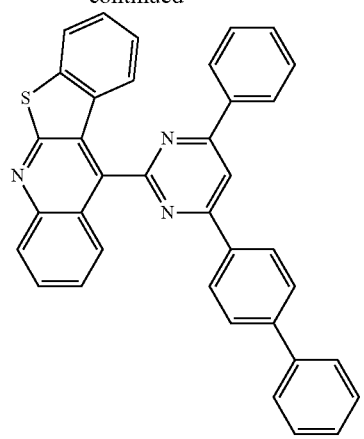
-continued
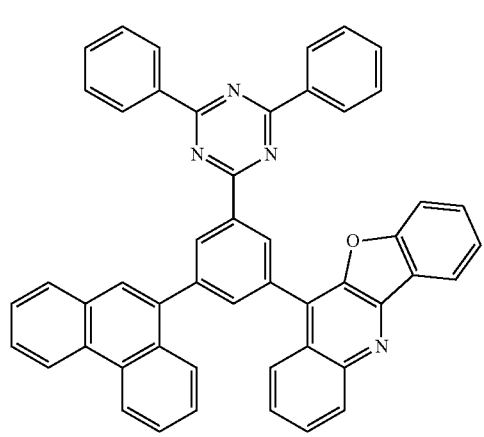
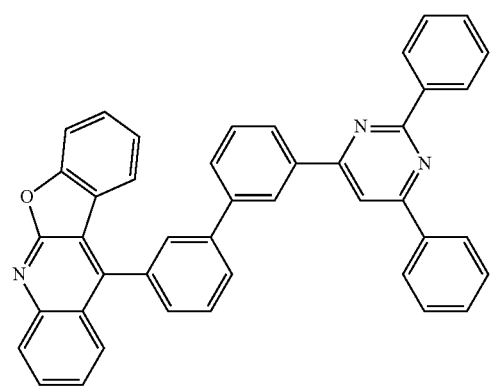
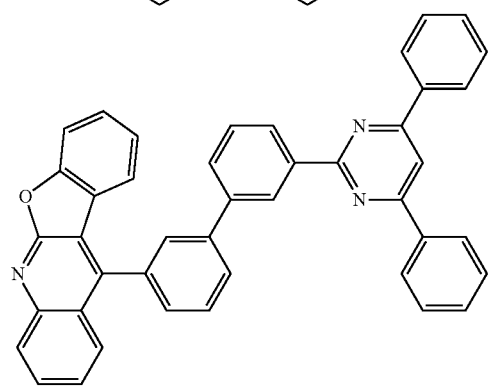
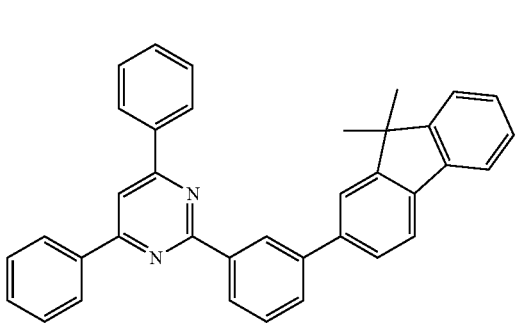
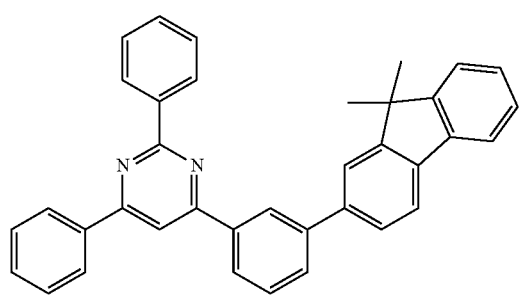
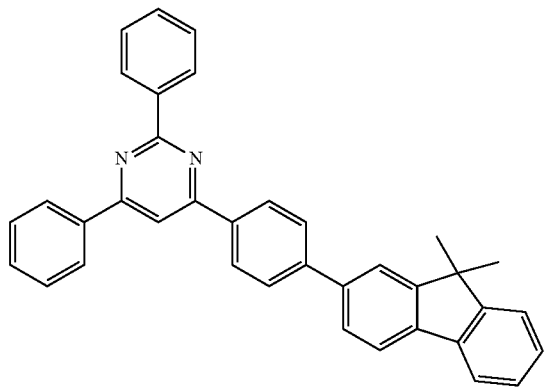

-continued
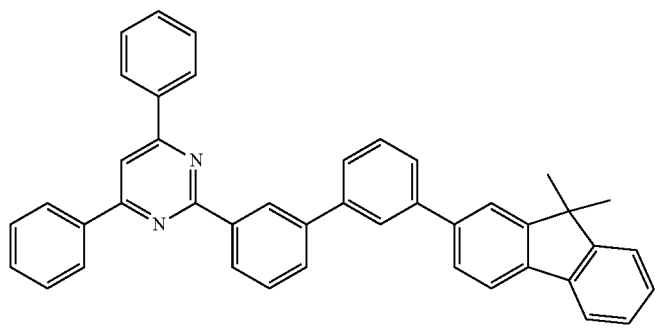
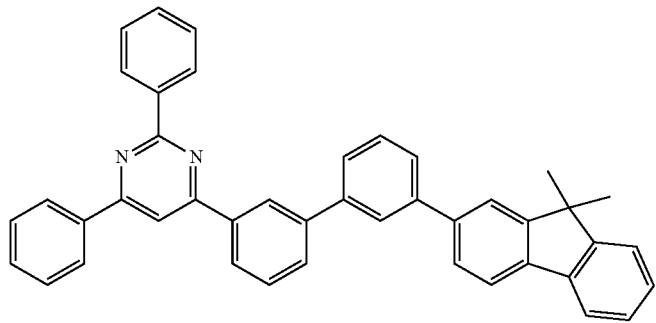
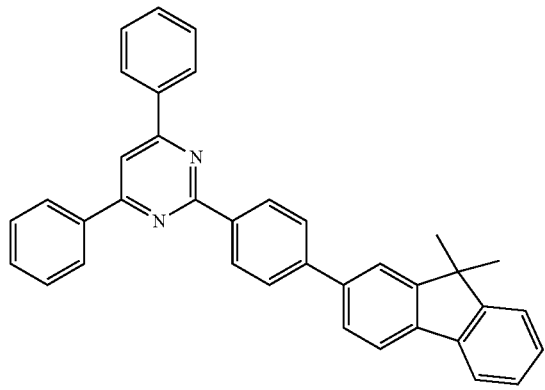
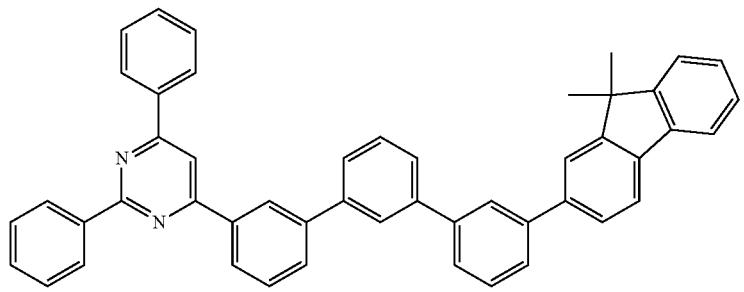
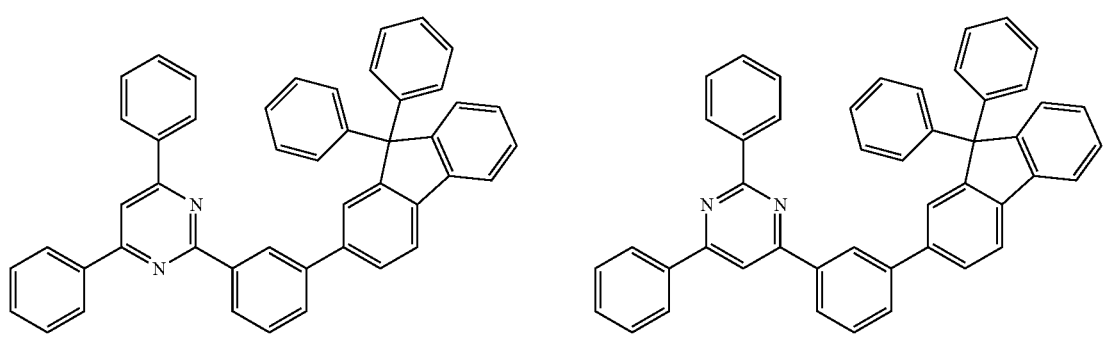

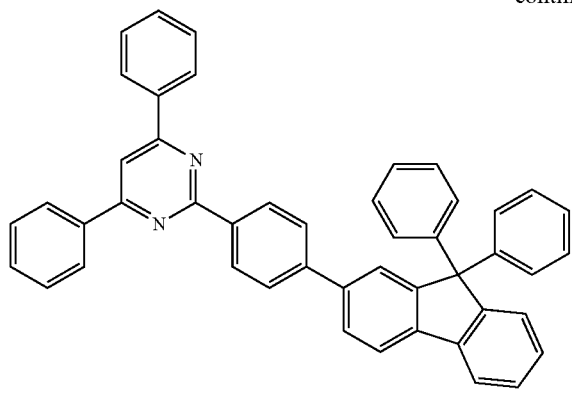
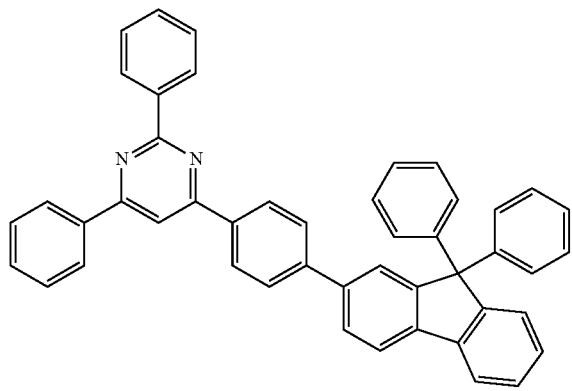
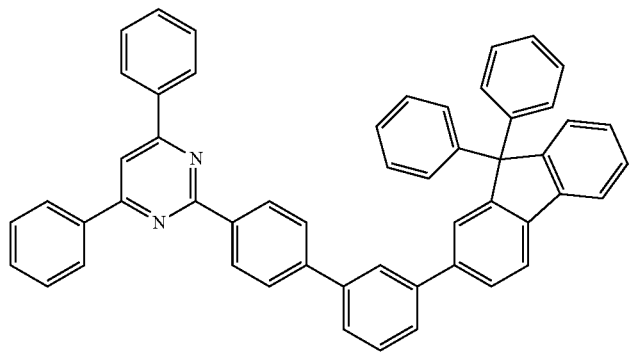
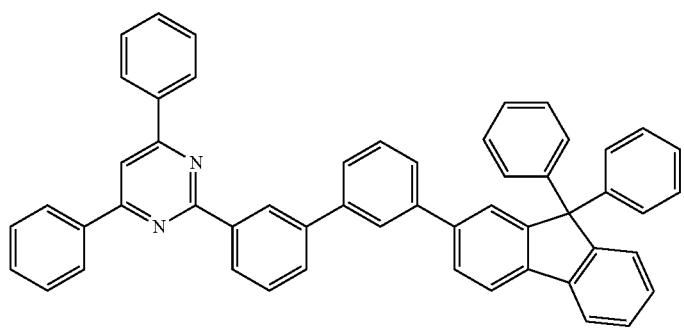

217
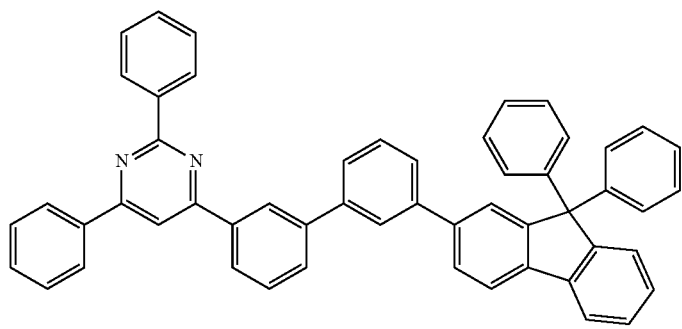
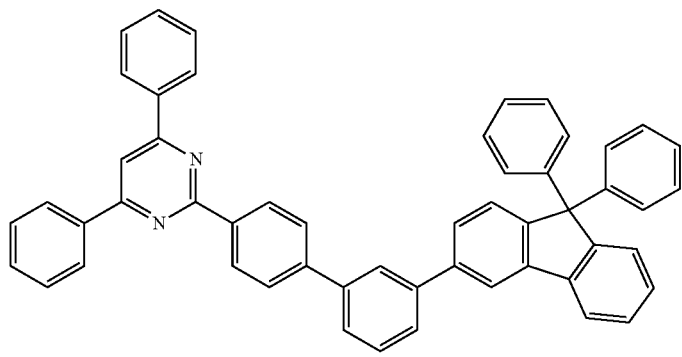
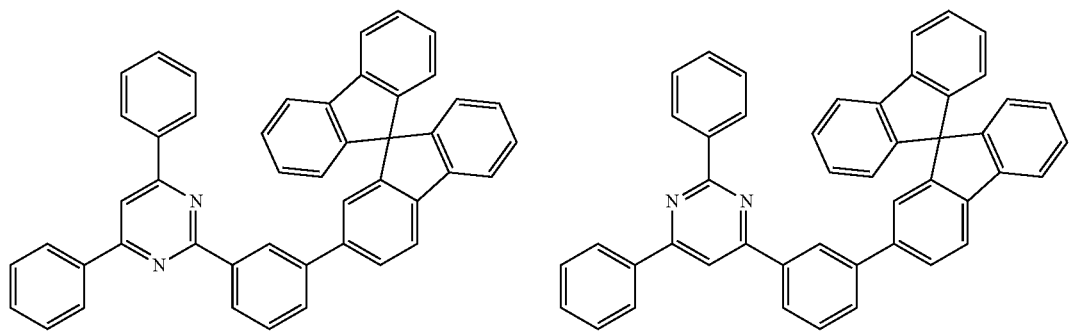
218
-continued
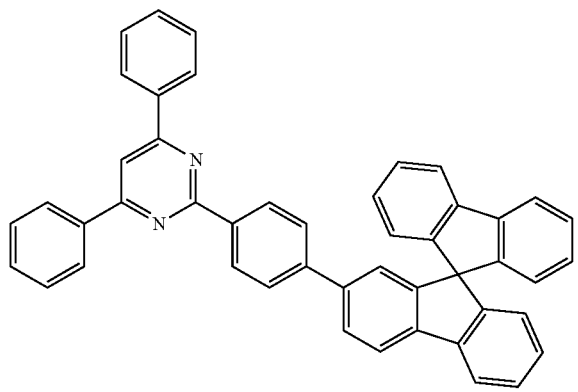

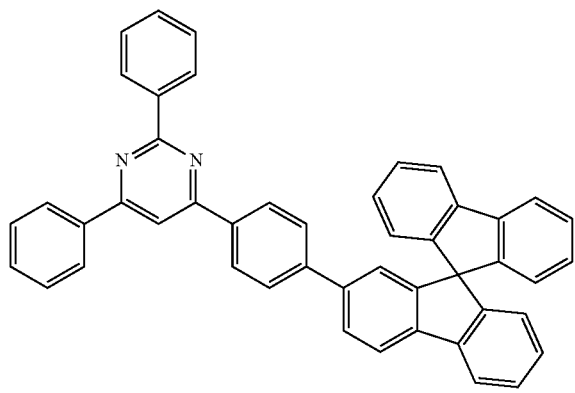
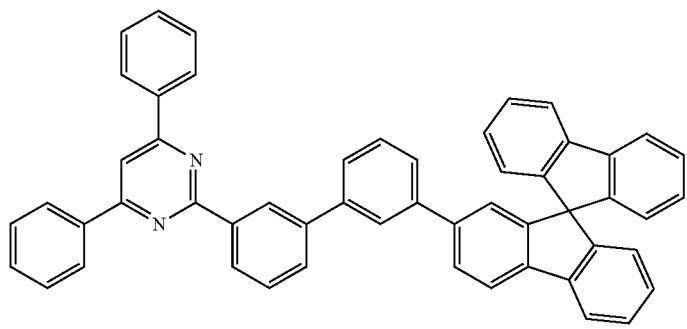
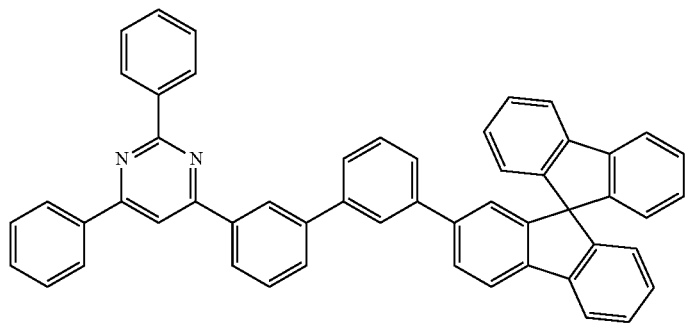
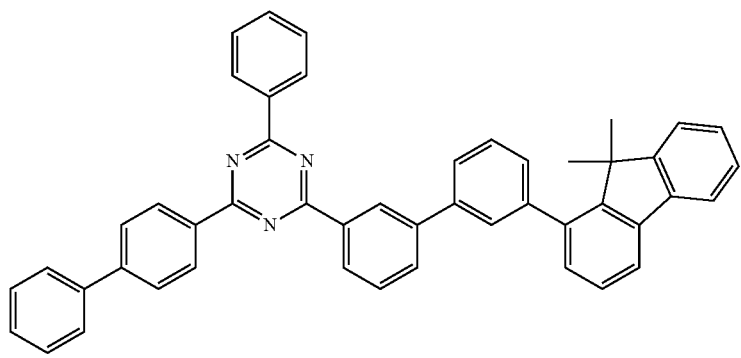

221 222
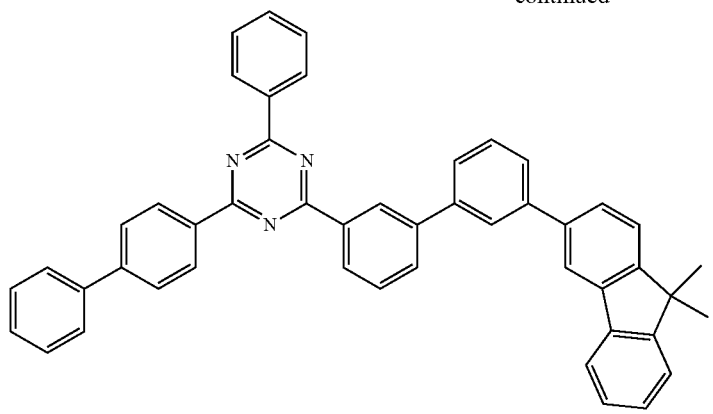
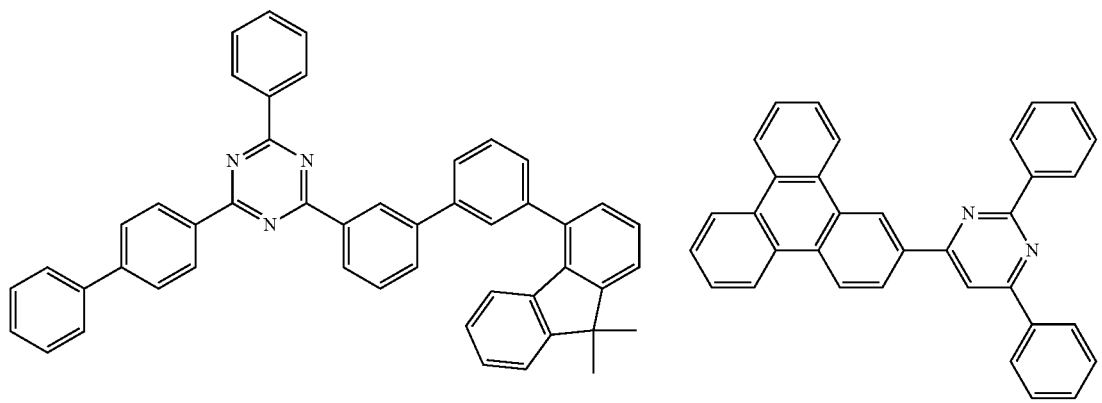
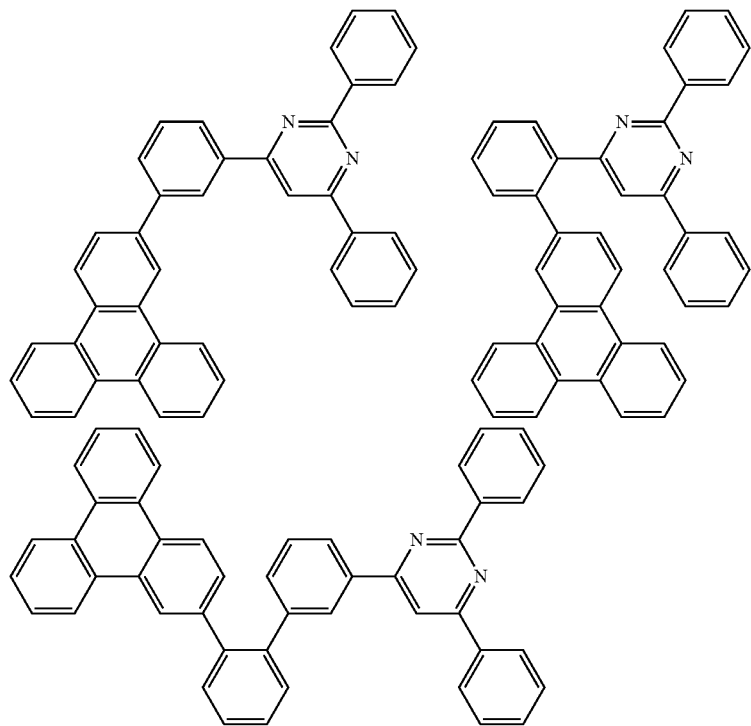

-continued
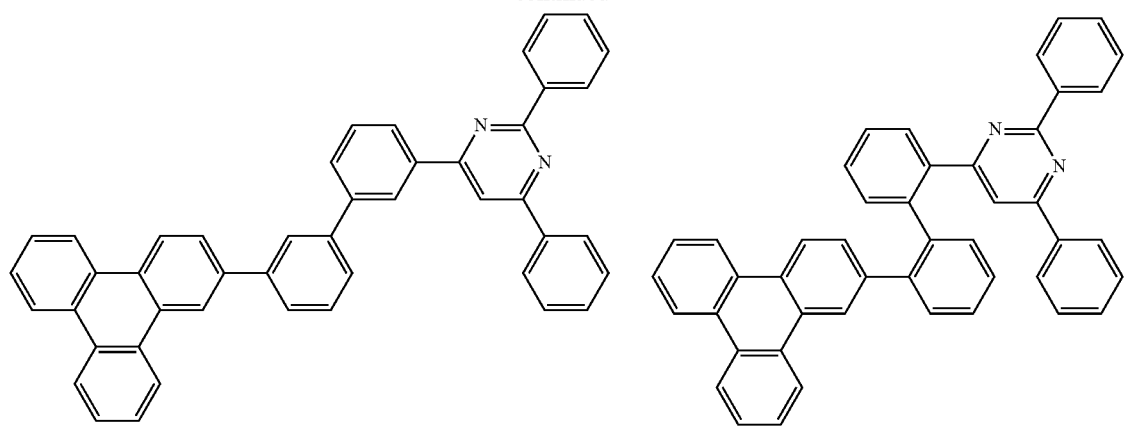
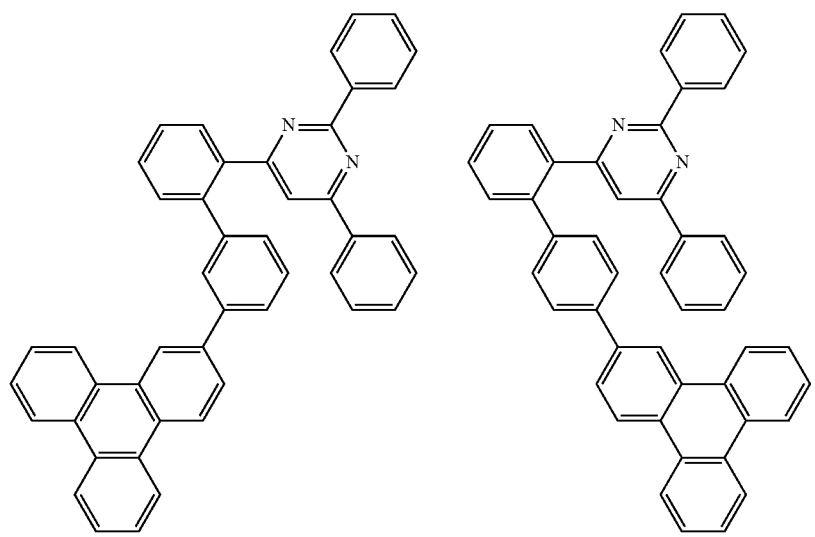
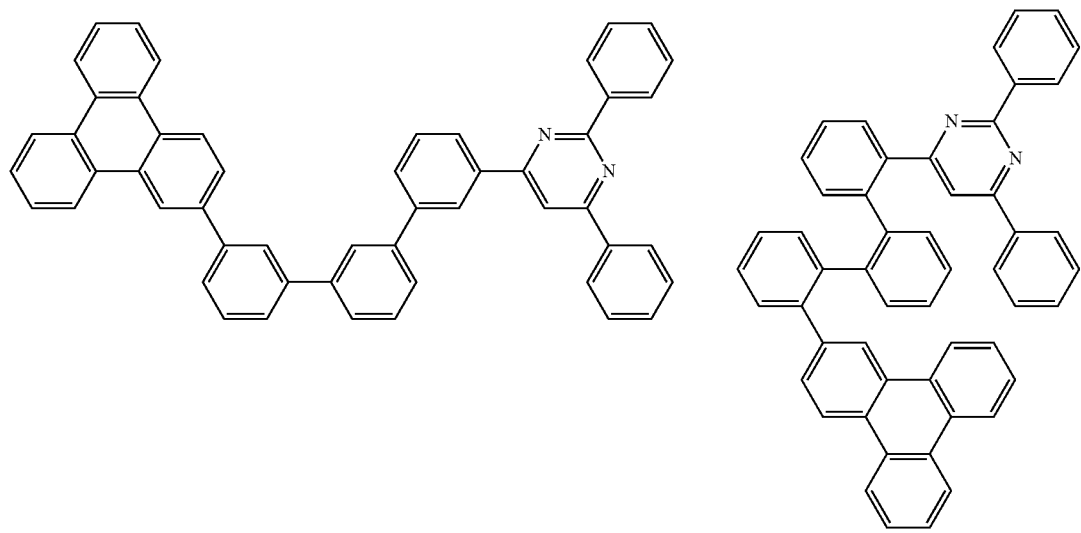

225
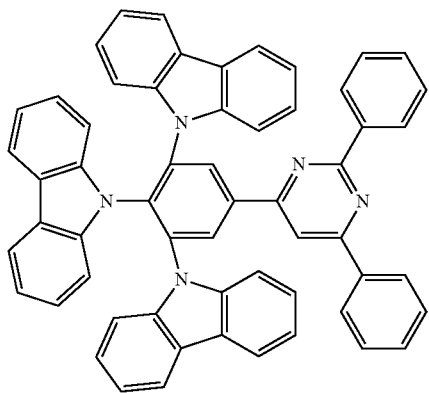
226
-continued
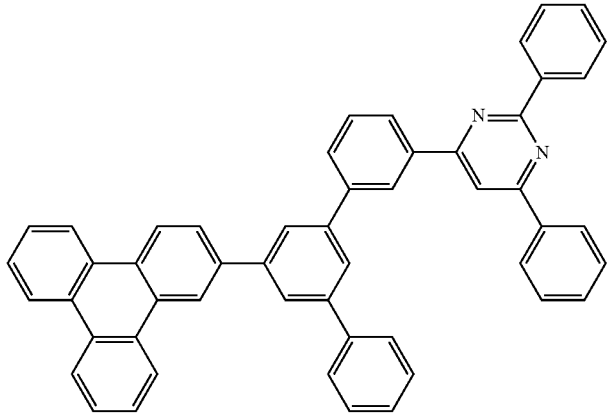
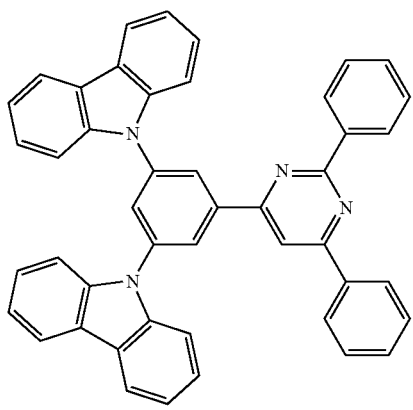
-continued
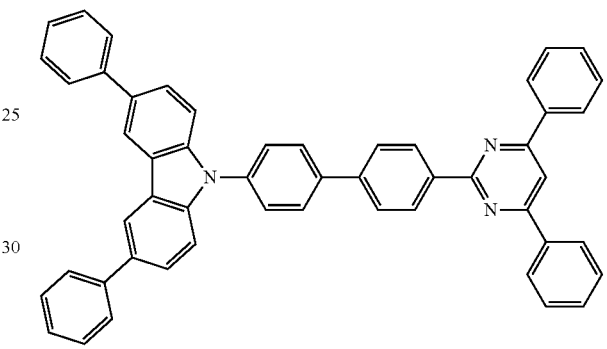
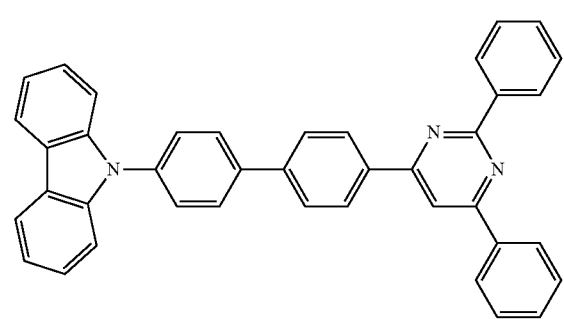
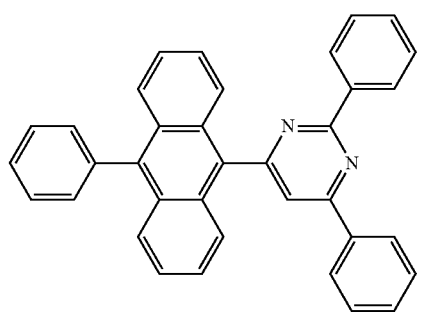
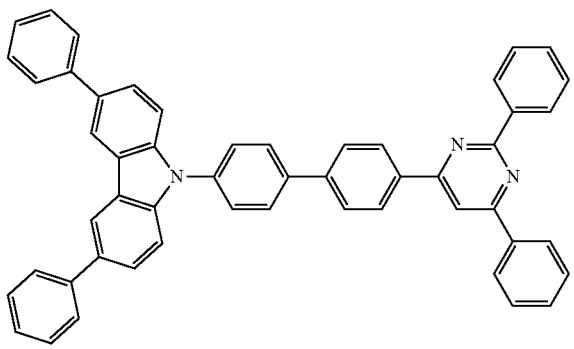
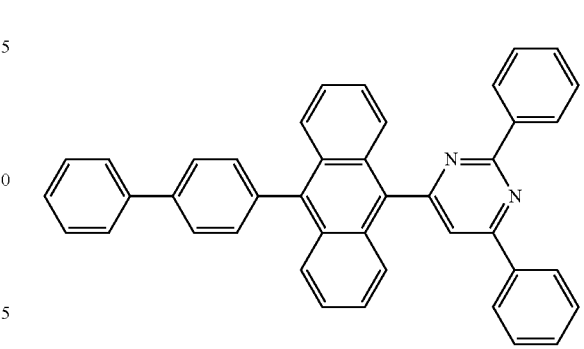

227
-continued
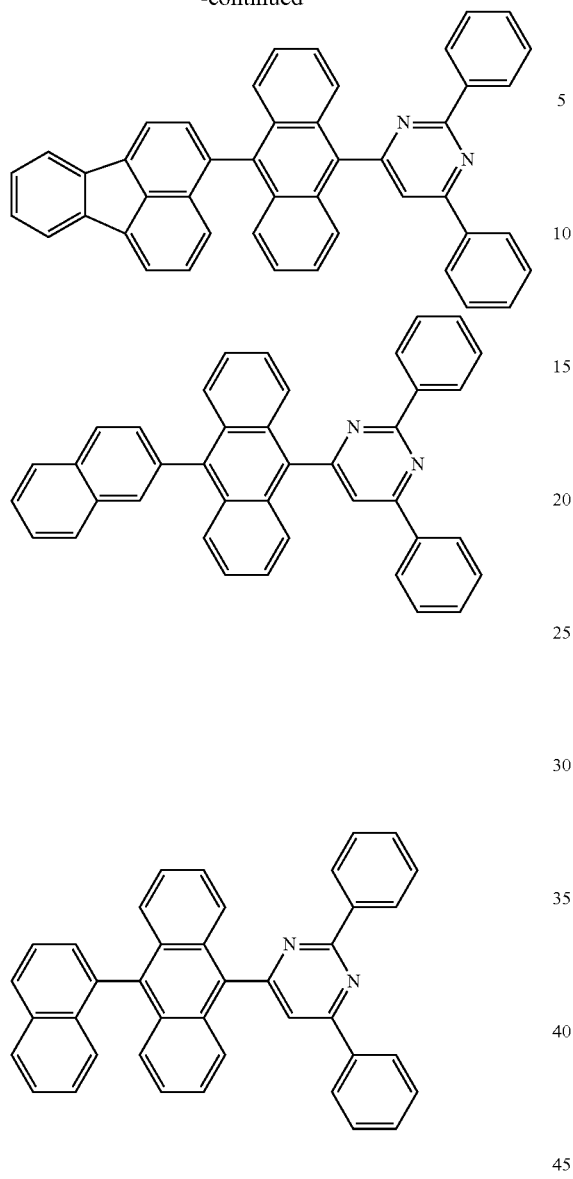
228
-continued
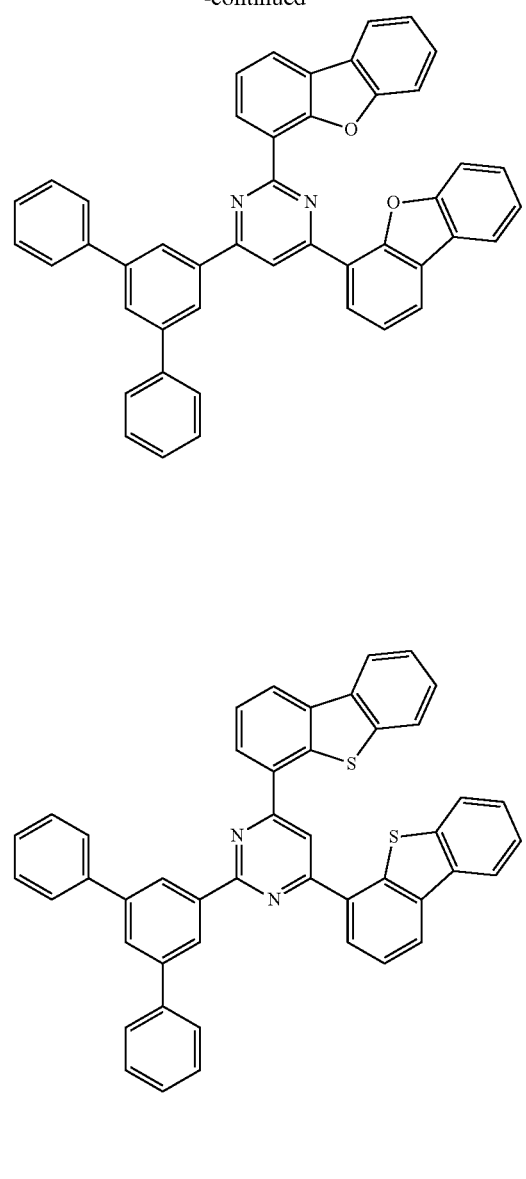
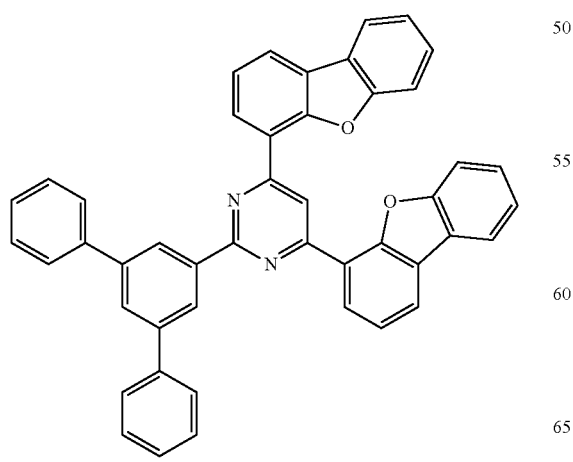

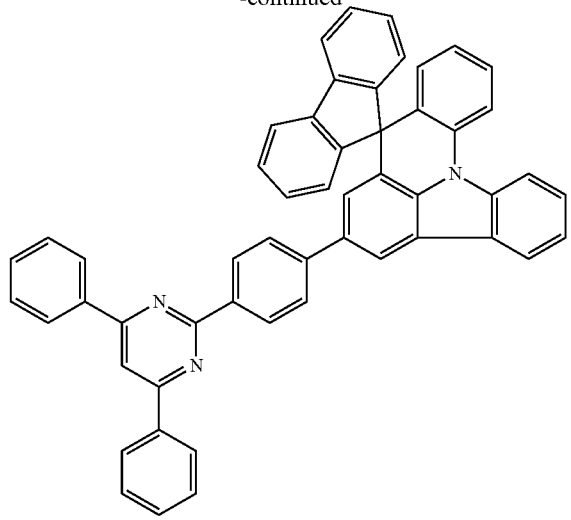
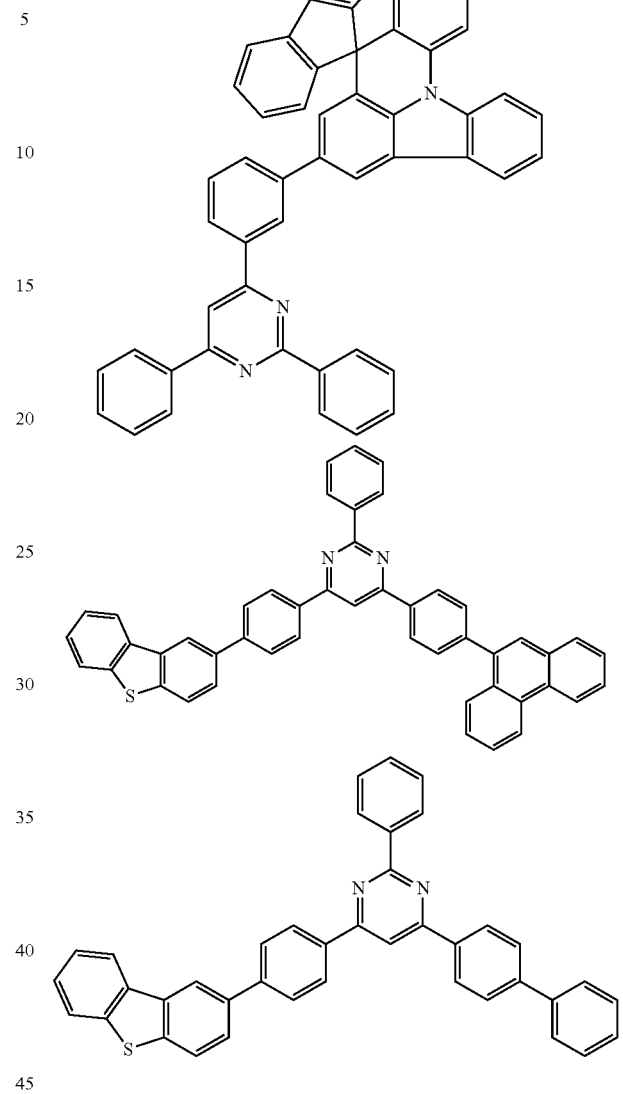
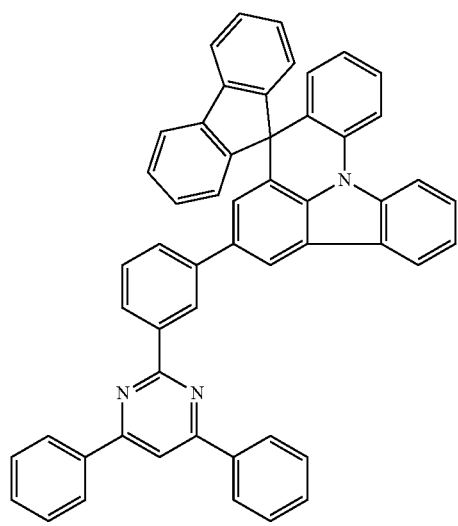

231
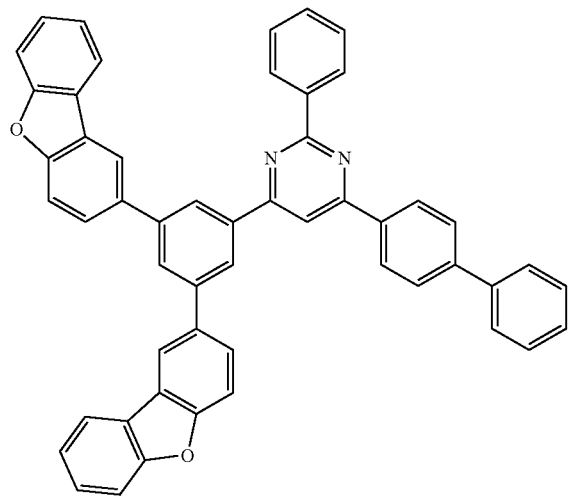
232
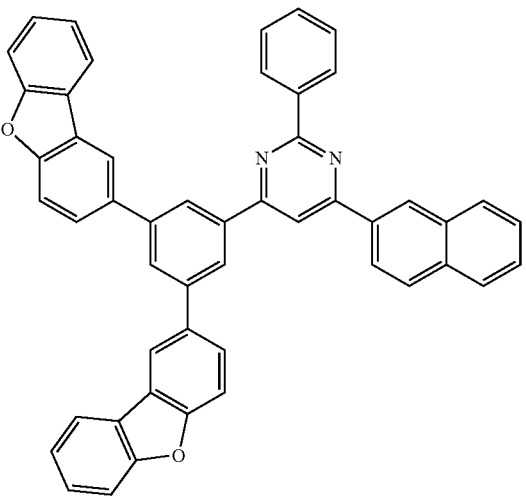
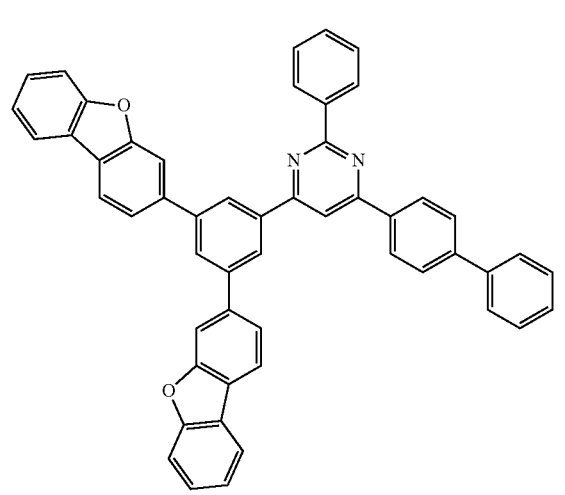
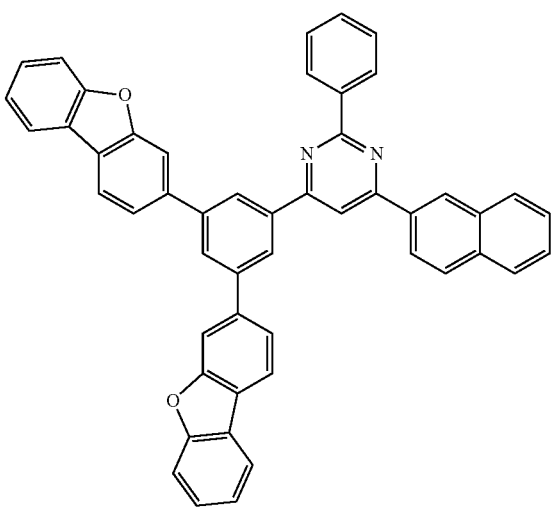
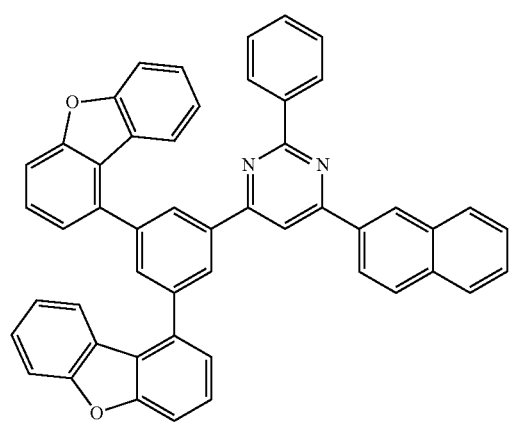
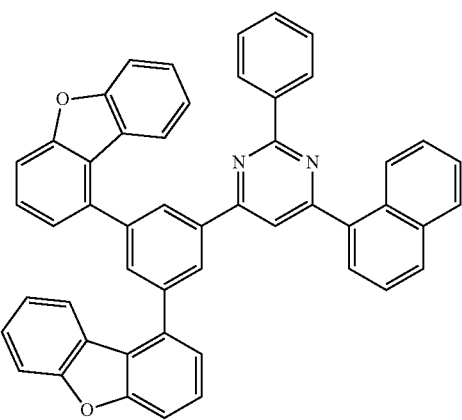

233
-continued
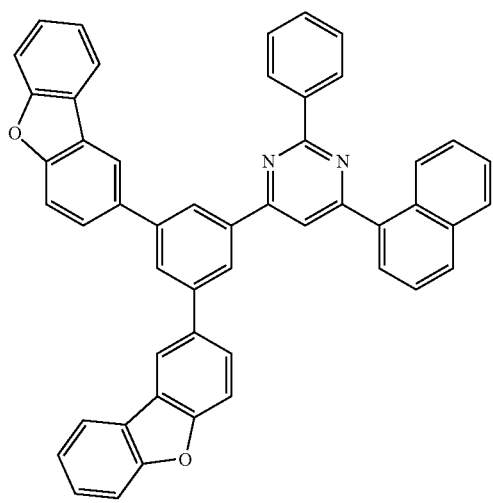
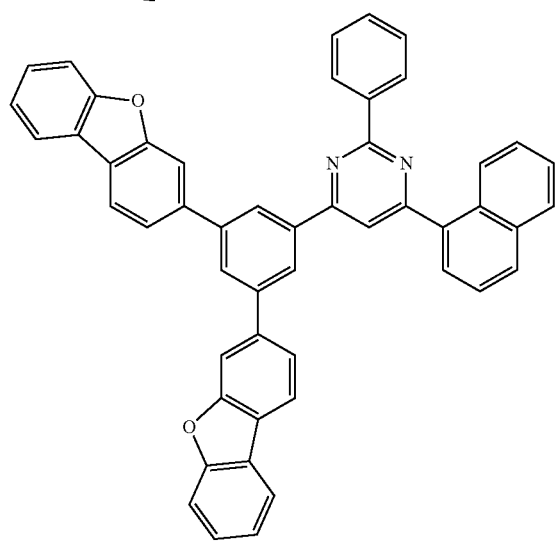
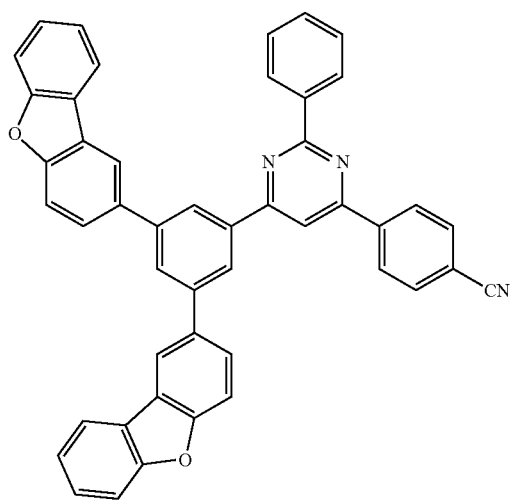
234
-continued
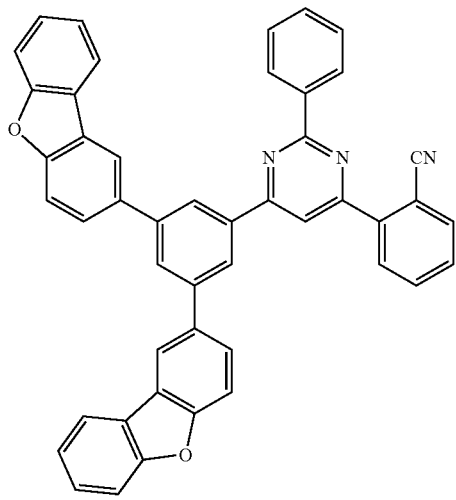
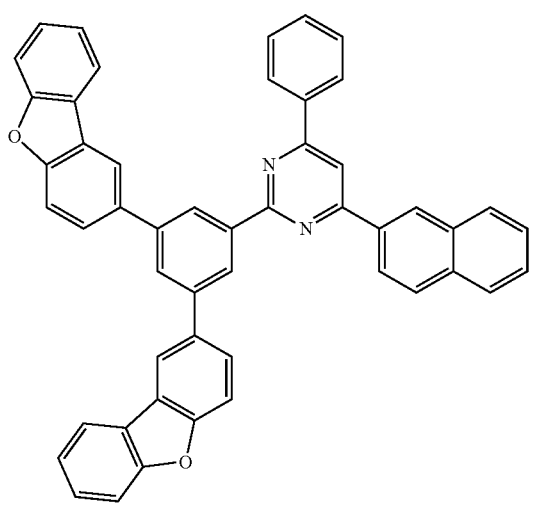
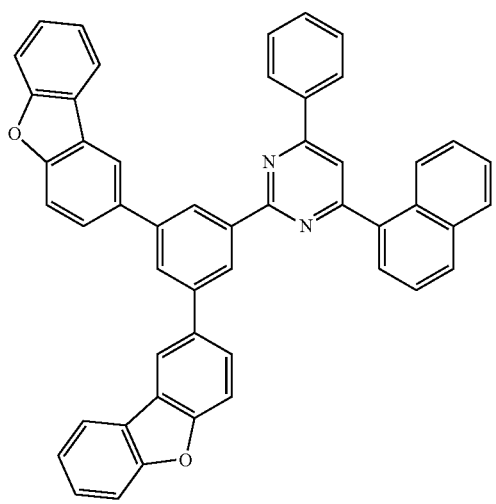

235
-continued
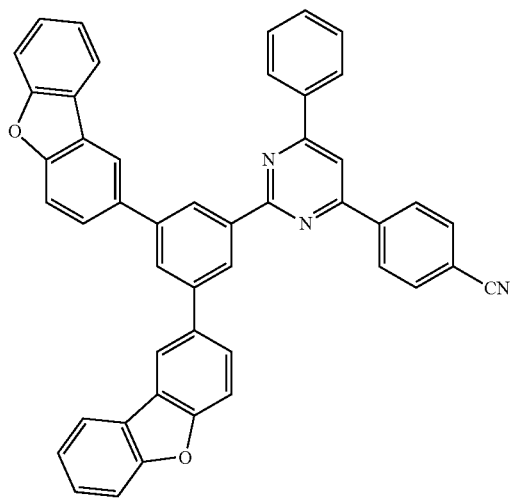
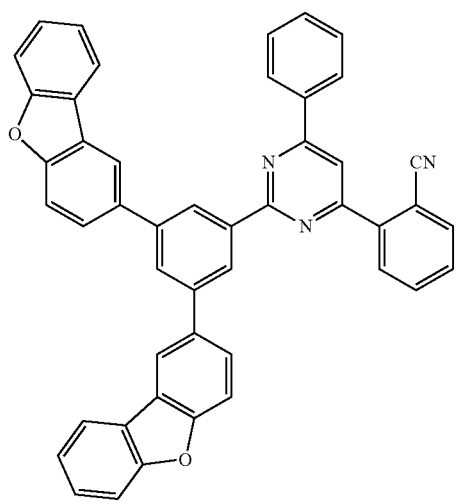
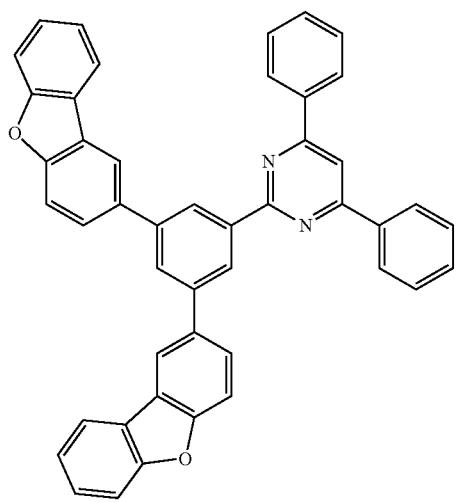
236
-continued
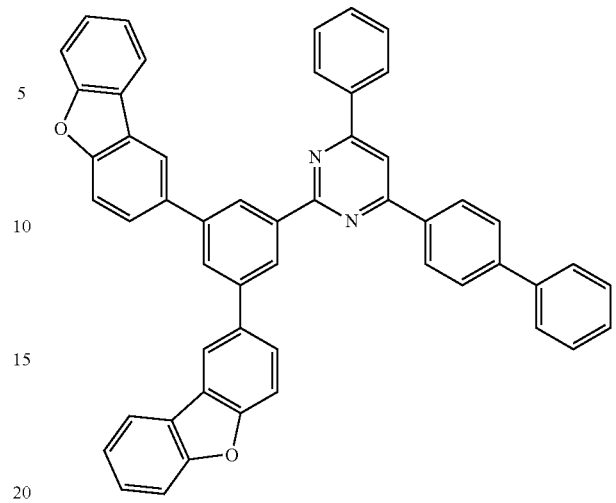
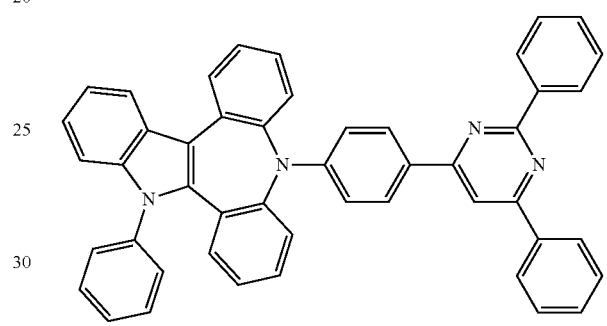
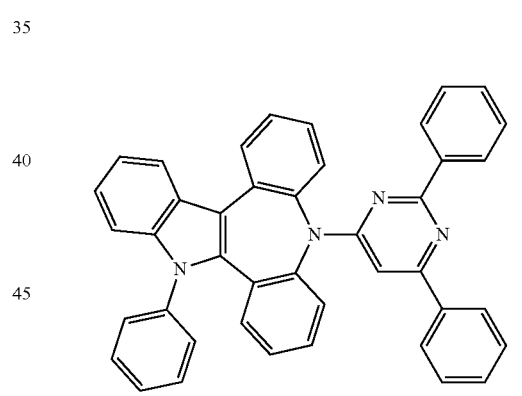
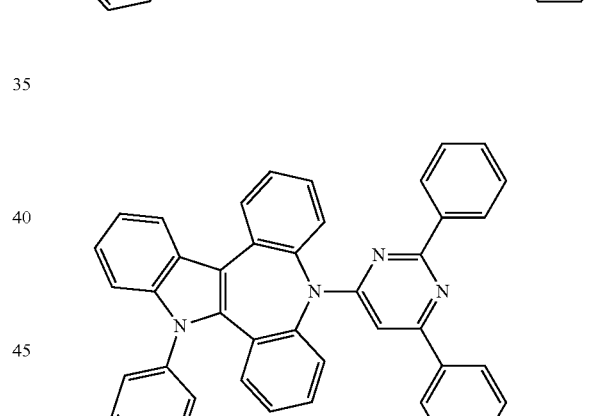

237
-continued
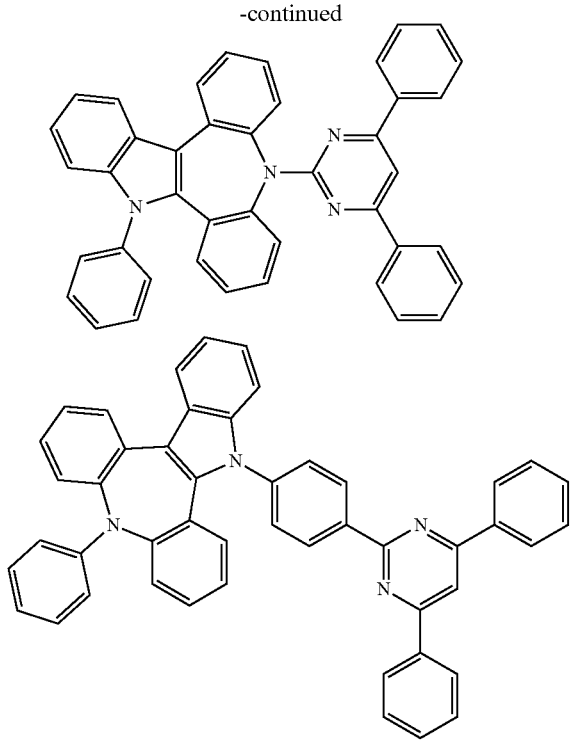
238
-continued
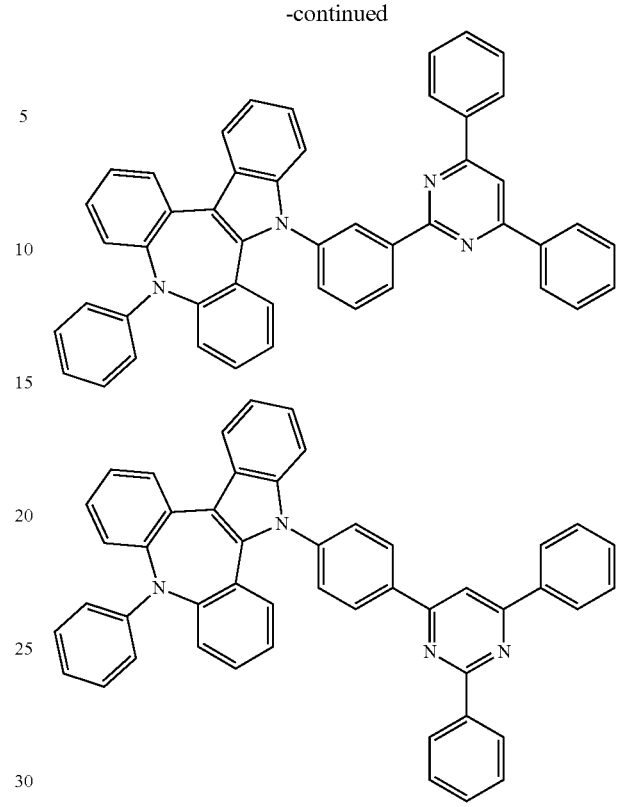
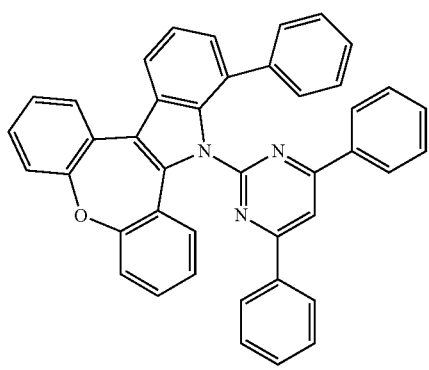
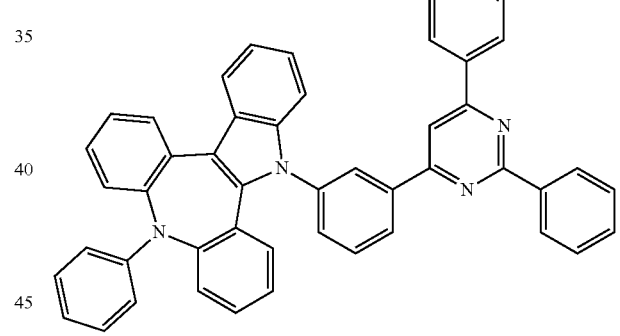
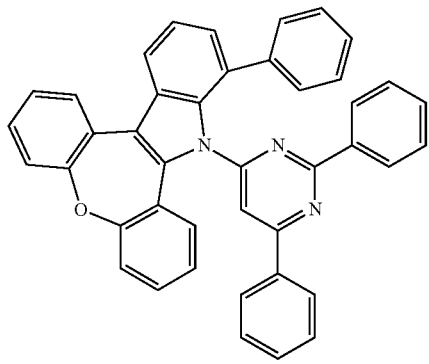
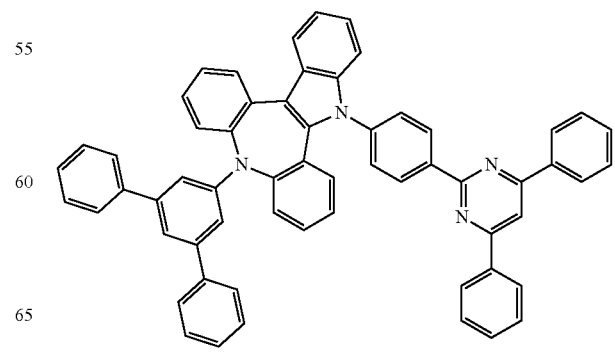

239
-continued
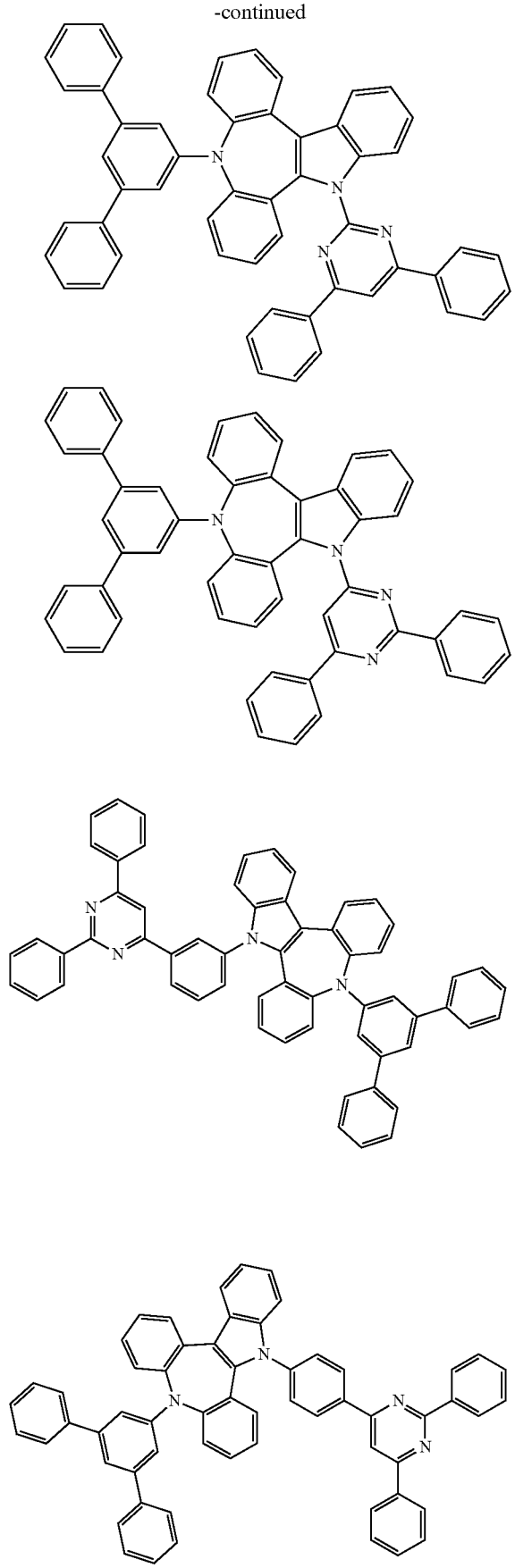
240
-continued
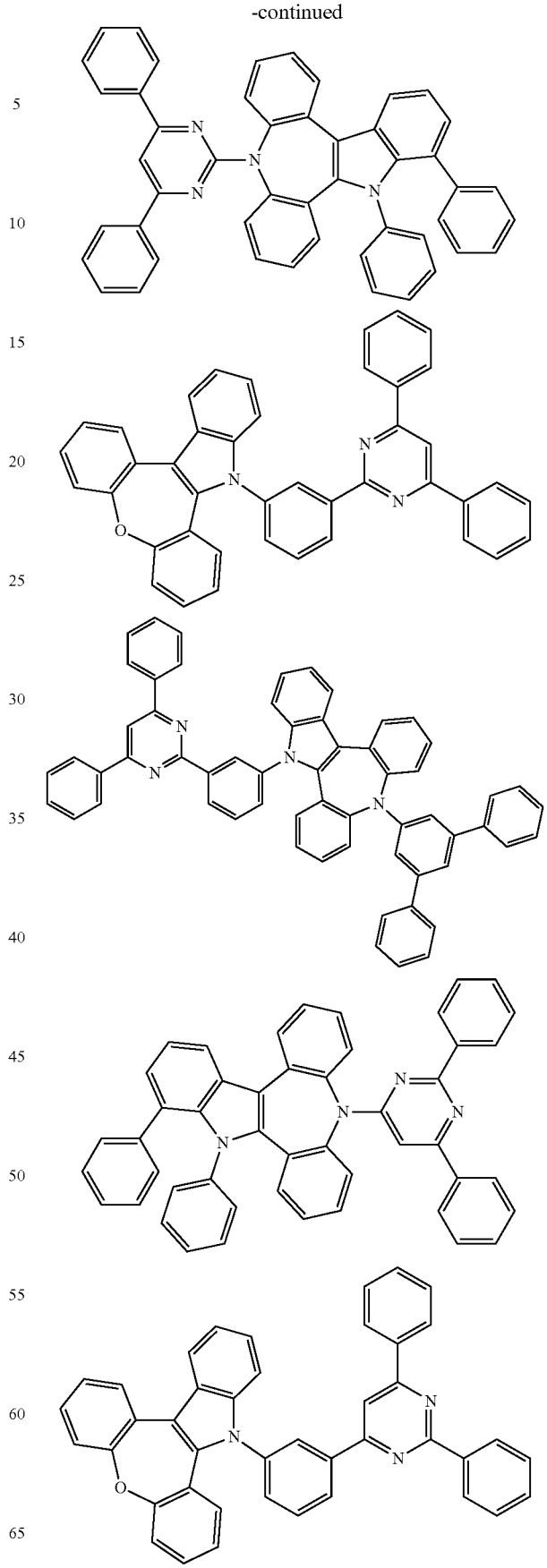

241
-continued
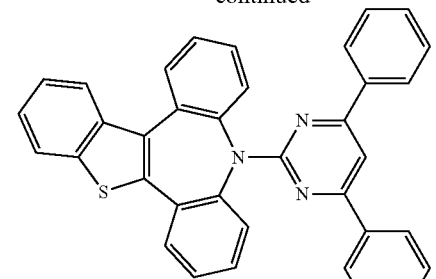
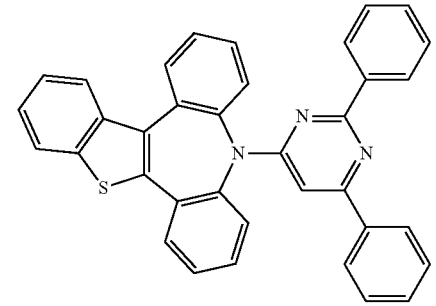
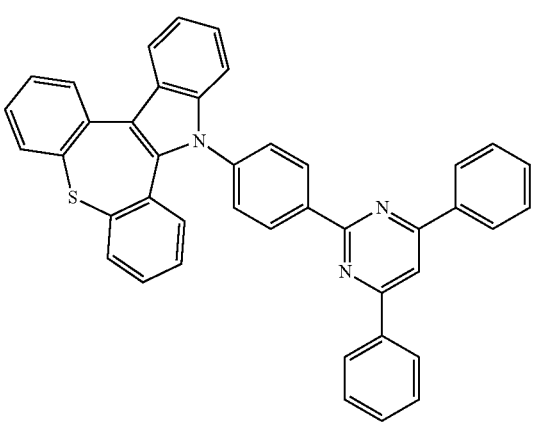
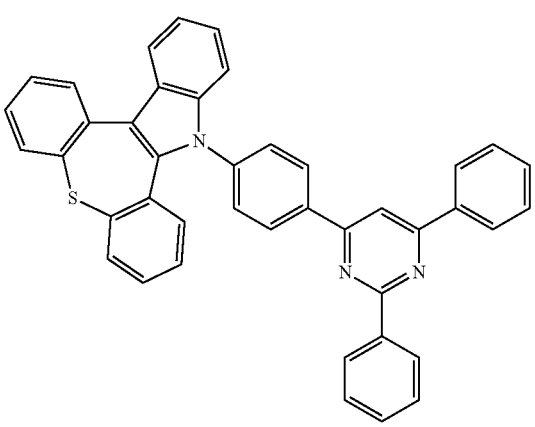
242
-continued
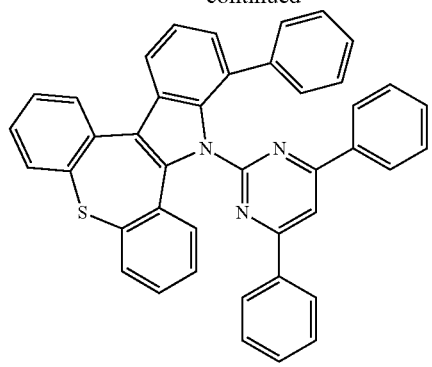
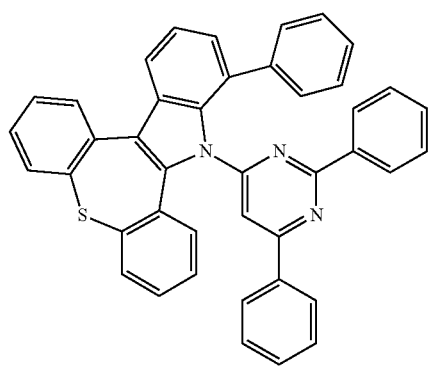
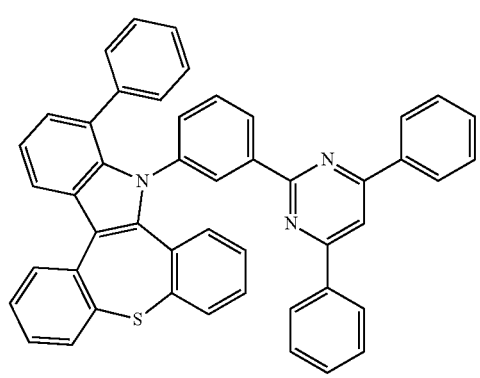
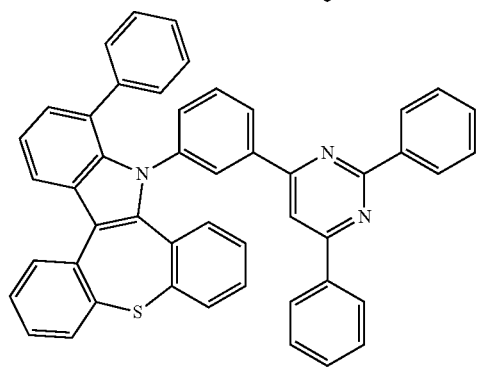

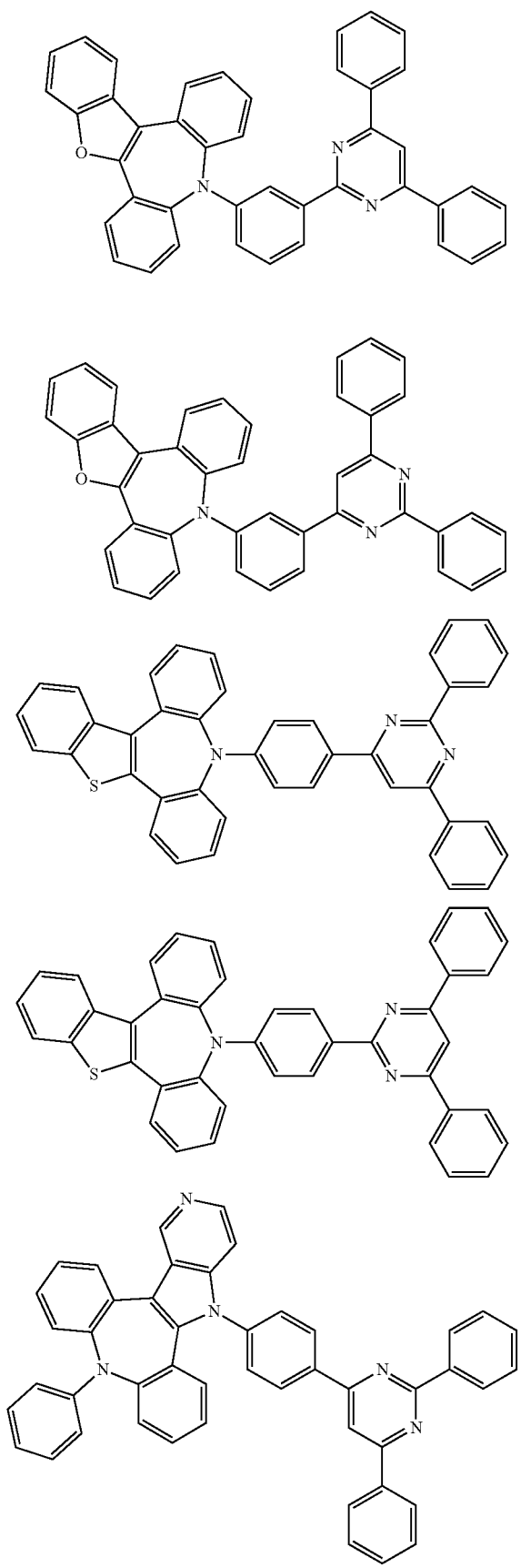

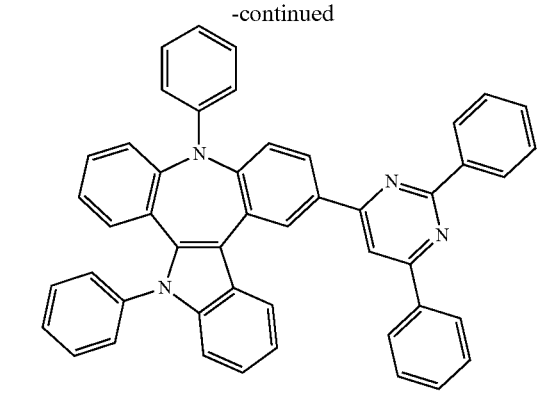
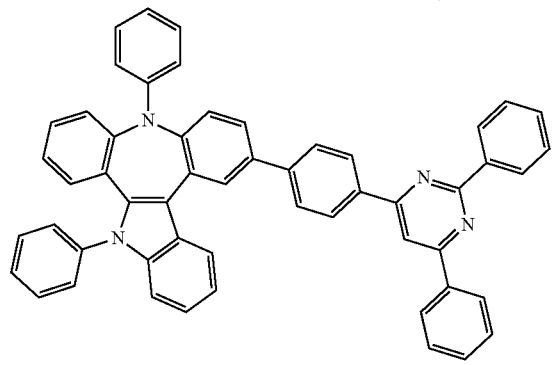
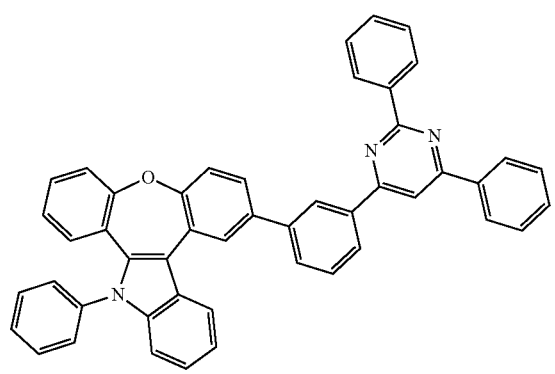
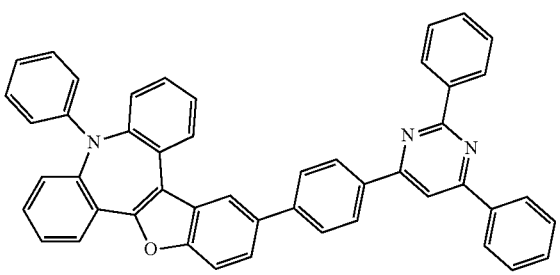
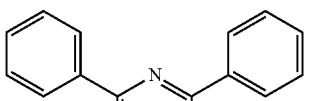
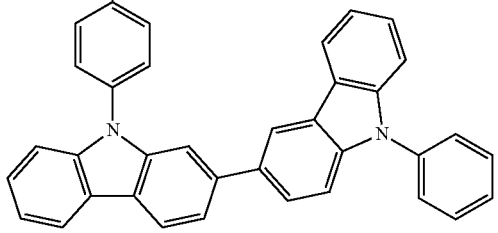
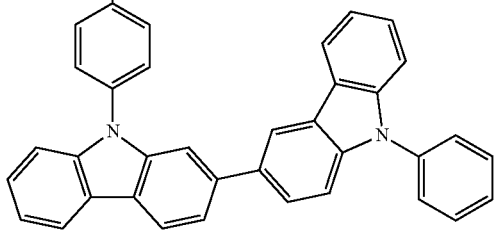
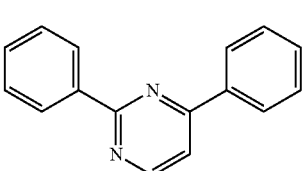
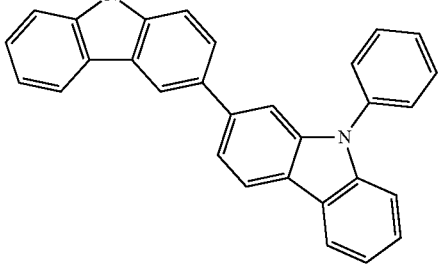

247
-continued
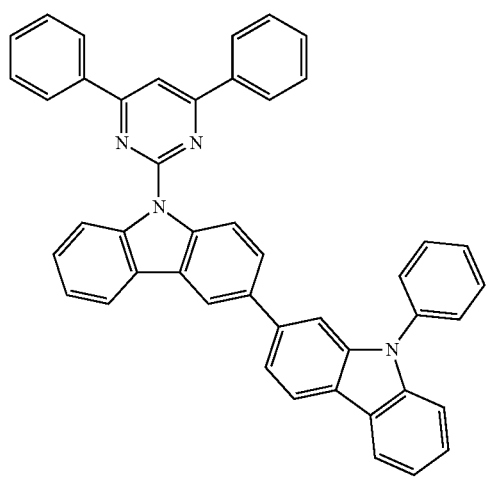
248
-continued
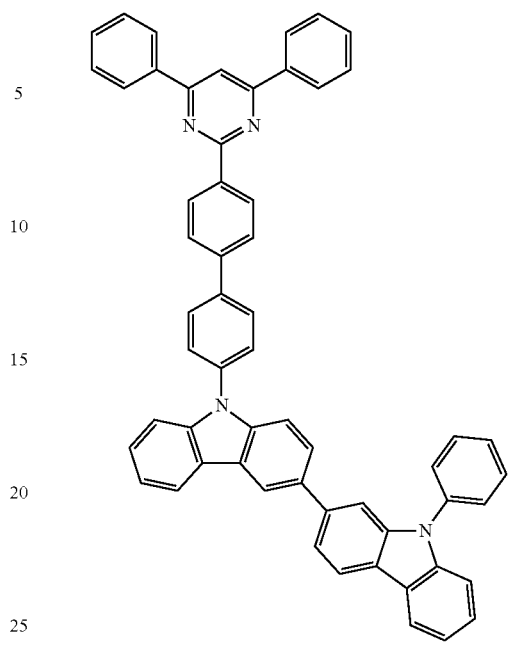
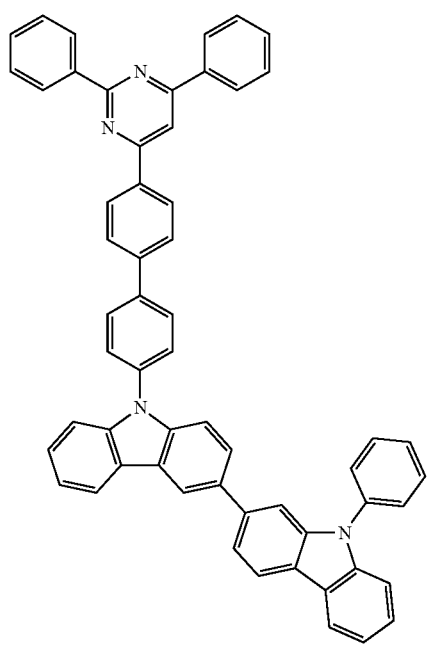
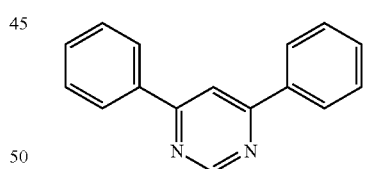
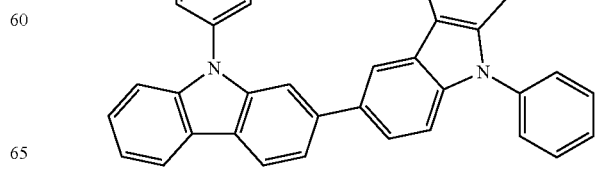

249
-continued
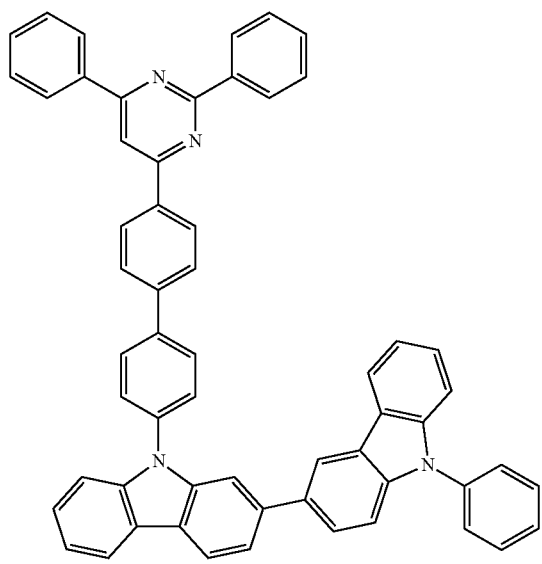
250
-continued
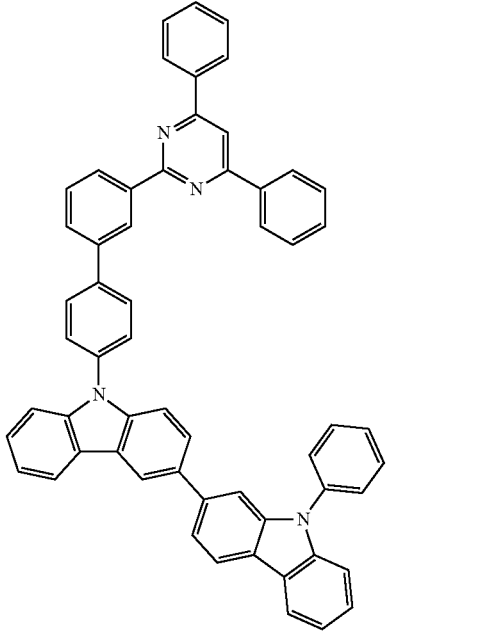
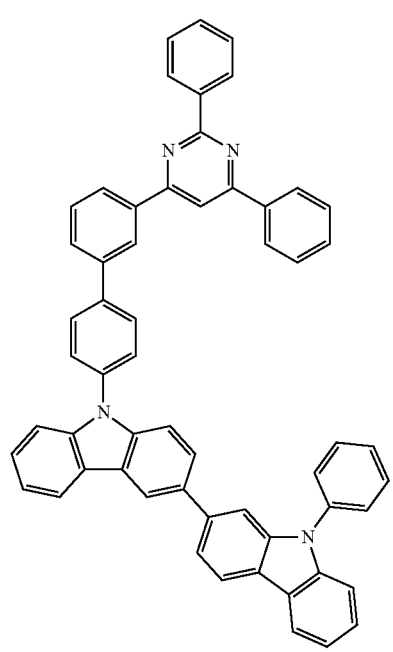
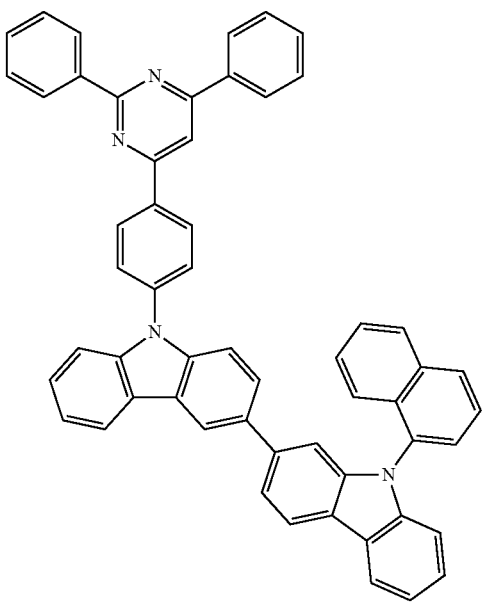

251
-continued
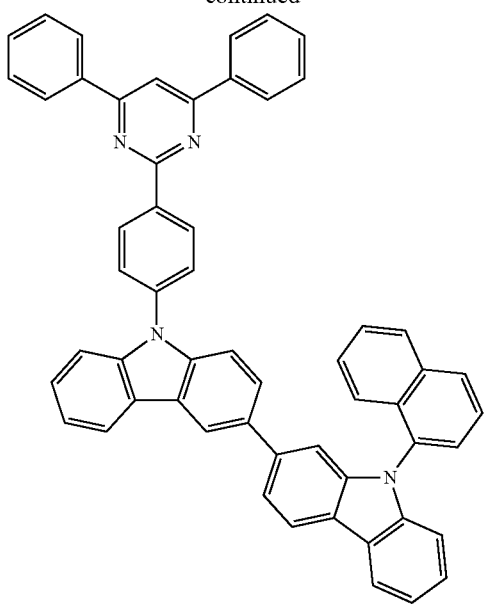
252
-continued
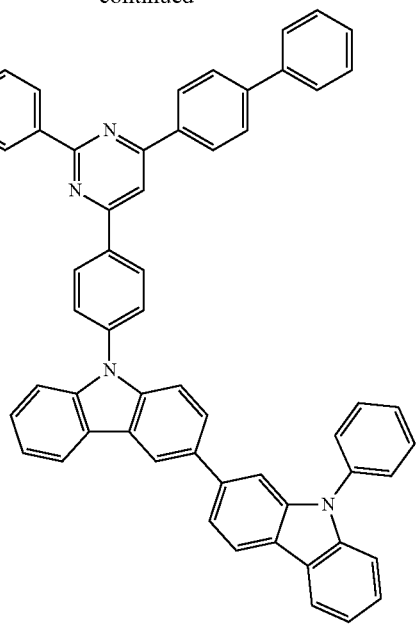
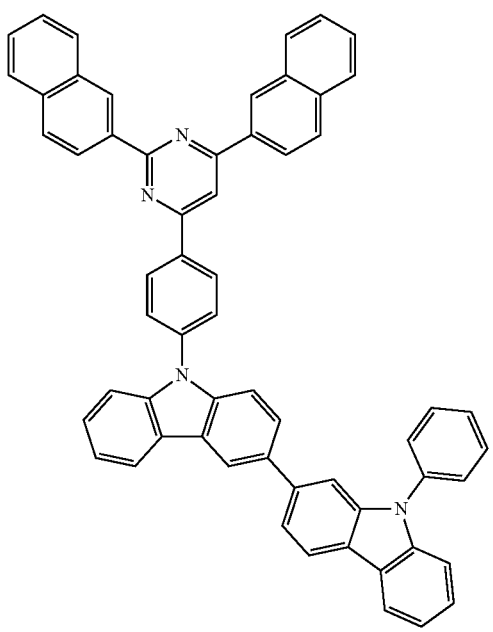
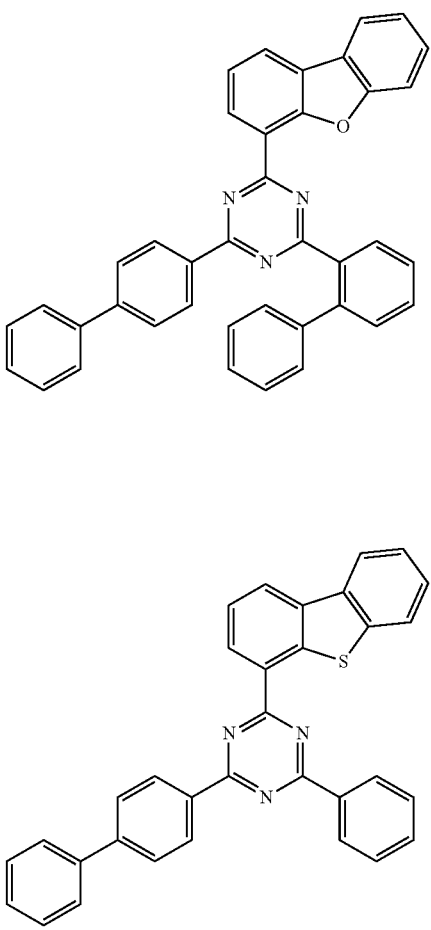

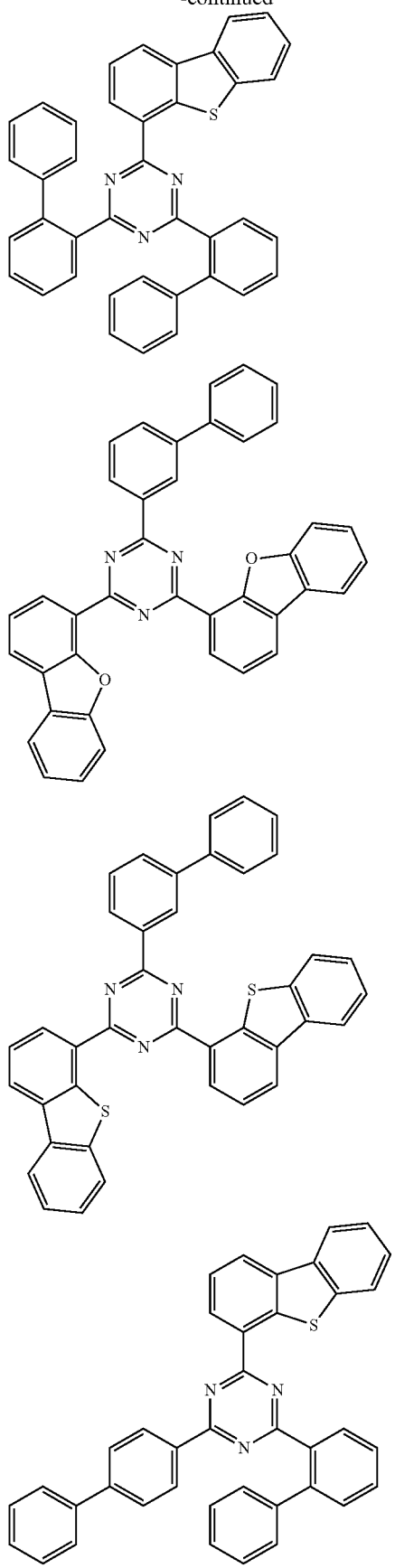
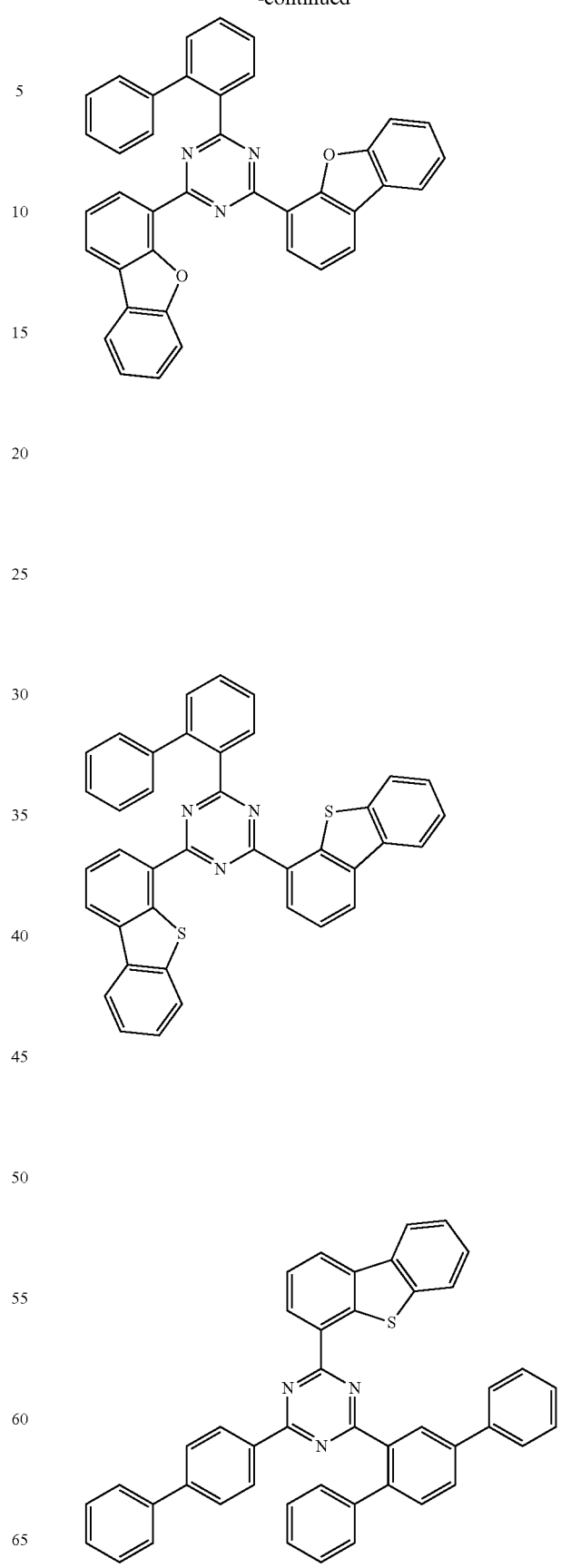

255
-continued
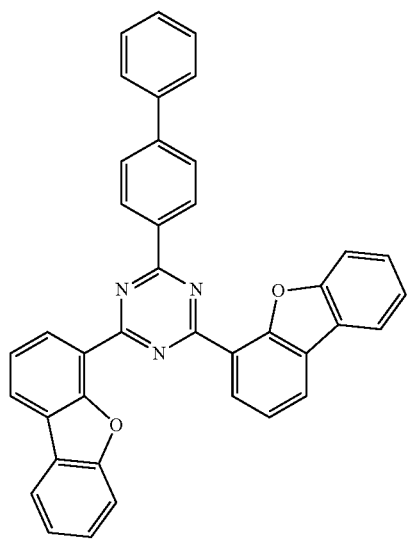
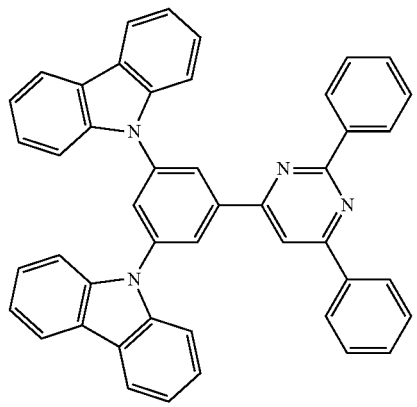
aET-3
256
-continued
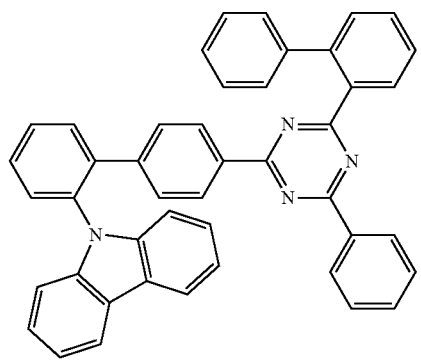
aET-6
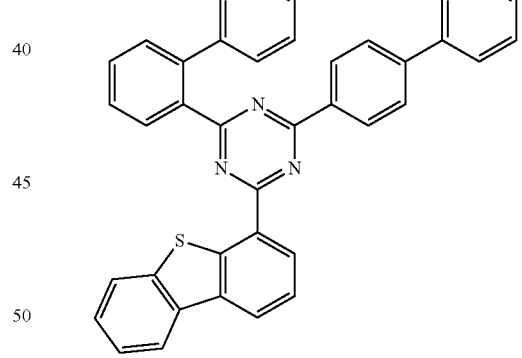
bET-1
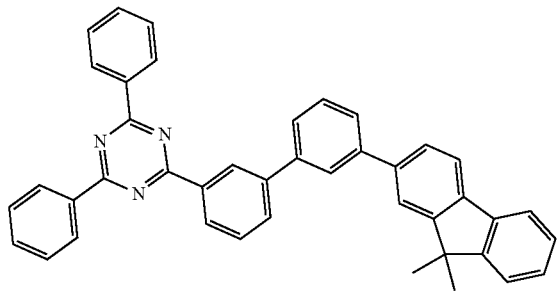
aET-1
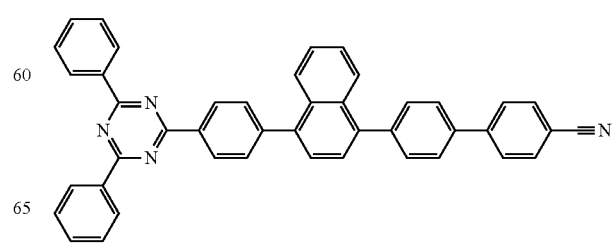
bET-2

In one embodiment, a second layer is disposed between the cathode and the first layer.

That is, the organic EL device of this embodiment has a layer configuration of at least cathode/second layer/first layer/emitting layer/anode. The second layer may or may not contain the compound represented by the formula (BE1).

<Compound Represented by the Formula (EB1)>

In one embodiment, the second layer contains a compound represented by the following formula (EB1)

(EB1)

In the formula (EB1),
$XEB_1$ is O, S, or $CR_{41}R_{42}$;
$R_{41}$ and $R_{42}$ are independently
a hydrogen atom,
a cyano group,
a substituted or unsubstituted alkyl group including 1 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
a substituted or unsubstituted aryl group including 6 to 50 ring carbon atoms, or
a substituted or unsubstituted monovalent heterocyclic group including 5 to 50 ring atoms;
$R_{901}$ to $R_{904}$ are as defined in the formula (1);
$YE_1$, $YE_2$, and $YE_3$ are independently CH or N;
provided that two or more of $YE_1$, $YE_2$, and $YE_3$ are N;
$ArE_1$, $ArE_3$, and $ArE^5$ are independently
a single bond,
a substituted or unsubstituted phenylene group,
a substituted or unsubstituted naphthylene group,
a substituted or unsubstituted phenanthrylene group, or
a substituted or unsubstituted anthrylene group;
$ArE_2$ and $ArE_4$ are independently
a substituted or unsubstituted phenyl group,
a substituted or unsubstituted naphthyl group,
a substituted or unsubstituted phenanthryl group, or
a substituted or unsubstituted anthryl group;
$ArE_1$ and $ArE_2$, and $ArE_3$ and $ArE_4$ independently form a substituted or unsubstituted, saturated or unsaturated ring constituted only by a 6-membered ring by bonding with each other, or do not form a ring.

In one embodiment, the compound represented by the formula (EB1) is the compound represented by the following formula (EB2).

(EB2)

In the formula (EB2), $YE_1$ to $YE_3$, $ArE_1$ to $ArE_4$, and $XEB_1$ are as defined in the formula (EB1).

In one embodiment, the compound represented by the formula (EB1) is the compound represented by the following formula (EB4).

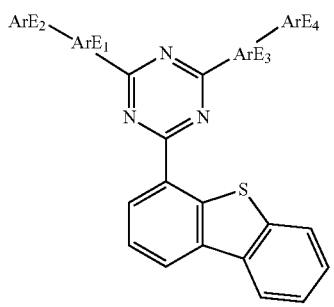

(EB4)

In the formula (EB4), $ArE_1$ to $ArE_4$ are as defined in the formula (EB1).

In one embodiment, $ArE_1$ and $ArE_2$, and $ArE_3$ and $ArE_4$ do not form a ring by bonding with each other, respectively.

In one embodiment, $ArE_2$ and $ArE_4$ are independently an unsubstituted phenyl group, an unsubstituted naphthyl group, an unsubstituted anthryl group, or an unsubstituted phenanthryl group.

In one embodiment, the compound represented by the formula (EB1) is the compound represented by the following formula (EB5).

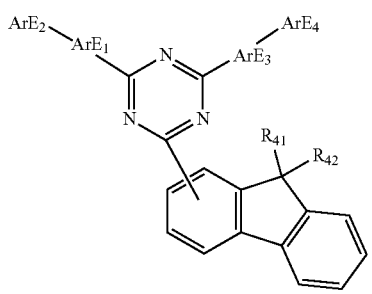

(EB5)

In the formula (EB5), $ArE_1$ to $ArE_4$, $R_{41}$, and $R_{42}$ are as defined in the formula (EB1).

In one embodiment, $ArE_1$ and $ArE_3$ are independently a single bond, an unsubstituted p-phenylene group, or an unsubstituted 1,4-naphthylene group.

Specific examples of the compound represented by the formula (EB1) are described below, but are not limited to these specific example compounds.

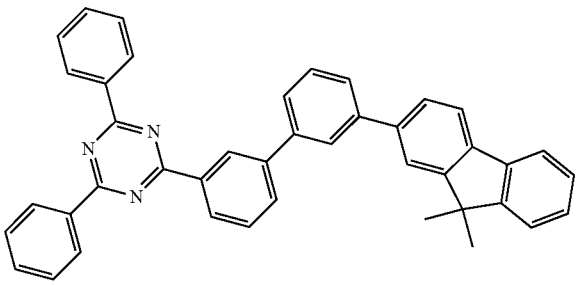

aET-1

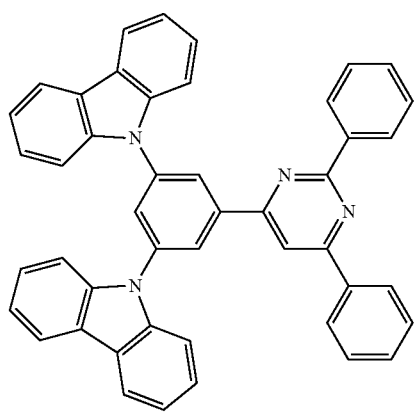

aET-3

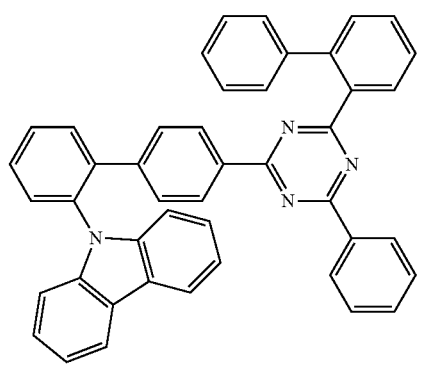

aET-6

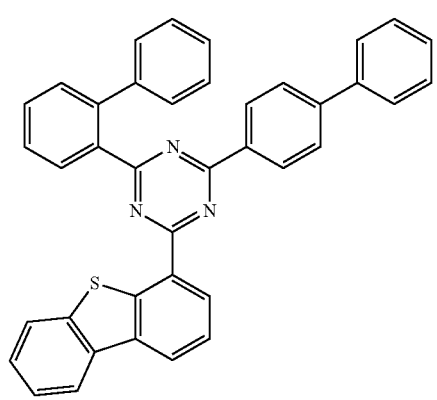

bET-1

-continued

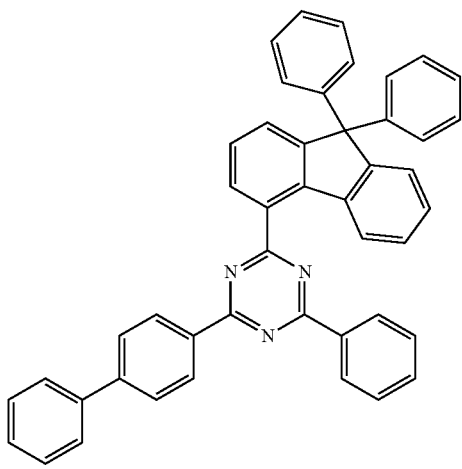

bET-3

In one embodiment, the organic layer further contains a third layer,
the third layer is disposed between the anode and the emitting layer; and
the third layer contains the compound represented by the following formula (B1).

That is, the organic EL device of this embodiment has a layer configuration of at least cathode/first layer/emitting layer/third layer/anode.

<Compound Represented by the Formula (B1)>

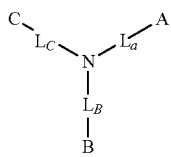

(B1)

In the formula (B1), $L_A$, $L_B$, and $L_C$ are independently a single bond, a substituted or unsubstituted arylene group including 6 to 50 ring carbon atoms, or a substituted or unsubstituted divalent heterocyclic group including 5 to 50 ring atoms;

A, B, and C are independently
a substituted or unsubstituted aryl group including 6 to 50 ring carbon atoms,
a substituted or unsubstituted monovalent heterocyclic group including 5 to 50 ring atoms, or
—Si(R'$_{901}$) (R'$_{902}$) (R'$_{903}$);

R'$_{901}$ to R'$_{903}$ are independently a substituted or unsubstituted aryl group including 6 to 50 ring carbon atoms; and when two or more of each of R'$_{901}$ to R'$_{903}$ are present, the two or more of each of R'$_{901}$ to R'$_{903}$ are the same or different.

In one embodiment, the third layer contains a compound represented by the formula (B1).

In one embodiment, $L_A$, $L_B$, and $L_C$ are independently a single bond, or a substituted or unsubstituted arylene group including 6 to 12 ring carbon atoms.

In one embodiment, $L_C$ is a phenylene group.

In one embodiment, A is a substituted or unsubstituted aryl group including 6 to 12 ring carbon atoms.

In one embodiment, A is
a substituted or unsubstituted phenyl group,
a substituted or unsubstituted biphenyl group, or
a substituted or unsubstituted naphthyl group.

In one embodiment, A is
an unsubstituted phenyl group,
an unsubstituted biphenyl group, or
an unsubstituted naphthyl group.

In one embodiment, B is a substituted or unsubstituted aryl group including 6 to 12 ring carbon atoms.

In one embodiment, B is
a substituted or unsubstituted phenyl group,
a substituted or unsubstituted biphenyl group, or
a substituted or unsubstituted naphthyl group.

In one embodiment, B is
an unsubstituted phenyl group,
an unsubstituted biphenyl group, or
an unsubstituted naphthyl group.

Specific examples of the compound represented by the formula (B1) are described below, but are not limited to these specific example compounds.

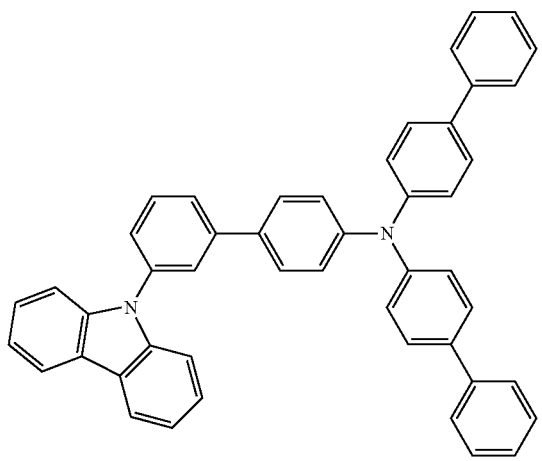

EBL-1

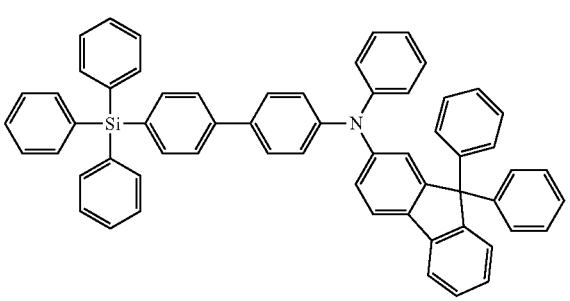

EBL-3

EBL-5
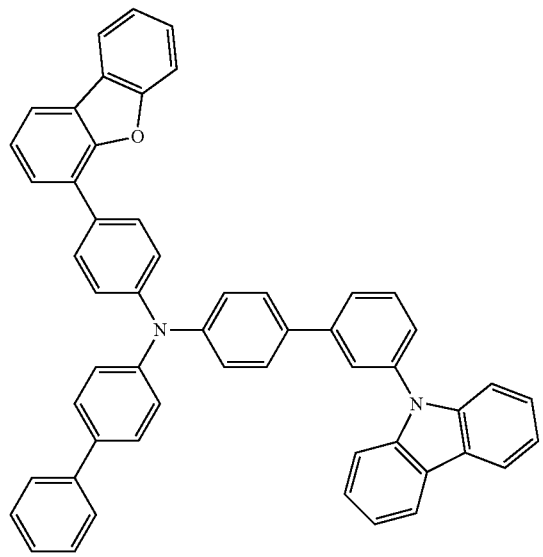
HT-1
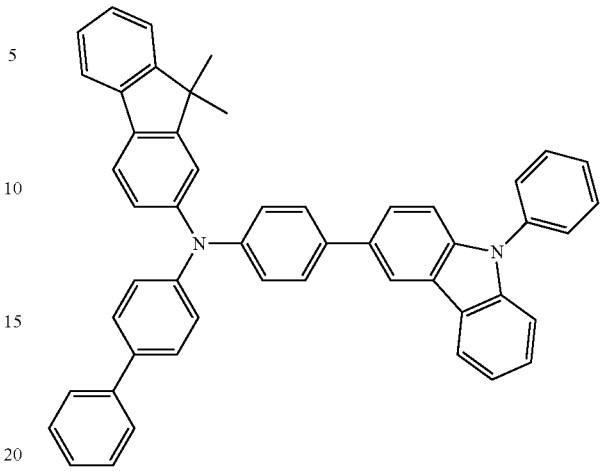
EBL-6
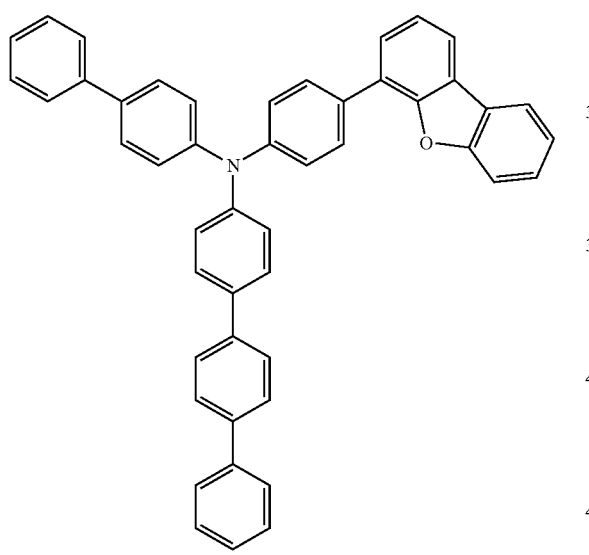
HT-2
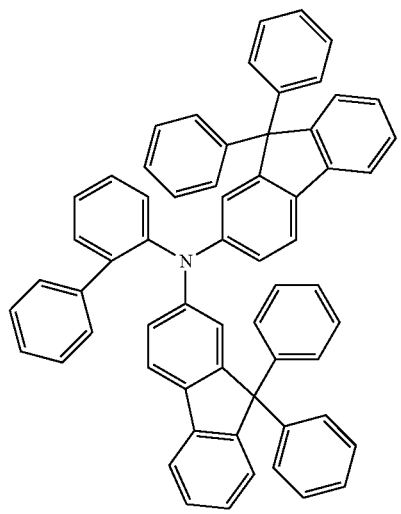
EBL-8
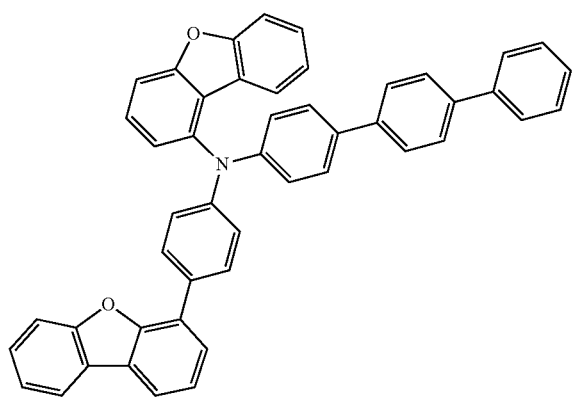
HT-4
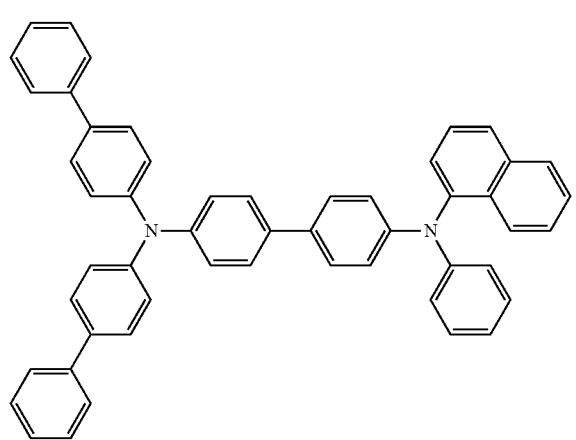

HT-5

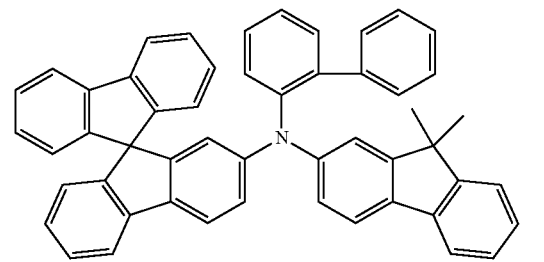

HT-6

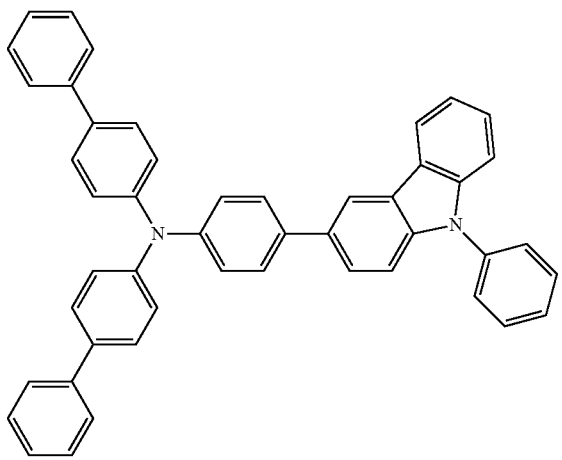

In one embodiment, the substituent in the case of "substituted or unsubstituted" in each of the formulas is selected from the group consisting of
an unsubstituted alkyl group including 1 to 50 carbon atoms,
an unsubstituted alkenyl group including 2 to 50 carbon atoms,
an unsubstituted alkynyl group including 2 to 50 carbon atoms,
an unsubstituted cycloalkyl group including 3 to 50 ring carbon atoms,
—Si($R_{901}$)($R_{902}$)($R_{903}$),
—O—($R_{904}$),
—S—($R_{903}$),
—N($R_{906}$)($R_{907}$),
a halogen atom, a cyano group, a nitro group,
an unsubstituted aryl group including 6 to 50 ring carbon atoms, or
an unsubstituted monovalent heterocyclic group including 5 to 50 ring atoms, wherein
$R_{901}$ to $R_{907}$ are independently
a hydrogen atom,
a substituted or unsubstituted alkyl group including 1 to 50 carbon atoms,
a substituted or unsubstituted aryl group including 6 to 50 ring carbon atoms, or
a substituted or unsubstituted monovalent heterocyclic group including 5 to 50 ring atoms;
when two or more of each of $R_{901}$ to $R_{907}$ are present, the two or more of each of $R_{901}$ to $R_{907}$ are the same or different.
In one embodiment, the substituent in the case of "substituted or unsubstituted" is
an unsubstituted alkyl group including 1 to 50 carbon atoms,
an unsubstituted alkenyl group including 2 to 50 carbon atoms,
an unsubstituted alkynyl group including 2 to 50 carbon atoms,
an unsubstituted cycloalkyl group including 3 to 50 ring carbon atoms,
—Si($R_{901a}$)($R_{902a}$)($R_{903a}$),
—O—($R_{904a}$),
—S—($R_{903a}$),
—N($R_{906a}$)($R_{907a}$),
a halogen atom, a cyano group, a nitro group,
an unsubstituted aryl group including 6 to 50 ring carbon atoms, or
an unsubstituted monovalent heterocyclic group including 5 to 50 ring atoms, wherein
$R_{901a}$ to $R_{907a}$ are independently
a hydrogen atom,
an unsubstituted alkyl group including 1 to 50 carbon atoms,
an unsubstituted aryl group including 6 to 50 ring carbon atoms, or
an unsubstituted monovalent heterocyclic group including 5 to 50 ring atoms; when two or more of each of $R_{901a}$ to $R_{907a}$ are present, the two or more of each of $R_{901a}$ to $R_{907a}$ are the same or different.
In one embodiment, the substituent in the case of "substituted or unsubstituted" is an unsubstituted alkyl group including 1 to 50 carbon atoms,
an unsubstituted aryl group including 6 to 50 ring carbon atoms, or
an unsubstituted monovalent heterocyclic group including 5 to 50 ring atoms.
In one embodiment, the substituent in the case of "substituted or unsubstituted" is an unsubstituted alkyl group including 1 to 18 carbon atoms,
an unsubstituted aryl group including 6 to 18 ring carbon atoms, or
an unsubstituted monovalent heterocyclic group including 5 to 18 ring atoms.
In one embodiment, the substituent in the case of "substituted or unsubstituted" is an unsubstituted alkyl group including 1 to 5 carbon atoms.

Hereinafter, a layer configuration of the organic EL device according to an aspect of the invention will be described.

The organic EL device according to an aspect of the invention has an organic layer between a pair of electrodes that are the cathode and the anode. The organic layer contains at least one layer containing an organic compound. Alternatively, the organic layer is formed by stacking a plurality of layers containing an organic compound. The organic layer may have a layer consisting only of one or a plurality of organic compounds. The organic layer may have a layer containing an organic compound and an inorganic compound together. The organic layer may have a layer consisting only of one or a plurality of inorganic compounds.

At least one of the layers contained by the organic layer is an emitting layer. The organic layer may be formed, for example, as one layer of the emitting layer, or may contain other layers which can be adopted in the layer configuration of an organic EL device. Examples of the layers that may be employed in the layer configuration of the organic EL device include, but are not limited to, a hole-transporting region (e.g., a hole-transporting layer, a hole-injecting layer, an electron-blocking layer, an exciton-blocking layer, etc.) disposed between an anode and an emitting layer, an emitting layer, a space layer, and an electron-transporting region (e.g., an electron-transporting layer, an electron-injecting layer, a hole-blocking layer, etc.) disposed between a cathode and an emitting layer.

The organic EL device according to an aspect of the invention may be, for example, a monochromatic emitting device of a fluorescent or phosphorescent type, or a white emitting device of a fluorescent/phosphorescent hybrid type. In addition, it may be a simple type including a single light emitting unit or a tandem type including a plurality of light emitting units.

The "emitting unit" refers to the smallest unit which includes organic layers, in which at least one of the organic layers is an emitting layer, and which emits light by recombination of injected holes and electrons.

The "emitting layer" described in this specification is an organic layer having an emitting function. The emitting layer is, for example, a phosphorescent emitting layer, a fluorescent emitting layer, or the like, and may be a single layer or a plurality of layers.

The light-emitting unit may be of a stacked type including a plurality of a phosphorescent emitting layer and a fluorescent emitting layer, and in this case, for example, it may include a spacing layer between each emitting layer for preventing excitons generated by the phosphorescent emitting layer from diffusing into the fluorescent emitting layer.

The simple type organic EL device includes, for example, a device configuration such as anode/emitting unit/cathode.

Typical layer configurations of the emitting unit are shown below. The layers in parentheses are optional layers.

(a) (hole-injecting layer) hole-transporting layer/fluorescent emitting layer (/electron-transporting layer/electron-injecting layer)
(b) (hole-injecting layer) hole-transporting layer/phosphorescent emitting layer (/electron-transporting layer/electron-injecting layer)
(c) (hole-injecting layer/) hole-transporting layer/first fluorescent emitting layer/second fluorescent emitting layer (/electron-transporting layer/electron-injecting layer)
(d) (hole-injecting layer) hole-transporting layer/first phosphorescent emitting layer/second phosphorescent emitting layer (/electron-transporting layer/electron-injecting layer)
(e) (hole-injecting layer) hole-transporting layer/phosphorescent emitting layer/spacing layer/fluorescent emitting layer (/electron-transporting layer/electron-injecting layer)
(f) (hole-injecting layer/) hole-transporting layer/first phosphorescent emitting layer/second phosphorescent emitting layer/spacing layer/fluorescent emitting layer (/electron-transporting layer/electron-injecting layer)
(g) (hole-injecting layer) hole-transporting layer/first phosphorescent layer/spacing layer/second phosphorescent emitting layer/spacing layer/fluorescent emitting layer (/electron-transporting layer/electron-injecting layer)
(h) (hole-injecting layer) hole-transporting layer/phosphorescent emitting layer/spacing layer/first fluorescent emitting layer/second fluorescent emitting layer (/electron-transporting layer/electron-injecting layer)
(i) (hole-injecting layer/) hole-transporting layer/electron-blocking layer/fluorescent emitting layer (/electron-transporting layer/electron-injecting layer)
(j) (hole-injecting layer/) hole-transporting layer/electron-blocking layer/phosphorescent emitting layer (/electron-transporting layer/electron-injecting layer)
(k) (hole-injecting layer/) hole-transporting layer/exciton-blocking layer/fluorescent emitting layer (/electron-transporting layer/electron-injecting layer)
(l) (hole-injecting layer/) hole-transporting layer/exciton-blocking layer/phosphorescent emitting layer (/electron-transporting layer/electron-injecting layer)
(m) (hole-injecting layer/first hole-transporting layer/second hole-transporting layer/fluorescent emitting layer (/electron-transporting layer/electron-injecting layer)
(n) (hole-injecting layer/first hole-transporting layer/second hole-transporting layer/fluorescent emitting layer (/first electron-transporting layer/second electron-transporting layer/electron-injecting layer)
(o) (hole-injecting layer/first hole-transporting layer/second hole-transporting layer/phosphorescent emitting layer (/electron-transporting layer/electron-injecting layer)
(p) (hole-injecting layer/first hole-transporting layer/second hole-transporting layer/phosphorescent emitting layer (/first electron-transporting layer/second electron-transporting layer/electron-injecting layer)
(q) (hole-injecting layer/) hole-transporting layer/fluorescent emitting layer/hole-blocking layer (/electron-transporting layer/electron-injecting layer)
(r) (hole-injecting layer/) hole-transporting layer/phosphorescent emitting layer/hole-blocking layer (/electron-transporting layer/electron-injecting layer)
(s) (hole-injecting layer/) hole-transporting layer/fluorescent emitting layer/exciton-blocking layer (/electron-transporting layer/electron-injecting layer)
(t) (hole-injecting layer) hole-transporting layer/phosphorescent emitting layer/exciton-blocking layer (/electron-transporting layer/electron-injecting layer)

However, the layer configuration of the organic EL device according to one aspect of the invention is not limited thereto. For example, when the organic EL device has a hole-injecting layer and a hole-transporting layer, it is preferred that a hole-injecting layer be provided between the hole-transporting layer and the anode. Further, when the organic EL device has an electron-injecting layer and an electron-transporting layer, it is preferred that an electron-injecting layer be provided between the electron-transporting layer and the cathode. Further, each of the hole-injecting layer, the hole-transporting layer, the electron-transporting layer and the electron-injecting layer may be constituted of a single layer or of a plurality of layers.

The plurality of phosphorescent emitting layers, and the plurality of the phosphorescent emitting layer and the fluorescent emitting layer may be emitting layers that emit mutually different colors. For example, the emitting unit (f) may contain a hole-transporting layer/first phosphorescent layer (red light emission)/second phosphorescent emitting layer (green light emission)/spacing layer/fluorescent emitting layer (blue light emission)/electron-transporting layer.

An electron-blocking layer may be provided between each light emitting layer and the hole-transporting layer or the spacing layer. Further, a hole-blocking layer may be provided between each emitting layer and the electron-transporting layer. By providing the electron-blocking layer or the hole-blocking layer, it is possible to confine electrons or holes in the emitting layer, thereby to improve the recombination probability of carriers in the emitting layer, and to improve luminous efficiency.

As a representative device configuration of a tandem type organic EL device, for example, a device configuration such as anode/first emitting unit/intermediate layer/second emitting unit/cathode can be given.

The first emitting unit and the second emitting unit are independently selected from the above-mentioned emitting units, for example.

The intermediate layer is also generally referred to as an intermediate electrode, an intermediate conductive layer, a charge generating layer, an electron withdrawing layer, a connecting layer, a connector layer, or an intermediate insulating layer. The intermediate layer is a layer that supplies electrons to the first emitting unit and holes to the second emitting unit, and can be formed of known materials.

Only one of the first and second emitting units may be an emitting layer of an aspect of the invention, or both may be an emitting layer of an aspect of the invention.

Hereinbelow, an explanation will be made on function, materials, etc. of each layer constituting the organic EL device described in this specification.

(Substrate)

The substrate is used as a support of the organic EL device. The substrate preferably has a light transmittance of 50% or more in the visible light region within a wavelength of 400 to 700 nm, and a smooth substrate is preferable. Examples of the material of the substrate include soda-lime glass, aluminosilicate glass, quartz glass, plastic and the like. As the substrate, a flexible substrate can be used. The flexible substrate means a substrate that can be bent (flexible), and examples thereof include a plastic substrate and the like. Specific examples of the material for forming the plastic substrate include polycarbonate, polyallylate, polyether sulfone, polypropylene, polyester, polyvinyl fluoride, polyvinyl chloride, polyimide, polyethylene naphthalate and the like. Also, an inorganic vapor deposited film can be used.

(Anode)

As the anode, for example, it is preferable to use a metal, an alloy, a conductive compound, a mixture thereof or the like, which has a high work function (specifically, 4.0 eV or more). Specific examples of the material of the anode include indium oxide-tin oxide (ITO: Indium Tin Oxide), indium oxide-tin oxide containing silicon or silicon oxide, indium oxide-zinc oxide, tungsten oxide, indium oxide containing zinc oxide, graphene and the like. In addition, it is possible to use gold, silver, platinum, nickel, tungsten, chromium, molybdenum, iron, cobalt, copper, palladium, titanium, nitrides of these metals (e.g., titanium nitride) and the like.

The anode is normally formed by depositing these materials on the substrate by a sputtering method. For example, indium oxide-zinc oxide can be formed by a sputtering method by using a target in which 1 to 10 mass % zinc oxide is added to indium oxide. Further, indium oxide containing tungsten oxide or zinc oxide can be formed by a sputtering method by using a target in which 0.5 to 5 mass % of tungsten oxide or 0.1 to 1 mass % of zinc oxide is added to indium oxide.

As the other methods for forming the anode, a vacuum deposition method, a coating method, an inkjet method, a spin coating method or the like can be given. When silver paste or the like is used, it is possible to use a coating method, an inkjet method or the like.

The hole-injecting layer formed in contact with the anode is formed by using a material that allows easy hole injection regardless of the work function of the anode. For this reason, in the anode, it is possible to use a common electrode material, for example, a metal, an alloy, a conductive compound and a mixture thereof. Specifically, materials having a small work function such as alkaline metals such as lithium and cesium; magnesium; alkaline earth metals such as calcium and strontium; alloys containing these metals (for example, magnesium-silver and aluminum-lithium); rare earth metals such as europium and ytterbium; and an alloy containing rare earth metals can also be used for the anode.

(Hole-Injecting Layer)

A hole-injecting layer is a layer that contains a substance having a high hole-injecting property and has a function of injecting holes from the anode to the organic layer. As the substance having a high hole-injecting property, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, an aromatic amine compound, an electron-attracting (acceptor) compound, a polymeric compound (oligomer, dendrimer, polymer, etc.) and the like can be given. Among these, an aromatic amine compound and an acceptor compound are preferable, with an acceptor compound being more preferable.

Specific examples of the aromatic amine compound include 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

The acceptor compound is preferably, for example, a heterocyclic ring derivative having an electron-attracting group, a quinone derivative having an electron-attracting group, an arylborane derivative, a heteroarylborane derivative, and the like, and specific examples include hexacyanohexaazatriphenylene, 2,3,5,6-tetrafluoro-7,7,8,8-tetracyanoquinodimethane (abbreviation: F4TCNQ), 1,2,3-tris[(cyano)(4-cyano-2,3,5,6-tetrafluorophenyl)methylene]cyclopropane, and the like.

When the acceptor compound is used, it is preferred that the hole-injecting layer further contain a matrix material. As the matrix material, a material known as the material for an organic EL device can be used. For example, an electron-donating (donor) compound is preferable.

(Hole-Transporting Layer)

The hole-transporting layer is a layer that comprises a high hole-transporting property, and has a function of transporting holes from the anode to the organic layer.

As the substance having a high hole-transporting property, a substance having a hole mobility of $10\text{-}6\ \text{cm}^2/(\text{V}\cdot\text{s})$ or more is preferable. Materials that can be used together with the compound represented by the formula (B1) used in one aspect of the invention include, for example, an aromatic amine compound, a carbazole derivative, an anthracene derivative, a polymeric compound, and the like.

Specific examples of the aromatic amine compound include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BAFLP), 4,4'-bis[N-(9,9-dimethylfluoren-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]

triphenylamine (abbreviation: MTDATA), 4,4'-bis[N-(spiro-9,9'-bifluoren-2-yl)-N-phenylamino]biphenyl (abbreviation: BSPB), and the like.

Specific examples of the carbazole derivative include 4,4'-di(9-carbazolyl)biphenyl (abbreviation: CBP), 9-[4-(9-carbazolyl)phenyl]-10-phenylanthracene (abbreviation: CzPA), 9-phenyl-3-[4-(10-phenyl-9-anthryl)phenyl]-9H-carbazole (abbreviation: PCzPA) and the like.

Specific examples of the anthracene derivative include 2-t-butyl-9,10-di(2-naphthyl)anthracene (t-BuDNA), 9,10-di(2-naphthyl)anthracene (DNA), 9,10-diphenylanthracene (DPAnth), and the like.

Specific examples of the polymeric compound include poly(N-vinylcarbazole) (abbreviation: PVK), poly(4-vinyltriphenylamine) (abbreviation: PVTPA) and the like.

As long as a compound other than those mentioned above, that has a higher hole-transporting property as compared with electron-transporting property, such a compound can be used for the hole-transporting layer.

The hole-transporting layer may be a single layer or may be a stacked layer of two or more layers. In this case, it is preferred to arrange a layer that contains a substance having a larger energy gap among substances having a higher hole-transporting property, on a side nearer to the emitting layer.

(Emitting Layer)

The emitting layer is a layer containing a substance having a high emitting property (dopant material). As the dopant material, various types of material can be used. For example, a fluorescent emitting compound (fluorescent dopant), a phosphorescent emitting compound (phosphorescent dopant) or the like can be used. A fluorescent emitting compound is a compound capable of emitting light from the singlet excited state, and an emitting layer containing a fluorescent emitting compound is called as a fluorescent emitting layer. Further, a phosphorescent emitting compound is a compound capable of emitting light from the triplet excited state, and an emitting layer containing a phosphorescent emitting compound is called as a phosphorescent emitting layer.

The emitting layer normally contains a dopant material and a host material that allows the dopant material to emit light efficiently. In some literatures, a dopant material may be called as a guest material, an emitter, or an emitting material. In some literatures, a host material is called as a matrix material.

A single emitting layer may include a plurality of dopant materials and a plurality of host materials. Further, a plurality of emitting layers may be present.

In this specification, a host material combined with the fluorescent dopant is referred to as a "fluorescent host" and a host material combined with the phosphorescent dopant is referred to as the "phosphorescent host". Note that the fluorescent host and the phosphorescent host are not classified only by the molecular structure. The phosphorescent host is a material for forming a phosphorescent emitting layer containing a phosphorescent dopant, but it does not mean that it cannot be used as a material for forming a fluorescent emitting layer. The same can be applied to the fluorescent host.

The content of the dopant material in the emitting layer is not particularly limited, but from the viewpoint of adequate luminescence and concentration quenching, it is preferable, for example, to be 0.1 to 70 mass %, more preferably 0.1 to 30 mass %, more preferably 1 to 30 mass %, still more preferably 1 to 20 mass %, and particularly preferably 1 to 10 mass %.

<Fluorescent Dopant>

As the fluorescent dopant, a fused polycyclic aromatic derivative, a styrylamine derivative, a fused ring amine derivative, a boron-containing compound, a pyrrole derivative, an indole derivative, a carbazole derivative can be given, for example. Among these, a fused ring amine derivative, a boron-containing compound, and a carbazole derivative are preferable.

As the fused ring amine derivative, a diaminopyrene derivative, a diaminochrysene derivative, a diaminoanthracene derivative, a diaminofluorene derivative, a diaminofluorene derivative with which one or more benzofuro skeletons are fused, and the like can be given.

As the boron-containing compound, a pyrromethene derivative, a triphenylborane derivative and the like can be given.

Examples of the blue fluorescent dopant, include a pyrene derivative, a styrylamine derivative, a chrysene derivative, a fluoranthene derivative, a fluorene derivative, a diamine derivative, a triarylamine derivative, and the like. Specifically, N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(10-phenyl-9-anthryl)-4'-(9-phenyl-9H-carbazol-3-yl)triphenylamine (abbreviation: PCBAPA) and the like can be given.

As the green fluorescent dopant, an aromatic amine derivative and the like can be given, for example. Specifically, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl) phenyl]-N-phenylanthracene-2-amine (abbreviation: 2YGABPhA), N,N,9-triphenylanthracene-9-amine (abbreviation: DPhAPhA), and the like can be given.

As the red fluorescent dopant, a tetracene derivative, a diamine derivative or the like can be given. Specifically, N,N,N',N'-tetrakis(4-methylphenyl)tetracen-5,11-diamine (abbreviation: p-mPhTD), 7,14-diphenyl-N,N,N',N'-tetrakis(4-methylphenyl)acenaphtho[1,2-a]fluoranthen-3,10-diamine (abbreviation: p-mPhAFD) and the like can be given.

<Phosphorescent Dopant>

As the phosphorescent dopant, a phosphorescent light-emitting heavy metal complex and a phosphorescent light-emitting rare earth metal complex can be given.

As the heavy metal complex, an iridium complex, an osmium complex, a platinum complex and the like can be given. As the heavy metal complex, an ortho-metalated complex of a metal selected from iridium, osmium and platinum.

As the rare earth metal complexes include a terbium complex, a europium complex and the like. Specifically, tris(acetylacetonate)(monophenanthroline)terbium (III) (abbreviation: Tb(acac)$_3$(Phen)), tris(1,3-diphenyl-1,3-propandionate)(monophenanthroline)europium (III) (abbreviation: Eu(DBM)$_3$(Phen)), tris[1-(2-thenoyl)-3,3,3-trifluoroacetonate](monophenanthroline)europium (III) (abbreviation: Eu(TTA)$_3$(Phen)) and the like can be given. These rare earth metal complexes are preferable as phosphorescent dopants since rare earth metal ions emit light due to electronic transition between different multiplicity.

As the blue phosphorescent dopant, an iridium complex, an osmium complex, a platinum complex, or the like can be given, for example. Specific examples include bis[2-(4',6'-difluorophenyl)pyridinato-N,C2']iridium (III) tetrakis(1-pyrazolyl)borate (abbreviation: Flr6), bis[2-(4',6'-difluorophenyl)pyridinato-N,C2']iridium (III) picolinate (abbreviation: Flrpic), bis[2-(3',5'-bistrofluoromethylphenyl)pyridinato-N,C2']iridium (III) picolinate (abbreviation: Ir(CF3ppy)$_2$(pic)), bis[2-(4',6'-difluorophenyl)pyridinato-N,C2']iridium (III) acetylacetonate (abbreviation: Flracac), and the like.

As the green phosphorescent dopant, an iridium complex or the like can be given, for example. Specific examples include tris(2-phenylpyridinato-N,C2')iridium (III) (abbreviation: Ir(ppy)$_3$), bis(2-phenylpyridinato-N,C2')iridium (III) acetylacetonate (abbreviation: Ir(ppy)$_2$(acac)), bis(1,2-diphenyl-1H benzimidazolate)iridium (III) acetylacetonate (abbreviation: Ir(pbi)$_2$(acac)), bis(benzo[h]quinolinato) iridium (III) acetylacetonate (abbreviation: Ir(bzq)$_2$(acac)), and the like.

As the red phosphorescent dopant, an iridium complex, a platinum complex, a terbium complex, a europium complex and the like can be given. Specifically, bis[2-(2'-benzo[4,5-a] thienyl)pyridinato-N,C3']iridium (III) acetylacetonate (abbreviation: Ir(btp)$_2$(acac)), bis(1-phenylisoquinolinato-N,C2')iridium (III) acetylacetonate (abbreviation: Ir(piq)$_2$(acac)), (acetylacetonate)bis[2,3-bis(4-fluorophenyl)quinoxalinato]iridium (III) (abbreviation: Ir(Fdpq)$_2$(acac)), 2,3,7,8,12,13,17,18-octaethyl-21H,23H-porphyrin platinum (II) (abbreviation: PtOEP), and the like.

<Host Material>

Examples of the host material, which can be used together with the host material used in an aspect of the invention, include metal complexes such as an aluminum complex, a beryllium complex, and a zinc complex; heterocyclic compounds such as an indole derivative, a pyridine derivative, a pyrimidine derivative, a triazine derivative, a quinoline derivative, an isoquinoline derivative, a quinazoline derivative, a dibenzofuran derivative, a dibenzothiophene derivative, an oxadiazole derivative, a benzimidazole derivative, a phenanthroline derivative; fused aromatic compounds such as a naphthalene derivative, a triphenylene derivative, a carbazole derivative, an anthracene derivative, a phenanthrene derivative, a pyrene derivative, a chrysene derivative, a naphthacene derivative, and a fluoranthene derivative; and aromatic amine compounds such as a tiarylamine derivative, and a fused polycyclic aromatic amine derivative, and the like. Plural types of host materials can be used in combination.

Specific examples of the metal complex include tris(8-quinolinolato)aluminum(II) (abbreviation: Alq), tris(4-methyl-8-quinolinolato)aluminum(III) (abbreviation: Almq3), bis(10-hydroxybenzo[h]quinolinato)beryllium(II) (abbreviation: BeBq2), bis(2-methyl-8-quinolinolato)(4-phenylphenolato)aluminum(III) (abbreviation: BAlq), bis (8-quinolinolato)zinc(II) (abbreviation: Znq), bis[2-(2-benzoxazolyl)phenolato]zinc(II) (abbreviation: ZnPBO), bis[2-(2-benzothiazolyl) phenolato]zinc(II) (abbreviation: ZnBTZ), and the like.

Specific examples of the heterocyclic compound include 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-tiazole (abbreviation: TAZ), 2,2',2''-(1,3,5-benzenetriyl)tris(1-phenyl-1H-benzimidazole) (abbreviation: TPBI), bathophenanthroline (abbreviation: BPhen), bathocuproine (abbreviation: BCP), and the like.

Specific examples of the fused aromatic compound include 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3''-(benzene-1,3,5-triyl)tripyrene (abbreviation: TPB3), 9,10-diphenylanthracene (abbreviation: DPAnth), 6,12-dimethoxy-5,11-diphenylchrysene, and the like.

Specific examples of the aromatic amine compound include N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(9,9-dimethylfluoren-2-yl)-N-phenylamino]biphenyl (abbreviation: DFLDPBi), 4,4'-bis[N-(spiro-9,9'-bifluoren-2-yl)-N-phenylamino]biphenyl (abbreviation: BSPB), and the like.

As the fluorescent host material, a compound having a higher singlet energy level as compared with a fluorescent dopant is preferable. For example, a heterocyclic compound, a fused aromatic compound, and the like can be given. As fused aromatic compounds, for example, anthracene derivatives, pyrene derivatives, chrysene derivatives, and naphthacene derivatives are preferred.

As the phosphorescent host, a compound having a higher triplet energy level as compared with a phosphorescent dopant is preferable. For example, a metal complex, a heterocyclic compound, a fused aromatic compound and the like can be given. Among these, an indole derivative, a carbazole derivative, a pyridine derivative, a pyrimidine derivative, a triazine derivative, a quinoline derivative, an isoquinoline derivative, a quinazoline derivative, a dibenzofuran derivative, a dibenzothiophene derivative, a naphthalene derivative, a triphenylene derivative, a phenanthrene derivative, a fluoranthene derivative and the like are preferable.

(Electron-Transporting Layer)

An electron-transporting layer is a layer that comprises a substance having a high electron-transporting property. As the substance having a high electron-transporting property, a substance having an electron mobility of 10-6 cm$^2$Vs or more is preferable. Materials that can be used together with the compound represented by the formula (BE1) and/or the compound represented by the formula (EB1) used in one aspect of the invention include, for example, a metal complex, an aromatic heterocyclic compound, an aromatic hydrocarbon compound, a polymeric compound, and the like.

As the metal complex, an aluminum complex, a beryllium complex, a zinc complex and the like can be given. Specific examples of the metal complex include tris (8-quinolinolato) aluminum (III) (abbreviation: Alq), tris (4-methyl-8-quinolinolato) aluminum (abbreviation: Almq3), bis (10-hydroxybenzo[h]quinolinato) beryllium (abbreviation: BeBq2), bis (2-methyl-8-quinolinolato) (4-phenylphenolato) aluminum (III) (abbreviation: BAlq), bis (8-quinolinolato) zinc (II) (abbreviation: Znq), bis [2-(2-benzoxazolyl) phenolato]zinc (II) (abbreviation: ZnPBO), bis [2-(2-benzothiazolyl) phenolato] zinc(II) (abbreviation: ZnBTZ), and the like.

As the aromatic heterocyclic compound, imidazole derivatives such as a benzimidazole derivative, an imidazopyridine derivative and a benzimidazophenanthridine derivative; azine derivatives such as a pyrimidine derivative and a triazine derivative; compounds having a nitrogen-containing 6-membered ring structure such as a quinoline derivative, an isoquinoline derivative, and a phenanthroline derivative (also including one having a phosphine oxide-based substituent on the heterocyclic ring) and the like can be given. Specifically, 2-(4-biphenylyl)-5-(4-tert-butylphenyl)-1,3,4-oxadiazole (abbreviation: PBD), 1,3-bis [5-(p-tert-butylphenyl)-1,3,4-oxadiazol-2-yl] benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), 4,4'-bis (5-methylbenzoxazol-2-yl) stilbene (abbreviation: BzOs), and the like can be given.

As the aromatic hydrocarbon compound, an anthracene derivative, a fluoranthene derivative and the like can be given, for example.

As specific examples of the polymeric compound, poly [(9,9-dihexylfluoren-2,7-diyl)-co-(pyridine-3,5-diyl)] (abbreviation: PF-Py), poly [(9,9-dioctylfluoren-2,7-diyl)-co-(2,2'-bipyridin-6,6'-diyl)] (abbreviation: PF-BPy) and the like can be given.

As long as a compound other than those mentioned above, that has a higher electron-transporting property as compared with hole-transporting property, such a compound may be used in the electron-transporting layer.

The electron-transporting layer may be a single layer, or a stacked layer of two or more layers. In this case, it is preferable to arrange a layer that contains a substance having a larger energy gap, among substances having a high electron-transporting property, on the side nearer to the emitting layer.

The electron-transporting layer may contain a metal such as an alkali metal, magnesium, an alkaline earth metal, or an alloy containing two or more of these metals; a metal compound such as an alkali metal compound such as 8-quinolinolato lithium (Liq), or an alkaline earth metal compound. When a metal such as an alkali metal, magnesium, an alkaline earth metal, or an alloy containing two or more of these metals is contained in the electron-transporting layer, the content of the metal is not particularly limited, but is preferably from 0.1 to 50 mass %, more preferably from 0.1 to 20 mass %, further preferably from 1 to 10 mass %. When a metal compound such as an alkali metal compound or an alkaline earth metal compound is contained in the electron-transporting layer, the content of the metal compound is preferably from 1 to 99 mass %, more preferably from 10 to 90 mass %. When plural electron-transporting layers are provided, the layer on the emitting layer side can be formed only from the metal compound as mentioned above.

(Electron-Injecting Layer)

The electron-injecting layer is a layer that contains a substance having a high electron-injecting property, and has the function of efficiently injecting electrons from a cathode to an emitting layer. Examples of the substance that has a high electron-injecting property include an alkali metal, magnesium, an alkaline earth metal, a compound thereof, and the like. Specific examples thereof include lithium, cesium, calcium, lithium fluoride, cesium fluoride, calcium fluoride, lithium oxide, and the like. In addition, a material in which an alkali metal, magnesium, an alkaline earth metal, or a compound thereof is incorporated to an electron-transporting substance having an electron-transporting property, for example, Alq incorporated with magnesium, may also be used.

Alternatively, a composite material that includes an organic compound and a donor compound may also be used in the electron-injecting layer. Such a composite material is excellent in the electron-injecting property and the electron-transporting property since the organic compound receives electrons from the donor compound.

The organic compound is preferably a substance excellent in transporting property of the received electrons, and specifically, for example, the metal complex, the aromatic heterocyclic compound, and the like, which are a substance that has a high electron-transporting property as mentioned above, can be used.

Any material capable of donating electrons to an organic compound can be used as the donor compound. Examples thereof include an alkali metal, magnesium, an alkaline earth metal, a rare earth metal and the like. Specific examples thereof include lithium, cesium, magnesium, calcium, erbium, ytterbium, and the like. Further, an alkali metal oxide and an alkaline earth metal oxide are preferred, and examples thereof include lithium oxide, calcium oxide, barium oxide, and the like. Lewis bases such as magnesium oxide can also be used. Alternatively, an organic compound such as tetrathiafulvalene (abbreviation: TTF) can be used.

(Cathode)

For the cathode, a metal, an alloy, an electrically conductive compound, and a mixture thereof, each having a small work function (specifically, a work function of 3.8 eV or less) are preferably used. Specific examples of the material for the cathode include alkali metals such as lithium and cesium; magnesium; alkaline earth metals such as calcium, and strontium; alloys containing these metals (for example, magnesium-silver, and aluminum-lithium); rare earth metals such as europium and ytterbium; alloys containing a rare earth metal, and the like.

The cathode is usually formed by a vacuum vapor deposition or a sputtering method. Further, in the case of using a silver paste or the like, a coating method, an inkjet method, or the like can be employed.

In the case where the electron-injecting layer is provided, a cathode can be formed from a substance selected from various electrically conductive materials such as aluminum, silver, ITO, graphene, indium oxide-tin oxide containing silicon or silicon oxide, regardless of the work function value. These electrically conductive materials are made into films by using a sputtering method, an inkjet method, a spin coating method, or the like.

When a top emission type is adopted, a capping layer may be provided above the cathode. By providing a capping layer, it is possible to adjust the peak intensity and peak wavelength of the emission.

Compounds that can be used for the capping layer are those whose molecular formula contains a carbon atom and a hydrogen atom as constituent elements, and which may contain an oxygen atom, a nitrogen atom, a fluorine atom, a silicon atom, a chlorine atom, a bromine atom, and an iodine atom, and which may have a substituent.

Examples of the preferred material include the following compounds.

(i) The aromatic hydrocarbon compound whose molecular formula contains a carbon atom and a hydrogen atom as constituent elements, and which may contain an oxygen atom, a nitrogen atom, a fluorine atom, a silicon atom, a chlorine atom, a bromine atom, and an iodine atom, and which may have a substituent.

(ii) The aromatic heterocyclic compound whose molecular formula contains a carbon atom and a hydrogen atom as constituent elements, and which may contain an oxygen atom, a nitrogen atom, a fluorine atom, a silicon atom, a chlorine atom, a bromine atom, and an iodine atom, and which may have a substituent.

(iii) The amine compound whose molecular formula contains a carbon atom and a hydrogen atom as constituent elements, and which may contain an oxygen atom, a nitrogen atom, a fluorine atom, a silicon atom, a chlorine atom, a bromine atom, and an iodine atom, and which may have a substituent.

The thickness of the capping layer is preferably 200 nm or less, more preferably 20 nm or more and 200 nm or less, and still more preferably 40 nm or more and 140 nm or less.

Figure 2:
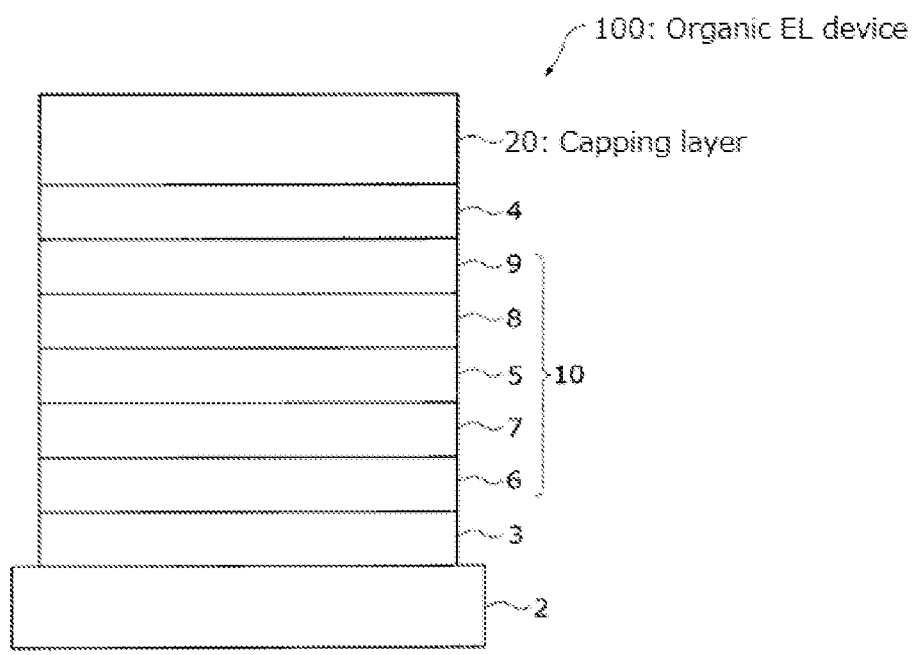
FIG. 2 is a diagram showing a schematic configuration of another embodiment of an organic EL device according to an aspect of the invention.

The schematic configuration of an example of an organic EL device containing a capping layer is shown in FIG. 2.

The organic EL device 100 contains an anode 3, an emitting unit 10, a cathode 4, and a capping layer 20 in this order on a substrate 2, and is configured to take out light from the capping layer 20 side. The emitting unit 10 is as described in FIG. 1.

(Insulating Layer)

In the organic EL device, pixel defects based on leakage or a short circuit are easily generated since an electric field is applied to a thin film. In order to prevent this, an insulating thin layer may be inserted between a pair of electrodes.

Examples of substances used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, vanadium oxide, and the like. A mixture thereof may be used in the insulating layer, and a stacked body of a plurality of layers that include these substances can be also used for the insulating layer.

(Spacing Layer)

The spacing layer is a layer provided between a fluorescent emitting layer and a phosphorescent emitting layer when the fluorescent emitting layer and the phosphorescent emitting layer are stacked, in order to prevent diffusion of excitons generated in the phosphorescent emitting layer to the fluorescent emitting layer or in order to adjust the carrier balance. Further, the spacing layer can be provided between plural phosphorescent emitting layers.

Since the spacing layer is provided between the emitting layers, the material used for the spacing layer is preferably a substance that has both electron-transporting property and hole-transporting property. In order to prevent diffusion of the triplet energy in adjacent phosphorescent emitting layers, it is preferred that the material used for the spacing layer have a triplet energy of 2.6 eV or more.

As the material used for the spacing layer, the same materials as those used in the above-mentioned hole-transporting layer can be given.

(Electron-Blocking Layer, Hole-Blocking Layer, Exciton-Blocking Layer)

An electron-blocking layer, a hole-blocking layer, an exciton (triplet)-blocking layer, and the like may be provided in adjacent to the emitting layer.

The electron-blocking layer has a function of preventing leakage of electrons from the emitting layer to the hole-transporting layer. The hole-blocking layer has a function of preventing leakage of holes from the emitting layer to the electron-transporting layer. The exciton-blocking layer has a function of preventing diffusion of excitons generated in the emitting layer to the adjacent layers to confine the excitons within the emitting layer.

(Intermediate Layer)

In tandem-type organic EL device, an intermediate layer is provided.

(Method for Forming a Layer)

The method for forming each layer of the organic EL device is not particularly limited unless otherwise specified. As the film forming method, a known film-forming method such as a dry film-forming method, a wet film-forming method or the like can be used. Specific examples of the dry film-forming method include a vacuum deposition method, a sputtering method, a plasma method, an ion plating method, and the like. Specific examples of the wet film-forming method include various coating methods such as a spin coating method, a dipping method, a flow coating method, and an inkjet method.

(Film Thickness)

The film thickness of each layer of the organic EL device is not particularly limited unless otherwise specified. If the film thickness is too small, defects such as pinholes are likely to occur to make it difficult to obtain an enough luminance. On the other hand, if the film thickness is too large, a high driving voltage is required to be applied, leading to a lowering in efficiency. In this respect, the film thickness is preferably 1 nm to 10 μm, and more preferably 1 nm to 0.2 μm.

[Electronic Apparatus]

The electronic apparatus according to one aspect of the invention is provided with the above-described organic EL device according to one aspect of the invention. Examples of the electronic apparatus include display parts such as an organic EL panel module; display devices of television sets, mobile phones, smart phones, personal computers, and the like; and emitting devices of a lighting device and a vehicle lighting device.

EXAMPLE

Hereinafter, the invention will be described in more detail by referring to Examples and Comparative Examples, but the invention is not limited in any way to the description of these Examples.

<Compound>

The compounds represented by the formula (1) used in the manufacturing of the organic EL devices in Examples 1 to 65 are shown below.

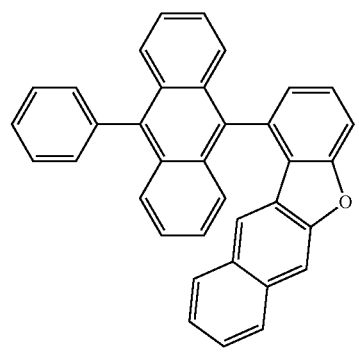

BH-1

BH-3
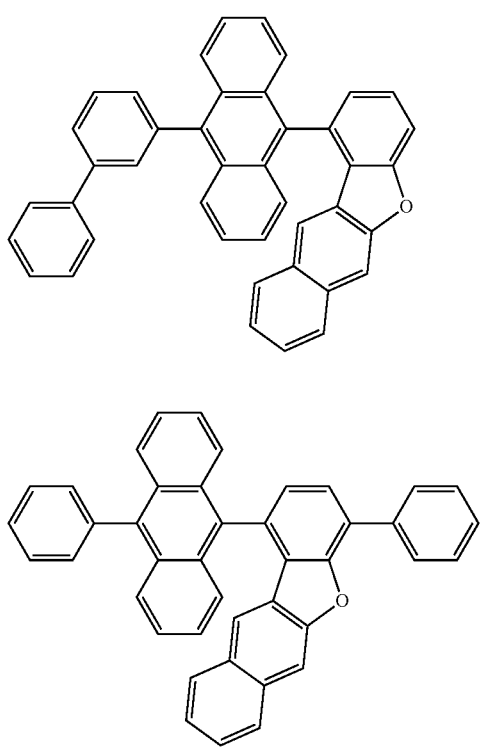
BH-15
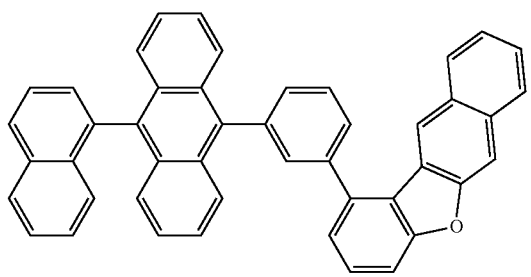
BH-17
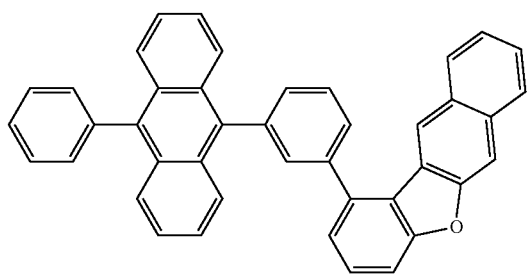
BH-5
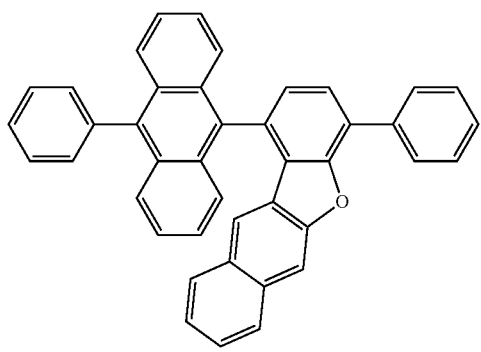
The structures of the comparative compounds used in the manufacturing of the organic EL devices of Comparative Examples 1 to 41 are shown below.
BH-11
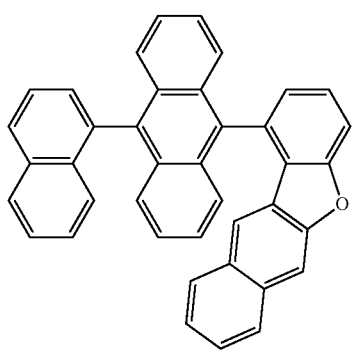
BH-R1
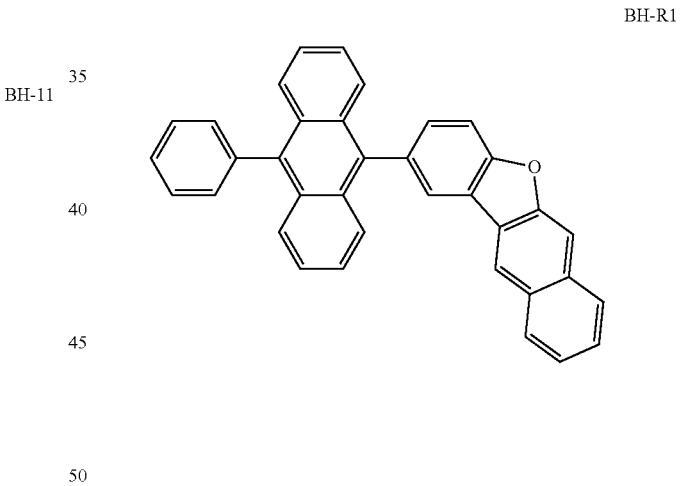
BH-12
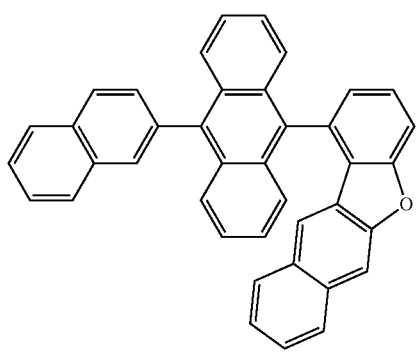
BH-R2
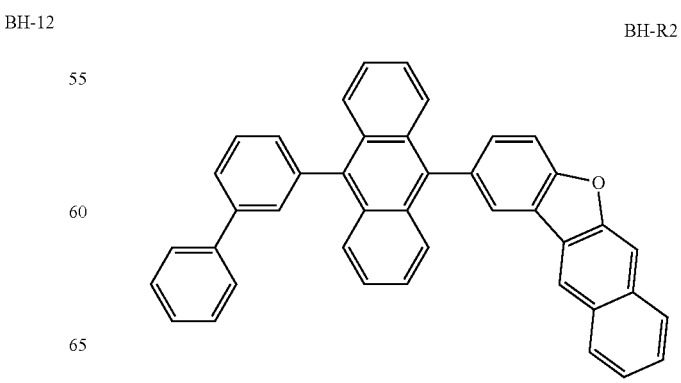

BH-R3
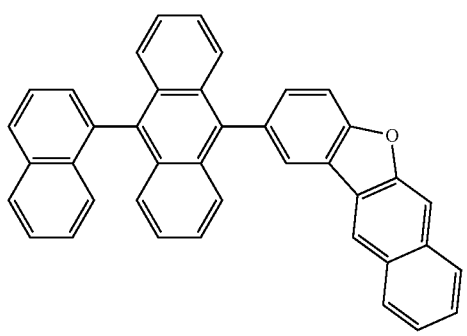
aET-1
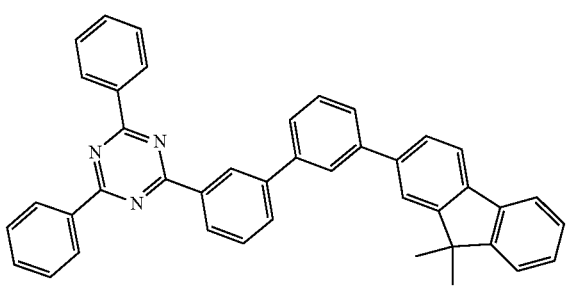
aET-3
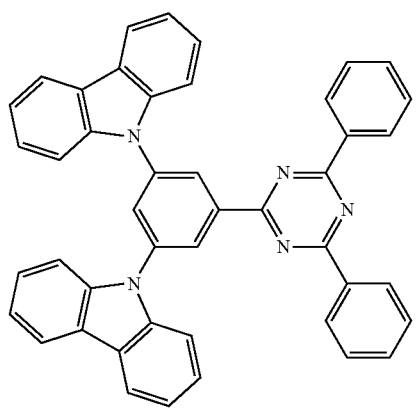
BH-R4
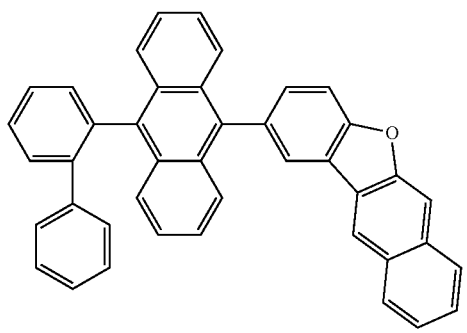
BH-R5
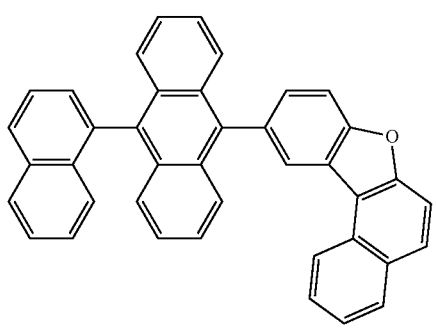
atET-6
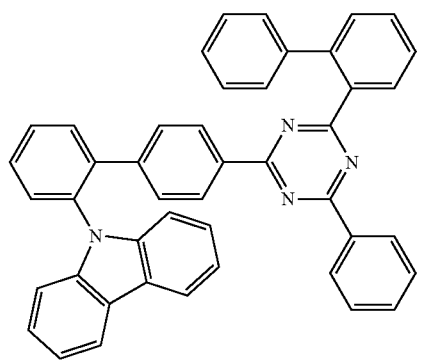
BH-R6
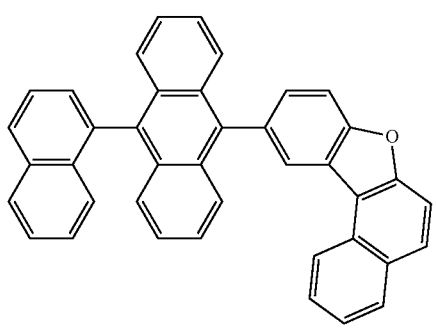
bET-1
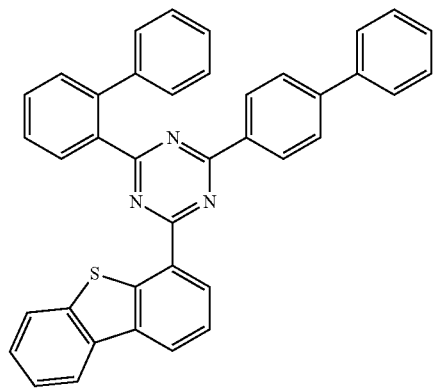
The compounds represented by the formula (BE1) used in the manufacturing of the organic EL devices in Examples 1 to 65 are shown below bET-2
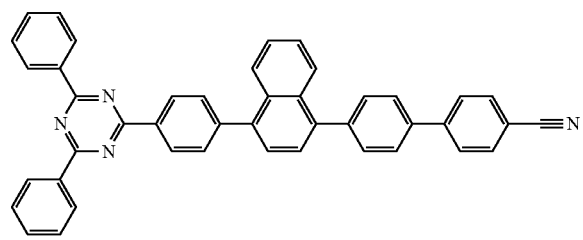
bET-3
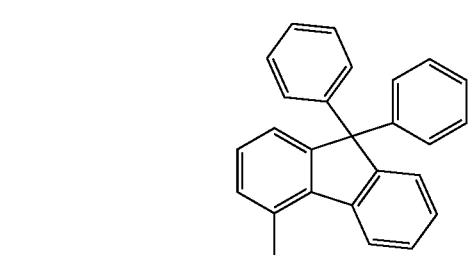
bET-5
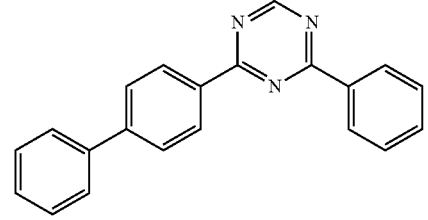
bET-6
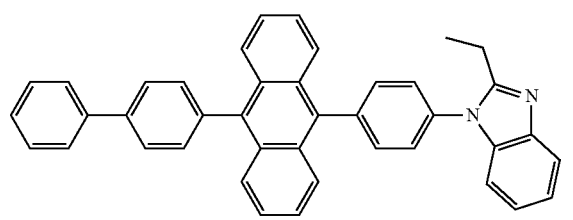
The compounds represented by the formula (B1) used in the manufacturing of the organic EL devices in Examples 1 to 65 are shown below
EBL-1
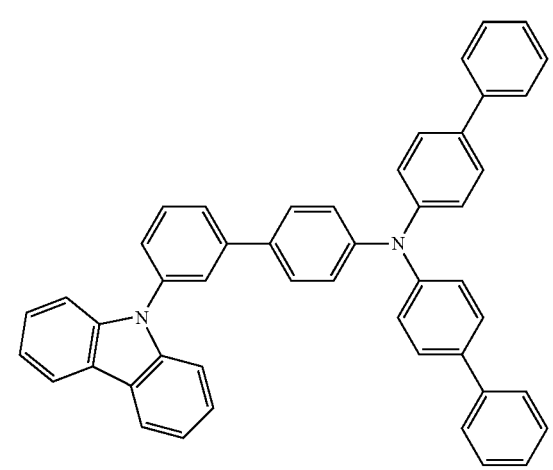
EBL-3
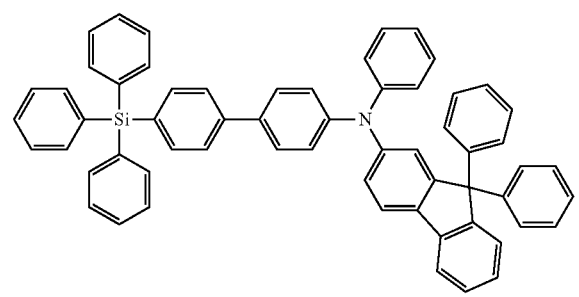
EBL-5
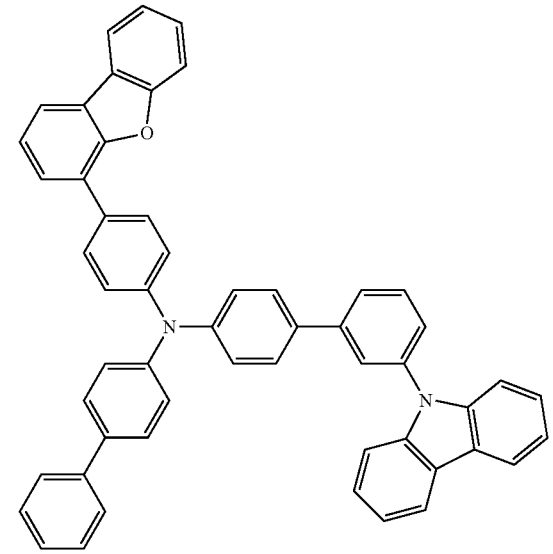

EBL-6
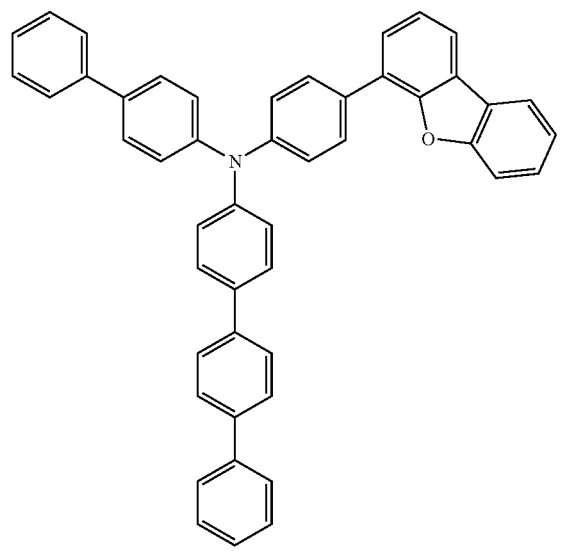
HT-2
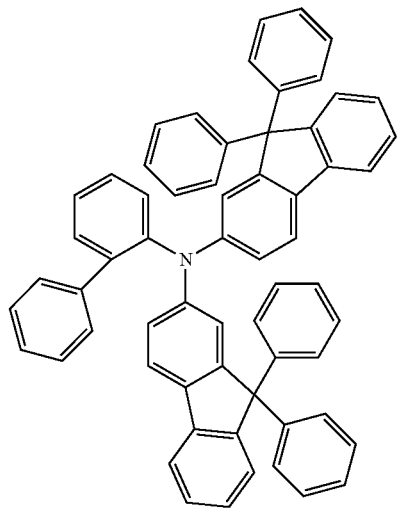
EBL-8
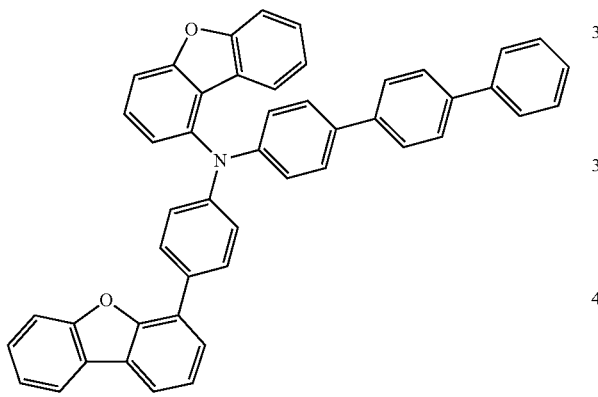
HT-4
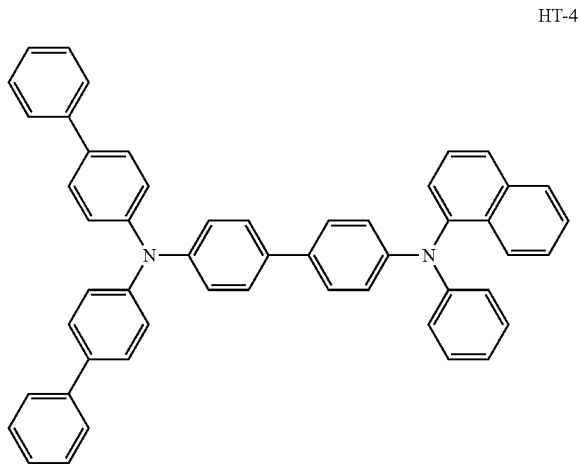
HT-1
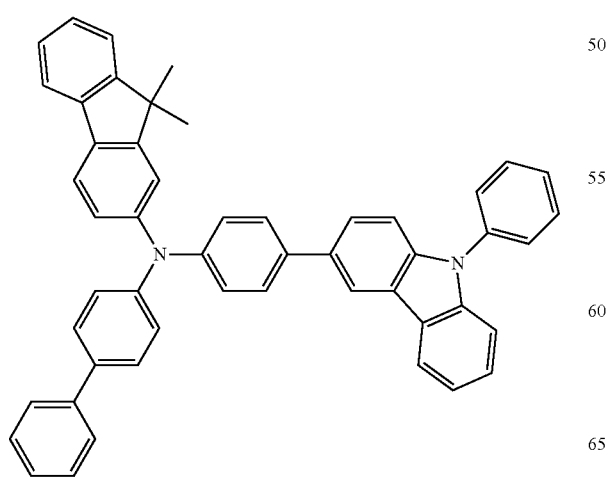
HT-5
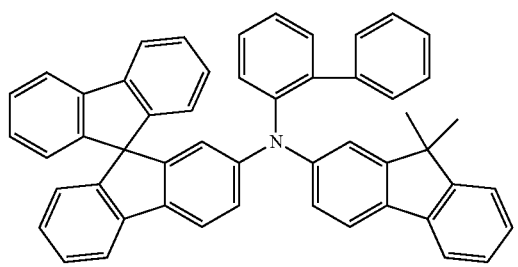

HT-6
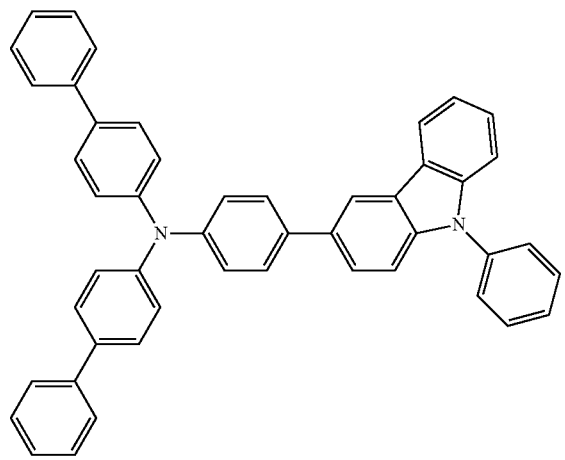
The structures of the other compounds used in the manufacturing of the organic EL devices in Examples 1 to 65 and Comparative Examples 1 to 41 are shown below.
HI-1
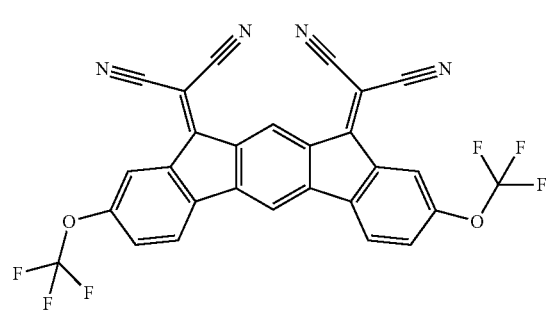
HI-2
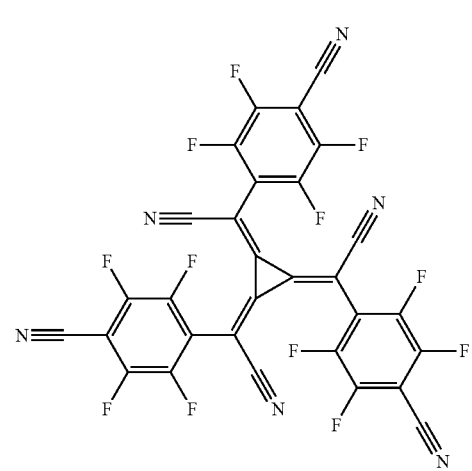
BD-1
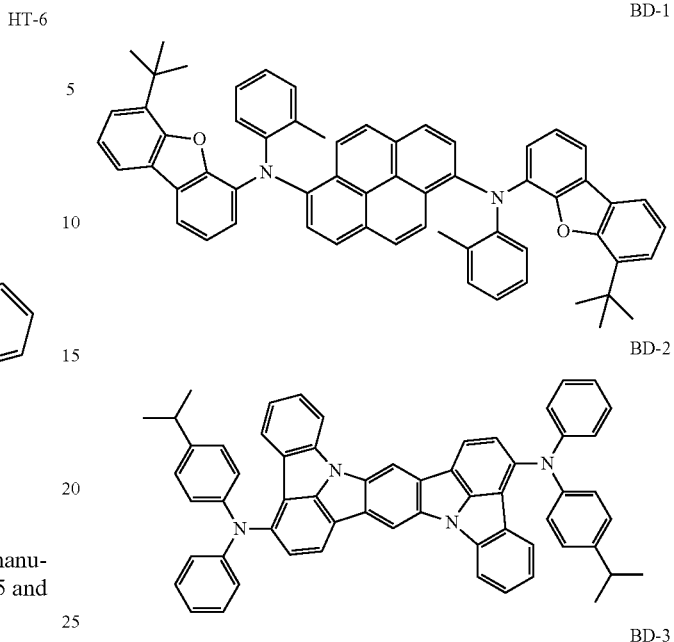
BD-2
BD-3
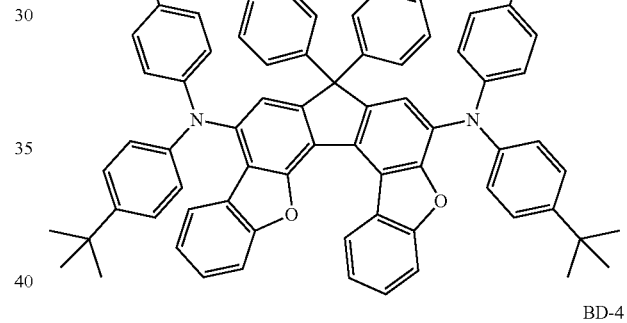
BD-4
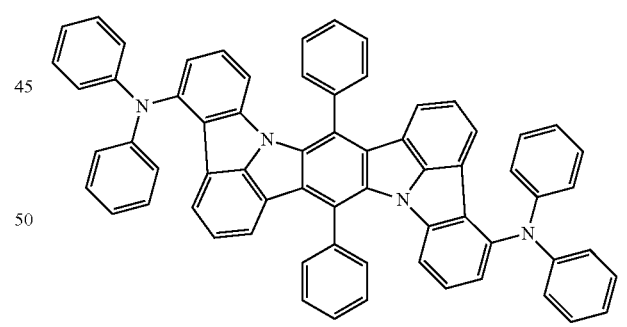
BD-5
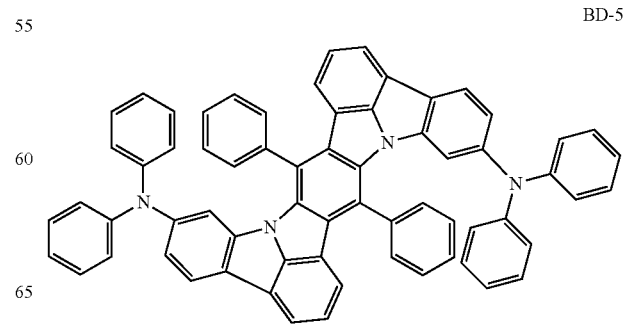

-continued
BD-6
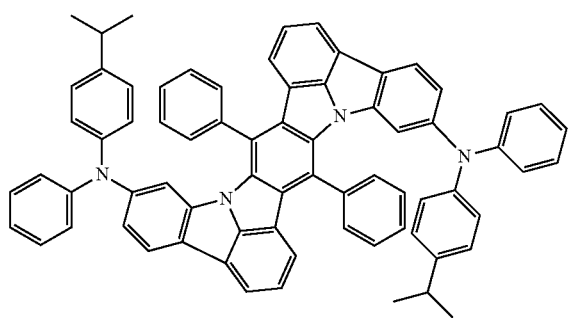
BD-10
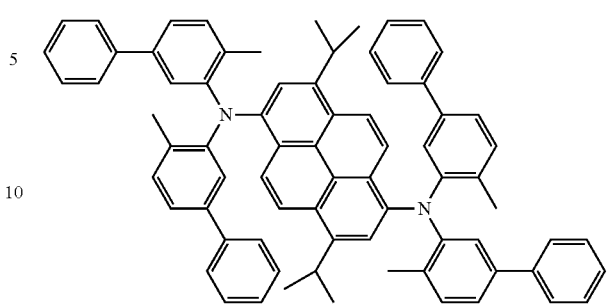
BD-7
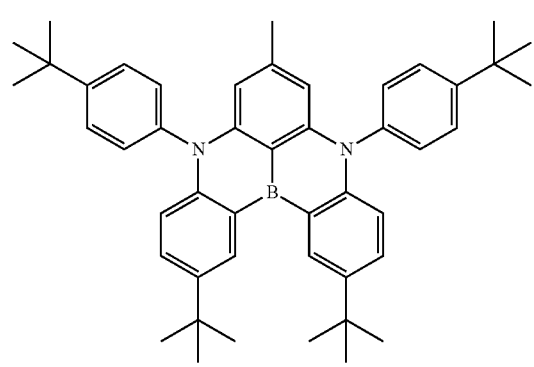
CAP-1
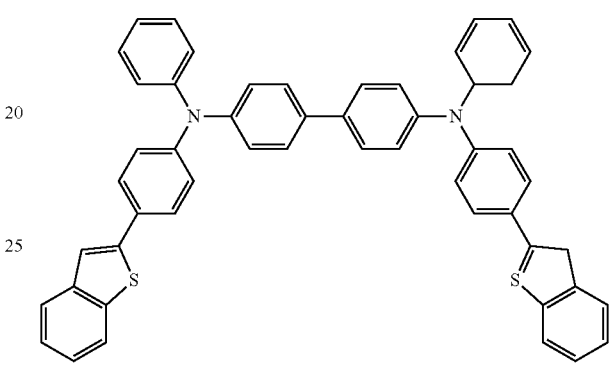
BD-8
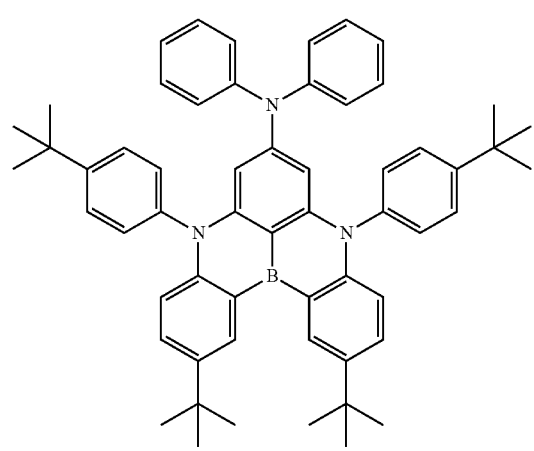
BD-11
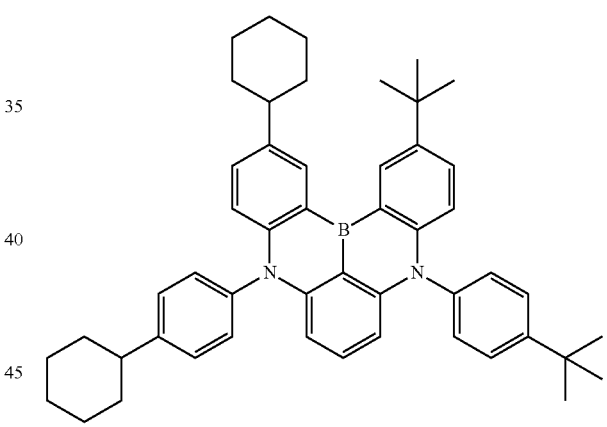
BD-9
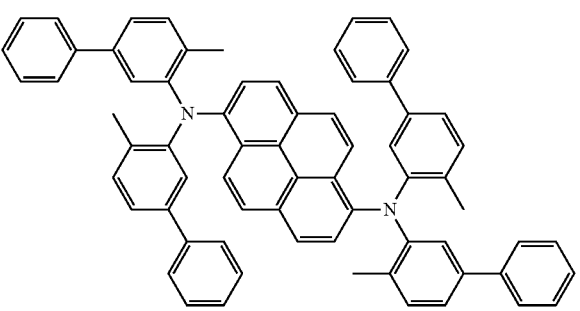
BD-12
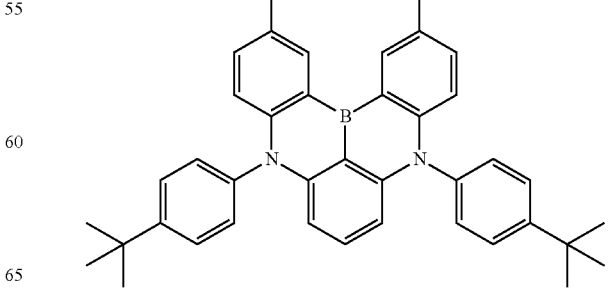

BD-13

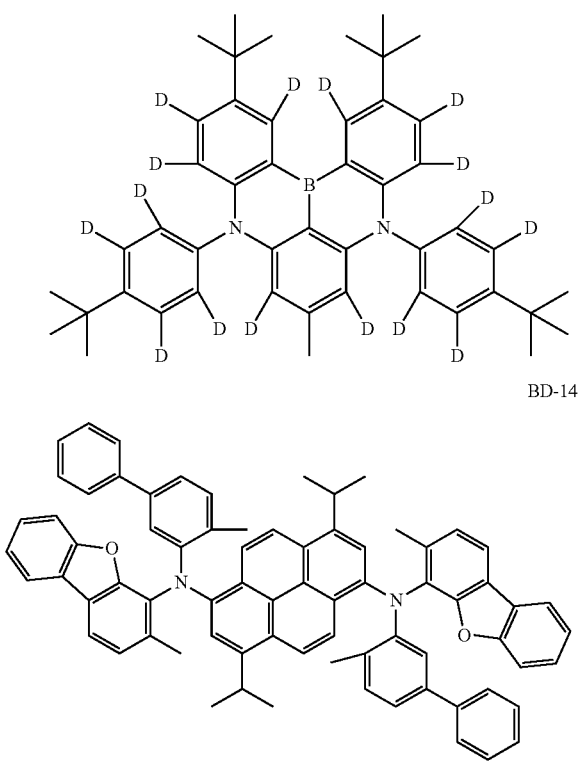

BD-14

BD-15

BD-16

BD-18

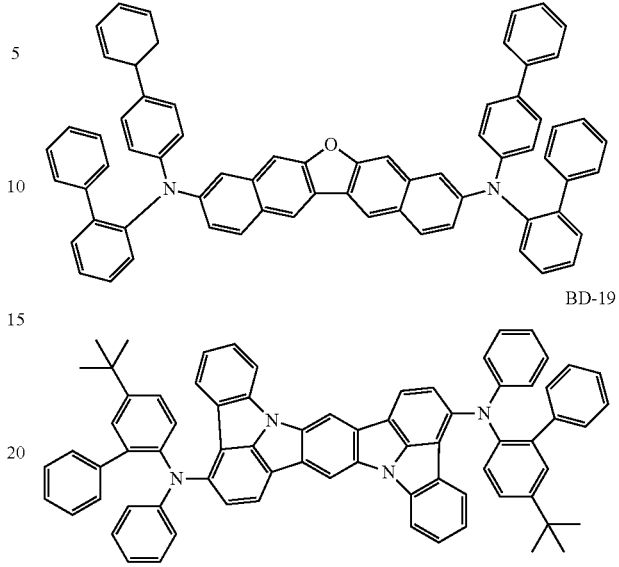

BD-19

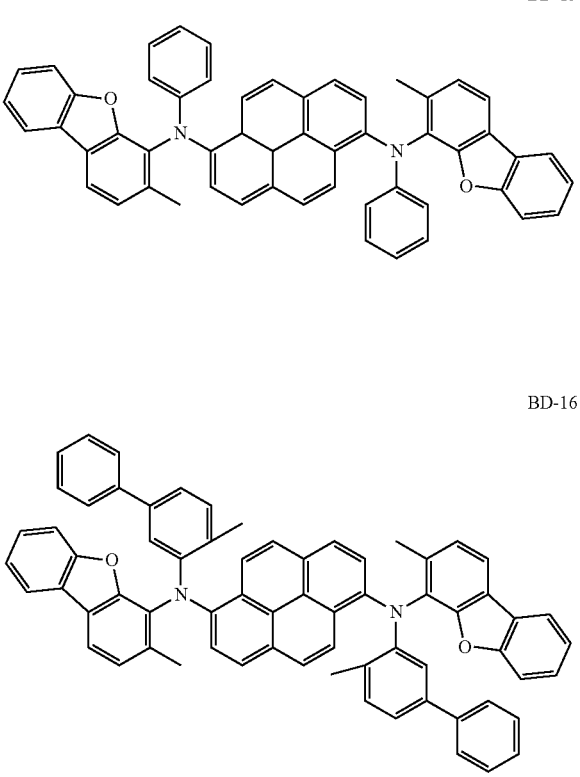

<Fabrication of Organic EL Device>

Example 1

[Manufacture of Bottom Emission Type Organic EL Device]

A 25 mm×75 mm×1.1 mm-thick glass substrate with ITO (Indium Tin Oxide) transparent electrode (anode) (manufactured by GEOMATEC Co., Ltd.) was subjected to ultrasonic cleaning in isopropyl alcohol for 5 minutes, followed by UV-ozone washing for 30 minutes. The thickness of the ITO transparent electrode was 130 nm. The glass substrate with the transparent electrode line after being cleaned was mounted onto a substrate holder in a vacuum vapor deposition apparatus, and a compound HI-1 was deposited on a surface on the side on which the transparent electrode line was formed so as to cover the transparent electrode to form a hole-injecting layer (HI) having a thickness of 5 nm. Subsequent to the formation of the hole-injecting layer, a compound HT-2 was deposited thereon to form a first hole-transporting layer (HT) having a thickness of 90 nm. Subsequent to the formation of the first hole-transporting layer, a compound EBL-1 was deposited thereon to form a second hole-transporting layer (also referred to as an electron barrier layer) (EBL) having a thickness of 10 nm. A compound BH-1 (a host material (BH)) and compound BD-2 (a dopant material (BD)) were co-deposited on the second hole-transporting layer to be 4 mass % in a proportion of BD-2 to form an emitting layer having a thickness of 20 nm. A compound aET-1 was deposited on the emitting layer to form a first electron-transporting layer (also referred to as a hole barrier layer) (HBL) having a thickness of 5 nm. A compound bET-1 was deposited on the first electron-transporting layer to forma second electron-transporting layer (ET) having a thickness of 20 nm. LiF was deposited on the second electron-transporting layer to form an electron-injecting layer having a thickness of 1 nm. A metal Al was deposited on the electron-injecting layer to form a cathode having a thickness of 80 nm.

The device configuration of the organic EL device of Example 1 is shown informality as follows. ITO(130)/HI-1 (5)/HT-2(90)/EBL-1(10)/BH-1:BD-2(20, 96%:4%)/aET-1 (5)/bET-1(20)/LiF(1)/Al(80)

The numerical values in parentheses indicate the film thickness (unit: nm). The numerical value represented in percentages in parentheses indicates the proportion (mass %) of the host material and the dopant material in the emitting layer.

<Evaluation of Organic EL Device>

Initial characteristics of the obtained organic EL devices were measured by driving at a constant current of 10 mA/cm$^2$ of DC (direct current) at room temperature. The measurement results of the voltage are shown in Table 1.

A voltage was applied to the obtained organic EL device so that the current density became 50 mA/cm$^2$, and the time until the luminance became 90% of the initial luminance (LT90 (unit: hours)) was measured. The results are shown in Table 1.

Comparative Example 1

The organic EL device was manufactured and evaluated in the same manner as in Example 1, except that the compounds listed in Table 1 were used. The results are shown in Table 1.

TABLE 1

| | HI | HT | EBL | BH | BD | HBL | ET | Voltage [V] | LT90 |
|---|---|---|---|---|---|---|---|---|---|
| Ex. 1 | HI-1 | HT-2 | EBL-1 | BH-1 | BD-2 | aET-1 | bET-1 | 3.1 | 280 |
| Comp. Ex. 1 | HI-1 | HT-2 | EBL-1 | BH-R1 | BD-2 | aET-1 | bET-1 | 3.2 | 248 |

Example 2 and Comparative Example 2

The organic EL devices were manufactured and evaluated in the same manner as in Example 1, except that the compounds listed in Table 2 were used. The results are shown in Table 2.

Example 3 and Comparative Example 3

TABLE 2

| | HI | HT | EBL | BH | BD | HBL | ET | Voltage [V] | LT90 |
|---|---|---|---|---|---|---|---|---|---|
| Ex. 2 | HI-1 | HT-1 | EBL-1 | BH-1 | BD-1 | aET-1 | bET-2 | 3.2 | 183 |
| Comp. Ex. 2 | HI-1 | HT-1 | EBL-1 | BH-R1 | BD-1 | aET-1 | bET-2 | 3.3 | 156 |

The organic EL devices were manufactured and evaluated in the same manner as in Example 1, except that the compounds listed in Table 3 were used. The results are shown in Table 3.

TABLE 3

| | HI | HT | EBL | BH | BD | HBL | ET | Voltage [V] | LT90 |
|---|---|---|---|---|---|---|---|---|---|
| Ex. 3 | HI-1 | HT-1 | EBL-1 | BH-1 | BD-3 | aET-1 | bET-1 | 3.2 | 120 |
| Comp. Ex. 3 | HI-1 | HT-1 | EBL-1 | BH-R1 | BD-3 | aET-1 | bET-1 | 3.4 | 105 |

Example 4 and Comparative Example 4

The organic EL devices were manufactured and evaluated in the same manner as in Example 1, except that the compounds listed in Table 4 were used. The results are shown in Table 4.

TABLE 4

|  | HI | HT | EBL | BH | BD | HBL | ET | Voltage [V] | LT90 |
|---|---|---|---|---|---|---|---|---|---|
| Ex. 4 | HI-1 | HT-1 | EBL-1 | BH-1 | BD-4 | aET-1 | bET-1 | 3.1 | 100 |
| Comp. Ex. 4 | HI-1 | HT-1 | EBL-1 | BH-R1 | BD-4 | aET-1 | bET-1 | 3.4 | 85 |

Example 5 and Comparative Example 5

The organic EL devices were manufactured and evaluated in the same manner as in Example 1, except that the compounds listed in Table 5 were used. The results are shown in Table 5.

TABLE 5

|  | HI | HT | EBL | BH | BD | HBL | ET | Voltage [V] | LT90 |
|---|---|---|---|---|---|---|---|---|---|
| Ex. 5 | HI-1 | HT-1 | EBL-1 | BH-1 | BD-5 | aET-1 | bET-1 | 3.1 | 122 |
| Comp. Ex. 5 | HI-1 | HT-1 | EBL-1 | BH-R1 | BD-5 | aET-1 | bET-1 | 3.4 | 98 |

Example 6 and Comparative Example 6

The organic EL devices were manufactured and evaluated in the same manner as in Example 1, except that the compounds listed in Table 6 were used. The results are shown in Table 6.

TABLE 6

|  | HI | HT | EBL | BH | BD | HBL | ET | Voltage [V] | LT90 |
|---|---|---|---|---|---|---|---|---|---|
| Ex. 6 | HI-1 | HT-1 | EBL-1 | BH-1 | BD-6 | aET-1 | bET-1 | 3.2 | 146 |
| Comp. Ex. 6 | HI-1 | HT-1 | EBL-1 | BH-R1 | BD-6 | aET-1 | bET-1 | 3.4 | 119 |

Example 7 and Comparative Example 7

The organic EL devices were manufactured and evaluated in the same manner as in Example 1, except that the compounds listed in Table 7 were used. The results are shown in Table 7.

TABLE 7

|  | HI | HT | EBL | BH | BD | HBL | ET | Voltage [V] | LT90 |
|---|---|---|---|---|---|---|---|---|---|
| Ex. 7 | HI-1 | HT-1 | EBL-1 | BH-1 | BD-7 | aET-1 | bET-1 | 3.1 | 120 |
| Comp. Ex. 7 | HI-1 | HT-1 | EBL-1 | BH-R1 | BD-7 | aET-1 | bET-1 | 3.4 | 98 |

Example 8 and Comparative Example 8

The organic EL devices were manufactured and evaluated in the same manner as in Example 1, except that the compounds listed in Table 8 were used. The results are shown in Table 8.

TABLE 8

|  | HI | HT | EBL | BH | BD | HBL | ET | Voltage [V] | LT90 |
|---|---|---|---|---|---|---|---|---|---|
| Ex. 8 | HI-1 | HT-1 | EBL-1 | BH-1 | BD-8 | aET-1 | bET-1 | 3.1 | 122 |
| Comp. Ex. 8 | HI-1 | HT-1 | EBL-1 | BH-R1 | BD-8 | aET-1 | bET-1 | 3.4 | 97 |

Example 9 and Comparative Example 9

The organic EL devices were manufactured and evaluated in the same manner as in Example 1, except that the compounds listed in Table 9 were used. The results are shown in Table 9.

TABLE 9

|  | HI | HT | EBL | BH | BD | HBL | ET | Voltage [V] | LT90 |
|---|---|---|---|---|---|---|---|---|---|
| Ex. 9 | HI-1 | HT-1 | EBL-1 | BH-1 | BD-9 | aET-1 | bET-1 | 3.2 | 172 |
| Comp. Ex. 9 | HI-1 | HT-1 | EBL-1 | BH-R1 | BD-9 | aET-1 | bET-1 | 3.4 | 148 |

Example 10 and Comparative Example 10

The organic EL devices were manufactured and evaluated in the same manner as in Example 1, except that the compounds listed in Table 10 were used. The results are shown in Table 10.

TABLE 10

|  | HI | HT | EBL | BH | BD | HBL | ET | Voltage [V] | LT90 |
|---|---|---|---|---|---|---|---|---|---|
| Ex. 10 | HI-1 | HT-1 | EBL-1 | BH-1 | BD-10 | aET-1 | bET-1 | 3.2 | 189 |
| Comp. Ex. 10 | HI-1 | HT-1 | EBL-1 | BH-R1 | BD-10 | aET-1 | bET-1 | 3.4 | 164 |

Comparative Examples 11 to 16

The organic EL devices were manufactured and evaluated in the same manner as in Example 1, except that the compounds listed in Table 11 were used. The results are shown in Table 11.

TABLE 11

|  | HI | HT | EBL | BH | BD | HBL | ET | Voltage [V] | LT90 |
|---|---|---|---|---|---|---|---|---|---|
| Comp. Ex. 11 | HI-1 | HT-1 | EBL-1 | BH-R3 | BD-1 | aET-1 | bET-1 | 3.3 | 65 |
| Comp. Ex. 12 | HI-1 | HT-1 | EBL-1 | BH-R4 | BD-1 | aET-1 | bET-1 | 3.6 | 75 |
| Comp. Ex. 13 | HI-1 | HT-1 | EBL-1 | BH-R3 | BD-6 | aET-1 | bET-1 | 3.3 | 63 |
| Comp. Ex. 14 | HI-1 | HT-1 | EBL-1 | BH-R4 | BD-6 | aET-1 | bET-1 | 3.6 | 67 |
| Comp. Ex. 15 | HI-1 | HT-1 | EBL-1 | BH-R3 | BD-7 | aET-1 | bET-1 | 3.4 | 52 |
| Comp. Ex. 16 | HI-1 | HT-1 | EBL-1 | BH-R4 | BD-7 | aET-1 | bET-1 | 3.6 | 64 |

From the results of Tables 1 to 10, it can be seen that the bottom emission type device of Examples has the same device lifetime (LT90) but lower driving voltage compared to the device of Comparative Examples.

From the results of Table 11, it can be seen that the devices of Comparative Examples 11 to 16 using BH-R3 or BH-R4 in place of BH-1 or BH-3 have inferior device lifetime and equal to or inferior driving voltage compared to the devices of Comparative Examples 1 to 10.

Example 11

[Manufacturing and Evaluation of Top Emission Type Organic EL Devices]

On the glass substrate, a layer of silver-alloy APC (Ag—Pd—Cu) (a reflective layer) (film thickness: 100 nm) and a layer of indium zinc oxide (IZO) (film thickness: 10 nm) were formed in this order by a sputtering method. Subsequently, this conductive material layer was patterned by etching using a resist pattern as a mask by using a normal lithography technique to form an anode layer. A substrate on which the lower electrode was formed was subjected to ultrasonic cleaning in isopropyl alcohol for 5 minutes, followed by UV-ozone washing for 30 minutes. Thereafter, a compound HI-2 was deposited by a vacuum deposition method to form a hole-injecting layer (HI) having a thickness of 5 nm. Subsequent to the formation of the hole-injecting layer, a compound HT-1 was deposited thereon to form a first hole-transporting layer (HT) having a thickness of 130 nm. Subsequent to the formation of the first hole-transporting layer, a compound EBL-1 was deposited thereon to form a second hole-transporting layer (also referred to as an electron barrier layer) (EBL) having a thickness of 10 nm. A compound BH-1 (a host material (BH)) and compound BD-3 (a dopant material (BD)) were co-deposited on the second hole-transporting layer to be 4 mass % in a proportion of BD-3 to form an emitting layer having a thickness of 20 nm. A compound aET-1 was deposited on the emitting layer to form a first electron-transporting layer (also referred to as a hole barrier layer) (HBL) having a thickness of 5 nm. A compound bET-1 was deposited on the first electron-transporting layer to form a second electron-transporting layer (ET) having a thickness of 20 nm. LiF was deposited on the second electron-transporting layer to form an electron-injecting layer having a thickness of 1 nm. On the electron-injecting layer, Mg and Ag were deposited in a thickness ratio of 1:9 to form a cathode made of semi-permeable MgAg alloys having a thickness of 15 nm. A CAP-1 film was formed on a cathode by vacuum deposition process to form a capping layer having a thickness of 65 nm.

The device configuration of the organic EL device of Example 11 is shown informality as follows.

APC(100)/IZO(10)/HI-2(5)/HT-1(130)/EBL-1(10)/BH-1:BD-3(20, 96%:4%)/aET-1(5)/bET-1(20)/LiF(1)/MgAg(15)/CAP-1(65)

The numerical values in parentheses indicate the film thickness (unit: nm). The numerical value represented in percentages in parentheses indicates the proportion (mass %) of the host material and the dopant material in the emitting layer.

<Evaluation of Organic EL Device>

Initial characteristics of the obtained organic EL devices were measured by driving at a constant current of 10 mA/cm$^2$ of DC (direct current) at room temperature. The measurement results of the voltage are shown in Table 12.

A voltage was applied to the obtained organic EL device so that the current density became 15 mA/cm$^2$, and the time until the luminance became 90% of the initial luminance (LT90 (unit: hours)) was measured. The results are shown in Table 12.

Comparative Example 17

The organic EL device was manufactured and evaluated in the same manner as in Example 11, except that the compounds listed in Table 12 were used. The results are shown in Table 12.

TABLE 12

|  | HI | HT | EBL | BH | BD | HBL | ET | Voltage [V] | LT90 |
|---|---|---|---|---|---|---|---|---|---|
| Ex. 11 | HI-2 | HT-1 | EBL-1 | BH-1 | BD-3 | aET-1 | bET-2 | 3.3 | 1250 |
| Comp. Ex. 17 | HI-2 | HT-1 | EBL-1 | BH-R1 | BD-3 | aET-1 | bET-2 | 3.5 | 1100 |

Example 12 and Comparative Example 18

The organic EL devices were manufactured and evaluated in the same manner as in Example 11, except that the compounds listed in Table 13 were used. The results are shown in Table 13.

TABLE 13

|  | HI | HT | EBL | BH | BD | HBL | ET | Voltage [V] | LT90 |
|---|---|---|---|---|---|---|---|---|---|
| Ex. 12 | HI-2 | HT-1 | EBL-1 | BH-3 | BD-3 | aET-1 | bET-2 | 3.4 | 1100 |
| Comp. Ex. 18 | HI-2 | HT-1 | EBL-1 | BH-R2 | BD-3 | aET-1 | bET-2 | 3.6 | 720 |

Example 13 and Comparative Example 19

The organic EL devices were manufactured and evaluated in the same manner as in Example 11, except that the compounds listed in Table 14 were used. The results are shown in Table 14.

TABLE 14

|  | HI | HT | EBL | BH | BD | HBL | ET | Voltage [V] | LT90 |
|---|---|---|---|---|---|---|---|---|---|
| Ex. 13 | HI-2 | HT-2 | EBL-1 | BH-1 | BD-2 | aET-1 | bET-2 | 3.2 | 2600 |
| Comp. Ex. 19 | HI-2 | HT-2 | EBL-1 | BH-R1 | BD-2 | aET-1 | bET-2 | 3.4 | 2200 |

Example 14 and Comparative Example 20

The organic EL devices were manufactured and evaluated in the same manner as in Example 11, except that the compounds listed in Table 15 were used. The results are shown in Table 15.

TABLE 15

|  | HI | HT | EBL | BH | BD | HBL | ET | Voltage [V] | LT90 |
|---|---|---|---|---|---|---|---|---|---|
| Ex. 14 | HI-2 | HT-2 | EBL-1 | BH-3 | BD-2 | aET-1 | bET-2 | 3.3 | 2300 |
| Comp. Ex. 20 | HI-2 | HT-2 | EBL-1 | BH-R2 | BD-2 | aET-1 | bET-2 | 3.5 | 1430 |

Example 15, Example 16 and Comparative Example 21

The organic EL devices were manufactured and evaluated in the same manner as in Example 11, except that the compounds listed in Table 16 were used. The results are shown in Table 16.

TABLE 16

|  | HI | HT | EBL | BH | BD | HBL | ET | Voltage [V] | LT90 |
|---|---|---|---|---|---|---|---|---|---|
| Ex. 15 | HI-2 | HT-1 | EBL-1 | BH-1 | BD-2 | aET-1 | bET-1 | 3.3 | 1420 |
| Ex. 16 | HI-2 | HT-1 | EBL-1 | BH-3 | BD-2 | aET-1 | bET-1 | 3.3 | 1240 |
| Comp. Ex. 21 | HI-2 | HT-1 | EBL-1 | BH-R1 | BD-2 | aET-1 | bET-1 | 3.4 | 1050 |

Example 17

The organic EL devices were manufactured and evaluated in the same manner as in Example 11, except that the compounds listed in Table 17 were used. The results are shown in Table 17.

TABLE 17

|  | HI | HT | EBL | BH | BD | HBL | ET | Voltage [V] | LT90 |
|---|---|---|---|---|---|---|---|---|---|
| Ex. 17 | HI-2 | HT-1 | EBL-1 | BH-3 | BD-2 | aET-1 | bET-1 | 3.3 | 1110 |

Example 18 and Comparative Example 22

The organic EL devices were manufactured and evaluated in the same manner as in Example 11, except that the compounds listed in Table 18 were used. The results are shown in Table 18.

TABLE 18

|  | HI | HT | EBL | BH | BD | HBL | ET | Voltage [V] | LT90 |
|---|---|---|---|---|---|---|---|---|---|
| Ex. 18 | HI-2 | HT-1 | EBL-3 | BH-1 | BD-3 | aET-1 | bET-2 | 3.2 | 920 |
| Comp. Ex. 22 | HI-2 | HT-1 | EBL-3 | BH-R1 | BD-3 | aET-1 | bET-2 | 3.5 | 740 |

From the results in Tables 12 to 18, it can be seen that the top emission type devices of the Examples have lower voltage and the same or better device lifetime (LT90) than the devices of the Comparative Examples.

Example 19

The organic EL device was manufactured and evaluated in the same manner as in Example 1, except that the compounds listed in Table 19 were used. The results are shown in Table 19. Comparative Example 4 is also shown in Table 19 as a contrast.

TABLE 19

| | HI | HT | EBL | BH | BD | HBL | ET | Voltage [V] | LT90 |
|---|---|---|---|---|---|---|---|---|---|
| Ex. 19 | HI-1 | HT-1 | EBL-1 | BH-3 | BD-4 | aET-1 | bET-1 | 3.2 | 95 |
| Comp. Ex. 4 | HI-1 | HT-1 | EBL-1 | BH-R1 | BD-4 | aET-1 | bET-1 | 3.4 | 85 |

Example 20

The organic EL device was manufactured and evaluated in the same manner as in Example 1, except that the compounds listed in Table 20 were used. The results are shown in Table 20. Comparative Example 5 is also shown in Table 20 as a contrast.

TABLE 20

| | HI | HT | EBL | BH | BD | HBL | ET | Voltage [V] | LT90 |
|---|---|---|---|---|---|---|---|---|---|
| Ex. 20 | HI-1 | HT-1 | EBL-1 | BH-3 | BD-5 | aET-1 | bET-1 | 3.2 | 108 |
| Comp. Ex. 5 | HI-1 | HT-1 | EBL-1 | BH-R1 | BD-5 | aET-1 | bET-1 | 3.4 | 98 |

Example 21

The organic EL device was manufactured and evaluated in the same manner as in Example 1, except that the compounds listed in Table 21 were used. The results are shown in Table 21. Comparative Example 6 is also shown in Table 21 as a contrast.

TABLE 21

| | HI | HT | EBL | BH | BD | HBL | ET | Voltage [V] | LT90 |
|---|---|---|---|---|---|---|---|---|---|
| Ex. 21 | HI-1 | HT-1 | EBL-1 | BH-3 | BD-6 | aET-1 | bET-1 | 3.2 | 130 |
| Comp. Ex. 6 | HI-1 | HT-1 | EBL-1 | BH-R1 | BD-6 | aET-1 | bET-1 | 3.4 | 119 |

Example 22

The organic EL device was manufactured and evaluated in the same manner as in Example 1, except that the compounds listed in Table 22 were used. The results are shown in Table 22. Comparative Example 7 is also shown in Table 19 as a contrast.

TABLE 22

| | HI | HT | EBL | BH | BD | HBL | ET | Voltage [V] | LT90 |
|---|---|---|---|---|---|---|---|---|---|
| Ex. 22 | HI-1 | HT-1 | EBL-1 | BH-3 | BD-7 | aET-1 | bET-1 | 3.1 | 108 |
| Comp. Ex. 7 | HI-1 | HT-1 | EBL-1 | BH-R1 | BD-7 | aET-1 | bET-1 | 3.4 | 98 |

Example 23

The organic EL device was manufactured and evaluated in the same manner as in Example 1, except that the compounds listed in Table 23 were used. The results are shown in Table 23. Comparative Example 8 is also shown in Table 23 as a contrast.

TABLE 23

|  | HI | HT | EBL | BH | BD | HBL | ET | Voltage [V] | LT90 |
|---|---|---|---|---|---|---|---|---|---|
| Ex. 23 | HI-1 | HT-1 | EBL-1 | BH-3 | BD-8 | aET-1 | bET-1 | 3.2 | 107 |
| Comp. Ex. 8 | HI-1 | HT-1 | EBL-1 | BH-R1 | BD-8 | aET-1 | bET-1 | 3.4 | 97 |

Example 24

The organic EL device was manufactured and evaluated in the same manner as in Example 1, except that the compounds listed in Table 24 were used. The results are shown in Table 24. Comparative Example 9 is also shown in Table 24 as a contrast.

TABLE 24

|  | HI | HT | EBL | BH | BD | HBL | ET | Voltage [V] | LT90 |
|---|---|---|---|---|---|---|---|---|---|
| Ex. 24 | HI-1 | HT-1 | EBL-1 | BH-3 | BD-9 | aET-1 | bET-1 | 3.2 | 163 |
| Comp. Ex. 9 | HI-1 | HT-1 | EBL-1 | BH-R1 | BD-9 | aET-1 | bET-1 | 3.4 | 148 |

Example 25

The organic EL device was manufactured and evaluated in the same manner as in Example 1, except that the compounds listed in Table 25 were used. The results are shown in Table 25. Comparative Example 10 is also shown in Table 25 as a contrast.

TABLE 25

|  | HI | HT | EBL | BH | BD | HBL | ET | Voltage [V] | LT90 |
|---|---|---|---|---|---|---|---|---|---|
| Ex. 25 | HI-1 | HT-1 | EBL-1 | BH-3 | BD-10 | aET-1 | bET-1 | 3.2 | 181 |
| Comp. Ex. 10 | HI-1 | HT-1 | EBL-1 | BH-R1 | BD-10 | aET-1 | bET-1 | 3.4 | 164 |

Example 26 and Comparative Example 23

The organic EL devices were manufactured and evaluated in the same manner as in Example 1, except that the compounds listed in Table 26 were used. The results are shown in Table 26.

TABLE 26

|  | HI | HT | EBL | BH | BD | HBL | ET | Voltage [V] | LT90 |
|---|---|---|---|---|---|---|---|---|---|
| Ex. 26 | HI-1 | HT-1 | EBL-1 | BH-3 | BD-11 | aET-1 | bET-1 | 3.2 | 132 |
| Comp. Ex. 23 | HI-1 | HT-1 | EBL-1 | BH-R1 | BD-11 | aET-1 | bET-1 | 3.4 | 120 |

Example 27 and Comparative Example 24

The organic EL devices were manufactured and evaluated in the same manner as in Example 1, except that the compounds listed in Table 27 were used. The results are shown in Table 27.

TABLE 27

|  | HI | HT | EBL | BH | BD | HBL | ET | Voltage [V] | LT90 |
|---|---|---|---|---|---|---|---|---|---|
| Ex. 27 | HI-1 | HT-1 | EBL-1 | BH-3 | BD-12 | aET-1 | bET-1 | 3.1 | 134 |
| Comp. Ex. 24 | HI-1 | HT-1 | EBL-1 | BH-R1 | BD-12 | aET-1 | bET-1 | 3.3 | 122 |

Example 28 and Comparative Example 25

The organic EL devices were manufactured and evaluated in the same manner as in Example 1, except that the compounds listed in Table 28 were used. The results are shown in Table 28.

TABLE 28

|  | HI | HT | EBL | BH | BD | HBL | ET | Voltage [V] | LT90 |
|---|---|---|---|---|---|---|---|---|---|
| Ex. 28 | HI-1 | HT-1 | EBL-1 | BH-3 | BD-13 | aET-1 | bET-1 | 3.2 | 152 |
| Comp. Ex. 25 | HI-1 | HT-1 | EBL-1 | BH-R1 | BD-13 | aET-1 | bET-1 | 3.4 | 137 |

Example 29 and Comparative Example 26

The organic EL devices were manufactured and evaluated in the same manner as in Example 1, except that the compounds listed in Table 29 were used. The results are shown in Table 29.

TABLE 29

|  | HI | HT | EBL | BH | BD | HBL | ET | Voltage [V] | LT90 |
|---|---|---|---|---|---|---|---|---|---|
| Ex. 29 | HI-1 | HT-1 | EBL-1 | BH-3 | BD-14 | aET-1 | bET-1 | 3.1 | 158 |
| Comp. Ex. 26 | HI-1 | HT-1 | EBL-1 | BH-R1 | BD-14 | aET-1 | bET-1 | 3.3 | 145 |

Example 30 and Comparative Example 27

The organic EL devices were manufactured and evaluated in the same manner as in Example 1, except that the compounds listed in Table 30 were used. The results are shown in Table 30.

TABLE 30

|  | HI | HT | EBL | BH | BD | HBL | ET | Voltage [V] | LT90 |
|---|---|---|---|---|---|---|---|---|---|
| Ex. 30 | HI-1 | HT-1 | EBL-1 | BH-5 | BD-2 | aET-1 | bET-1 | 3.0 | 115 |
| Comp. Ex. 27 | HI-1 | HT-1 | EBL-1 | BH-R1 | BD-2 | aET-1 | bET-1 | 3.3 | 102 |

Example 31

The organic EL devices were manufactured and evaluated in the same manner as in Example 1, except that the compounds listed in Table 31 were used. The results are shown in Table 31. Comparative Example 7 is also shown in Table 31 as a contrast.

TABLE 31

|  | HI | HT | EBL | BH | BD | HBL | ET | Voltage [V] | LT90 |
|---|---|---|---|---|---|---|---|---|---|
| Ex. 31 | HI-1 | HT-1 | EBL-1 | BH-5 | BD-7 | aET-1 | bET-1 | 3.1 | 112 |
| Comp. Ex. 7 | HI-1 | HT-1 | EBL-1 | BH-R1 | BD-7 | aET-1 | bET-1 | 3.4 | 98 |

Example 32

The organic EL devices were manufactured and evaluated in the same manner as in Example 1, except that the compounds listed in Table 32 were used. The results are shown in Table 32. Comparative Example 8 is also shown in Table 32 as a contrast.

TABLE 32

| | HI | HT | EBL | BH | BD | HBL | ET | Voltage [V] | LT90 |
|---|---|---|---|---|---|---|---|---|---|
| Ex. 32 | HI-1 | HT-1 | EBL-1 | BH-5 | BD-8 | aET-1 | bET-1 | 3.1 | 110 |
| Comp. Ex. 8 | HI-1 | HT-1 | EBL-1 | BH-R1 | BD-8 | aET-1 | bET-1 | 3.4 | 97 |

Example 33

The organic EL devices were manufactured and evaluated in the same manner as in Example 1, except that the compounds listed in Table 33 were used. The results are shown in Table 33. Comparative Example 9 is also shown in Table 33 as a contrast.

TABLE 33

| | HI | HT | EBL | BH | BD | HBL | ET | Voltage [V] | LT90 |
|---|---|---|---|---|---|---|---|---|---|
| Ex. 33 | HI-1 | HT-1 | EBL-1 | BH-5 | BD-9 | aET-1 | bET-1 | 3.1 | 170 |
| Comp. Ex. 9 | HI-1 | HT-1 | EBL-1 | BH-R1 | BD-9 | aET-1 | bET-1 | 3.4 | 148 |

Example 34

The organic EL devices were manufactured and evaluated in the same manner as in Example 1, except that the compounds listed in Table 34 were used. The results are shown in Table 34. Comparative Example 10 is also shown in Table 34 as a contrast.

TABLE 34

| | HI | HT | EBL | BH | BD | HBL | ET | Voltage [V] | LT90 |
|---|---|---|---|---|---|---|---|---|---|
| Ex. 34 | HI-1 | HT-1 | EBL-1 | BH-5 | BD-10 | aET-1 | bET-1 | 3.1 | 185 |
| Comp. Ex. 10 | HI-1 | HT-1 | EBL-1 | BH-R1 | BD-10 | aET-1 | bET-1 | 3.4 | 164 |

Example 35 and Comparative Example 28

The organic EL devices were manufactured and evaluated in the same manner as in Example 1, except that the compounds listed in Table 35 were used. The results are shown in Table 35.

TABLE 35

| | HI | HT | EBL | BH | BD | HBL | ET | Voltage [V] | LT90 |
|---|---|---|---|---|---|---|---|---|---|
| Ex. 35 | HI-1 | HT-1 | EBL-1 | BH-5 | BD-11 | aET-1 | bET-1 | 3.1 | 135 |
| Comp. Ex. 28 | HI-1 | HT-1 | EBL-1 | BH-R1 | BD-11 | aET-1 | bET-1 | 3.4 | 120 |

Example 36 and Comparative Example 29

The organic EL devices were manufactured and evaluated in the same manner as in Example 1, except that the compounds listed in Table 36 were used. The results are shown in Table 36.

TABLE 36

|  | HI | HT | EBL | BH | BD | HBL | ET | Voltage [V] | LT90 |
|---|---|---|---|---|---|---|---|---|---|
| Ex. 36 | HI-1 | HT-1 | EBL-1 | BH-5 | BD-12 | aET-1 | bET-1 | 3.0 | 138 |
| Comp. Ex. 29 | HI-1 | HT-1 | EBL-1 | BH-R1 | BD-12 | aET-1 | bET-1 | 3.3 | 122 |

Example 37 and Comparative Example 30

The organic EL devices were manufactured and evaluated in the same manner as in Example 1, except that the compounds listed in Table 37 were used. The results are shown in Table 37.

TABLE 37

|  | HI | HT | EBL | BH | BD | HBL | ET | Voltage [V] | LT90 |
|---|---|---|---|---|---|---|---|---|---|
| Ex. 37 | HI-1 | HT-1 | EBL-1 | BH-5 | BD-13 | aET-1 | bET-1 | 3.1 | 154 |
| Comp. Ex. 30 | HI-1 | HT-1 | EBL-1 | BH-R1 | BD-13 | aET-1 | bET-1 | 3.4 | 137 |

Example 38 and Comparative Example 31

The organic EL devices were manufactured and evaluated in the same manner as in Example 1, except that the compounds listed in Table 38 were used. The results are shown in Table 38.

TABLE 38

|  | HI | HT | EBL | BH | BD | HBL | ET | Voltage [V] | LT90 |
|---|---|---|---|---|---|---|---|---|---|
| Ex. 38 | HI-1 | HT-1 | EBL-1 | BH-5 | BD-14 | aET-1 | bET-1 | 3.0 | 164 |
| Comp. Ex. 31 | HI-1 | HT-1 | EBL-1 | BH-R1 | BD-14 | aET-1 | bET-1 | 3.3 | 145 |

Example 39

The organic EL devices were manufactured and evaluated in the same manner as in Example 1, except that the compounds listed in Table 39 were used. The results are shown in Table 39. Comparative Example 28 is also shown in Table 39 as a contrast.

TABLE 39

|  | HI | HT | EBL | BH | BD | HBL | ET | Voltage [V] | LT90 |
|---|---|---|---|---|---|---|---|---|---|
| Ex. 39 | HI-1 | HT-1 | EBL-1 | BH-1 | BD-11 | aET-1 | bET-1 | 3.2 | 136 |
| Comp. Ex. 28 | HI-1 | HT-1 | EBL-1 | BH-R1 | BD-11 | aET-1 | bET-1 | 3.4 | 120 |

Example 40

The organic EL devices were manufactured and evaluated in the same manner as in Example 1, except that the compounds listed in Table 40 were used. The results are shown in Table 40. Comparative Example 29 is also shown in Table 40 as a contrast.

TABLE 40

|  | HI | HT | EBL | BH | BD | HBL | ET | Voltage [V] | LT90 |
|---|---|---|---|---|---|---|---|---|---|
| Ex. 40 | HI-1 | HT-1 | EBL-1 | BH-1 | BD-12 | aET-1 | bET-1 | 3.1 | 139 |
| Comp. Ex. 29 | HI-1 | HT-1 | EBL-1 | BH-R1 | BD-12 | aET-1 | bET-1 | 3.3 | 122 |

Example 41

The organic EL devices were manufactured and evaluated in the same manner as in Example 1, except that the compounds listed in Table 41 were used. The results are shown in Table 41. Comparative Example 30 is also shown in Table 41 as a contrast.

TABLE 41

|  | HI | HT | EBL | BH | BD | HBL | ET | Voltage [V] | LT90 |
|---|---|---|---|---|---|---|---|---|---|
| Ex. 41 | HI-1 | HT-1 | EBL-1 | BH-1 | BD-13 | aET-1 | bET-1 | 3.2 | 157 |
| Comp. Ex. 30 | HI-1 | HT-1 | EBL-1 | BH-R1 | BD-13 | aET-1 | bET-1 | 3.4 | 137 |

Example 42

The organic EL devices were manufactured and evaluated in the same manner as in Example 1, except that the compounds listed in Table 42 were used. The results are shown in Table 42. Comparative Example 31 is also shown in Table 42 as a contrast.

TABLE 42

|  | HI | HT | EBL | BH | BD | HBL | ET | Voltage [V] | LT90 |
|---|---|---|---|---|---|---|---|---|---|
| Ex. 42 | HI-1 | HT-1 | EBL-1 | BH-1 | BD-14 | aET-1 | bET-1 | 3.1 | 165 |
| Comp. Ex. 31 | HI-1 | HT-1 | EBL-1 | BH-R1 | BD-14 | aET-1 | bET-1 | 3.3 | 145 |

From the results in Tables 19 to 42, it can be seen that the bottom emission type devices of the Examples have lower voltage and the same or better device lifetime (LT90) than the devices of the Comparative examples.

Example 43

[Manufacture of Bottom Emission Type Organic EL Device]

A 25 mm×75 mm×1.1 mm-thick glass substrate with ITO (Indium Tin Oxide) transparent electrode (anode) (manufactured by GEOMATEC Co., Ltd.) was subjected to ultrasonic cleaning in isopropyl alcohol for 5 minutes, followed by UV-ozone washing for 30 minutes. The thickness of the ITO transparent electrode was 130 nm. The glass substrate with the transparent electrode line after being cleaned was mounted onto a substrate holder in a vacuum vapor deposition apparatus, and a compound HI-1 was deposited on a surface on the side on which the transparent electrode line was formed so as to cover the transparent electrode to form a hole-injecting layer (HI) having a thickness of 5 nm. Subsequent to the formation of the hole-injecting layer, a compound HT-1 was deposited thereon to form a first hole-transporting layer (HT) having a thickness of 80 nm. Subsequent to the formation of the first hole-transporting layer, a compound EBL-5 was deposited thereon to form a second hole-transporting layer (also referred to as an electron barrier layer) (EBL) having a thickness of 10 nm. A compound BH-1 (a host material (BH)) and compound BD-14 (a dopant material (BD)) were co-deposited on the second hole-transporting layer to be 4 mass % in a proportion of BD-14 to form an emitting layer having a thickness of 25 nm. A compound aET-3 was deposited on the emitting layer to forma first electron-transporting layer (also referred to as a hole barrier layer) (HBL) having a thickness of 10 nm. A compound bET-5 was deposited on the first electron-transporting layer to form a second electron-transporting layer (ET) having a thickness of 15 nm. LiF was deposited on the second electron-transporting layer to form an electron-injecting layer having a thickness of 1 nm. A metal Al was deposited on the electron-injecting layer to form a cathode having a thickness of 80 nm.

The device configuration of the organic EL device of Example 43 is shown informality as follows.

ITO(130)/HI-1(5)/HT-1(80)/EBL-5(10)/BH-1:BD-14 (25.96%:4%)/aET-3(10)/bET-5(15)/LiF(1)/Al(80)

The numerical values in parentheses indicate the film thickness (unit: nm). The numerical value represented in percentages in parentheses indicates the proportion (mass %) of the host material and the dopant material in the emitting layer.

<Evaluation of Organic EL Device>

Initial characteristics of the obtained organic EL devices were measured by driving at a constant current of 10 mA/cm² of DC (direct current) at room temperature. The measurement results of the voltage are shown in Table 43.

A voltage was applied to the obtained organic EL device so that the current density became 50 mA/cm², and the time until the luminance became 95% of the initial luminance (LT95 (unit: hours)) w as measured. Results are shown in Table 43.

Comparative Example 32

The organic EL devices were manufactured and evaluated in the same manner as in Example 43, except that the compounds listed in Table 43 were used. The results are shown in Table 43.

TABLE 43

|  | HI | HT | EBL | BH | BD | HBL | ET | Voltage [V] | LT90 |
|---|---|---|---|---|---|---|---|---|---|
| Ex. 43 | HI-1 | HT-1 | EBL-5 | BH-1 | BD-14 | aET-3 | bET-5 | 3.4 | 95 |
| Comp. Ex. 32 | HI-1 | HT-1 | EBL-5 | BH-R1 | BD-14 | aET-3 | bET-5 | 3.5 | 72 |

Example 44 and Comparative Example 33

The organic EL devices were manufactured and evaluated in the same manner as in Example 43, except that the compounds listed in Table 44 were used. The results are shown in Table 44.

TABLE 44

|  | HI | HT | EBL | BH | BD | HBL | ET | Voltage [V] | LT90 |
|---|---|---|---|---|---|---|---|---|---|
| Ex. 44 | HI-1 | HT-1 | EBL-5 | BH-1 | BD-15 | aET-3 | bET-5 | 3.4 | 70 |
| Comp. Ex. 33 | HI-1 | HT-1 | EBL-5 | BH-R1 | BD-15 | aET-3 | bET-5 | 3.5 | 54 |

Example 45

The organic EL devices were manufactured and evaluated in the same manner as in Example 43, except that the compounds listed in Table 45 were used. The results are shown in Table 45.

TABLE 45

|  | HI | HT | EBL | BH | BD | HBL | ET | Voltage [V] | LT90 |
|---|---|---|---|---|---|---|---|---|---|
| Ex. 45 | HI-1 | HT-1 | EBL-5 | BH-1 | BD-16 | aET-3 | bET-5 | 3.4 | 72 |

Example 46 and 47

The organic EL devices were manufactured and evaluated in the same manner as in Example 43, except that the compounds listed in Table 46 were used. The results are shown in Table 46.

TABLE 46

|  | HI | HT | EBL | BH | BD | HBL | ET | Voltage [V] | LT90 |
|---|---|---|---|---|---|---|---|---|---|
| Ex. 46 | HI-1 | HT-1 | EBL-5 | BH-3 | BD-14 | aET-3 | bET-5 | 3.4 | 83 |
| Ex. 47 | HI-1 | HT-1 | EBL-5 | BH-3 | BD-15 | aET-3 | bET-5 | 3.4 | 62 |

From the results in Tables 43 to 46, it can be seen that the bottom emission type devices of the Examples have lower voltage and the same or better device lifetime (LT95) than the devices of the Comparative examples.

Example 48

[Manufacture of Bottom Emission Type Organic EL Device]

A 25 mm×75 mm×1.1 mm-thick glass substrate with ITO (Indium Tin Oxide) transparent electrode (anode) (manufactured by GEOMATEC Co., Ltd.) was subjected to ultrasonic cleaning in isopropyl alcohol for 5 minutes, followed by UV-ozone washing for 30 minutes. The thickness of the ITO transparent electrode was 130 nm. The glass substrate with the transparent electrode line after being cleaned was mounted onto a substrate holder in a vacuum vapor deposition apparatus, and a compound HI-2 was deposited on a surface on the side on which the transparent electrode line was formed so as to cover the transparent electrode to form a hole-injecting layer (HI) having a thickness of 5 nm. Subsequent to the formation of the hole-injecting layer, a compound HT-2 was deposited thereon to form a first hole-transporting layer (HT) having a thickness of 85 nm. Subsequent to the formation of the first hole-transporting layer, a compound EBL-6 was deposited thereon to form a second hole-transporting layer (also referred to as an electron barrier layer) (EBL) having a thickness of 5 nm. A compound BH-1 (a host material (BH)) and compound BD-9 (a dopant material (BD)) were co-deposited on the second hole-transporting layer to be 4 mass % in a proportion of BD-9 to form an emitting layer having a thickness of 25 nm. A compound aET-3 was deposited on the emitting layer to form a first electron-transporting layer (also referred to as a hole barrier layer) (HBL) having a thickness of 10 nm. A compound bET-3 was deposited on the first electron-transporting layer to forma second electron-transporting layer (ET) having a thickness of 15 nm. LiF was deposited on the second electron-transporting layer to form an electron-injecting layer having a thickness of 1 nm. A metal Al was deposited on the electron-injecting layer to form a cathode having a thickness of 80 nm.

The device configuration of the organic EL device of Example 48 is shown informality as follows.

ITO(130)/HI-2(5)/HT-2(85)/EBL-6(5)/BH-1:BD-9(25, 96%:4%)/aET-3(10)/bET-3(15)/LiF(1)/Al(80)

The numerical values in parentheses indicate the film thickness (unit: nm). The numerical value represented in percentages in parentheses indicates the proportion (mass %) of the host material and the dopant material in the emitting layer.

<Evaluation of Organic EL Device>

Initial characteristics of the obtained organic EL devices were measured by driving at a constant current of 10 mA/cm$^2$ of DC (direct current) at room temperature. The measurement results of the voltage are shown in Table 43.

A voltage was applied to the obtained organic EL device so that the current density became 50 mA/cm$^2$, and the time until the luminance became 95% of the initial luminance (LT90 (unit: hours)) w as measured. Results are shown in Table 47.

Example 49, and Comparative Example 34

The organic EL devices were manufactured and evaluated in the same manner as in Example 48, except that the compounds listed in Table 47 were used. The results are shown in Table 47.

TABLE 47

| (Thickness: nm) | HI (5) | HT (85) | EBL (5) | BH | BD (25) | HBL (10) | ET (15) | Voltage [V] | LT90 |
|---|---|---|---|---|---|---|---|---|---|
| Ex. 48 | HI-2 | HT-2 | EBL-6 | BH-1 | BD-9 | aET-3 | bET-3 | 3.0 | 308 |
| Ex. 49 | HI-2 | HT-2 | EBL-6 | BH-3 | BD-9 | aET-3 | bET-3 | 3.1 | 275 |
| Comp. Ex. 34 | HI-2 | HT-2 | EBL-6 | BH-R5 | BD-9 | aET-3 | bET-3 | 3.3 | 120 |

Examples 50 and 51, and Comparative Examples 35 and 36

The organic EL devices were manufactured and evaluated in the same manner as in Example 48, except that the compounds listed in Table 48 were used and the film thickness of each layer was set as described in Table 48. The results are shown in Table 48.

The device configuration of the organic EL device of Example 50 is shown informality as follows.
ITO(130)/HI-2(5)/HT-4(110)/EBL-5(20)/BH-1:BD-2(25, 96%:4%)/aET-3(5)/bET-3(20)/LiF(1)/Al(80)

TABLE 48

| (Thickness: nm) | HI (5) | HT (110) | EBL (20) | BH | BD (25) | HBL (5) | ET (20) | Voltage [V] | LT90 |
|---|---|---|---|---|---|---|---|---|---|
| Ex. 50 | HI-2 | HT-4 | EBL-5 | BH-1 | BD-2 | aET-3 | bET-3 | 3.6 | 236 |
| Ex. 51 | HI-2 | HT-4 | EBL-5 | BH-3 | BD-2 | aET-3 | bET-3 | 3.6 | 228 |
| Comp. Ex. 35 | HI-2 | HT-4 | EBL-5 | BH-R5 | BD-2 | aET-3 | bET-3 | 3.8 | 102 |
| Comp. Ex. 36 | HI-2 | HT-4 | EBL-5 | BH-R6 | BD-2 | aET-3 | bET-3 | 3.9 | 120 |

Example 52, and Comparative Example 37

The organic EL devices were manufactured and evaluated in the same manner as in Example 48, except that the compounds listed in Table 49 were used and the film thickness of each layer was set as described in Table 49. The results are shown in Table 49.

The device configuration of the organic EL device of Example 52 is shown informality as follows.
ITO(130)/HI-2(5)/HT-6(10)/EBL-3(5)/BH-3:BD-2(25, 96%:4%)/aET-1(5)/bET-3(25)/LiF(1)/Al(80)

TABLE 49

| (Thickness: nm) | HI (5) | HT (10) | EBL (5) | BH | BD (25) | HBL (5) | ET (25) | Voltage [V] | LT90 |
|---|---|---|---|---|---|---|---|---|---|
| Ex. 52 | HI-2 | HT-6 | EBL-3 | BH-3 | BD-2 | aET-1 | bET-3 | 3.0 | 140 |
| Comp. Ex. 37 | HI-2 | HT-6 | EBL-3 | BH-R1 | BD-2 | aET-1 | bET-3 | 3.2 | 115 |

Examples 53 and 54, and Comparative Example 38

The organic EL devices were manufactured and evaluated in the same manner as in Example 48, except that the compounds listed in Table 50 were used and the film thickness of each layer was set as described in Table 50. The results are shown in Table 50.

The device configuration of the organic EL device of Example 53 is shown informality as follows.
ITO(130)/HI-2(5)/HT-5(75)/EBL-8(15)/BH-3:BD-2(25, 96%:4%)/aET-1(3)/bET-3(30)/LiF(1)/Al(80)

TABLE 50

| (Thickness: nm) | HI (5) | HT (75) | EBL (15) | BH (25) | BD (3) | HBL (30) | ET | Voltage [V] | LT90 |
|---|---|---|---|---|---|---|---|---|---|
| Ex. 53 | HI-2 | HT-5 | EBL-8 | BH-3 | BD-2 | aET-1 | bET-3 | 3.1 | 150 |
| Ex. 54 | HI-2 | HT-5 | EBL-8 | BH-1 | BD-2 | aET-1 | bET-3 | 3.1 | 145 |
| Comp. Ex. 38 | HI-2 | HT-5 | EBL-8 | BH-R1 | BD-2 | aET-1 | bET-3 | 3.2 | 130 |

Example 55, and Comparative Example 39

The organic EL devices were manufactured and evaluated in the same manner as in Example 48, except that the compounds listed in Table 51 were used and the film thickness of each layer was set as described in Table 51. The results are shown in Table 51.

The device configuration of the organic EL device of Example 55 is shown informality as follows.
ITO(130)/HI-1(5)/HT-1(85)/EBL-1(5)/BH-1:BD-18(25, 96%:4%)/aET-1(10)/bET-1(15)/LiF(1)/Al(80)

TABLE 51

| (Thickness: nm) | HI (5) | HT (85) | EBL (5) | BH (25) | BD | HBL (10) | ET (15) | Voltage [V] | LT90 |
|---|---|---|---|---|---|---|---|---|---|
| Ex. 55 | HI-1 | HT-1 | EBL-1 | BH-1 | BD-18 | aET-1 | bET-1 | 3.2 | 203 |
| Comp. Ex. 39 | HI-1 | HT-1 | EBL-1 | BH-R1 | BD-18 | aET-1 | bET-1 | 3.4 | 150 |

Examples 56 to 60, and Comparative Example 40

The organic EL devices were manufactured and evaluated in the same manner as in Example 48, except that the compounds listed in Table 52 were used and the film thickness of each layer was set as described in Table 52. The results are shown in Table 52.

The device configuration of the organic EL device of Example 56 is shown informality as follows.
ITO(130)/HI-1(5)/HT-1(85)/EBL-1(5)/BH-1:BD-19(25, 96%:4%)/aET-1(10)/bET-1(15)/LiF(1)/Al(80)

TABLE 52

| (Thickness: nm) | HI (5) | HT (85) | EBL (5) | BH (25) | BD | HBL (10) | ET (15) | Voltage [V] | LT90 |
|---|---|---|---|---|---|---|---|---|---|
| Ex. 56 | HI-1 | HT-1 | EBL-1 | BH-1 | BD-19 | aET-1 | bET-1 | 3.2 | 257 |
| Ex. 57 | HI-1 | HT-1 | EBL-1 | BH-11 | BD-19 | aET-1 | bET-1 | 3.1 | 190 |
| Ex. 58 | HI-1 | HT-1 | EBL-1 | BH-12 | BD-19 | aET-1 | bET-1 | 3.1 | 196 |
| Ex. 59 | HI-1 | HT-1 | EBL-1 | BH-15 | BD-19 | aET-1 | bET-1 | 3.2 | 203 |
| Ex. 60 | HI-1 | HT-1 | EBL-1 | BH-17 | BD-19 | aET-1 | bET-1 | 3.2 | 206 |
| Comp. Ex. 40 | HI-1 | HT-1 | EBL-1 | BH-R1 | BD-19 | aET-1 | bET-1 | 3.4 | 165 |

Examples 61 to 65, and Comparative Example 41

The organic EL devices were manufactured and evaluated in the same manner as in Example 48, except that the compounds listed in Table 53 were used and the film thickness of each layer was set as described in Table 53. The results are shown in Table 53.

The device configuration of the OLED device of Example 61 is shown in the following schematic.

The device configuration of the organic EL device of Example 61 is shown informality as follows.
ITO(430)/HI-1(5)/HT-1(85)/EBL-1(5)/BH-1 BD-19(25, 96%:4%)/aET-6(10)/bET-6(35)/LiF(1)/Al(80)

TABLE 53

| (Thickness: nm) | HI (5) | HT (85) | EBL (5) | BH | BD (25) | HBL (10) | ET (15) | Voltage [V] | LT90 |
|---|---|---|---|---|---|---|---|---|---|
| Ex. 61 | HI-1 | HT-1 | EBL-1 | BH-1 | BD-19 | aET-6 | bET-6 | 3.1 | 272 |
| Ex. 62 | HI-1 | HT-1 | EBL-1 | BH-11 | BD-19 | aET-6 | bET-6 | 3.1 | 196 |
| Ex. 63 | HI-1 | HT-1 | EBL-1 | BH-12 | BD-19 | aET-6 | bET-6 | 3.1 | 204 |
| Ex. 64 | HI-1 | HT-1 | EBL-1 | BH-15 | BD-19 | aET-6 | bET-6 | 3.2 | 200 |
| Ex. 65 | HI-1 | HT-1 | EBL-1 | BH-17 | BD-19 | aET-6 | bET-6 | 3.2 | 210 |
| Comp. Ex. 41 | HI-1 | HT-1 | EBL-1 | BH-R1 | BD-19 | aET-6 | bET-6 | 3.3 | 165 |

From the results in Tables 47 to 53, it can be seen that the bottom emission type devices of the Examples have lower voltage and the same or better device lifetime (LT90) than the devices of the Comparative examples.

<Synthesis of Compounds>

Synthesis Example 1: Synthesis of Compound 1BH-1

A compound 1BH-1 was synthesized according to the synthetic scheme below.

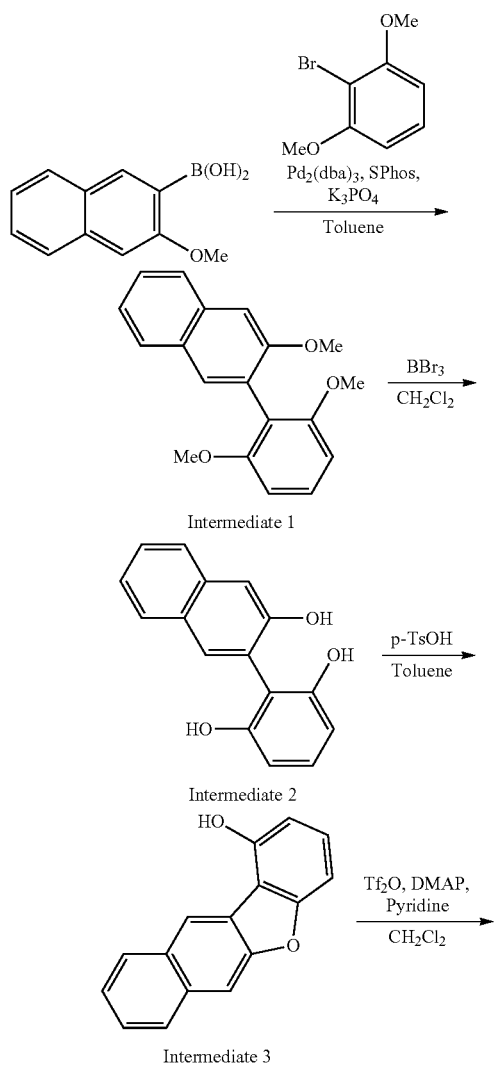

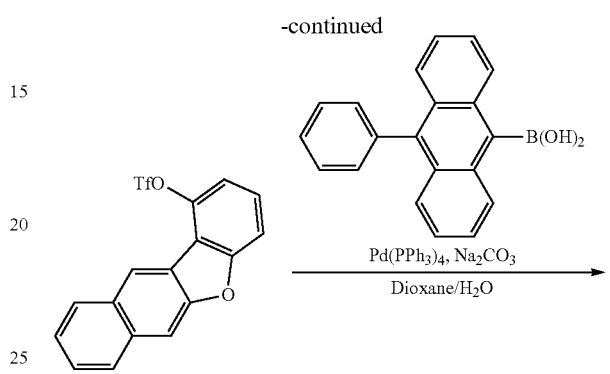

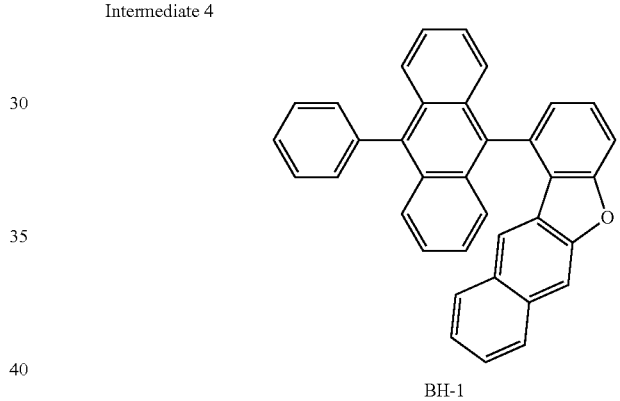

(1) Synthesis of 2-(2,6-dimethoxyphenyl)-3-methoxynaphthalene (Intermediate 1)

Under an argon atmosphere, 18.6 g of (3-methoxynaphthalene-2-yl)boronic acid, 10.0 g of 2-bromo-1,3-dimethoxybenzene, 2.11 g of tris(dibenzylideneacetone)dipalladium (0), 1.89 g of 2-dicyclohexylphosphino-2',6'-dimethoxybiphenyl (SPhos), 29.3 g of tripotassium phosphate, and 23 mL of toluene (dehydrated) were charged into flasks, and heated and stirred at refluxing for 5 hours. After cooling to room temperature, the reaction solution was extracted using toluene, and after removing the aqueous phase, the organic phase was washed with saturated saline. The organic phase was dried with anhydrous sodium sulfate and concentrated, and the residue was purified by silica gel column chromatography to obtain 12.1 g (yield: 89%) of 2-(2,6-dimethoxyphenyl)-3-methoxynaphthalene (Intermediate 1).

(2) Synthesis of 2-(3-hydroxynaphthalene-2-yl)benzene-1,3-diol (Intermediate 2)

Under an argon atmosphere, 12.1 g of 2-(2,6-dimethoxyphenyl)-3-methoxynaphthalene (Intermediate 1) and 520 mL of dichloromethane (dehydrated) were placed in a flask and cooled to 0° C. 156 mL of 1.0 mol/l solution of boron tribromide in dichloromethane was added to the flask, followed by stirring at room temperature for 4 hours. After completion of the reaction, the solution was cooled to −78° C., carefully deactivated with methanol, and further deactivated with a sufficient amount of water. The solution was transferred to a separatory funnel, extracted with dichloromethane, dried over anhydrous sodium sulfate, and then passed through a silica gel short column to remove the origin impurities, and the solution was concentrated, and the obtained sample was dried under vacuum at room temperature for 3 hours to obtain 10.2 g (99%) of a white solid of 2-(3-hydroxynaphthalene-2-yl)benzene-1,3-diol (Intermediate 2).

(3) Synthesis of naphtho[2,3-b]benzofuran-1-ol (Intermediate 3)

10.1 g of 2-(3-hydroxynaphthalene-2-yl)benzene-1,3-diol (Intermediate 2), 14.0 g of p-toluenesulfonic acid monohydrate, and 500 mL of toluene were placed in a flask, and then heated and stirred at refluxing for 8 hours. After completion of the reaction, the solution was cooled to room temperature and further deactivated with a sufficient amount of water. The solution was transferred to a separatory funnel, extracted with toluene, dried over anhydrous sodium sulfate, and then passed through a silica gel short column to remove the origin impurities, and the solution was concentrated, and the obtained sample was dried under vacuum at room temperature for 3 hours to obtain 6.52 g (70%) of a white solid of naphtho[2,3-b]benzofuran-1-ol (Intermediate 3).

(4) Synthesis of naphtho[2,3-b]benzofuran-1-yl trifluoromethanesulfonate (Intermediate 4)

Under an argon atmosphere, 6.52 g of naphtho[2,3-b]benzofuran-1-ol (Intermediate 4), 0.34 g of N,N-dimethyl-4-aminopyridine, 5.62 mL of trifluoromethanesulfonic anhydride, and 140 mL of dichloromethane (dehydrated) were placed in a flask and cooled to 0° C. 55.7 mL of pyridine (dehydrated) was added dropwise and then stirred at room temperature for 2 hours. After completion of the reaction, the reaction solution was deactivated with a sufficient amount of water. The solution was transferred to a separatory funnel, extracted with dichloromethane, dried over anhydrous sodium sulfate, and then passed through a silica gel short column to remove the origin impurities, and the solution was concentrated, and the obtained sample was dried under vacuum at room temperature for 3 hours to obtain 7.77 g (76%) of a white solid of naphtho[2,3-b]benzofuran-1-yl trifluoromethanesulfonate (Intermediate 4).

(5) Synthesis of anthracene derivative (compound BH-1)

Under an argon atmosphere, 2.31 g of naphtho[2,3-b]benzofuran-1-yl trifluoromethanesulfonate (Intermediate 4), 1.88 g of 10-phenylanthracene-9-boronic acid synthesized by a known method, 0.29 g of tetrakis(triphenylphosphine) palladium (0), 1.34 g of sodium carbonate, 47 mL of 1,4-dioxane, and 16 mL of ion-exchanged water were added to the flask, and the mixture was stirred at refluxing for 4 hours. After cooling to room temperature, the precipitated solid was collected by filtration. The resulting solid was washed with water and acetone, and then recrystallized with a mixed solvent of toluene and hexane to obtain 1.44 g of a white solid. This white solid was a compound BH-1 as a consequence of mass spectral analyses, with m/e=470 for a molecular weight of 470.17.

Synthesis Example 2: Synthesis of Compound BH-3

A compound BH-3 was synthesized according to the synthetic scheme below.

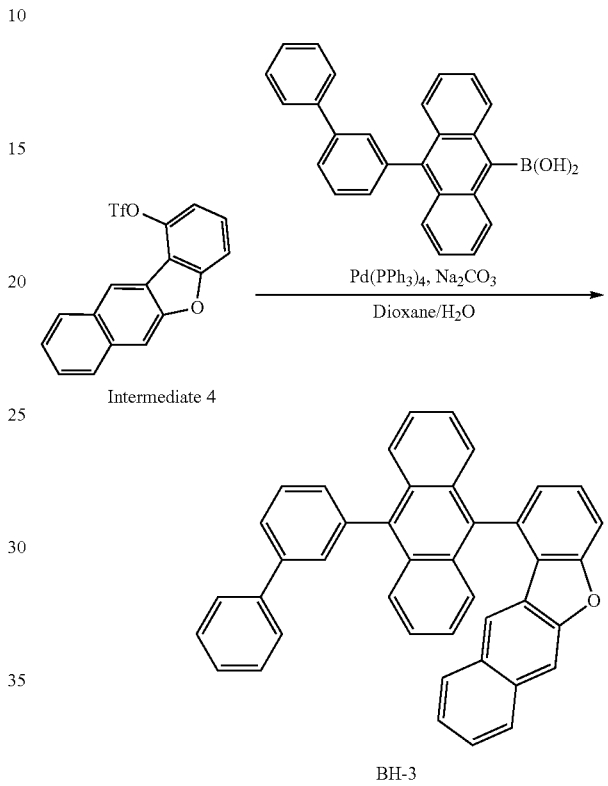

BH-3

A reaction was carried out in the same manner as in Synthesis Example 1 except that 10-(3-biphenyl)anthracene-9-boronic acid synthesized by a known method was used in place of 10-phenylanthracene-9-boronic acid in the synthesis of the compound BH-1 of Synthesis Example 1 to obtain a white solid. This white solid was a compound BH-3 as a consequence of mass spectral analyses, with m/e=546 for a molecular weight of 546.20.

Synthesis Example 3: Synthesis of Compound BH-5

A compound BH-5 was synthesized according to the synthetic scheme below.

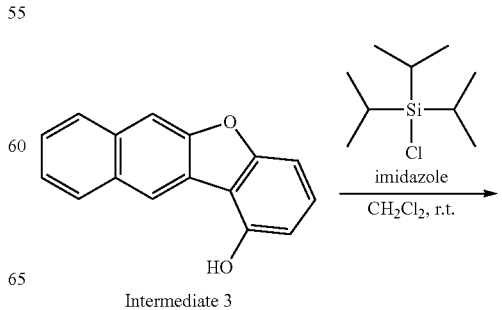

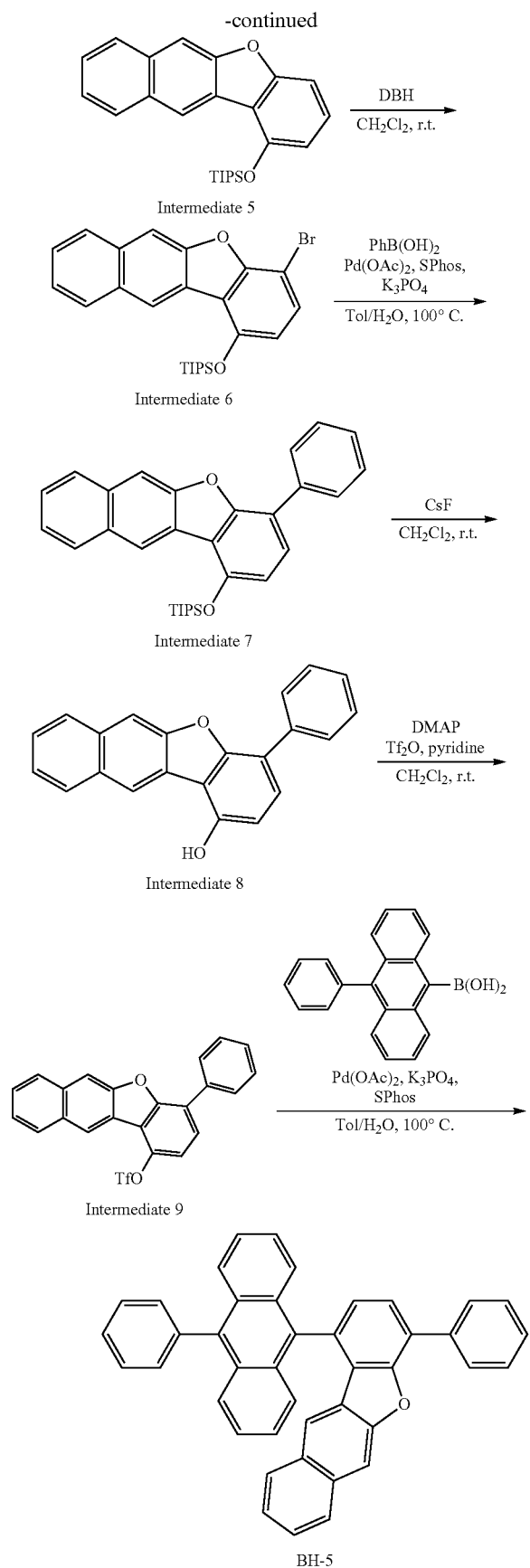

(1) Synthesis of triisopropyl(naphtho[2,3-b]benzo-furan-1-yloxy)silane (Intermediate 5)

Under an argon atmosphere, 9.88 g of naphtho[2,3-b]benzofuran-1-ol (Intermediate 3), 13.6 mL of chlorotriisopropylsilane, 4.33 g of imidazole, and 200 mL of dichloromethane (dehydrated) were charged into a flask and stirred at room temperature for 5 hours. The reaction solution was extracted using dichloromethane, and after removing the aqueous phase, the organic phase was washed with saturated saline. The organic phase was dried with anhydrous sodium sulfate and concentrated, and the residue was purified by silica gel column chromatography to obtain 16.3 g (yield: 98%) of a transparent oil of triisopropyl(naphtho[2,3-b]benzofuran-1-yloxy)silane (Intermediate 5).

(2) Synthesis of ((4-bromonaphtho[2,3-b]benzo-furan-1-yl)oxy)triisopropylsilane (Intermediate 6)

Under an argon atmosphere, 15.8 g of triisopropyl(naphtho[2,3-b]benzofuran-1-yloxy)silane (Intermediate 5), 9.17 g of 1,3-dibromo-5,5-dimethylhydantoin (DBH), and 200 mL of dichloromethane (dehydrated) were placed in a flask and then stirred at room temperature for 4 hours. After completion of the reaction, the reaction solution was deactivated with a sufficient amount of water. The solution was transferred to a separatory funnel, extracted with dichloromethane, and the organic phase was dried with anhydrous sodium sulfate, and then concentrated, and the residue was purified by silica gel column chromatography, and the obtained sample was dried under vacuum at room temperature for 3 hours to obtain 18.7 g (99%) of a transparent oil of ((4-bromonaphtho[2,3-b]benzofuran-1-yl)oxy)triisopropylsilane (Intermediate 6).

(3) Synthesis of triisopropyl((4-phenylnaphtho[2,3-b]benzofuran-1-yl)oxy)silane (Intermediate 7)

17.7 g of ((4-bromonaphtho[2,3-b]benzofuran-1-yl)oxy)triisopropylsilane (Intermediate 6), 6.03 g of phenylboronic acid (PhB(OH)$_2$), 0.23 g of palladium (II) acetate, 0.90 g of 2-dicyclohexylphosphino-2',6'-dimethoxybiphenyl (SPhos), 16.8 g of tripotassium phosphate, 360 mL of toluene, and 110 mL of ion-exchanged water were placed in a flask, and then heated and stirred at refluxing for 6 hours. After completion of the reaction, the solution was cooled to room temperature and further deactivated with a sufficient amount of water. The solution was transferred to a separatory funnel, extracted with toluene, dried over anhydrous sodium sulfate, and then passed through a silica gel short column to remove the origin impurities, and the solution was concentrated, and the obtained sample was dried under vacuum at room temperature for 3 hours to obtain 17.0 g (97%) of a white solid of triisopropyl((4-phenylnaphtho[2,3-b]benzofuran-1-yl)oxy)silane (Intermediate 7).

(4) Synthesis of 4-phenylnaphtho[2,3-b]benzofuran-1-ol (Intermediate 8)

3.66 g of triisopropyl((4-phenylnaphtho[2,3-b]benzofuran-1-yl)oxy)silane (Intermediate 7), 4.60 g of cesium fluoride, and 30 mL of dichloromethane (dehydrated) were placed in a flask, and then heated and stirred at refluxing for 6 hours. After completion of the reaction, the solution was cooled to room temperature and further deactivated with a sufficient amount of water. The solution was transferred to a separatory funnel, extracted with toluene, dried over anhydrous sodium sulfate, and then passed through a silica gel short column to remove the origin impurities, and the solution was concentrated, and the obtained sample was dried under vacuum at room temperature for 3 hours to obtain 1.95 g (80%) of a white solid of 4-phenylnaphtho[2,3-b]benzofuran-1-ol (Intermediate 8).

(5) Synthesis of 4-phenylnaphtho[2,3-b]benzofuran-1-yl trifluoromethanesulfonate (Intermediate 9)

1.60 g of 4-phenylnaphtho[2,3-b]benzofuran-1-ol (Intermediate 8), 1.75 g of trifluoromethanesulfonic anhydride (Tf$_2$O), 0.06 g of N,N-dimethyl-4-aminopyridine, and 25 mL of dichloromethane (dehydrated) were placed in a flask and cooled to 0° C. in an ice bath. Thereafter, 10 mL of pyridine was added dropwise with a dropping funnel, and the mixture was stirred at room temperature for 3 hours. After completion of the reaction, the solution was cooled to 0° C., and further deactivated with a sufficient amount of water. The solution was transferred to a separatory funnel, extracted with dichloromethane, dried over anhydrous sodium sulfate, and then concentrated, and the residue was purified by silica gel column chromatography, and the obtained sample was dried under vacuum at room temperature for 3 hours to obtain 1.83 g (80%) of a white solid of 4-phenylnaphtho[2,3-b]benzofuran-1-yl trifluoromethanesulfonate (Intermediate 9).

(6) Synthesis of Anthracene Derivative (Compound BH-5)

Under an argon atmosphere, 3.90 g of 4-phenylnaphtho[2,3-b]benzofuran-1-yl trifluoromethanesulfonate (Intermediate 9), 2.50 g of (10-phenylanthracene-9-yl)phenylboronic acid synthesized by known methods, 0.04 g of palladium (II) acetate, 0.15 g of 2-dicydohexylphosphino-2',6'-dimethoxybiphenyl (SPhos), 3.80 g of tripotassium phosphate, 80 mL of toluene, and 10 mL of ion-exchanged water were placed in a flask, and the mixture was heated and stirred for 6 hours. After completion of the reaction, the solution was cooled to room temperature and further deactivated with a sufficient amount of water. The solution was transferred to a separatory funnel, extracted with toluene, dried over anhydrous sodium sulfate, and then passed through a silica gel short column to remove the origin impurities, and the solution was concentrated, and the obtained sample was dried under vacuum at room temperature for 3 hours, cooled to room temperature, and then the precipitated solid was collected by filtration. The resulting solid was washed with water, acetone, and then recrystallized with a mixed solvent of toluene and hexane to obtain 2.51 (52%) of a white solid. This white solid was a compound BH-5 as a consequence of mass spectral analyses, with m/e=547 for a molecular weight of 546.67.

Synthesis Example 4: Synthesis of Compound BH-7

A compound BH-7 was synthesized according to the synthetic scheme below.

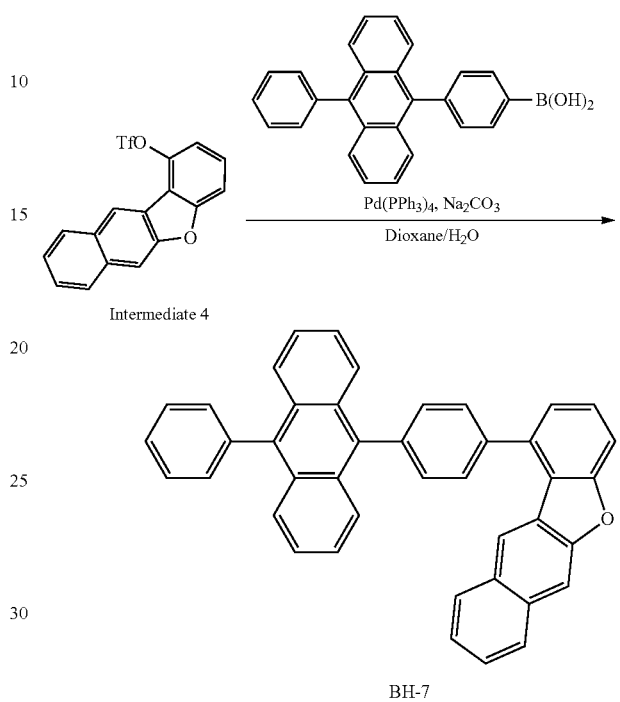

A reaction was carried out in the same manner as in Synthesis Example 1 except that (4-(10-phenylanthracen-9-yl) phenyl)boronic acid synthesized by a known method was used in place of 10-phenylanthracene-9-boronic acid in the synthesis of the compound BH-1 of Synthesis Example 1 to obtain a white solid. This white solid was a compound BH-7 as a consequence of mass spectral analyses, with m/e=546 for a molecular weight of 546.20.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The invention claimed is:
1. An organic electroluminescence device comprising:
a cathode,
an anode, and
an organic layer disposed between the cathode and the anode, wherein
the organic layer comprises an emitting layer, a first layer, and a second layer,
the first layer is disposed between the cathode and the emitting layer,
the second layer is disposed between the cathode and the first layer,
the second layer comprises a compound represented by the following formula (EB4),
the emitting layer comprises a compound represented by the following formula (1), and the first layer comprises a compound represented by the following formula (BE1):

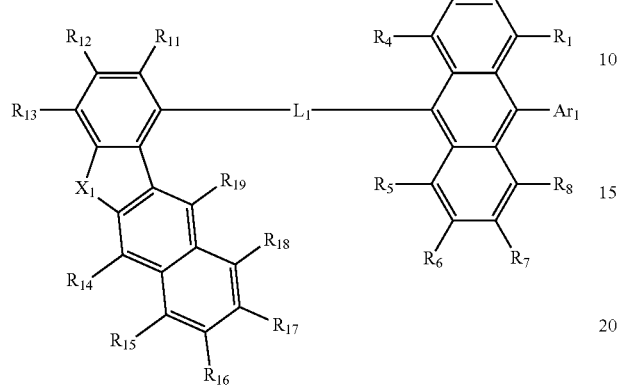
(1)

wherein in the formula (1),
$X_1$ is an oxygen atom or a sulfur atom;
$Ar_1$ is a substituted or unsubstituted aryl group including 6 to 50 ring carbon atoms, or
a substituted or unsubstituted monovalent heterocyclic group including 5 to 50 ring atoms;
$L_1$ is a single bond,
a substituted or unsubstituted arylene group including 6 to 50 ring carbon atoms, or
a substituted or unsubstituted divalent heterocyclic group including 5 to 50 ring atoms;
$R_1$ to $R_8$ and $R_{11}$ to $R_{19}$ are independently
a hydrogen atom, a halogen atom, a cyano group, a nitro group,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
—S—($R_{905}$),
—N($R_{906}$)($R_{907}$),
a substituted or unsubstituted aryl group including 6 to 50 ring carbon atoms, or
a substituted or unsubstituted monovalent heterocyclic group including 5 to 50 ring atoms;
$R_{901}$ to $R_{907}$ are independently
a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted monovalent heterocyclic group including 5 to 50 ring atoms; and
when two or more of each of $R_{901}$ to $R_{907}$ are present, the two or more of each of $R_{901}$ to $R_{907}$ are the same or different;

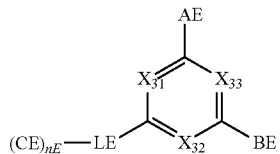
(BE1)

wherein in the formula (BE1),
two or more of $X_{31}$ to $X_{33}$ are nitrogen atoms, and the rest which is not a nitrogen atom is CR;
R is
a hydrogen atom,
a cyano group,
a substituted or unsubstituted alkyl group including 1 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
a substituted or unsubstituted aryl group including 6 to 50 ring carbon atoms, or
a substituted or unsubstituted monovalent heterocyclic group including 5 to 50 ring atoms;
$R_{901}$ to $R_{904}$ are as defined in the formula (1);
when a plurality of R's are present, the plurality of R's may be the same as or different from each other;
AE is a substituted or unsubstituted aryl group including 6 to 50 ring carbon atoms, or a substituted or unsubstituted monovalent heterocyclic group including 5 to 50 ring atoms;
BE is a substituted or unsubstituted aryl group including 6 to 50 ring carbon atoms, or a substituted or unsubstituted monovalent heterocyclic group including 5 to 50 ring atoms;
LE is a single bond, a substituted or unsubstituted (nE+1)-valent aromatic hydrocarbon ring group including 6 to 50 ring carbon atoms, or a substituted or unsubstituted (nE+1)-valent heterocyclic group including 5 to 50 ring atoms; the aromatic hydrocarbon ring group may have a structure in which two or more different aromatic hydrocarbon rings are bonded;
CE's are independently a substituted or unsubstituted aryl group including 6 to 50 ring carbon atoms, or a substituted or unsubstituted monovalent heterocyclic group including 5 to 50 ring atoms;
nE is an integer of 1 to 3; and when nE is 2 or more, LE is not a single bond;

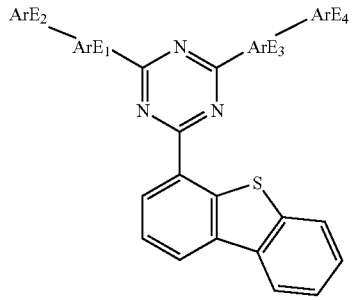
(EB4)

wherein in the formula (EB4),
ArE$_1$ and ArE$_3$ are independently
a single bond,
a substituted or unsubstituted phenylene group,
a substituted or unsubstituted naphthylene group,
a substituted or unsubstituted phenanthrylene group, or
a substituted or unsubstituted anthrylene group;
ArE$_2$ and ArE$_4$ are independently
a substituted or unsubstituted phenyl group,
a substituted or unsubstituted naphthyl group,
a substituted or unsubstituted phenanthryl group, or
a substituted or unsubstituted anthryl group;
ArE$_1$ and ArE$_2$, and ArE$_3$ and ArE$_4$ independently form a substituted or unsubstituted, saturated or unsaturated ring constituted only by a 6-membered ring by bonding with each other, or do not form a ring.

2. The organic electroluminescence device according to claim 1, wherein the compound represented by the formula (BE1) is a compound represented by the following formula (BE10):

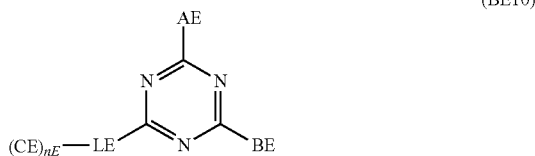

(BE10)

wherein in the formula (BE10),
AE, BE, LE, CE, and nE are as defined in the formula (BE1).

3. The organic electroluminescence device according to claim 1, wherein L$_1$ is
a single bond, or
a substituted or unsubstituted arylene group including 6 to 14 ring carbon atoms.

4. The organic electroluminescence device according to claim 1, wherein the compound represented by the formula (1) is a compound represented by the following formula (1-1):

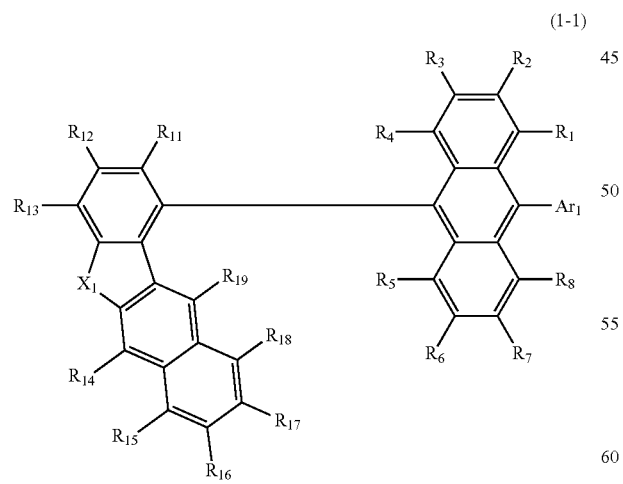

(1-1)

wherein in the formula (1-1), X$_1$, Ar$_1$, R$_1$ to R$_8$, and R$_{11}$ to R$_{19}$ are as defined in the formula (1).

5. The organic electroluminescence device according to claim 1, wherein Ar$_1$ is a substituted or unsubstituted aryl group including 6 to 50 ring carbon atoms.

6. The organic electroluminescence device according to claim 1, wherein Ar$_1$ is selected from the group represented by the following formulas (a1) to (a4),

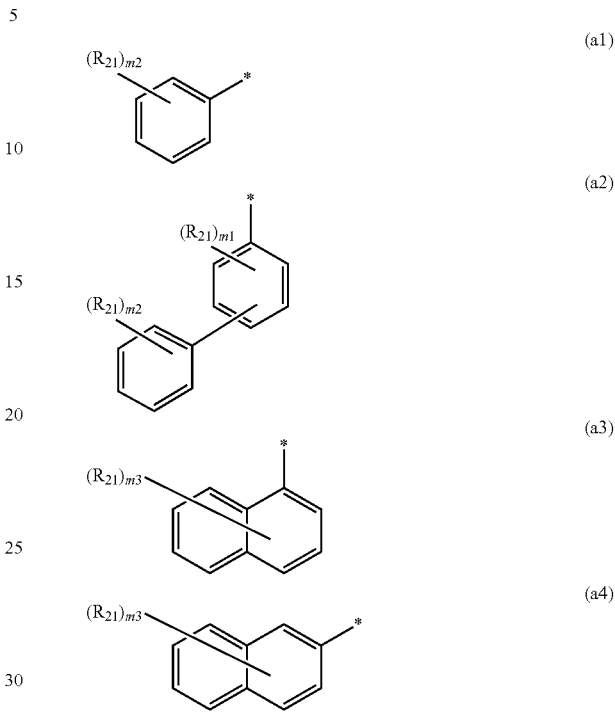

wherein in the formulas (a1) to (a4), "*" is bonded to a carbon atom of the anthracene skeleton;
R$_{21}$ is
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si(R$_{901}$)(R$_{902}$)(R$_{903}$),
—O—(R$_{904}$),
—S—(R$_{905}$),
—N(R$_{906}$)(R$_{907}$),
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms;
R$_{901}$ to R$_{907}$ are as defined in the formula (1);
m1 is an integer of 0 to 4;
m2 is an integer of 0 to 5;
m3 is an integer of 0 to 7;
when each of m1 to m3 is 2 or more, a plurality of R$_{21}$'s may be the same as or different from each other;
when each of m1 to m3 is 2 or more, a plurality of adjacent R$_{21}$'s form a substituted or unsubstituted, saturated or unsaturated ring by bonding with each other, or do not form a substituted or unsubstituted saturated or unsaturated ring.

7. The organic electroluminescence device according to claim 1, wherein $R_1$ to $R_8$ and $R_{11}$ to $R_{19}$ are hydrogen atoms;

$L_1$ is a single bond, an unsubstituted arylene group including 6 to 50 ring carbon atoms, or an unsubstituted divalent heterocyclic group including 5 to 50 ring atoms; and $Ar_1$ is an unsubstituted aryl group including 6 to 50 ring carbon atoms or an unsubstituted monovalent heterocyclic group including 5 to 50 ring atoms.

8. The organic electroluminescence device according to claim 1, wherein $X_1$ is an oxygen atom.

9. The organic electroluminescence device according to claim 2, wherein the compound represented by the formula (BE10) is a compound represented by the following formula (BE11) or formula (BE12),

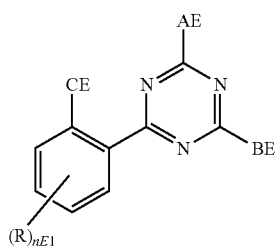

(BE11)

wherein in the formula (BE11),

AE, BE, and CE are as defined in the formula (BE1);

when a plurality of R's are present, one or more sets of adjacent two or more among the plurality of R's are bonded with each other to form a substituted or unsubstituted and saturated or unsaturated ring, or do not form a substituted or unsubstituted and saturated or unsaturated ring;

R which does not form the substituted or unsubstituted, saturated or unsaturated ring is a cyano group, a substituted or unsubstituted alkyl group including 1 to 50 carbon atoms, a substituted or unsubstituted cycloalkyl group including 3 to 50 ring carbon atoms, —Si($R_{901}$)($R_{902}$)($R_{903}$),

—O—($R_{904}$), a substituted or unsubstituted aryl group including 6 to 50 ring carbon atoms, or a substituted or unsubstituted monovalent heterocyclic group including 5 to 50 ring atoms;

$R_{901}$ to $R_{904}$ are as defined in the formula (1);

nE1 is an integer of 0 to 4;

when a plurality of R's are present, the plurality of R's may be the same as or different from each other;

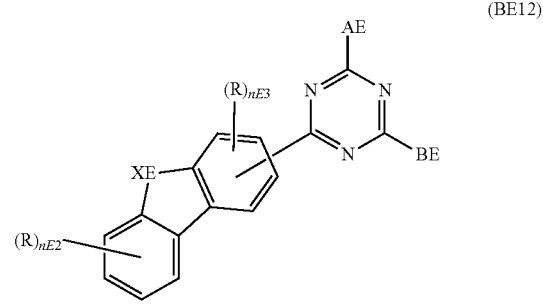

(BE12)

wherein in the formula (BE12),

AE and BE are as defined in the formula (BE1);

XE is $CR_{51}R_{52}$, $NR_{53}$, an oxygen atom, or a sulfur atom;

when XE is $CR_{51}R_{52}$, $R_{51}$ and $R_{52}$ form a substituted or unsubstituted, saturated or unsaturated ring by bonding with each other, or do not form a substituted or unsubstituted, saturated or unsaturated ring;

when a plurality of R's are present, one or more sets of adjacent two or more among the plurality of R's are bonded with each other to form a substituted or unsubstituted and saturated or unsaturated ring, or do not form the ring;

$R_{53}$, and R's, $R_{51}$ and $R_{52}$ which do not form the substituted or unsubstituted, saturated or unsaturated ring, are independently a hydrogen atom, a cyano group, a substituted or unsubstituted alkyl group including 1 to 50 carbon atoms, a substituted or unsubstituted cycloalkyl group including 3 to 50 ring carbon atoms, —Si($R_{901}$)($R_{902}$)($R_{903}$),

—O—($R_{904}$), a substituted or unsubstituted aryl group including 6 to 50 ring carbon atoms, or a substituted or unsubstituted monovalent heterocyclic group including 5 to 50 ring atoms;

$R_{901}$ to $R_{904}$ are as defined in the formula (1);

nE2 is an integer of 0 to 4, and nE3 is an integer of 0 to 3; and when a plurality of R's are present, the plurality of R's may be the same as or different from each other.

10. The organic electroluminescence device according to claim 1, wherein the compound represented by the formula (BE1) is a compound represented by the following formula (BE14):

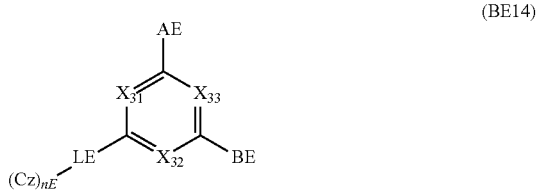

(BE14)

wherein in the formula (BE14), $X_{31}$ to $X_{33}$, AE, BE, LE, and nE are as defined in the formula (BE1);

Cz is a group represented by any one of the following formula (Cz1), (Cz2), and (Cz3):

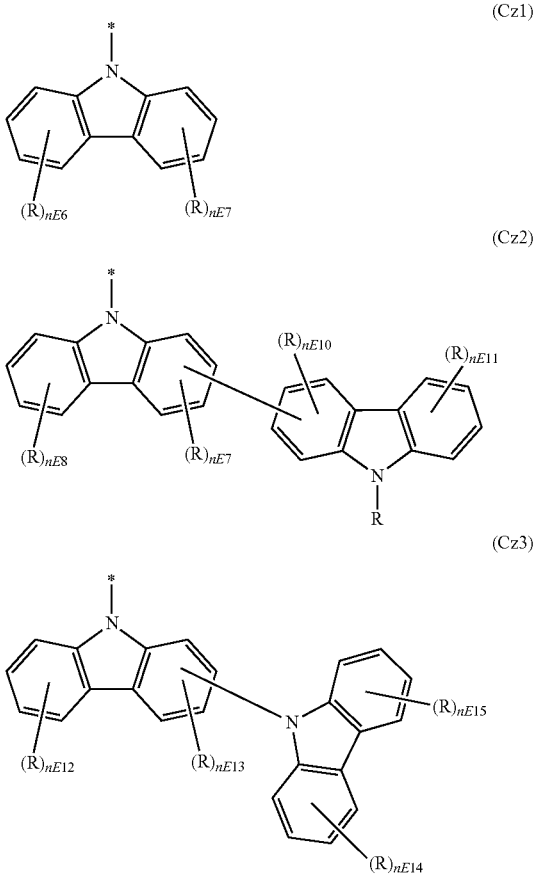

wherein in the formulas (Cz1), (Cz2), and (Cz3),
when a plurality of R's are present, one or more sets of adjacent two or more among the plurality of R's are bonded with each other to form a substituted or unsubstituted and saturated or unsaturated ring, or do not form a substituted or unsubstituted and saturated or unsaturated ring;
R which does not form the substituted or unsubstituted, saturated or unsaturated ring is
a cyano group,
a substituted or unsubstituted alkyl group including 1 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
a substituted or unsubstituted aryl group including 6 to 50 ring carbon atoms, or
a substituted or unsubstituted monovalent heterocyclic group including 5 to 50 ring atoms;
$R_{901}$ to $R_{904}$ are as defined in the formula (1);
nE6 and nE7 are independently an integer of 0 to 4;
nE8 and nE11 are independently an integer of 0 to 4, and nE9 and nE10 are independently an integer of 0 to 3;
nE12, nE14, and nE15 are independently an integer of 0 to 4, and nE13 is an integer of 0 to 3;
when a plurality of R's are present, the plurality of R's may be the same as or different from each other; and
"*" is bonded to LE.

11. The organic electroluminescence device according to claim 1, wherein LE is a single bond, or a substituted or unsubstituted (nE+1)-valent aromatic hydrocarbon ring group including 6 to 12 ring carbon atoms.

12. The organic electroluminescence device according to claim 1, wherein BE is a substituted or unsubstituted aryl group including 6 to 12 ring carbon atoms.

13. The organic electroluminescence device according to claim 1, wherein the first layer is directly adjacent to the emitting layer.

14. The organic electroluminescence device according to claim 1, wherein
the organic layer further comprises a third layer,
the third layer is disposed between the anode and the emitting layer, and
the third layer comprises a compound represented by the following formula (B1):

wherein in the formula (B1),
$L_A$, $L_B$, and $L_C$ are independently a single bond, a substituted or unsubstituted arylene group including 6 to 50 ring carbon atoms, or a substituted or unsubstituted divalent heterocyclic group including 5 to 50 ring atoms;
A, B, and C are independently
a substituted or unsubstituted aryl group including 6 to 50 ring carbon atoms,
a substituted or unsubstituted monovalent heterocyclic group including 5 to 50 ring atoms, or
—Si($R'_{901}$)($R'_{902}$)($R'_{903}$);
$R'_{901}$ to $R'_{903}$ are independently a substituted or unsubstituted aryl group including 6 to 50 ring carbon atoms; and
when two or more of each of $R'_{901}$ to $R'_{903}$ are present, the two or more of each of $R'_{901}$ to $R'_{903}$ are the same or different.

15. The organic electroluminescence device according to claim 1, wherein the substituent in the case of "substituted or unsubstituted" is a group selected from the group consisting of
an unsubstituted alkyl group including 1 to 50 carbon atoms,
an unsubstituted alkenyl group including 2 to 50 carbon atoms,
an unsubstituted alkynyl group including 2 to 50 carbon atoms,
an unsubstituted cycloalkyl group including 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
an unsubstituted aryl group including 6 to 50 ring carbon atoms, and
an unsubstituted monovalent heterocyclic group including 5 to 50 ring atoms; wherein $R_{901}$ to $R_{907}$ are independently
a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted monovalent heterocyclic group including 5 to 50 ring atoms; and
when two or more of each of $R_{901}$ to $R_{907}$ are present, the two or more of each of $R_{901}$ to $R_{907}$ are the same or different.

16. The organic electroluminescence device according to claim 1, wherein the substituent in the case of "substituted or unsubstituted" is
an unsubstituted alkyl group including 1 to 50 carbon atoms,
an unsubstituted alkenyl group including 2 to 50 carbon atoms,
an unsubstituted alkynyl group including 2 to 50 carbon atoms,
an unsubstituted cycloalkyl group including 3 to 50 ring carbon atoms,
—Si($R_{901}$a)($R_{902}$a)($R_{903}$a),
—O—($R_{904}$a),
—S—($R_{905}$a),
—N($R_{906}$a)($R_{907}$a),
a halogen atom, a cyano group, a nitro group,
an unsubstituted aryl group including 6 to 50 ring carbon atoms, or
an unsubstituted monovalent heterocyclic group including 5 to 50 ring atoms; wherein
$R_{901}$a to $R_{907}$a are independently
a hydrogen atom,
an unsubstituted alkyl group including 1 to 50 carbon atoms,
an unsubstituted aryl group including 6 to 50 ring carbon atoms, or
an unsubstituted monovalent heterocyclic group including 5 to 50 ring atoms; and
when two or more of each of $R_{901}$a to $R_{907}$a are present, the two or more of each of $R_{901}$a to $R_{907}$a are the same or different.

17. The organic electroluminescence device according to claim 1, wherein the substituent in the case of "substituted or unsubstituted" is
an unsubstituted alkyl group including 1 to 50 carbon atoms,
an unsubstituted aryl group including 6 to 50 ring carbon atoms, or
an unsubstituted monovalent heterocyclic group including 5 to 50 ring atoms.

18. An electronic apparatus, wherein the organic electroluminescence device according to claim 1 is provided.

* * * * *

UNITED STATES PATENT AND TRADEMARK OFFICE
CERTIFICATE OF CORRECTION

PATENT NO. : 12,284,916 B2
APPLICATION NO. : 17/602273
DATED : April 22, 2025
INVENTOR(S) : Hiroaki Itoi et al.

Page 1 of 1

It is certified that error appears in the above-identified patent and that said Letters Patent is hereby corrected as shown below:

In the Claims

In Claim 6, Column 332, Line 3, please delete "(al) to (a4)," and replace with --(a1) to (a4).--

In Claim 6, Column 332, Line 34, please delete "(al)" and replace with --(a1)--

In Claim 9, Column 333, Line 18, please delete "(BE12)," and replace with --(BE12).--

In Claim 10, Column 335, please replace formula (Cz2) drawing with:

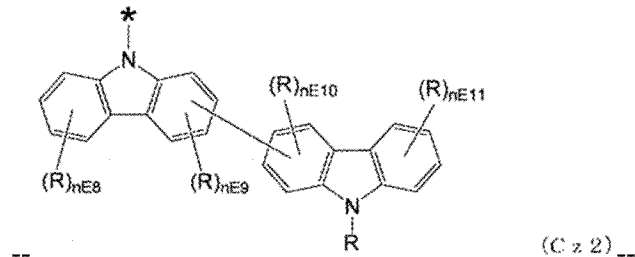

Signed and Sealed this
Twenty-fifth Day of November, 2025

John A. Squires
*Director of the United States Patent and Trademark Office*